(12) United States Patent
Ahmad et al.

(10) Patent No.: US 11,053,197 B2
(45) Date of Patent: Jul. 6, 2021

(54) CARBAZOLE DERIVATIVES

(71) Applicant: BRISTOL-MYERS SQUIBB COMPANY, Princeton, NJ (US)

(72) Inventors: Saleem Ahmad, Wall, NJ (US); Douglas G. Batt, Wilmington, DE (US); Qingjie Liu, Newtown, PA (US); John E. Macor, Washington Crossing, PA (US); Joseph A. Tino, Lawrenceville, NJ (US); Scott Hunter, Pennington, NJ (US); Satheesh Kesavan Nair, Bangalore (IN); Tarun Kumar Maishal, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/859,103

(22) Filed: Apr. 27, 2020

(65) Prior Publication Data

US 2020/0255377 A1    Aug. 13, 2020

Related U.S. Application Data

(63) Continuation of application No. 16/289,878, filed on Apr. 10, 2019, now Pat. No. 10,676,434, which is a continuation of application No. 15/521,194, filed as application No. PCT/US2015/057077 on Oct. 23, 2015, now Pat. No. 10,266,491.

(Continued)

(51) Int. Cl.
| | |
|---|---|
| *C07D 401/04* | (2006.01) |
| *C07D 403/04* | (2006.01) |
| *C07D 487/04* | (2006.01) |
| *C07D 487/10* | (2006.01) |
| *C07D 209/88* | (2006.01) |
| *A61K 31/4523* | (2006.01) |
| *C07D 471/04* | (2006.01) |
| *A61K 31/403* | (2006.01) |
| *C07D 401/06* | (2006.01) |
| *C07D 403/06* | (2006.01) |
| *C07D 403/12* | (2006.01) |
| *C07D 471/10* | (2006.01) |
| *C07D 495/04* | (2006.01) |

(52) U.S. Cl.
CPC ......... *C07D 209/88* (2013.01); *A61K 31/403* (2013.01); *A61K 31/4523* (2013.01); *C07D 401/04* (2013.01); *C07D 401/06* (2013.01); *C07D 403/04* (2013.01); *C07D 403/06* (2013.01); *C07D 403/12* (2013.01); *C07D 471/04* (2013.01); *C07D 471/10* (2013.01); *C07D 487/04* (2013.01); *C07D 487/10* (2013.01); *C07D 495/04* (2013.01)

(58) Field of Classification Search
None
See application file for complete search history.

(56) References Cited

U.S. PATENT DOCUMENTS

| 5,604,236 A | 2/1997 | Jakubowski et al. |
| 7,723,336 B2 | 5/2010 | Vaccaro et al. |

(Continued)

FOREIGN PATENT DOCUMENTS

| CN | 101475571 | 7/2009 |
| WO | WO 2005/005429 | 1/2005 |

(Continued)

OTHER PUBLICATIONS

International Preliminary Report on Patentability PCT/US2015/057077, dated Apr. 24, 2017.
Kalgutkar, Amit S., et al., "Drug Discover for a New Generation of Covalent Drugs", Expert Opinion Drug Discov., vol. 7(7), (2012) pp. 561-581.
Lou, Yan, et al., "Bruton's Tyrosine Kinase Inhibitors: Approaches to Potent and Selective Inhibition, Preclinical and Clinical Evaluation for Inflammatory Diseases and B Cell Malignancies", J. Med. Chem, vol. 55, (2012) pp. 4539-4550.
Barf, T. et al., "Irreversible Protein Kinase Inhibitors: Balancing the Benefits and Risks," Journal of Medicinal Chemistry, vol. 55, (2012) pp. 6243-6262.
Liu, Qingsong, et al., Developing Irreversible Inhibitors for the Protein Kinase Cysteinome, Chemistry & Biology, vol. 20, (2013) pp. 146-159.

(Continued)

*Primary Examiner* — Brian E McDowell
(74) *Attorney, Agent, or Firm* — Gary Greenblatt

(57) ABSTRACT

Disclosed are compounds of Formula (I):

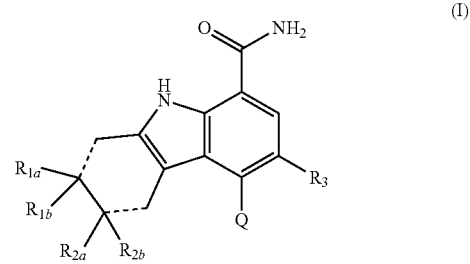

or a salt thereof, wherein Q, $R_{1a}$, $R_{1b}$, $R_{2a}$, $R_{2b}$, $R_3$, $R_4$, $R_{5a}$, $R_{5b}$, $R_{6a}$, $R_{6c}$, $R_{7a}$, $R_{7b}$, $R_{7c}$, and $R_{7d}$ are defined herein. Also disclosed are methods of using such compounds as inhibitors of Bruton's tyrosine kinase (Btk), and pharmaceutical compositions comprising such compounds. These compounds are useful in treating, preventing, or slowing the progression of diseases or disorders in a variety of therapeutic areas, such as autoimmune diseases and vascular disease.

23 Claims, 1 Drawing Sheet

Related U.S. Application Data

(60) Provisional application No. 62/068,234, filed on Oct. 24, 2014.

(56) References Cited

U.S. PATENT DOCUMENTS

| | | | |
|---|---|---|---|
| 8,084,620 | B2 | 12/2011 | Liu et al. |
| 8,362,065 | B2 | 1/2013 | Liu et al. |
| 8,685,969 | B2 | 4/2014 | Liu et al. |
| 9,334,290 | B2 | 5/2016 | Batt et al. |
| 9,688,629 | B2 | 6/2017 | Liu et al. |
| 2006/0084650 | A1 | 4/2006 | Dong et al. |
| 2008/0045536 | A1 | 2/2008 | Vaccaro et al. |
| 2009/0281131 | A1 | 11/2009 | Gopalan et al. |
| 2012/0136023 | A1 | 5/2012 | Bell et al. |
| 2016/0200710 | A1 | 7/2016 | Ko et al. |

FOREIGN PATENT DOCUMENTS

| | | |
|---|---|---|
| WO | WO 2005/014599 | 2/2005 |
| WO | WO 2005/047290 | 5/2005 |
| WO | WO 2006/053121 | 5/2006 |
| WO | WO 2006/064355 | 6/2006 |
| WO | WO 2007/061764 | 5/2007 |
| WO | WO 2008/032171 | 3/2008 |
| WO | WO 2008/033858 | 3/2008 |
| WO | WO 2009/024819 | 2/2009 |
| WO | WO 2009/075830 | 6/2009 |
| WO | WO 2009/102498 | 8/2009 |
| WO | WO 2009/141627 | 11/2009 |
| WO | WO 2009/158571 A1 | 12/2009 |
| WO | WO 2010/015636 | 2/2010 |
| WO | WO 2012/059232 | 5/2012 |
| WO | WO 2012/156334 | 11/2012 |
| WO | WO 2014/064131 | 5/2014 |
| WO | WO2016065222 A1 | 4/2016 |

OTHER PUBLICATIONS

D'Cruz, Osmond J., et al., "Novel Bruton's Tyrosine Kinase Inhibitors Currently in Development", OncoTargets and Therapy, vol. 6, (2013) pp. 161-176.

Whang, Jennifer A., et al., "Bruton's tyrosine kinase inhibitors for the treatment of rheumatoid arthritis," Drug Discovery Today vol. 19, No. 8 (2014) pp. 1200-1204.

Bauer, Renato A., "Covalent inhibitors in drug discovery: from accidental discoveries to avoided liabilities and designed therapies", Drug Discovery Today, vol. 20, No. 9 (2015) pp. 1061-1073.

Patani, et al., "Bioisosterism: A Rational Approach in Drug Design", Chem. Rev., 1996, 96, 3147-3176.

Lim, Jongwon, et al., "Discovery of 1-Amino-5H-pyrido[4,3-b]indol-4-carboxamide Inhibitors of Janus Kinase 2 (JAK2) for the Treatment of Myeloproliferative Disorders", Journal of Medicinal Chemistry, 2011, vol. 54, pp. 7334-7349.

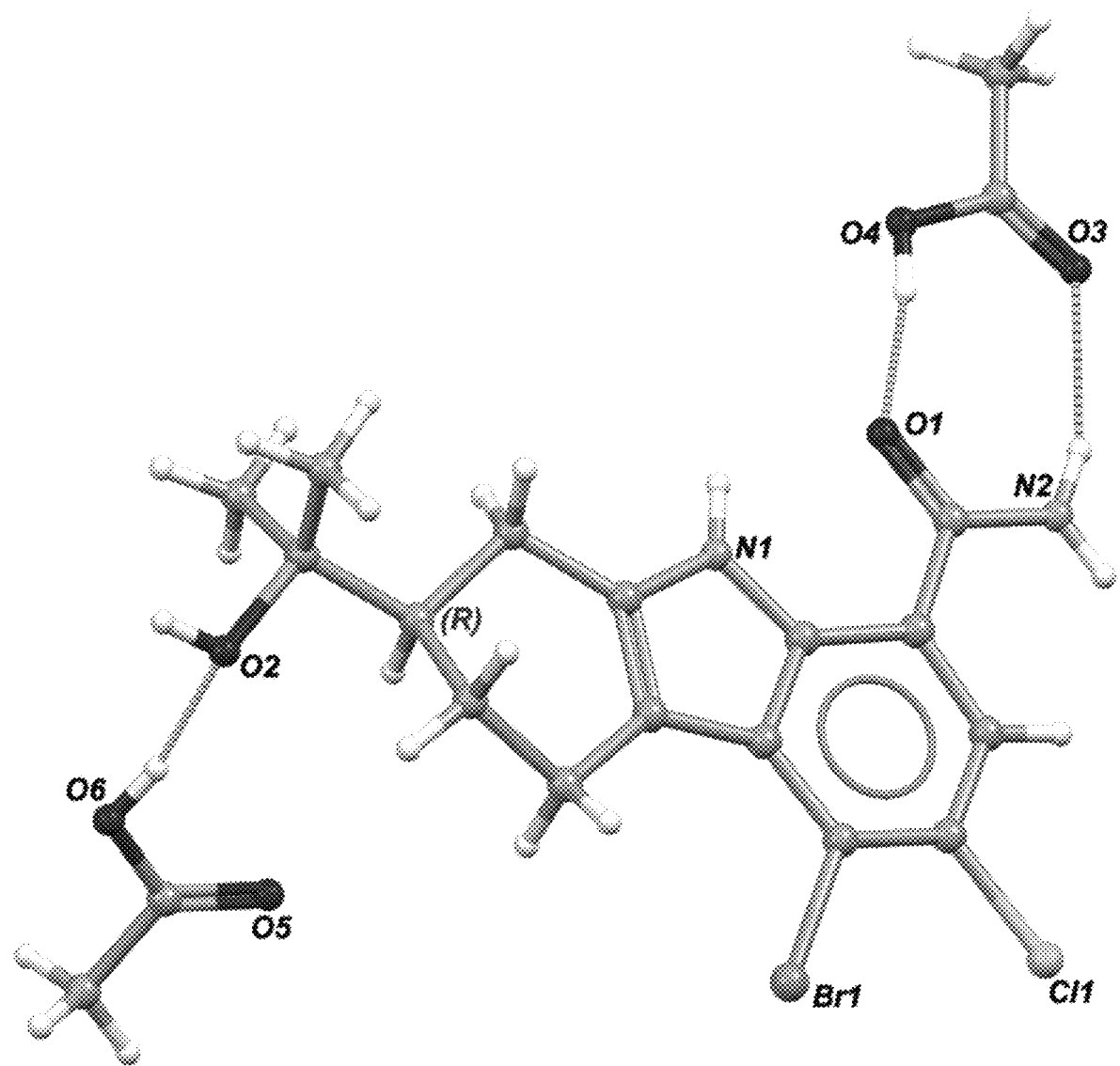

CARBAZOLE DERIVATIVES

CROSS-REFERENCE TO RELATED APPLICATIONS

This application is a continuation application of U.S. application Ser. No. 16/289,878, filed Apr. 10, 2019, which is a continuation application of U.S. application Ser. No. 15/521,194, filed Apr. 21, 2017, which is a national phase application under 35 U.S.C. § 371 of International Patent Application No. PCT/US2015/057077, filed Oct. 23, 2015, which claims priority to U.S. Application Ser. No. 62/068,234, filed Oct. 24, 2014, which are expressly incorporated fully herein by reference.

DESCRIPTION

The present invention generally relates to tricyclic compounds useful as kinase inhibitors, including the modulation of Bruton's tyrosine kinase (Btk) and other Tec family kinases such as Itk. Provided herein are tricyclic compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk and other Tec family kinases such as Itk, in a mammal.

Protein kinases, the largest family of human enzymes, encompass well over 500 proteins. Btk is a member of the Tec family of tyrosine kinases, and is a regulator of early B-cell development, as well as mature B-cell activation, signaling, and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis.

A large body of evidence supports the role of B-cells and the humoral immune system in the pathogenesis of autoimmune and/or inflammatory diseases. Protein-based therapeutics such as RITUXAN®, developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

A compound that inhibits an enzyme by reacting with the enzyme to form a covalent bond can offer advantages over a compound that does not form such a covalent bond. (See, for example, Liu, Q. et al., *Chem. Biol.*, 20:146 (2013); Barf, T. et al., *J. Med. Chem.*, 55:6243 (2012); Kalgutkar, A. et al., *Expert Opin. Drug Discov.*, 7:561 (2012); and Garuti, L. et al., *Curr. Med. Chem.*, 18:2981 (2011); and references cited therein). A compound that does not form a covalent bond can dissociate from the enzyme, releasing the enzyme from the inhibition resulting from its binding. Such reversible inhibition may require a relatively high and continuous concentration of the inhibitory compound to drive the binding equilibrium toward sufficient enzyme occupancy by the inhibitor to achieve useful enzyme inhibition. A higher concentration of the compound could require administration of a higher dose of the compound to a mammal in need of such inhibition, and at a higher concentration the inhibitor could have undesired effects due to inhibition of other, non-targeted enzymes. Such off-target inhibition could include toxicity. Additionally, more frequent dosing may be required since the inhibitory compound, after dissociation from the target enzyme, can be removed from the body by metabolism and/or elimination, lowering the concentration available to achieve inhibition of the target enzyme.

In contrast, an inhibitor that forms a covalent bond with its target enzyme irreversibly inhibits the enzyme. The irreversible inhibition would result from either slow or negligible dissociation of the inhibitor, since such dissociation would require breaking a covalent bond. If the affinity of such a covalent inhibitor for its target enzyme is sufficiently great relative to affinities for other, off-target enzymes, a significantly lower concentration of the inhibitor can result in useful inhibition relative to a concentration required for reversible inhibition. The lower concentration could reduce the likelihood of undesired off-target inhibition and potential toxicity. Also, since the covalent inhibitor can bind essentially irreversibly to the target enzyme, the free (non-bound) concentration of the inhibitor can become extremely low as non-bound inhibitor is removed from the body by metabolism and/or elimination, even while useful enzyme inhibition is maintained. This can reduce the likelihood of undesired effects. Additionally, since the enzyme can be irreversibly inhibited, less frequent dosing may be required to achieve useful inhibition.

Certain reactive functional groups can be attached to a compound with good affinity for the target enzyme, which will allow formation of a covalent bond with a functional group in the target enzyme. For example, an electrophilic group such as a vinylic or acetylenic group attached to an electron-withdrawing group such as a ketone, amide, sulfone, sulfonamide, or an electron-withdrawing heterocyclic ring such as a pyridyl ring can react with a nucleophilic group present in the target enzyme, such as the thiol or thiolate group of a cysteine residue, to form a covalent bond. Such a reaction can be essentially irreversible under normal physiological conditions. In order for such a reaction to be achieved, the inhibitor compound must bind to the target enzyme and present the attached electrophilic group in a correct spatial orientation to allow favorable interaction with the attacking nucleophile. If the orientation is not correct, the covalent bond may not easily form, and the desired irreversible inhibition may not be achieved. In this case, the compound would behave like a reversible inhibitor and the benefits of irreversible inhibition may not be realized. Also, if the orientation of the electrophile on the bound inhibitor is not suitable for reaction with the nucleophilic group of the target enzyme, the inhibitor will be capable of dissociation from the target enzyme, resulting in a higher concentration of the inhibitor and a greater likelihood that the reactive electrophilic group can react with other, non-target nucleophiles and cause undesired effects such as toxicity.

U.S. Pat. Nos. 8,084,620 and 8,685,969 disclose tricyclic carboxamide compounds useful as kinase inhibitors, including the modulation of Btk and other Tec family kinases.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

There still remains a need for compounds useful as Btk inhibitors. Further, there still remains a need for compounds useful as Btk inhibitors that can be administered at lower doses or are effective at lower concentrations. Additionally, there still remains a need for compounds that have a combination of improved potency as Btk inhibitors and improved potency in the Ramos FLIPR assay.

Applicants have found potent compounds that have activity as Btk inhibitors. These compounds are provided to be useful as pharmaceuticals with desirable stability, bioavailability, therapeutic index, and toxicity values that are important to their drugability.

SUMMARY OF THE INVENTION

The present invention provides tricyclic compounds, including prodrugs thereof, which are useful as inhibitors of Btk, and are useful for the treatment of proliferative diseases, allergic diseases, autoimmune diseases and inflammatory diseases.

The present invention also provides pharmaceutical compositions comprising at least one compound of Formula (IIa) and a pharmaceutically acceptable carrier.

The present invention also provides a method of inhibiting Btk activity comprising administering to a mammal in need thereof at least one compound of Formula (IIa).

The present invention also provides a method for treating allergic disorders and/or autoimmune and/or inflammatory diseases, comprising administering to a mammal in need thereof at least one compound of Formula (IIa).

The present invention also provides a method for treating proliferative diseases, such as cancer, comprising administering to a mammal in need thereof at least one compound of Formula (IIa).

The present invention also provides a method of treating a disease or disorder associated with Btk activity, the method comprising administering to a mammal in need thereof, at least one compound of Formula (IIa).

The present invention also provides processes and intermediates for making the compounds of Formula (I).

The present invention also provides a compound of Formula (IIa) for use in therapy.

The present invention also provides the use of the compounds of Formula (IIa) for the manufacture of a medicament for the treatment or prophylaxis of Btk related conditions, such as proliferative diseases, allergic diseases, autoimmune diseases and inflammatory diseases.

The present invention also provides the use of the compounds of Formula (IIa) for the manufacture of a medicament for treatment of cancer.

The compounds of Formula (IIa) and compositions comprising the compounds of Formula (IIa) may be used in treating, preventing, or curing various Btk related conditions. Pharmaceutical compositions comprising these compounds are useful in treating, preventing, or slowing the progression of diseases or disorders in a variety of therapeutic areas, such as proliferative diseases, allergic diseases, autoimmune diseases and inflammatory diseases.

These and other features of the invention will be set forth in expanded form as the disclosure continues.

BRIEF DESCRIPTION OF THE DRAWINGS

The invention is illustrated by reference to the accompanying drawings described below.

FIG. 1 shows the absolute stereochemistry of Intermediate 13 diacetic acid solvate.

DETAILED DESCRIPTION

The second aspect of the present invention provides a compound of Formula (I)

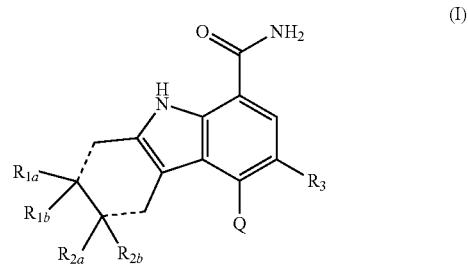

or a salt thereof, wherein:
the two dotted lines represent either two single or two double bonds; and $R_{1b}$ and $R_{2b}$ are present only if said two dotted lines are two single bonds;

Q is:
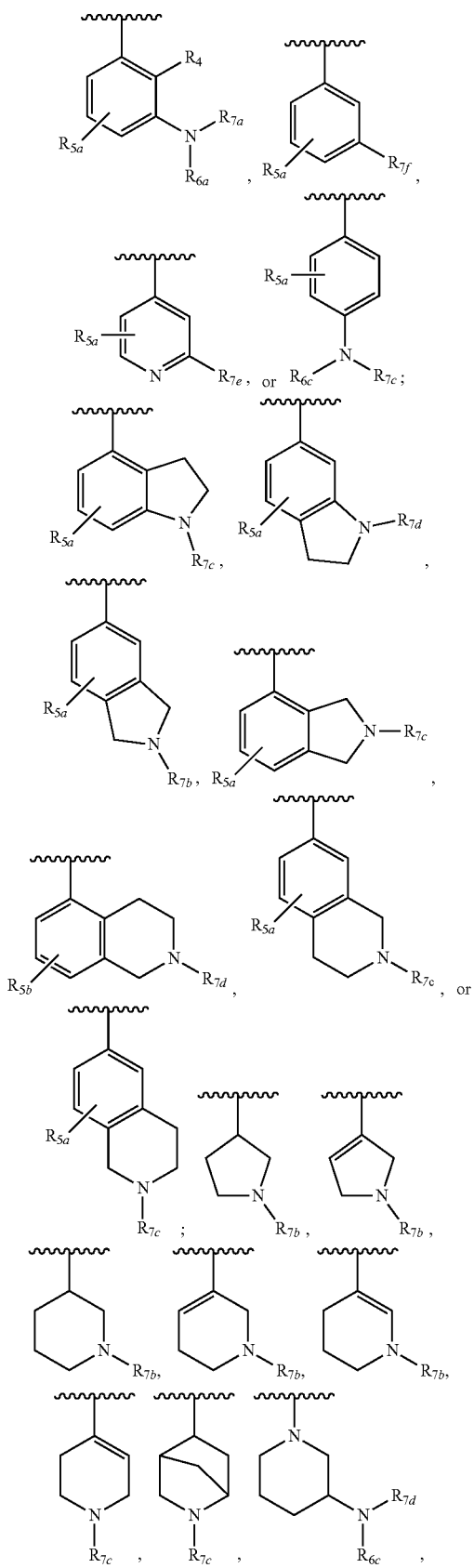
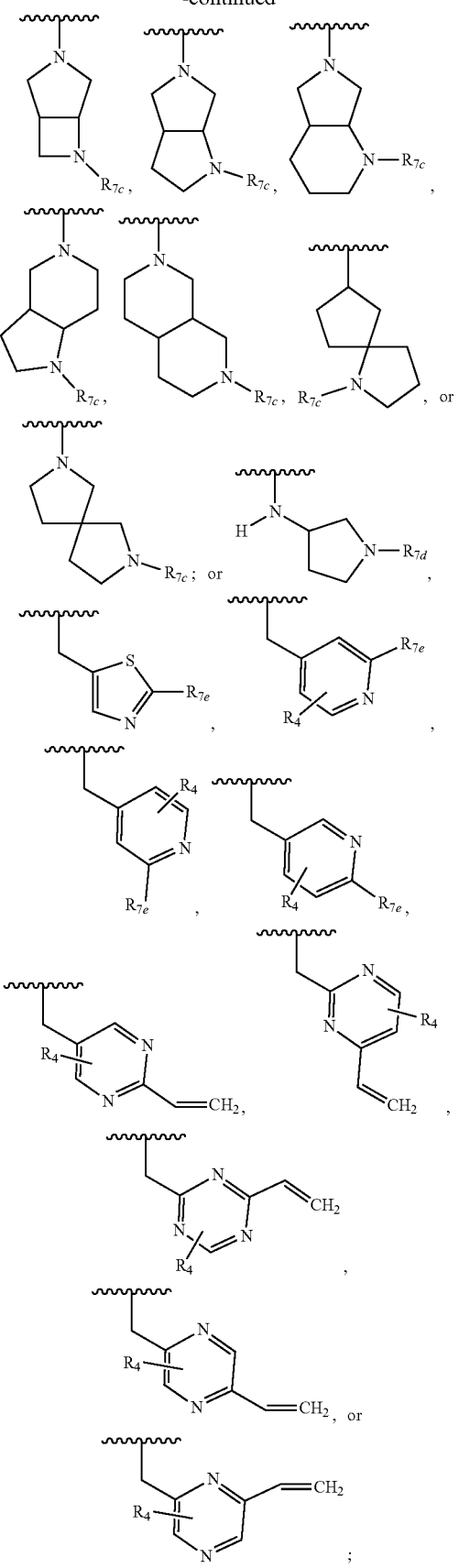

$R_{1a}$ is:
(i) H, —CN, —CF$_3$, —CH$_3$, —CR$_{8a}$R$_{8b}$OH, —CR$_{8a}$R$_{8b}$OH, —C$_{8a}$R$_{8b}$CR$_{8a}$R$_{8b}$OH, —CH(OH)CH$_2$OH, —NHR$_9$, —C(O)NR$_{10a}$R$_{10b}$, —C(O)(morpholinyl), —C(O)(piperazinyl), or —C(O)(methyl piperazinyl); or

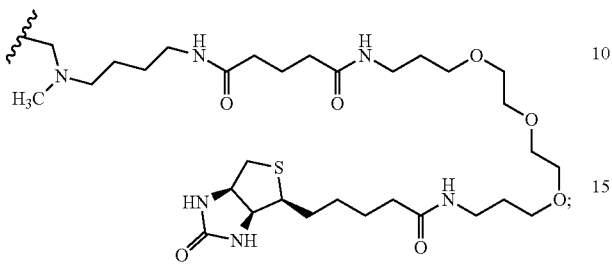

$R_{1b}$, when present, is H or —CH$_3$, provided that if $R_{1a}$ is H then $R_{1b}$ is also H;
$R_{2a}$ is H, F, or Cl, provided that if $R_{1a}$ is other than H then $R_{2a}$ is H;
$R_{2b}$, when present, is the same as $R_{2a}$;
$R_3$ is H, F, or Cl;
$R_4$ is H, F, Cl, or —CH$_3$;
$R_{5a}$ is H, F, Cl, —OCH$_3$, or —OCF$_3$;
$R_{5b}$ is H, F, Cl, —OCH$_3$, or —OCF$_3$;
$R_{6a}$ is H, —CH$_3$ or cyclopropyl;
$R_{6c}$ is H, —CH$_3$ or cyclopropyl;
$R_{7a}$ is —C(O)CH=CH(R$_{11}$), —C(O)C≡CR$_{12}$, or —S(O)$_2$CH=CH$_2$;
$R_{7b}$ is —C(O)CH=CH$_2$;
$R_{7c}$ is —C(O)CH=CH$_2$ or —C(O)C≡CR$_{12}$;
$R_{7d}$ is —CN, —C(O)CH=CH$_2$, or —C(O)C≡CR$_{13}$;
$R_{7e}$ is —CH=CH$_2$ or —C≡CR$_{13}$;
$R_{7f}$ is pyrrolidinyl substituted with R$_{7c}$, —CH=CHC(O)(morpholinyl), or —CH=CHC(O)(pyrrolidinyl);
$R_{8a}$ is H or —CH$_3$;
$R_{8b}$ is H or —CH$_3$;
$R_9$ is C$_{1-4}$ alkyl;
$R_{10a}$ and $R_{10b}$ are independently H or —CH$_3$;
$R_{11}$ is H or —CH$_3$;
$R_{12}$ is H, C$_{1-4}$ alkyl, or cyclopropyl; and
$R_{13}$ is H, C$_{1-4}$ alkyl, or cyclopropyl;
with the provisos that:
(a) if Q is

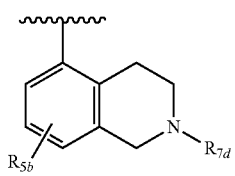

and $R_{7d}$ is —CN or —C(O)CH=CH$_2$, then $R_3$ is H; and
(b) if the dotted lines represent two single bonds, then:
(i) Q is not

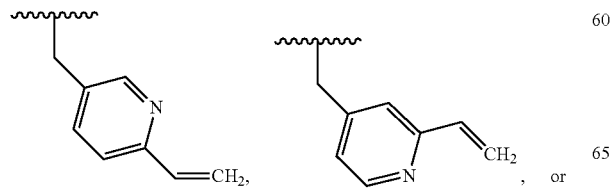

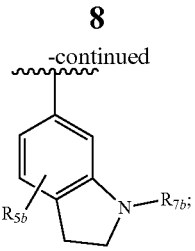

(ii) $R_{11}$, if present, is H; and
(iii) the compound of Formula (I) is not:

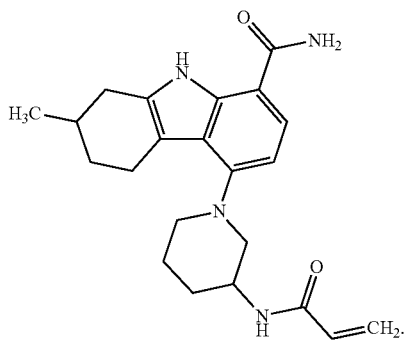 [SMILES: C=CC(=O)NC1CCCN(c2ccc(C(N)=O)c3[nH]c4c(c23)CCC(C)C4)C1]

The second aspect of the present invention provides a compound of Formula (I)

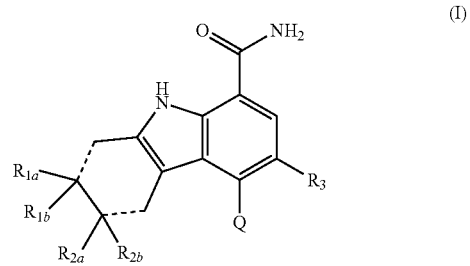

or a salt thereof, wherein:
the two dotted lines represent either two single or two double bonds; and $R_{1b}$ and $R_{2b}$ are present only if said two dotted lines are two single bonds;

Q is:

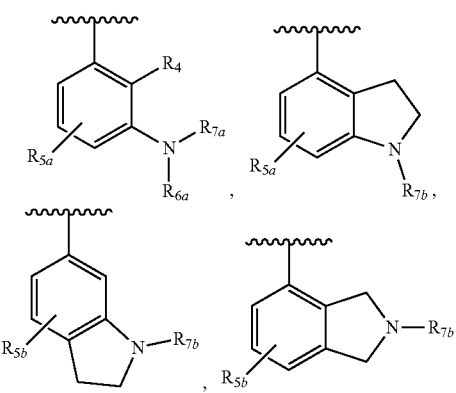

-continued

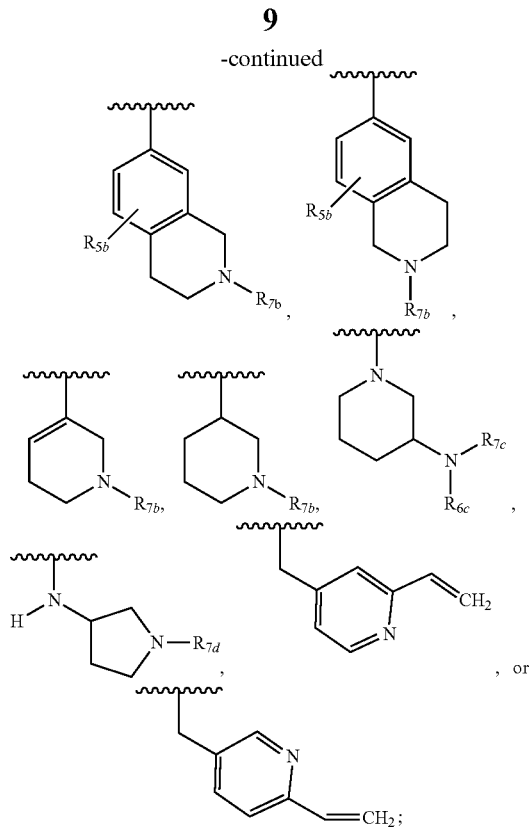

$R_{1a}$ is:
(i) H, —CN, —CF$_3$, —CH$_3$, —CR$_{8a}$R$_{8b}$OH, —CH(OH)CH$_2$OH, —NHR$_9$, or —C(O)NR$_{10a}$R$_{10b}$; or
(ii)

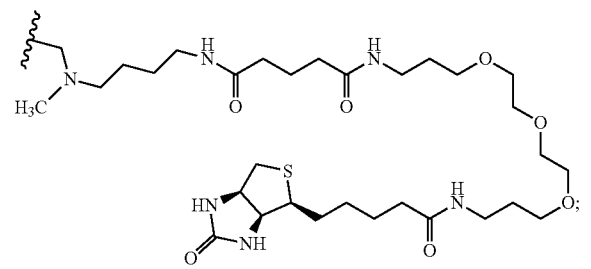 [SMILES: *CN(C)CCCCNC(=O)CCCC(=O)NCCCOCCOCCOCCCNC(=O)CCCC[C@@H]1SC[C@@H]2NC(=O)N[C@@H]21]

$R_{1b}$, when present, is H or —CH$_3$, provided that if $R_{1a}$ is H then $R_{1b}$ is also H;
$R_{2a}$ is H or F, provided that if $R_{1a}$ is other than H then $R_{2a}$ is H;
$R_{2b}$, when present, is the same as $R_{2a}$;
$R_3$ is H, F, or Cl;
$R_4$ is H, F, Cl, or —CH$_3$;
$R_{5a}$ is H, F, Cl, —OCH$_3$, or —OCF$_3$;
$R_{5b}$ is H, F, Cl, —OCH$_3$, or —OCF$_3$;
$R_{6a}$ is H, —CH$_3$ or cyclopropyl;
$R_{6c}$ is H, —CH$_3$ or cyclopropyl;
$R_{7a}$ is —C(O)CH=CH(R$_{11}$), —C(O)C≡CR$_{12}$, or —S(O)$_2$CH=CH$_2$;
$R_{7b}$ is —C(O)CH=CH$_2$;
$R_{7c}$ is —C(O)CH=CH$_2$ or —C(O)C≡CR$_{12}$;
$R_{7d}$ is —C(O)CH=CH$_2$ or —C(O)C≡CR$_{13}$;
$R_{8a}$ is H or —CH$_3$;
$R_{8b}$ is H or —CH$_3$;
$R_9$ is C$_{1-4}$ alkyl;
$R_{10a}$ and $R_{10b}$ are independently H or —CH$_3$;
$R_{11}$ is H or —CH$_3$;
$R_{12}$ is H, C$_{1-4}$ alkyl, or cyclopropyl; and
$R_{13}$ is H, C$_{1-4}$ alkyl, or cyclopropyl;
provided that if the dotted lines represent two single bonds, then:
(i) Q is not

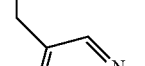

(ii) $R_{11}$, if present, is H; and
(iii) the compound of Formula (I) is not

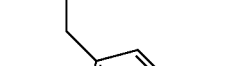

One embodiment provides a compound of Formula (I) or a salt thereof, wherein the two dotted lines represent two double bonds. Compounds of this embodiment have the structure of Formula (Ia):

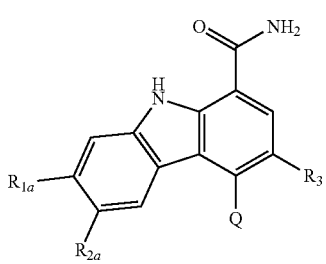

(Ia)

wherein Q, $R_{1a}$, $R_{2a}$, and $R_3$ are defined in the first aspect. Also included in this embodiment are compounds in which Q, $R_{1a}$, $R_{2a}$, and $R_3$ are defined in the second aspect.

One embodiment provides a compound of Formula (I) or a salt thereof, wherein the two dotted lines represent two single bonds. Compounds of this embodiment have the structure of Formula (Ib):

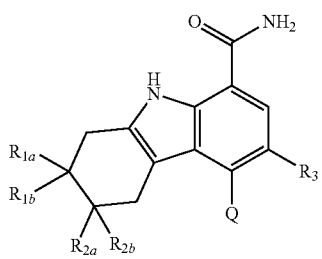

(Ib)

wherein Q, $R_{1a}$, $R_{1b}$, $R_{2a}$, $R_{2b}$, and $R_3$ are defined in the first aspect. Also included in this embodiment are compounds in which Q, $R_{1a}$, $R_{2a}$, and $R_3$ are defined in the second aspect. The tetrahydrocarbazole compounds represented by Formula (Ib), wherein $R_{1a}$ is other than H, also have a chiral center at the carbon atom to which $R_{1a}$ is attached, and thus can exist as S- and R-isomers at this chiral center. These isomers are separable and stable. One embodiment provides such compounds of Formula (Ib) with the carbon chiral center to which $R_{1a}$ is attached as the S-isomer. One embodiment provides such compounds of Formula (Ib) with the carbon chiral center to which $R_{1a}$ is attached as the R-isomer.

One embodiment provides a compound of Formula (I) or a salt thereof, wherein $R_{1a}$ is H, —CN, —CF$_3$, —CH$_3$, —CR$_{8a}$R$_{8b}$OH, —CR$_{8a}$R$_{8b}$CR$_{8a}$R$_{8b}$OH, —CH(OH)CH$_2$OH, —NHR$_9$, —C(O)NR$_{10a}$R$_{10b}$, —C(O)(morpholinyl), —C(O)(piperazinyl), or —C(O)(methyl piperazinyl); and Q, $R_{1b}$, $R_{2a}$, $R_{2b}$, $R_3$, $R_{8a}$, $R_{8b}$, $R_9$, $R_{10a}$, and $R_{10b}$ are defined in the first aspect. The compounds of this embodiment are referred to herein as compounds of Formula (IIa). Included in this embodiment are compounds in which $R_{1a}$ is H, —CN, —CH$_3$, —CF$_3$, —CR$_{8a}$R$_{8b}$OH, —CH(OH)CH$_2$OH, —NHR$_9$, or —C(O)NR$_{10a}$R$_{10b}$.

One embodiment provides a compound of Formula (I) or a salt thereof, wherein $R_{1a}$ is:

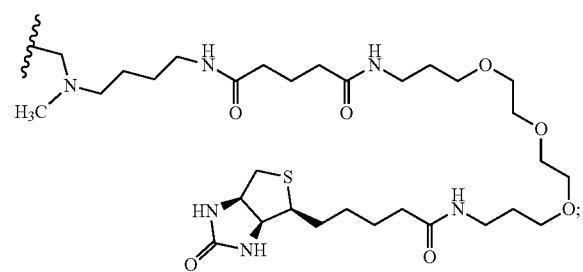 [SMILES: *CN(C)CCCCNC(=O)CCCC(=O)NCCCOCCOCCOCCCNC(=O)CCCC[C@@H]1SC[C@@H]2NC(=O)N[C@@H]21]

and Q, $R_{1b}$, $R_{2a}$, $R_{2b}$, and $R_3$ are defined in the first aspect or the second aspect. The compounds of this embodiment are referred to herein as compounds of Formula (IIb).

One embodiment provides a compound of Formula (I), Formula (Ia), or Formula (Ib), or a salt thereof, wherein $R_{6a}$ is H or —CH$_3$; $R_{6c}$ is H or —CH$_3$; $R_{7a}$ is —C(O)CH=CH(R$_{11}$) or —S(O)$_2$CH=CH$_2$; $R_{13}$ is H; and Q, $R_{1a}$, $R_{1b}$, $R_{2a}$, $R_{2b}$, $R_3$, and $R_{11}$ are defined in the first aspect or the second aspect.

One embodiment provides a compound of Formula (I), Formula (Ia), or Formula (Ib), or a salt thereof, wherein Q is

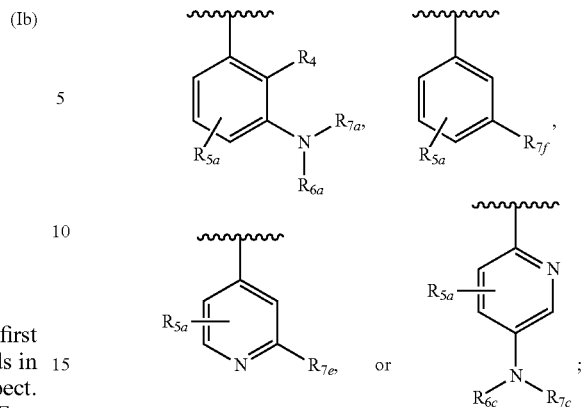

and $R_{1a}$, $R_{1b}$, $R_{2a}$, $R_{2b}$, $R_3$, $R_4$, $R_{5a}$, $R_{6a}$, $R_{6c}$, $R_{7a}$, $R_{7c}$, $R_{7e}$, and $R_{7f}$ are defined in the first aspect or the second aspect. Included in embodiment are compounds in which $R_{1a}$ is H, —CH$_3$, —CF$_3$, —CH$_2$OH, —C(CH$_3$)$_2$OH, —CH(OH)CH$_2$OH, —C(O)NH$_2$, —C(O)N(CH$_3$)$_2$, or —NHCH(CH$_3$)$_2$; $R_{1b}$ is H or —CH$_3$; $R_{2a}$ is H; $R_3$ is H, F, or Cl; $R_4$ is H or —CH$_3$; $R_{5a}$ is H or —CH$_3$; $R_{6a}$ is H or —CH$_3$; $R_{6c}$ is H or —CH$_3$; $R_{7a}$ is —C(O)CH=CH(R$_{11}$) or —S(O)$_2$CH=CH$_2$; $R_{7c}$ is —C(O)CH=CH$_2$; $R_{7e}$ is —C=CH$_2$; $R_{7f}$ is pyrrolidinyl substituted with $R_{7c}$, —CH=CHC(O)(morpholinyl), or —CH=CHC(O)(pyrrolidinyl); and $R_{11}$ is H or —CH$_3$.

One embodiment provides a compound of Formula (I), Formula (Ia), or Formula (Ib), or a salt thereof, wherein Q is

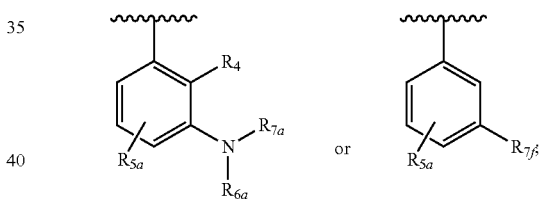

and $R_{1a}$, $R_{1b}$, $R_{2a}$, $R_{2b}$, $R_3$, $R_4$, $R_{5a}$, $R_{6a}$, $R_{7a}$, and $R_{7f}$ are defined in the first aspect or the second aspect. Included in embodiment are compounds in which $R_{1a}$ is H, —CH$_3$, —CF$_3$, —CH$_2$OH, —C(CH$_3$)$_2$OH, —CH(OH)CH$_2$OH, —C(O)NH$_2$, —C(O)N(CH$_3$)$_2$, or —NHCH(CH$_3$)$_2$; $R_{1b}$ is H or —CH$_3$; $R_{2a}$ is H; $R_3$ is H, F, or Cl; $R_4$ is H or —CH$_3$; $R_{5a}$ is H or —CH$_3$; $R_{6a}$ is H or —CH$_3$; $R_{7a}$ is —C(O)CH=CH(R$_{11}$) or —S(O)$_2$CH=CH$_2$; $R_{7c}$ is —C(O)CH=CH$_2$; $R_{7f}$ is pyrrolidinyl substituted with $R_{7c}$, —CH=CHC(O)(morpholinyl), or —CH=CHC(O)(pyrrolidinyl); and $R_{11}$ is H or —CH$_3$.

One embodiment provides a compound of Formula (I), Formula (Ia), or Formula (Ib), or a salt thereof, wherein Q is

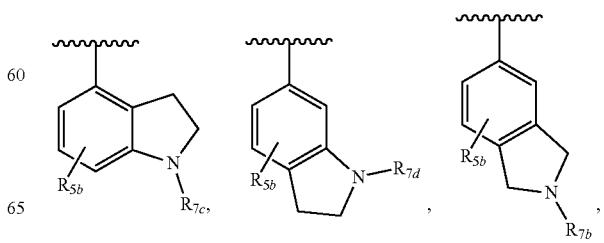

-continued

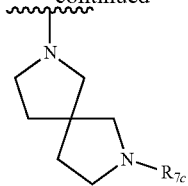

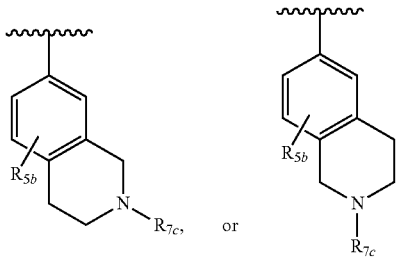

and $R_{1a}$, $R_{1b}$, $R_{2a}$, $R_{2b}$, $R_3$, $R_{5b}$, $R_{7b}$, $R_{7c}$, and $R_{7d}$ are defined in the first aspect or the second aspect. Included in embodiment are compounds in which $R_{1a}$ is H, —CF$_3$, —CH$_3$, —CR$_{8a}$R$_{8b}$OH, —CR$_{8a}$R$_{8b}$CR$_{8a}$R$_{8b}$OH, —C(O)NR$_{10a}$R$_{10b}$, or —C(O)(methyl piperazinyl); $R_{1b}$ is H; $R_{2a}$ is H, F, or Cl; $R_{2b}$ is H, F, or Cl; $R_3$ is H, F, or Cl; $R_{6c}$ is H; $R_{7b}$ is —C(O)CH=CH$_2$; $R_{7c}$ is —C(O)CH=CH$_2$ or —C(O)C≡CCH$_3$; $R_{7d}$ is —CN, —C(O)CH=CH$_2$, or —C(O)C≡CR$_{13}$; and $R_{13}$ is —CH$_3$ or cyclopropyl.

One embodiment provides a compound of Formula (I), Formula (Ia), or Formula (Ib), or a salt thereof, wherein Q is

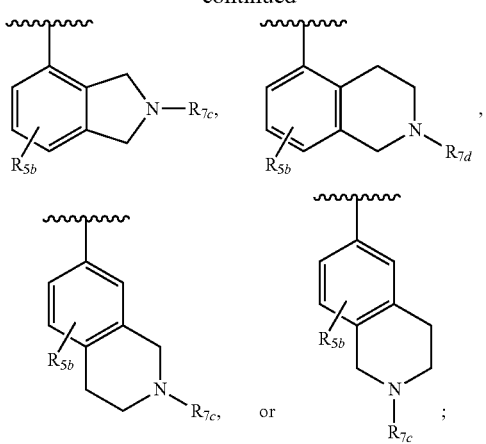

and $R_{1a}$, $R_{1b}$, $R_{2a}$, $R_{2b}$, $R_3$, $R_{5b}$, $R_{7b}$, $R_{7c}$, and $R_{7d}$ are defined in the first aspect or the second aspect. Included in embodiment are compounds in which $R_{1a}$ is H, —CF$_3$, —CH$_2$CH$_2$OH, —C(CH$_3$)$_2$OH, or —C(O)(morpholinyl); $R_{1b}$ is H; $R_{2a}$ is H; $R_3$ is H or F; $R_{7b}$ is —C(O)CH=CH$_2$; $R_{7c}$ is —C(O)CH=CH$_2$ or —C(O)C≡CR$_{12}$; $R_{7d}$ is —CN, —C(O)CH=CH$_2$, or —C(O)C≡CR$_{13}$; $R_{1a}$ is —CH$_3$; and $R_{13}$ is —CH$_3$.

One embodiment provides a compound of Formula (I), Formula (Ia), or Formula (Ib), or a salt thereof, wherein Q is

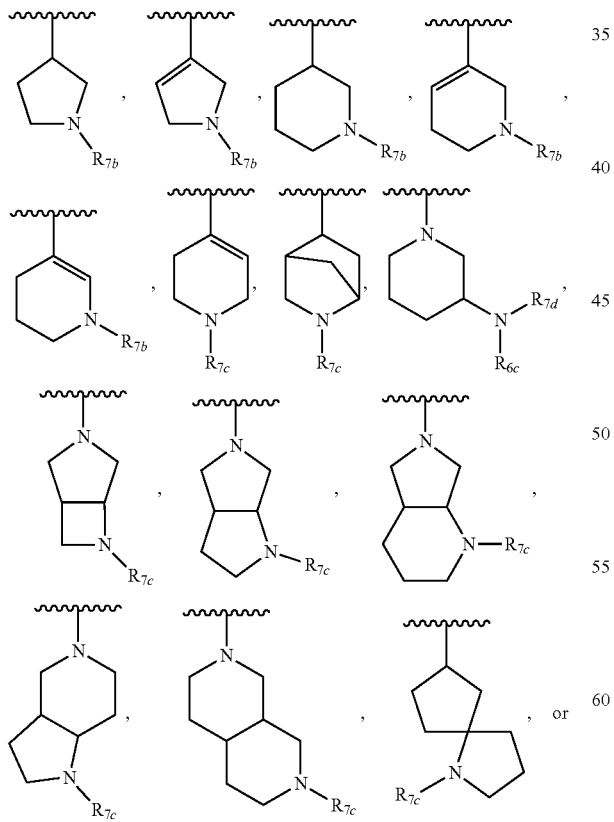

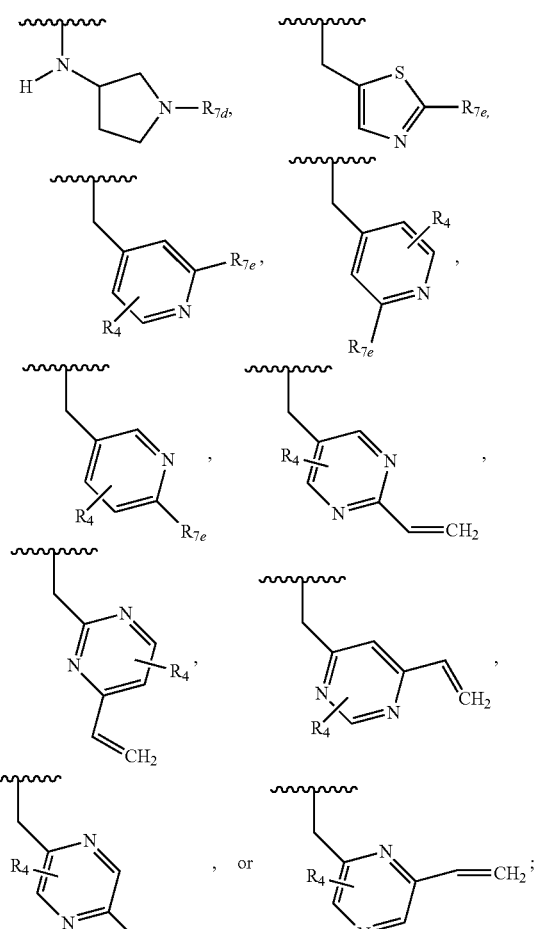

and $R_{1a}$, $R_{1b}$, $R_{2a}$, $R_{2b}$, $R_3$, $R_4$, $R_{7d}$, and $R_{7e}$ are defined in the first aspect or the second aspect. Included in embodiment are compounds in which $R_{1a}$ is H, —CF$_3$, —CR$_{8a}$R$_{8b}$OH, —C(O)NR$_{10a}$R$_{10b}$, or —C(O)(methyl piperazinyl); $R_{1b}$ is H; $R_{2a}$ is H; $R_3$ is H, F, or Cl; $R_4$ is H or —CH$_3$; $R_{7d}$ is —CN, —C(O)CH=CH$_2$, or —C(O)C≡CH; and $R_{7e}$ is —CH=CH$_2$ or —C≡CCH$_3$.

One embodiment provides a compound of Formula (I), Formula (Ia), or Formula (Ib), or a salt thereof, wherein Q is

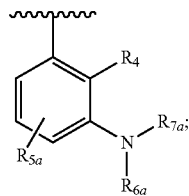

and $R_{1a}$, $R_{1b}$, $R_{2a}$, $R_{2b}$, $R_3$, $R_4$, $R_{5a}$, $R_{6a}$, and $R_{7a}$ are defined in the first aspect or the second aspect. Included in embodiment are compounds in which $R_{1a}$ is H, —CN, —CF$_3$, —CH$_3$, —CH$_2$OH, —C(CH$_3$)$_2$OH, —CH(OH)CH$_2$OH, —NHCH(CH$_3$)$_2$, —C(O)NH$_2$, or —C(O)N(CH$_3$)$_2$; $R_{2a}$ is H; $R_{2b}$ is H; $R_{5a}$ is H, F, —OCH$_3$, or —OCF$_3$; $R_{6a}$ is H or —CH$_3$; and $R_{7a}$ is —C(O)CH=CH$_2$, —C(O)CH=CHCH$_3$, or —S(O)$_2$CH=CH$_2$.

One embodiment provides a compound of Formula (Ia) or a salt thereof, wherein Q is

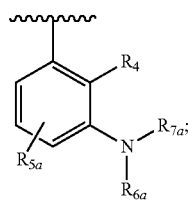

and $R_{1a}$, $R_{2a}$, $R_3$, $R_4$, $R_{5a}$, $R_{6a}$, and $R_{7a}$ are defined in the first aspect or the second aspect. Included in this embodiment are compounds in which $R_{1a}$ is —CN, —C(CH$_3$)$_2$OH, or —CH(OH)CH$_2$OH; $R_{2a}$ is H; $R_4$ is H or —CH$_3$; $R_{5a}$ is H; $R_{6a}$ is H or —CH$_3$; and $R_{7a}$ is —C(O)CH=CH$_2$, —C(O)CH=CHCH$_3$, or —S(O)$_2$CH=CH$_2$.

One embodiment provides a compound of Formula (Ib) or a salt thereof, wherein Q is

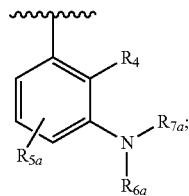

and $R_{1a}$, $R_{1b}$, $R_{2a}$, $R_{2b}$, $R_3$, $R_4$, $R_{5a}$, $R_{6a}$, and $R_{7a}$ are defined in the first aspect or the second aspect. Included in this embodiment are compounds in which $R_{1a}$ is H, —CF$_3$, —CH$_3$, —CH$_2$OH, —C(CH$_3$)$_2$OH, —C(O)NH$_2$, or —C(O)N(CH$_3$)$_2$; $R_{2a}$ is H; $R_{2b}$ is H; $R_3$ is H, F, or Cl; $R_{5a}$ is F, —OCH$_3$, or —OCF$_3$; $R_{6a}$ is H or —CH$_3$; and $R_{7a}$ is —C(O)CH=CH$_2$ or —S(O)$_2$CH=CH$_2$.

One embodiment provides a compound of Formula (Ib) or a salt thereof, wherein Q is

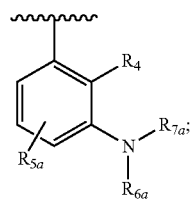

$R_{1a}$ is H, —CN, —CF$_3$, —CR$_{8a}$R$_{8b}$OH, or —NHR$_9$; $R_{2a}$ is H; $R_3$ is H, F, or Cl; $R_3$ is H, F, or Cl; $R_4$ is H, F, Cl, or —CH$_3$; $R_{5a}$ is H, F, Cl, or —OCH$_3$; $R_{6a}$ is H, —CH$_3$, or cyclopropyl; $R_{7a}$ is —C(O)CH=CH$_2$ or —S(O)$_2$CH=CH$_2$; $R_{8a}$ is H or —CH$_3$; RR, is H or —CH$_3$; and $R_9$ is $C_{2-3}$ alkyl.

One embodiment provides a compound of Formula (I), Formula (Ia), or Formula (Ib), or a salt thereof, wherein Q is

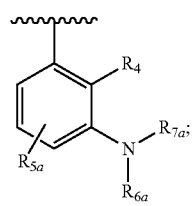

$R_{1a}$ is:

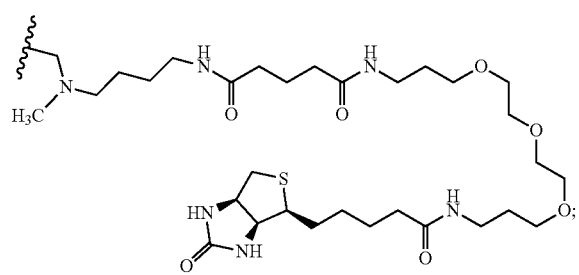 [SMILES: *CN(C)CCCCNC(=O)CCCC(=O)NCCCOCCOCCOCCCNC(=O)CCCC[C@@H]1SC[C@@H]2NC(=O)N[C@@H]21]

and $R_{1b}$, $R_{2a}$, $R_{2b}$, $R_3$, $R_4$, $R_{5a}$, $R_{6a}$, and $R_{7a}$ are defined in the first aspect or the second aspect.

One embodiment provides a compound of Formula (I), Formula (Ia), or Formula (Ib), or a salt thereof, wherein Q is

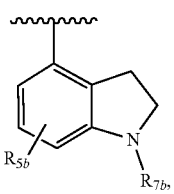 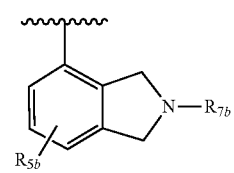

-continued

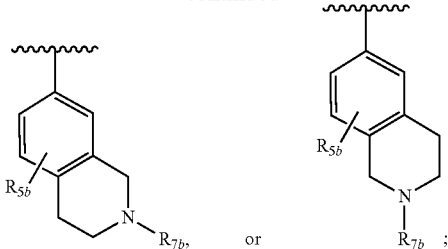

and $R_{1a}$, $R_{1b}$, $R_{2a}$, $R_{2b}$, $R_3$, $R_{5b}$, and $R_{7b}$ are defined in the first aspect or the second aspect. Included in this embodiment are compounds in which $R_{1a}$ is H, —$CF_3$, or —$C(CH_3)_2OH$; $R_3$ is F; and $R_{5b}$ is H.

One embodiment provides a compound of Formula (I), Formula (Ia), or Formula (Ib), or a salt thereof, wherein Q is

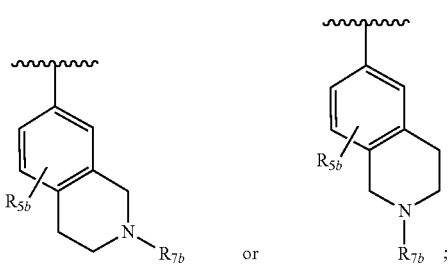

$R_{1a}$ is H, —$CF_3$, or —$C(CH_3)_2OH$; and $R_{1b}$, $R_{2a}$, $R_{2b}$, $R_3$, $R_{5b}$, and $R_{7b}$ are defined in the first aspect or the second aspect. Also included in this embodiment are compounds in which $R_3$ is H or F; and $R_{5b}$ is H.

One embodiment provides a compound of Formula (I), Formula (Ia), or Formula (Ib), or a salt thereof, wherein Q is

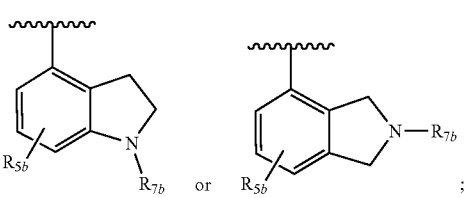

and $R_{1a}$, $R_{1b}$, $R_{2a}$, $R_{2b}$, $R_3$, $R_{5b}$, and $R_{7b}$ are defined in the first aspect or the second aspect. Included in this embodiment are compounds in which $R_{5b}$ is H. Also included in this embodiment are compounds of Formula (Ia) in which $R_3$ is H or F; and $R_{5b}$ is H.

One embodiment provides a compound of Formula (I), Formula (Ia), or Formula (Ib), or a salt thereof, wherein Q is

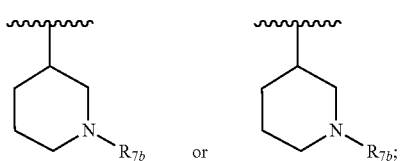

and $R_{1a}$, $R_{1b}$, $R_{2a}$, $R_{2b}$, $R_3$, and $R_{7b}$ are defined in the first aspect or the second aspect. Included in this embodiment are compounds of Formula (Ia) in which $R_3$ is H or F.

One embodiment provides a compound of Formula (I), Formula (Ia), or Formula (Ib), or a salt thereof, wherein Q is

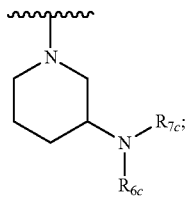

and $R_{1a}$, $R_{1b}$, $R_{2a}$, $R_{2b}$, $R_3$, $R_{6c}$, and $R_{7c}$ are defined in the first aspect or the second aspect. Included in this embodiment are compounds in which $R_{6c}$ is H; and $R_{7c}$ is —C(O)CH=$CH_2$, —C(O)C≡$CCH_3$, or —C(O)(cyclopropyl). Also included in this embodiment are compounds of Formula (Ib) in which $R_3$ is F; $R_{6c}$ is H; and $R_{7c}$ is —C(O)CH=$CH_2$, —C(O)C≡$CCH_3$, or —C(O)(cyclopropyl).

One embodiment provides a compound of Formula (I), Formula (Ia), or Formula (Ib), or a salt thereof, wherein Q is

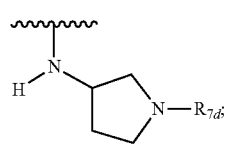

and $R_{1a}$, $R_{1b}$, $R_{2a}$, $R_{2b}$, $R_3$, and $R_{7d}$ are defined in the first aspect or the second aspect. Included in this embodiment are compounds in which $R_{1a}$ is H or —$CF_3$; and $R_{7d}$ is —C(O)CH=$CH_2$ or —C(O)C≡CH. Also included in this embodiment are compounds of Formula (Ib) in which $R_{1a}$ is H or —$CF_3$; $R_{1b}$ is H; $R_{2a}$ is H; $R_{2b}$ is H; and $R_{7d}$ is —C(O)CH=$CH_2$ or —C(O)C≡CH.

One embodiment provides a compound of Formula (I), Formula (Ia), or a salt thereof, wherein Q is

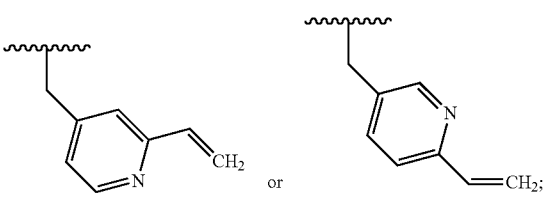

and $R_{1a}$, $R_{2a}$, and $R_3$ are defined in the first aspect or the second aspect. Included in this embodiment are compounds in which $R_3$ is H or F. Also included are compounds in which $R_{1a}$ is H and $R_{2a}$ is H.

One embodiment provides a compound of Formula (Ia) or a salt thereof, wherein Q is

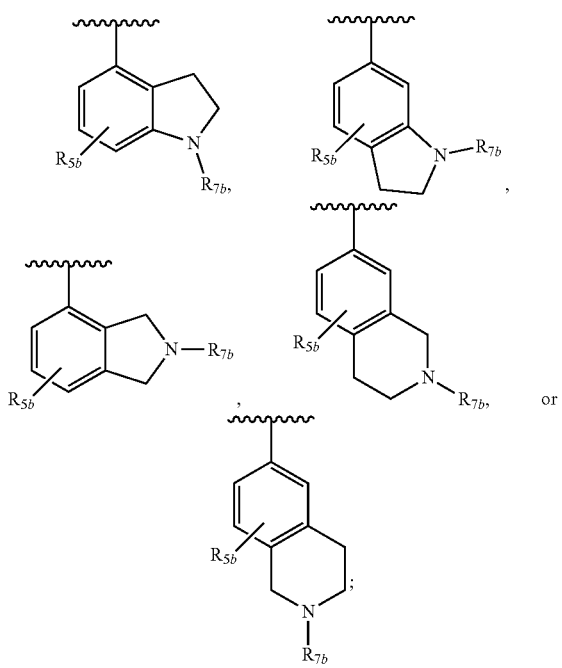

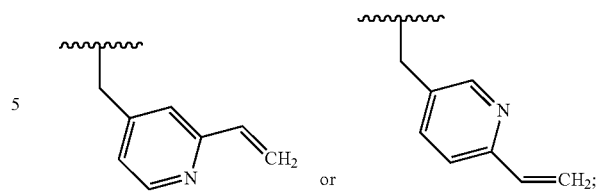

$R_{1a}$ is H, —CN, —CF$_3$, —CR$_{8a}$R$_{8b}$OH, or —NHR$_9$; R$_{2a}$ is H; R$_3$ is H, F, or Cl; R$_{5b}$ is H, F, Cl, or —OCH$_3$; R$_7$ is —C(O)CH═CH$_2$; R$_{8a}$ is H or —CH$_3$; R$_{8b}$ is H or —CH$_3$; and R$_9$ is C$_{2-3}$ alkyl.

One embodiment provides a compound of Formula (Ia) or a salt thereof, wherein Q is

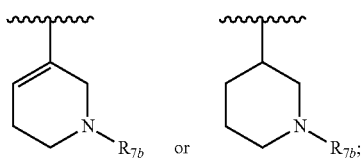

$R_{1a}$ is H, —CN, —CF$_3$, —CR$_{8a}$R$_{8b}$OH, or —NHR$_9$; R$_{2a}$ is H; R$_3$ is H, F, or Cl; R$_{7b}$ is —C(O)CH═CH$_2$; R$_{8a}$ is H or —CH$_3$; R$_{8b}$ is H or —CH$_3$; and R$_9$ is C$_{2-3}$ alkyl.

One embodiment provides a compound of Formula (Ia) or a salt thereof, wherein Q is

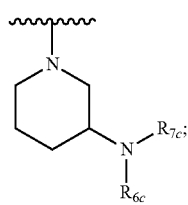

$R_{1a}$ is H, —CN, —CF$_3$, —CR$_{8a}$R$_{8b}$OH, or —NHR$_9$; R$_{2a}$ is H; R$_3$ is H, F, or Cl; R$_{6c}$ is H, —CH$_3$, or cyclopropyl; R$_{7c}$ is —C(O)CH═CH$_2$ or —C(O)C≡CR$_{12}$; R$_{8a}$ is H or —CH$_3$; R$_{8b}$ is H or —CH$_3$; R$_9$ is C$_{2-3}$ alkyl; and R$_{12}$ is H, C$_{1-4}$ alkyl, or cyclopropyl.

One embodiment provides a compound of Formula (Ia) or a salt thereof, wherein Q is $R_{1a}$ is H, —CN, —CF$_3$, —CR$_{8a}$R$_{8b}$OH, or —NHR$_9$; R$_{2a}$ is H; R$_3$ is H, F, or Cl; R$_{8a}$ is H or —CH$_3$; R$_{8b}$ is H or —CH$_3$; and R$_9$ is C$_{2-3}$ alkyl.

One embodiment provides a compound of Formula (Ib) or a salt thereof, wherein: Q is

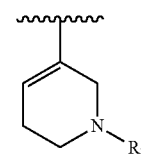 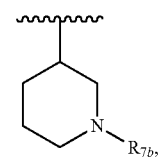

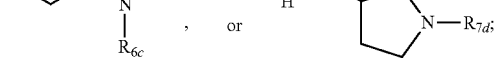

$R_{1a}$ is:
(i) H, —CH$_3$, —CF$_3$, —CR$_{8a}$R$_{8b}$OH, or —C(O)NR$_{10a}$R$_{10b}$; or
(ii)

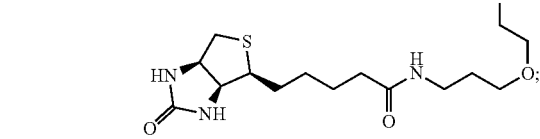

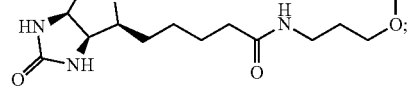

$R_{1b}$ is H; R$_{2a}$ is H or F, provided that if R$_{1a}$ is other than H then R$_{2a}$ is H; R$_{2b}$ is H or F, provided that if R$_{2a}$ and R$_{2b}$ are the same; R$_3$ is H, F, or Cl; R$_4$ is H, F, Cl, or —CH$_3$; R$_{5a}$ is H, F, Cl, or —OCH$_3$; R$_{5b}$ is H, F, Cl, or —OCH$_3$; R$_{6a}$ is H, —CH$_3$, or cyclopropyl; R$_{6c}$ is H, —CH$_3$, or cyclopropyl; R$_{7a}$ is —C(O)CH═CH$_2$ or —S(O)$_2$CH═CH$_2$; R$_{7c}$ is —C(O)CH═CH$_2$ or —C(O)C≡CR$_{12}$; R$_{7d}$ is —C(O)CH═CH$_2$ or —C(O)C≡CR$_{13}$; R$_{8a}$ is H or —CH$_3$; R$_{8b}$ is H or —CH$_3$; R$_{10a}$ and R$_{10b}$ are each —CH$_3$; R$_{1a}$ is H, C$_{1-4}$ alkyl, or cyclopropyl; and R$_{13}$ is H, C$_{1-4}$ alkyl or cyclopropyl; provided that the compound of Formula (Ib) is not

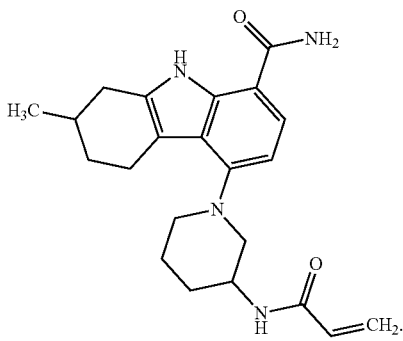

One embodiment provides a compound of Formula (Ib) or a salt thereof, wherein: Q is

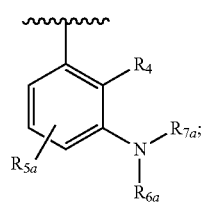

$R_{1a}$ is:
(i) H, —$CH_3$, —$CF_3$, —$CR_{8a}R_{8b}OH$, or —$C(O)NR_{10a}R_{10b}$; or
(ii)

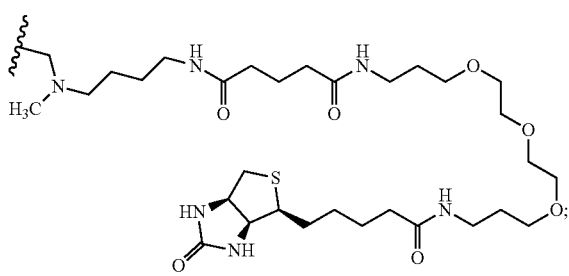 [SMILES: *CN(C)CCCCNC(=O)CCCC(=O)NCCCOCCOCCOCCCNC(=O)CCCC[C@@H]1SC[C@@H]2NC(=O)N[C@@H]21]

$R_{1b}$ is H; $R_{2a}$ is H or F, provided that if $R_{1a}$ is other than H then $R_{2a}$ is H; $R_{2b}$ is H or F, provided that if $R_{2a}$ and $R_{2b}$ are the same; $R_3$ is H, F, or Cl; $R_4$ is H, —$CH_3$, F, or Cl; $R_{5a}$ is H, F, Cl, or —$OCH_3$; $R_{6a}$ is H, —$CH_3$, or cyclopropyl; $R_{7a}$ is —$C(O)CH=CH_2$ or —$S(O)_2CH=CH_2$; $R_{8a}$ is H or —$CH_3$; $R_{8b}$ is H or —$CH_3$; and $R_{10a}$ and $R_{10b}$ are each —$CH_3$.

One embodiment provides a compound of Formula (Ib) or a salt thereof, wherein Q is

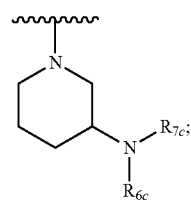

$R_{1a}$ is H, —$CH_3$, —$CF_3$, —$CR_{8a}R_{8b}OH$, or —$C(O)NR_{10a}R_{10b}$; $R_{1b}$ is H; $R_{2a}$ is H or F, provided that if $R_{1a}$ is other than H then $R_{2a}$ is H; $R_{2b}$ is H or F, provided that if $R_{2a}$ and $R_{2b}$ are the same; $R_3$ is H, F, or Cl; $R_{6c}$ is H, —$CH_3$ or cyclopropyl; $R_{7c}$ is —$C(O)CH=CH_2$ or —$C(O)C≡CR_{12}$; $R_{8a}$ is H or —$CH_3$; $R_{8b}$ is H or —$CH_3$; $R_{10a}$ and $R_{10b}$ are —$CH_3$; and Rig is H, $C_{1-4}$ alkyl, or cyclopropyl; provided that the compound of Formula (Ib) is not

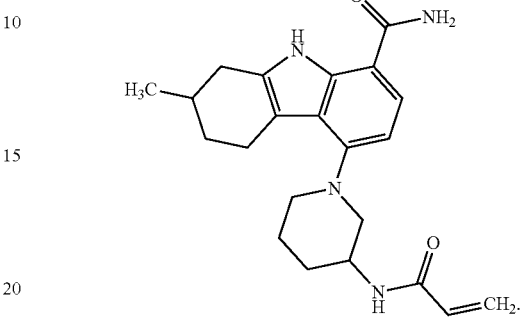

One embodiment provides a compound of Formula (Ib) or a salt thereof, wherein Q is

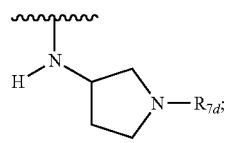

$R_{1a}$ is H, —$CH_3$, —$CF_3$, —$CR_{8a}R_{8b}OH$, or —$C(O)NR_{10a}R_{10b}$; $R_{1b}$ is H; $R_{2a}$ is H or F, provided that if $R_{1a}$ is other than H then $R_{2a}$ is H; $R_{2b}$ is H or F, provided that if $R_{2a}$ and $R_{2b}$ are the same; $R_3$ is H, F, or Cl; $R_{7d}$ is —$C(O)CH=CH_2$ or —$C(O)C≡CR_{13}$; $R_{8a}$ is H or —$CH_3$; $R_{8b}$ is H or —$CH_3$; $R_{10a}$ and $R_{10b}$ are each —$CH_3$; and $R_{13}$ is H, $C_{1-4}$ alkyl, or cyclopropyl.

One embodiment includes are compounds of Formula (I) or a salt thereof, wherein Q is

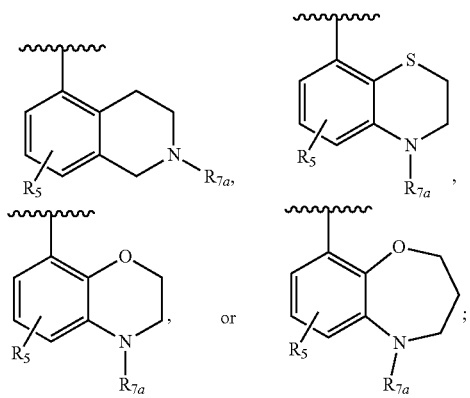

$R_3$ is H; and $R_{1a}$, $R_{1b}$, $R_{2a}$, $R_{2b}$, $R_5$ and $R_{7a}$ are defined in the first aspect or the second aspect.

One embodiment provides a compound of Formula (I) or a salt thereof, wherein $R_3$ is H; and $R_{1a}$, $R_{1b}$, $R_{2a}$, $R_{2b}$, $R_4$, $R_{5a}$, $R_{5b}$, $R_{6a}$, $R_{7a}$, $R_{7c}$, $R_{7d}$, $R_{7f}$, and Q are defined in the first aspect or the second aspect. Included in this embodiment are compounds in which Q is

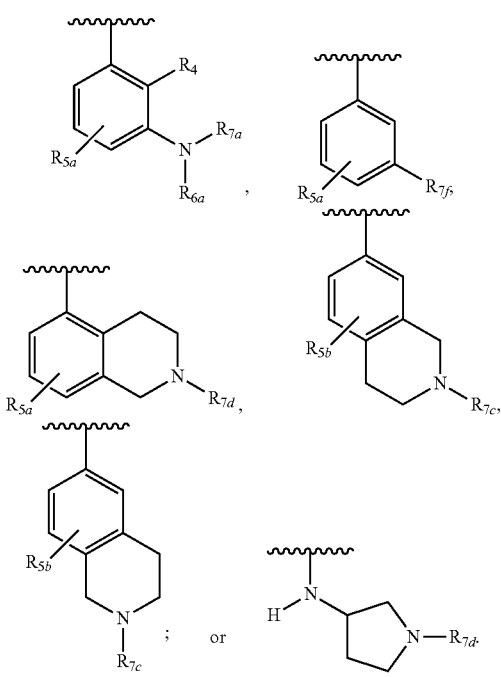

One embodiment provides a compound of Formula (I) or a salt thereof, wherein $R_3$ is F or Cl; and $R_{1a}$, $R_{1b}$, $R_{2a}$, $R_{2b}$, and Q are defined in the first aspect or the second aspect.

One embodiment provides a compound of Formula (I) or a salt thereof, wherein $R_3$ is F; and $R_{1a}$, $R_{1b}$, $R_{2a}$, $R_{2b}$, and Q are defined in the first aspect or the second aspect. Included in this embodiment are compounds in which $R_{1a}$ is H, —$CF_3$, —$CH_2CH_2OH$, —$C(CH_3)_2OH$, or —$C(O)N(CH_3)_2$.

One embodiment provides a compound of Formula (I) or a salt thereof, wherein $R_3$ is Cl; and $R_{1a}$, $R_{1b}$, $R_{2a}$, $R_{2b}$, $R_4$, $R_{5a}$, $R_{6a}$, $R_{7a}$, $R_{7c}$, $R_{7d}$, and Q are defined in the first aspect or the second aspect. Included in this embodiment are compounds in which Q is

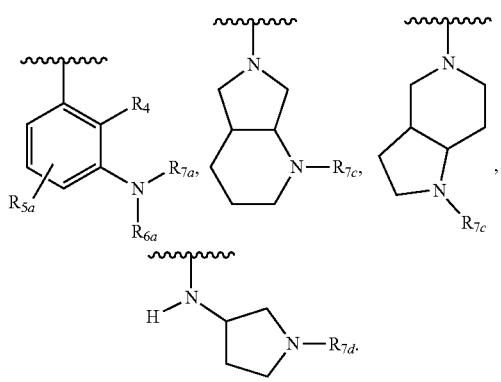

Atropisomers are stereoisomers resulting from hindered rotation about a single bond axis where the rotational barrier is high enough to allow for the isolation of the individual rotational isomers. (LaPlante et al., *J. Med. Chem.*, 54:7005 (2011)). The compounds of Formula (I) where $R_3$ is other than hydrogen, and Q is substituted phenyl with $R_4$ other than hydrogen, substituted 1,2,3,4-tetrahydroisoquinolin-5-yl, substituted 3,4-dihydro-2H-benzo[b][1,4]oxazin-8-yl, 2,3,4,5-tetrahydro[b][1,4]oxazepin-9-yl, or substituted isoindolin-4-yl, have a stereogenic axis at the bond between the tricyclic tetrahydrocarbazole/carbazole and group Q. Due to the non-symmetric nature of the substitutions on the rings connected by this bond, and due to limited rotation about this bond caused by steric hindrance, such compounds of Formula (I) can form rotational isomers. If the rotational energy barrier is sufficiently high, hindered rotation about this bond occurs at a rate that is slow enough to allow isolation of the separated atropisomers as different compounds. Thus, these compounds of Formula (I) can form two rotational isomers which under certain circumstances, such as chromatography on a chiral stationary phase, can be separated into individual atropisomers. Such compounds of Formula (I) can be provided as a mixture of two atropisomers, or as single atropisomers. Such compounds of Formula (I) were found to be separable and stable in solution at ambient and physiological temperatures. The absolute spatial configurations of the atropisomers can be determined by single crystal x-ray crystallography. These compounds of Formula (I) can be provided as individual atropisomers or as mixtures comprising the two atropisomers of Formula (I) in any proportions.

One embodiment provides compounds of Formula (I) or a salt thereof, wherein only one atropisomer is provided, or wherein only one atropisomer mixed with a smaller amount of the other atropisomer is provided. Where the absolute configuration is not assigned, the provided atropisomer can be defined by the order of elution relative to the other atropisomer during chromatography on a chiral stationary phase under specific conditions.

One embodiment provides compounds of Formula (I) or a salt thereof, wherein said compound is (RS)-5-(3-acrylamidophenyl)-2-(2-hydroxypropan-2-yl)-2,3,4,9-tetrahydro-1H-carbazole-8-carboxamide (1); (RS)-2-(2-hydroxypropan-2-yl)-5-(2-methyl-3-(N-methylvinylsulfonamido)phenyl)-2,3,4,9-tetrahydro-1H-carbazole-8-carboxamide (2); 5-(3-acrylamido-2-methylphenyl)-2,2-dimethyl-2,3,4,9-tetrahydro-1H-carbazole-8-carboxamide (3); 4-(3-acrylamido-2-methylphenyl)-7-(2-hydroxypropan-2-yl)-9H-carbazole-1-carboxamide (4); (RS)-2-(2-hydroxypropan-2-yl)-5-(3-(vinylsulfonamido)phenyl)-2,3,4,9-tetrahydro-1H-carbazole-8-carboxamide (5); (RS)-4-(3-acrylamido-2-methylphenyl)-3-chloro-7-(2-hydroxypropan-2-yl)-9H-carbazole-1-carboxamide (6); 5-(3-acrylamido-2-methylphenyl)-2-(hydroxymethyl)-2,3,4,9-tetrahydro-1H-carbazole-8-carboxamide (7); (RS)-5-(3-acrylamido-2-methylphenyl)-6-chloro-2-(hydroxymethyl)-2,3,4,9-tetrahydro-1H-carbazole-8-carboxamide, mixture of diastereomers (8); 5-(3-acrylamido-2-methylphenyl)-6-chloro-2,3,4,9-tetrahydro-1H-carbazole-2,8-dicarboxamide, mixture of diastereomers (9); (RS)-5-(3-acrylamido-2-methylphenyl)-2-(2-hydroxypropan-2-yl)-2,3,4,9-tetrahydro-1H-carbazole-8-carboxamide (10); (RS)-(E)-4-(3-(but-2-enamido)-2-methylphenyl)-3-chloro-7-(2-hydroxypropan-2-yl)-9H-carbazole-1-carboxamide (11); 5-(3-acrylamido-2-methylphenyl)-2,3,4,9-tetrahydro-1H-carbazole-8-carboxamide (12); (RS)-2-(2-hydroxypropan-2-yl)-5-(2-methyl-3-(vinylsulfonamido)phenyl)-2,3,4,9-tetrahydro-1H-carbazole-8-carboxamide (13); (RS)-5-(3-acrylamido-2-methylphenyl)-2,3,4,9-tetrahydro-1H-carbazole-2,8-dicarboxamide (14); 4-(3-acrylamido-2-methylphenyl)-7-cyano-9H-carbazole-1-carboxamide (15); (RS)-4-(3-acrylamido-2-methylphenyl)-7-(1,2-dihydroxyethyl)-9H-carbazole-1-carboxamide (16); 4-(3-acrylamido-2-methylphenyl)-7-(isopropylamino)-9H-carbazole-1- carboxamide (17); (RS)-5-(3-acrylamido-2-methylphenyl)-N²,N²-dimethyl-2,3,4,9-tetrahydro-1H-carbazole-2,8-dicarboxamide (18); (RS)-2-(2-hydroxypropan-2-yl)-5-(2-methyl-3-(N-methylacrylamido)phenyl)-2,3,4,9-tetrahydro-1H-carbazole-8-carboxamide (19); (RS)-2-(hydroxymethyl)-5-(2-methyl-3-(N-methylacrylamido)phenyl)-2,3,4,9-tetrahydro-1H-carbazole-8-carboxamide (20); (RS)-N²,N²-dimethyl-5-(2-methyl-3-(N-methylacrylamido)phenyl)-2,3,4,9-tetrahydro-1H-carbazole-2,8-dicarboxamide (21); (2R)-6-fluoro-2-(2-hydroxypropan-2-yl)-5-(2-methyl-3-(N-methylvinylsulfonamido)phenyl)-2,3,4,9-tetrahydro-1H-carbazole-8-carboxamide, mixture of diastereomers (22); (2R)-6-chloro-2-(2-hydroxypropan-2-yl)-5-(2-methyl-3-(N-methylvinylsulfonamido) phenyl)-2,3,4,9-tetrahydro-1H-carbazole-8-carboxamide, mixture of diastereomers (23); (2R)-6-fluoro-2-(2-hydroxypropan-2-yl)-5-(3-(N-methylvinylsulfonamido)phenyl)-2,3,4,9-tetrahydro-1H-carbazole-8-carboxamide, single enantiomer (24); (2R)-6-chloro-2-(2-hydroxypropan-2-yl)-5-(3-(N-methylvinylsulfonamido)phenyl)-2,3,4,9-tetrahydro-1H-carbazole-8-carboxamide, single enantiomer (25); (RS)-2-(2-hydroxypropan-2-yl)-5-(3-(N-methylvinylsulfonamido)phenyl)-2,3,4,9-tetrahydro-1H-carbazole-8-carboxamide (26); 7-(2-hydroxypropan-2-yl)-4-(2-methyl-3-(N-methylvinylsulfonamido)phenyl)-9H-carbazole-1-carboxamide (27); 7-(2-hydroxypropan-2-yl)-4-(3-(N-methylvinylsulfonamido)phenyl)-9H-carbazole-1-carboxamide (28); (RS)-3-fluoro-7-(2-hydroxypropan-2-yl)-4-(2-methyl-3-(vinylsulfonamido)phenyl)-9H-carbazole-1-carboxamide (29); (RS)-3-fluoro-7-(2-hydroxypropan-2-yl)-4-(2-methyl-3-(N-methylvinylsulfonamido)phenyl)-9H-carbazole-1-carboxamide (30); 3-fluoro-7-(2-hydroxypropan-2-yl)-4-(3-(N-methylvinylsulfonamido)phenyl)-9H-carbazole-1-carboxamide (31); 7-(2-hydroxypropan-2-yl)-4-(2-methyl-3-(vinylsulfonamido)phenyl)-9H-carbazole-1-carboxamide (32); 7-(2-hydroxypropan-2-yl)-4-(3-(vinylsulfonamido)phenyl)-9H-carbazole-1-carboxamide (33); 3-fluoro-7-(2-hydroxypropan-2-yl)-4-(3-(vinylsulfonamido)phenyl)-9H-carbazole-1-carboxamide (34); (RS)-2-(2-hydroxypropan-2-yl)-5-(3-(N-methylacrylamido)phenyl)-2,3,4,9-tetrahydro-1H-carbazole-8-carboxamide (35); (R)-6-fluoro-2-(2-hydroxypropan-2-yl)-5-(3-(N-methylacrylamido)phenyl)-2,3,4,9-tetrahydro-1H-carbazole-8-carboxamide (36); 7-(2-hydroxypropan-2-yl)-4-(3-(N-methylacrylamido)phenyl)-9H-carbazole-1-carboxamide (37); 3-fluoro-7-(2-hydroxypropan-2-yl)-4-(3-(N-methylacrylamido)phenyl)-9H-carbazole-1-carboxamide (38); (R)-6-chloro-2-(2-hydroxypropan-2-yl)-5-(3-(N-methylacrylamido)phenyl)-2,3,4,9-tetrahydro-1H-carbazole-8-carboxamide (39); (S)-2-(2-hydroxypropan-2-yl)-5-(3-(vinylsulfonamido)phenyl)-2,3,4,9-tetrahydro-1H-carbazole-8-carboxamide (40); (R)-2-(2-hydroxypropan-2-yl)-5-(3-(vinylsulfonamido)phenyl)-2,3,4,9-tetrahydro-1H-carbazole-8-carboxamide (41); (RS)-5-(2-fluoro-3-(N-methylacrylamido)phenyl)-2-(2-hydroxypropan-2-yl)-2,3,4,9-tetrahydro-1H-carbazole-8-carboxamide (42); (R)-6-fluoro-2-(2-hydroxypropan-2-yl)-5-(3-(vinylsulfonamido)phenyl)-2,3,4,9-tetrahydro-1H-carbazole-8-carboxamide (43); (2R)-6-chloro-2-(2-hydroxypropan-2-yl)-5-(2-methyl-3-(vinylsulfonamido)phenyl)-2,3,4,9-tetrahydro-1H-carbazole-8-carboxamide, mixture of diastereomers (44); (RS)-5-(2-fluoro-3-(N-methylvinylsulfonamido)phenyl)-2-(2-hydroxypropan-2-yl)-2,3,4,9-tetrahydro-1H-carbazole-8-carboxamide (45); (RS)-5-(2-chloro-3-(N-methylvinylsulfonamido)phenyl)-2-(2-hydroxypropan-2-yl)-2,3,4,9-tetrahydro-1H-carbazole-8-carboxamide (46); (2R)-6-fluoro-2-(2-hydroxypropan-2-yl)-5-(2-methyl-3-(vinylsulfonamido)phenyl)-2,3,4,9-tetrahydro-1H-carbazole-8-carboxamide, mixture of diastereomers (47); 5-(3-(vinylsulfonamido)phenyl)-2,3,4,9-tetrahydro-1H-carbazole-8-carboxamide (48); 5-(2-methyl-3-(vinylsulfonamido)phenyl)-2,3,4,9-tetrahydro-1H-carbazole-8-carboxamide (49); (RS)-5-(3-acrylamido-4-methoxyphenyl)-2-(2-hydroxypropan-2-yl)-2,3,4,9-tetrahydro-1H-carbazole-8-carboxamide (50); (RS)-5-(3-acrylamido-4-(trifluoromethoxy)phenyl)-2-(2-hydroxypropan-2-yl)-2,3,4,9-tetrahydro-1H-carbazole-8-carboxamide (51); (RS)-5-(3-acrylamido-4-fluorophenyl)-2-(2-hydroxypropan-2-yl)-2,3,4,9-tetrahydro-1H-carbazole-8-carboxamide (52); (RS)-5-(3-acrylamido-2-methylphenyl)-2-methyl-2,3,4,9-tetrahydro-1H-carbazole-8-carboxamide (53); (RS)-5-(3-acrylamido-2-methylphenyl)-2-(trifluoromethyl)-2,3,4,9-tetrahydro-1H-carbazole-8-carboxamide (54); 5-(3-acrylamido-2-methylphenyl)-6-chloro-2-(hydroxymethyl)-2-methyl-2,3,4,9-tetrahydro-1H-carbazole-8-carboxamide, single racemic diastereomers (55 and 56); 5-(3-acrylamido-2-methylphenyl)-6-chloro-N²,N²-dimethyl-2,3,4,9-tetrahydro-1H-carbazole-2,8-dicarboxamide, single racemic diastereomers (57 and 58); 5-(3-acrylamido-2-methylphenyl)-6-chloro-2-(2-hydroxypropan-2-yl)-2,3,4,9-tetrahydro-1H-carbazole-8-carboxamide, single racemic diastereomers (59 and 60); 5-(3-acrylamido-2-methylphenyl)-6-chloro-2-(2-hydroxypropan-2-yl)-2-methyl-2,3,4,9-tetrahydro-1H-carbazole-8-carboxamide, single racemic diastereomers (61 and 62); (S)-5-((1-acryloylpyrrolidin-3-yl)amino)-2,3,4,9-tetrahydro-1H-carbazole-8-carboxamide (63); (E)-4-(3-(but-2-enamido)-2-methylphenyl)-7-(2-hydroxypropan-2-yl)-9H-carbazole-1-carboxamide (64); 5-(((S)-1-acryloylpyrrolidin-3-yl)amino)-2-(trifluoromethyl)-2,3,4,9-tetrahydro-1H-carbazole-8-carboxamide, mixture of diastereomers (65); (S)-5-(3-acrylamidopiperidin-1-yl)-3,3,6-trifluoro-2,3,4,9-tetrahydro-1H-carbazole-8-carboxamide (66); (S)-4-(3-acrylamidopiperidin-1-yl)-3-fluoro-9H-carbazole-1-carboxamide (69); 5-(((S)-1-propioloylpyrrolidin-3-yl)amino)-2-(RS)-(trifluoromethyl)-2,3,4,9-tetrahydro-1H-carbazole-8-carboxamide, mixture of diastereomers (72); (S)-5-(3-(but-2-ynamido) piperidin-1-yl)-3,3,6-trifluoro-2,3,4,9-tetrahydro-1H-carbazole-8-carboxamide (73); (S)-3-fluoro-4-(3-(N-methylbut-2-ynamido)piperidin-1-yl)-9H-carbazole-1-carboxamide (74); (S)-4-(3-(but-2-ynamido)piperidin-1-yl)-3-fluoro-9H-carbazole-1-carboxamide (75); (S)-4-(3-(3-cyclopropylpropiolamido)piperidin-1-yl)-3-fluoro-9H-carbazole-1-carboxamide (76); 5-(((S)-1-acryloylpyrrolidin-3-yl)amino)-2-(trifluoromethyl)-2,3,4,9-tetrahydro-1H-carbazole-8-carboxamide, single diastereomers (77 and 78); 3-fluoro-4-((6-vinylpyridin-3-yl)methyl)-9H-carbazole-1-carboxamide (87); (RS)-4-(2-acryloylisoindolin-4-yl)-3-fluoro-9H-carbazole-1-carboxamide (89); 4-(2-acryloyl-1,2,3,4-tetrahydroisoquinolin-7-yl)-3-fluoro-9H-carbazole-1-carboxamide (90); 4-(2-acryloyl-1,2,3,4-tetrahydroisoquinolin-6-yl)-3-fluoro-9H-carbazole-1-carboxamide (91); 4-(1-acryloylindolin-4-yl)-3-fluoro-9H-carbazole-1-carboxamide (92); 4-(1-acryloylindolin-6-yl)-3-fluoro-9H-carbazole-1-carboxamide (95); 4-(1-acryloyl-1,2,5,6-tetrahydropyridin-3-yl)-3-fluoro-9H-carbazole-1-carboxamide (96); (RS)-4-(1-acryloylpiperidin-3-yl)-3-fluoro-9H-carbazole-1-carboxamide (97); 4-(1-acryloylpiperidin-3-yl)-3-fluoro-9H-carbazole-1-carboxamide, single enantiomers (98 and 99); 3-fluoro-4-((2-vinylpyridin-4-yl)methyl)-9H-carbazole-1-carboxamide (100); 4-(1-acryloylpyrrolidin-3-yl)-3-fluoro-9H-carbazole-1-carboxamide (112); 4-(1-acryloylpyrrolidin-3-yl)-3-fluoro-9H-carbazole-1-carboxamide (113 and 114); cis-4-(1-(but-2-ynoyl)octahydro-6H-pyrrolo[3,4-b]pyridin-6-yl)-3- fluoro-9H-carbazole-1-carboxamide (115); cis-4-(1-(but-2-ynoyl)octahydro-6H-pyrrolo[3,4-b]pyridin-6-yl)-3-fluoro-9H-carbazole-1-carboxamide (116 and 117); (S)-4-(3-(but-2-ynamido)piperidin-1-yl)-3-fluoro-9H-carbazole-1-carboxamide (118); cis-4-(1-acryloyloctahydro-6H-pyrrolo[3,4-b]pyridin-6-yl)-3-fluoro-9H-carbazole-1-carboxamide (119); cis-4-(1-acryloyloctahydro-6H-pyrrolo[3,4-b]pyridin-6-yl)-3-fluoro-9H-carbazole-1-carboxamide (120 and 121); 3-fluoro-4-((2-vinylpyrimidin-5-yl)methyl)-9H-carbazole-1-carboxamide (122); cis-4-(1-acryloylhexahydropyrrolo[3,4-b]pyrrol-5(1H)-yl)-3-fluoro-9H-carbazole-1-carboxamide (123); cis-4-(1-acryloylhexahydropyrrolo[3,4-b]pyrrol-5(1H)-yl)-3-fluoro-9H-carbazole-1-carboxamide (124 and 125); 4-(1-(but-2-ynoyl)octahydro-6H-pyrrolo[3,4-b]pyridin-6-yl)-3-chloro-9H-carbazole-1-carboxamide (126); 4-((4aS,7aS)-1-(but-2-ynoyl)octahydro-6H-pyrrolo[3,4-b]pyridin-6-yl)-3-chloro-9H-carbazole-1-carboxamide and 4-((4aR,7aR)-1-(but-2-ynoyl)octahydro-6H-pyrrolo[3,4-b]pyridin-6-yl)-3-chloro-9H-carbazole-1-carboxamide (127 and 128); 3-fluoro-4-((2-(prop-1-yn-1-yl)pyridin-4-yl)methyl)-9H-carbazole-1-carboxamide (129); 5-((S)-3-(but-2-ynamido) piperidin-1-yl)-6-fluoro-2-(2-hydroxypropan-2-yl)-2,3,4,9-tetrahydro-1H-carbazole-8-carboxamide (130, 131, and 132); 4-(2-acryloylisoindolin-5-yl)-3-fluoro-9H-carbazole-1-carboxamide (133); 4-(1-acryloyl-2,5-dihydro-1H-pyrrol-3-yl)-3-fluoro-9H-carbazole-1-carboxamide (134); 5-(1-acryloylpyrrolidin-3-yl)-6-fluoro-2,3,4,9-tetrahydro-1H-carbazole-8-carboxamide (135); (R)-4-(3-(but-2-ynamido)piperidin-1-yl)-3-fluoro-9H-carbazole-1-carboxamide (136); 4-(1-(but-2-ynoyl)hexahydropyrrolo[3,4-b]pyrrol-5(1H)-yl)-3-fluoro-9H-carbazole-1-carboxamide (137); 4-(1-acryloyl-1,4,5,6-tetrahydropyridin-3-yl)-3-fluoro-9H-carbazole-1-carboxamide (138); 4-(7-(but-2-ynoyl)-2,7-diazaspiro[4.4]nonan-2-yl)-3-fluoro-9H-carbazole-1-carboxamide (139); 4-(7-acryloyl-2,7-diazaspiro[4.4]nonan-2-yl)-3-fluoro-9H-carbazole-1-carboxamide (140); 4-(1-acryloyloctahydro-5H-pyrrolo[3,2-c]pyridin-5-yl)-3-fluoro-9H-carbazole-1-carboxamide (141); 4-(1-(but-2-ynoyl)octahydro-5H-pyrrolo[3,2-c]pyridin-5-yl)-3-fluoro-9H-carbazole-1-carboxamide (142); 4-((6-acryloyl-3,6-diazabicyclo[3.2.0]heptan-3-yl)-3-fluoro-9H-carbazole-1-carboxamide (143); 4-(6-(but-2-ynoyl)-3,6-diazabicyclo[3.2.0]heptan-3-yl)-3-fluoro-9H-carbazole-1-carboxamide (144); 4-(7-acryloyloctahydro-2,7-naphthyridin-2(1H)-yl)-3-fluoro-9H-carbazole-1-carboxamide (145); 4-(1-acryloyloctahydro-6H-pyrrolo[3,4-b]pyridin-6-yl)-3-chloro-9H-carbazole-1-carboxamide (146); 4-(1-(but-2-ynoyl)indolin-4-yl)-3-fluoro-9H-carbazole-1-carboxamide (147); 4-(2-(but-2-ynoyl)-1,2,3,4-tetrahydroisoquinolin-7-yl)-3-fluoro-9H-carbazole-1-carboxamide (148); 4-(2-(but-2-ynoyl)-1,2,3,4-tetrahydroisoquinolin-6-yl)-3-fluoro-9H-carbazole-1-carboxamide (149); 4-(2-(but-2-ynoyl)isoindolin-4-yl)-3-fluoro-9H-carbazole-1-carboxamide (150); 4-(1-(but-2-ynoyl)indolin-6-yl)-3-fluoro-9H-carbazole-1-carboxamide (151); 3-fluoro-4-((6-vinylpyrazin-2-yl)methyl)-9H-carbazole-1-carboxamide (152); 3-chloro-4-((6-vinylpyrazin-2-yl)methyl)-9H-carbazole-1-carboxamide (153); 4-((6-ethynylpyridin-3-yl)methyl)-3-fluoro-9H-carbazole-1-carboxamide (154); 3-chloro-4-((6-vinylpyridin-3-yl)methyl)-9H-carbazole-1-carboxamide (155); 4-(2-ethynylpyridin-4-yl)methyl)-3-fluoro-9H-carbazole-1-carboxamide (156); 3-fluoro-4-((2-vinylthiazol-5-yl)methyl)-9H-carbazole-1-carboxamide (157); 3-fluoro-4-((6-(prop-1-yn-1-yl)pyridin-3-yl)methyl)-9H-carbazole-1-carboxamide (158); 3-fluoro-4-(5-vinylpyrazin-2-yl)methyl)-9H-carbazole-1-carboxamide (159); 4-(1-acryloyl-1,2,5,6-tetrahydropyridin-3-yl)-3-fluoro-7-(trifluoromethyl)-9H-carbazole-1-carboxamide (160); 4-(1-acryloylpiperidin-3-yl)-3-fluoro-7-(trifluoromethyl)-9H-carbazole-1-carboxamide (161 and 162); (S)-4-(3-acrylamidopiperidin-1-yl)-3-fluoro-7-(trifluoromethyl)-9H-carbazole-1-carboxamide (163); (S)-4-(3-(but-2-ynamido) piperidin-1-yl)-3-fluoro-7-(trifluoromethyl)-9H-carbazole-1-carboxamide (164); (R)-4-(3-(but-2-ynamido)piperidin-1-yl)-3-fluoro-7-(trifluoromethyl)-9H-carbazole-1-carboxamide (165); (S)-4-(3-(3-cyclopropylpropiolamido)piperidin-1-yl)-3-fluoro-7-(trifluoromethyl)-9H-carbazole-1-carboxamide (166); (S)-4-(3-cyanamidopiperidin-1-yl)-3-fluoro-7-(trifluoromethyl)-9H-carbazole-1-carboxamide (167); 4-(2-acryloylisoindolin-4-yl)-3-fluoro-7-(trifluoromethyl)-9H-carbazole-1-carboxamide (168); 4-(1-acryloylindolin-4-yl)-3-fluoro-7-(trifluoromethyl)-9H-carbazole-1-carboxamide (169); 4-(1-acryloylindolin-6-yl)-3-fluoro-7-(trifluoromethyl)-9H-carbazole-1-carboxamide (170); 4-(1-acryloyl-1-azaspiro[4.4]nonan-7-yl)-3-fluoro-7-(trifluoromethyl)-9H-carbazole-1-carboxamide (171); (S)-4-(3-(but-2-ynamido)piperidin-1-yl)-3-fluoro-7-(4-methylpiperazine-1-carbonyl)-9H-carbazole-1-carboxamide (172); (S)-4-(3-(but-2-ynamido)piperidin-1-yl)-3-fluoro-N7,N7-dimethyl-9H-carbazole-1,7-dicarboxamide (173); 3-fluoro-N7,N7-dimethyl-4-((2-vinylpyridin-4-yl)-9H-carbazole-1,7-dicarboxamide (174); (S)-4-((1-cyanopyrrolidin-3-yl)amino)-3-fluoro-N7,N7-dimethyl-9H-carbazole-1,7-dicarboxamide (175); (S)-4-((1-cyanopyrrolidin-3-yl) amino)-3-fluoro-7-(4-methylpiperazine-1-carbonyl)-9H-carbazole-1-carboxamide (176); 4-(2-acryloyl-1,2,3,4-tetrahydroisoquinolin-5-yl)-7-(morpholine-4-carbonyl)-9H-carbazole-1-carboxamide (177); 4-(2-(but-2-ynoyl)-1,2,3,4-tetrahydroisoquinolin-5-yl)-7-(morpholine-4-carbonyl)-9H-carbazole-1-carboxamide (178); 4-(2-cyano-1,2,3,4-tetrahydroisoquinolin-5-yl)-7-(morpholine-4-carbonyl)-9H-carbazole-1-carboxamide (179); 4-(1-acryloylindolin-6-yl)-3-fluoro-7-(2-hydroxyethyl)-9H-carbazole-1-carboxamide (180); 4-(1-cyanoindolin-6-yl)-3-fluoro-7-(2-hydroxyethyl)-9H-carbazole-1-carboxamide (181); 4-(1-acryloyloctahydro-6H-pyrrolo[3,4-b]pyridin-6-yl)-6-chloro-3-fluoro-9H-carbazole-1-carboxamide (182); 4-(1-(but-2-ynoyl)octahydro-6H-pyrrolo[3,4-b]pyridin-6-yl)-6-chloro-3-fluoro-9H-carbazole-1-carboxamide (183); 5-(1-acryloyl-1,2,5,6-tetrahydropyridin-3-yl)-6-fluoro-2-(2-hydroxypropan-2-yl)-2,3,4,9-tetrahydro-1H-carbazole-8-carboxamide (184); (R)-6-fluoro-2-(2-hydroxypropan-2-yl)-5-((6-vinylpyridin-3-yl)methyl)-2,3,4,9-tetrahydro-1H-carbazole-8-carboxamide (185); 5-(2-acryloyl-1,2,3,4-tetrahydroisoquinolin-5-yl)-6-fluoro-2-(2-hydroxypropan-2-yl)-2,3,4,9-tetrahydro-1H-carbazole-8-carboxamide (186 and 187); 6-fluoro-2-(2-hydroxypropan-2-yl)-5-((6-(prop-1-yn-1-yl)pyridin-3-yl)methyl)-2,3,4,9-tetrahydro-1H-carbazole-8-carboxamide (188); 3-fluoro-4-(2-vinylpyridin-4-yl)-9H-carbazole-1-carboxamide (189); 4-(7-(but-2-ynoyl)octahydro-2,7-naphthyridin-2(1H)-yl)-3-fluoro-9H-carbazole-1-carboxamide (190); 4-(1-acryloyl-1,2,3,6-tetrahydropyridin-4-yl)-3-fluoro-9H-carbazole-1-carboxamide (191); 4-(1-(but-2-ynoyl)-1,2,3,6-tetrahydropyridin-4-yl)-3-fluoro-9H-carbazole-1-carboxamide (192); 3-fluoro-4-(5-(N-methylacrylamido) pyridin-2-yl)-9H-carbazole-1-carboxamide (193); 4-((1S,4S)-2-acryloyl-2-azabicyclo[2.2.1]heptan-5-yl)-3-fluoro-9H-carbazole-1-carboxamide (194); 3-fluoro-4-((2-methyl-6-vinylpyridin-4-yl)methyl)-9H-carbazole-1-carboxamide (195); 3-fluoro-4-((2-methyl-6-vinylpyrimidin-4-yl)methyl)-9H-carbazole-1-carboxamide (196); 3-fluoro-4-((4-methyl-6-vinylpyrimidin-2-yl)methyl)-9H-carbazole-1-carboxamide (197); 3-fluoro-4-((3-fluoro-2-vinylpyridin-4-yl)

methyl)-9H-carbazole-1-carboxamide (198); 4-(3-(1-acryloylpyrrolidin-2-yl)phenyl)-3-fluoro-9H-carbazole-1-carboxamide (199); 4-(3-(1-(but-2-ynoyl)pyrrolidin-2-yl)phenyl)-3-fluoro-9H-carbazole-1-carboxamide (200); (E)-3-fluoro-4-(3-(3-morpholino-3-oxoprop-1-en-1-yl)phenyl)-9H-carbazole-1-carboxamide (201); (E)-3-fluoro-4-(3-(3-oxo-3-(pyrrolidin-1-yl)prop-1-en-1-yl)phenyl)-9H-carbazole-1-carboxamide (202); or 5-(2-acryloyl-1,2,3,4-tetrahydroisoquinolin-5-yl)-2-(2-hydroxypropan-2-yl)-2,3,4,9-tetrahydro-1H-carbazole-8-carboxamide (203 and 204).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to six carbon atoms.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

Certain compounds of Formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic salts formed with inorganic and/or organic acids. Pharmaceutically acceptable (i.e., non-toxic, physiologically acceptable) salts are preferred, such as, for example, salts in which the anion does not contribute significantly to the toxicity or biological activity of the salt. However, other salts may be useful, e.g., in isolation or purification steps which may be employed during preparation, and thus, are contemplated within the scope of the invention. Salts of the compounds of the Formula (I) may be formed, for example, by reacting a compound of the Formula (I) with an amount of acid such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example, when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and d) Testa, B. et al., Hydrolysis in Drug and Prodrug Metabolism, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to Btk, or effective to treat or prevent autoimmune and/or inflammatory and/or proliferative disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with Formula (IIa) can be administered by any means suitable for the condition to be treated, which can depend on the need for site-specific treatment or quantity of Formula (IIa) compound to be delivered.

Also embraced within this invention is a class of pharmaceutical compositions comprising a compound of Formula (IIa) and one or more non-toxic, pharmaceutically-acceptable carriers and/or diluents and/or adjuvants (collectively referred to herein as "carrier" materials) and, if desired, other active ingredients. The compounds of Formula (IIa) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (IIa) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (IIa) with at least one inert solid diluent, such as, for example, calcium carbonate; calcium phosphate; and kaolin.

Soft gelatin capsules can, for example, be prepared by mixing at least one compound of Formula (IIa) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (IIa) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (IIa) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (IIa) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (IIa) thereof can, for example, be prepared as an oil-in-water emulsion. The oily phase of the emulsions comprising compounds of Formula (IIa) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (IIa) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (IIa) and optionally an additional agent selected from any pharmaceutically acceptable carrier, adjuvant, and vehicle. Alternate compositions of this invention comprise a compound of the Formula (IIa) described herein, or a prodrug thereof, and a pharmaceutically acceptable carrier, adjuvant, or vehicle.

Utility

The compounds of the invention modulate kinase activity, including the modulation of Btk. Other types of kinase activity that may be modulated by the compounds of the instant invention include, but are not limited to, the Tec family of kinases, such as BMX, Btk, ITK, TXK and Tec, and mutants thereof.

Accordingly, compounds of Formula (IIa) have utility in treating conditions associated with the modulation of kinase activity, and particularly the selective inhibition of Btk activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (IIa) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, Sjögren's syndrome, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, Kawasaki disease, chronic inflammatory demyelinating polyneuropathy (CIDP), dermatomyositis, uveitis, anti-factor-VIII disease, ankylosing spondylitis, myasthenia gravis, Goodpasture's disease, antiphospholipid syndrome, ANCA-associated vasculitis, dermatomyositis/polymyositis, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris.

Preferred methods of treatment are those wherein the condition is selected from Crohn's and ulcerative colitis, allograft rejection, rheumatoid arthritis, psoriasis, ankylosing spondylitis, psoriatic arthritis, pemphigus vulgaris and multiple sclerosis. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

"Therapeutically effective amount" is intended to include an amount of a compound of the present invention that is effective when administered alone or in combination to inhibit Btk.

One embodiment provides methods for treating such Btk kinase-associated conditions, comprising administering to a subject in need thereof at least one compound of Formula (IIa). A therapeutically-effective amount for treating such conditions may be administered. The methods of the present embodiment may be employed to treat Btk kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating Btk kinase-associated conditions may comprise administering at least one compound of Formula (IIa) alone or in combination with each other and/or other suitable therapeutic agents useful in treating such conditions. Therapeutically-effective amounts of at least one compound of Formula (IIa) and other suitable therapeutic agents for treating such conditions may be administered. Accordingly, "therapeutically effective amount" is also intended to include an amount of the combination of compounds claimed that is effective to treat Btk kinase-associated conditions. The combination of compounds is preferably a synergistic combination. Synergy, as described, for example, by Chou et al., *Adv. Enzyme Regul.*, 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-a] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti- TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (IIa) for use in therapy. In the present embodiment, the use in therapy may include the administration of a therapeutically-effective amount of a compound of Formula (IIa).

The present invention also provides the use of the compounds of Formula (IIa) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (IIa) for the treatment of prophylaxis of an allergic disorder and/or autoimmune and/or inflammatory disease.

The present invention also provides the use of the compounds of Formula (IIa) for the manufacture of a medicament for treatment of cancer. The present embodiment may include the use for the manufacture of a medicament includes the administration of a therapeutically-effective amount of a compound of Formula (IIa) for the treatment of prophylaxis of an allergic disorder and/or autoimmune and/or inflammatory disease.

The present invention further includes compositions comprising one or more compounds of Formula (IIa) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula (IIa) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of compounds of Formula (I) as specified in the "Examples" section below, have been tested in one or more of the assays described below.

In one embodiment, the compounds of Formula (IIa) inhibit Btk enzymes with $IC_{50}$ values of 2 nM or less, for example, from 0.001 to 2 nM, as measured by the Human Recombinant Btk enzyme assay. Included in this embodiment are compounds of Formula (IIa) which inhibit Btk enzymes with $IC_{50}$ values of 1 nM and less, for example, from 0.001 to 1 nM. Other compounds of this embodiment inhibit Btk enzymes with $IC_{50}$ values of 0.5 nM and less, for example, from 0.001 to 0.5 nM.

In one embodiment, the compounds of Formula (IIa) have useful potency in the inhibition of intracellular calcium flux in Ramos RA1 B cells stimulated with anti-human IgM, with $IC_{50}$ values of 450 nM or less, for example, from 0.1 to 450 nM. Included in this embodiment are compounds of Formula (IIa) that have potency in the inhibition of intracellular calcium flux in Ramos RA1 B cells stimulated with anti-human IgM with $IC_{50}$ values of 150 nM or less, for example, from 0.1 to 150 nM; and with $IC_{50}$ values of 60 nM or less, for example, from 0.1 to 60 nM.

In one embodiment, the compounds of Formula (IIa) inhibit Btk enzymes with $IC_{50}$ values of 2 nM or less, for example, from 0.001 to 2 nM, as measured by the Human Recombinant Btk enzyme assay, and inhibit the intracellular calcium flux in Ramos RA1 B cells stimulated with anti-human IgM, with $IC_{50}$ values of 450 nM or less, for example, from 0.1 to 450 nM.

In one embodiment, the compounds of Formula (IIa) inhibit Btk enzymes with $IC_{50}$ values of 2 nM or less, for example, from 0.001 to 2 nM, as measured by the Human Recombinant Btk enzyme assay, and inhibit the intracellular calcium flux in Ramos RA1 B cells stimulated with anti-human IgM, with $IC_{50}$ values of 150 nM or less, for example, from 0.1 to 150 nM.

In one embodiment, the compounds of Formula (IIa) inhibit Btk enzymes with $IC_{50}$ values of 2 nM or less, for example, from 0.001 to 2 nM, as measured by the Human Recombinant Btk enzyme assay, and inhibit the intracellular calcium flux in Ramos RA1 B cells stimulated with anti-human IgM, with $IC_{50}$ values of 60 nM or less, for example, from 0.1 to 60 nM.

In one embodiment, the compounds of Formula (IIa) inhibit Btk enzymes with $IC_{50}$ values of 1 nM and less, for example, from 0.001 to 1 nM, as measured by the Human Recombinant Btk enzyme assay, and inhibit the intracellular calcium flux in Ramos RA1 B cells stimulated with anti-human IgM, with $IC_{50}$ values of 450 nM or less, for example, from 0.1 to 450 nM.

In one embodiment, the compounds of Formula (IIa) inhibit Btk enzymes with $IC_{50}$ values of 1 nM and less, for example, from 0.001 to 1 nM, as measured by the Human Recombinant Btk enzyme assay, and inhibit the intracellular calcium flux in Ramos RA1 B cells stimulated with anti-human IgM, with $IC_{50}$ values of 150 nM or less, for example, from 0.1 to 150 nM.

In one embodiment, the compounds of Formula (IIa) inhibit Btk enzymes with $IC_{50}$ values of 1 nM or less, for example, from 0.001 to 1 nM, as measured by the Human Recombinant Btk enzyme assay, and inhibit the intracellular calcium flux in Ramos RA1 B cells stimulated with anti-human IgM, with $IC_{50}$ values of 60 nM or less, for example, from 0.1 to 60 nM.

In one embodiment, the compounds of Formula (IIa) inhibit Btk enzymes with $IC_{50}$ values of 0.5 nM and less, for example, from 0.001 to 0.5 nM, as measured by the Human Recombinant Btk enzyme assay, and inhibit the intracellular calcium flux in Ramos RA1 B cells stimulated with anti-human IgM, with $IC_{50}$ values of 450 nM or less, for example, from 0.1 to 450 nM.

In one embodiment, the compounds of Formula (IIa) inhibit Btk enzymes with $IC_{50}$ values of 0.5 nM and less, for example, from 0.001 to 0.5 nM, as measured by the Human Recombinant Btk enzyme assay, and inhibit the intracellular calcium flux in Ramos RA1 B cells stimulated with anti-human IgM, with $IC_{50}$ values of 150 nM or less, for example, from 0.1 to 150 nM.

In one embodiment, the compounds of Formula (IIa) inhibit Btk enzymes with $IC_{50}$ values of 0.5 nM or less, for example, from 0.001 to 0.5 nM, as measured by the Human Recombinant Btk enzyme assay, and inhibit the intracellular calcium flux in Ramos RA1 B cells stimulated with anti-human IgM, with $IC_{50}$ values of 60 nM or less, for example, from 0.1 to 60 nM.

The compounds of Formula (I %) have utility as probe molecules in assays, such as the Human Whole Blood Btk inactivation assay disclosed herein.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will be recognized by one skilled in the art of organic synthesis that some functional groups present in intermediate compounds, or in compounds of Formula (I), may be unstable to, or otherwise unsuited for, some of the reaction conditions used to prepare them or to convert them to other intermediates or to compounds of Formula (I). In these cases, the functional groups may be protected by conversion to alternative functional groups which are stable to, or more suited for, the reaction conditions to be employed. These protected functional group can then be converted back to the original functional group at a later stage of the synthesis. Examples are the protection of a carboxylic acid as a carboxylate ester, the protection of a primary or secondary amine as a tert-butyloxycarbonyl (Boc) derivative or benzyloxycarbonyl (Cbz) derivative, or the protection of a carbazole or tetrahydrocarbazole nitrogen as a 2-trimethylsilylethoxymethyl (SEM) derivative. The use of protecting groups is well known in the literature; an authoritative account describing the many alternatives to the trained practitioner is Wuts, P. et al., *Greene's Protective Groups in Organic Synthesis*, Fourth Edition, Wiley-Interscience (2006).

Compounds 3, representing certain compounds of Formula (I), can be prepared using methods shown in Scheme 1.

drocarbazole moiety is located on a benzene ring of Q, to provide a compound 3. This reaction may be performed by using a suitable base such as potassium carbonate, cesium carbonate or tripotassium phosphate, and a suitable catalyst such as tetrakis(triphenylphosphine)palladium, 1,1'-bis(diphenylphosphino)ferrocene palladium(II) chloride, or 1,1'-bis(di-tert-butylphosphino)ferrocene palladium(II) chloride, in a suitable solvent such as 1,4-dioxane, N,N-dimethylformamide or tetrahydrofuran, optionally with one or more suitable cosolvents such as water or ethanol. Such coupling reactions are commonly known as Suzuki-Miyaura coupling reactions, and are known in the chemical literature (see, for example, Heravi, M. et al., Tetrahedron, 68:9145 (2012), and references cited therein).

Alternatively, a substituted carbazolecarboxamide or tetrahydrocarbazolecarboxamide 1 can be converted to the corresponding boronic acid or boronic acid ester 4 (where R is, for example, H, alkyl, or taken together form an optionally substituted 1,3,2-dioxaboralane or 1,3,2-dioxaborinane), using methods known in the chemical literature (see, for example, Ishiyama, T. et al., Tetrahedron, 57:9813 (2001), and references cited therein). Examples of such methods are the reaction of 1 with a reagent such as 4,4,4',4',5,5,5',5'-octamethyl-2,2'-bi(1,3,2-dioxaborolane) in the presence of a base such as potassium acetate and a suitable catalyst such as 1,1'-bis(diphenylphosphino)ferrocene palladium(II) chloride in a suitable solvent. Alternatively, reaction of a compound 1 where Y is Br with an organometallic reagent such as butyllithium or isopropylmagnesium chloride, followed by treatment with a boric

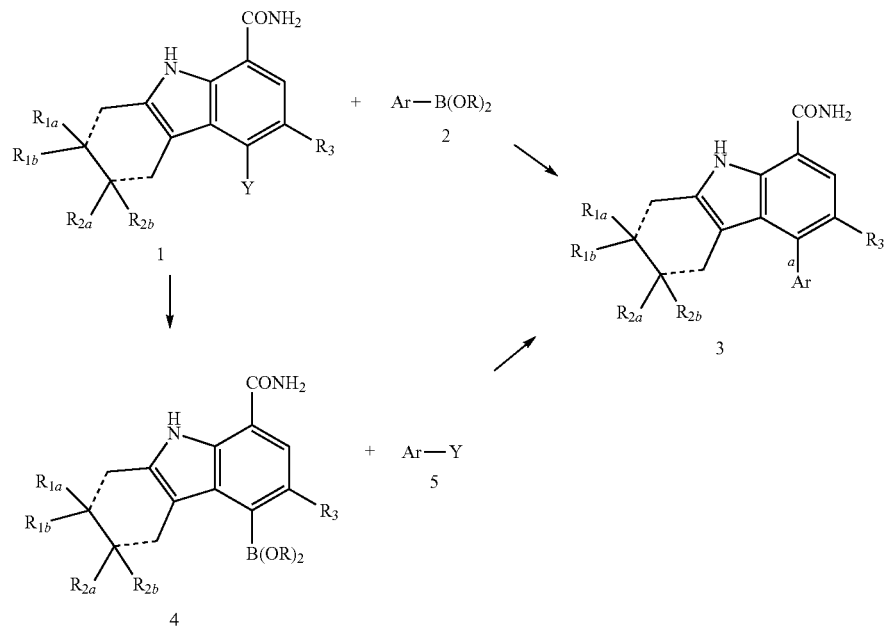

Scheme 1

A substituted carbazolecarboxamide or tetrahydrocarbazolecarboxamide 1, where Y is an appropriate group such as Br, Cl, or trifluoromethanesulfonyloxy, can be reacted with a boronic acid or boronic acid ester 2 (where R is, for example, H, alkyl, or taken together form an optionally substituted 1,3,2-dioxaboralane or 1,3,2-dioxaborinane), where Ar represents one of the groups Q of Formula (I) in which the point of attachment to the carbazole or tetrahyacid ester such as trimethyl borate or tri-isopropyl borate, then followed by hydrolysis of the resulting boronic acid ester, can provide a boronic acid 4 (R=H). Reaction of a compound 4 with a suitable compound 5, wherein Ar represents one of the groups Q of Formula (I) in which the point of attachment to the carbazole or tetrahydrocarbazole moiety is located on a benzene ring of Q, and Y is an appropriate group such as Br, Cl, or trifluoromethanesulfonyloxy, using the Suzuki-Miyaura coupling reaction as described above, can also provide a compound 3.

A compound 2 can be prepared from a compound 5 using the same method described for the preparation of a compound 4 from a compound 1.

In cases where a compound 3 is a tetrahydrocarbazole-carboxamide (where the dashed lines represent single bonds) and $R_{1a}$ and $R_{1b}$ are different from each other, a chiral center will exist at the point of attachment of $R_{1a}$ and $R_{1b}$, and such a compound will exist as two enantiomers. Thus, a compound 3 can be isolated as a racemic mixture, or if the compound 3 is prepared from a compound 1 or a compound 4 which is a single enantiomer or non-racemic enantiomer mixture, the compound 3 can be isolated as a single enantiomer or a non-racemic enantiomer mixture. If a compound 3 contains a chiral center and is not a single enantiomer, it can be separated into two single enantiomers using methods known in the art, such as preparative chromatography on a chiral stationary phase.

as shown in Scheme 2. Under certain conditions, such as chromatography on a chiral stationary phase, the enantiomeric atropisomers can be observed as two separate peaks in the chromatogram. Such compounds can be isolated as mixtures of enantiomers, or the enantiomers can be separated using methods known in the art, such as preparative chromatography on a stationary phase. The separated enantiomers can be isolable and stable under appropriate storage and handling conditions.

In certain cases, a compound 3 is a tetrahydrocarbazole-carboxamide (where the dashed lines represent single bonds) and $R_{1a}$ and $R_{1b}$ are different from each other; $R_3$ is not hydrogen; and Ar is a phenyl ring with $R_4$ other than H. In this case, two chiral centers are present: the point of attachment of $R_{1a}$, and the bond labeled a as described above. Thus, four diastereomers are possible (3e, 3f, 3g and 3h) as shown in Scheme 3. Compound 3d may therefore exist as a mixture of all four diastereomers, or as single diastereomers, Scheme 2

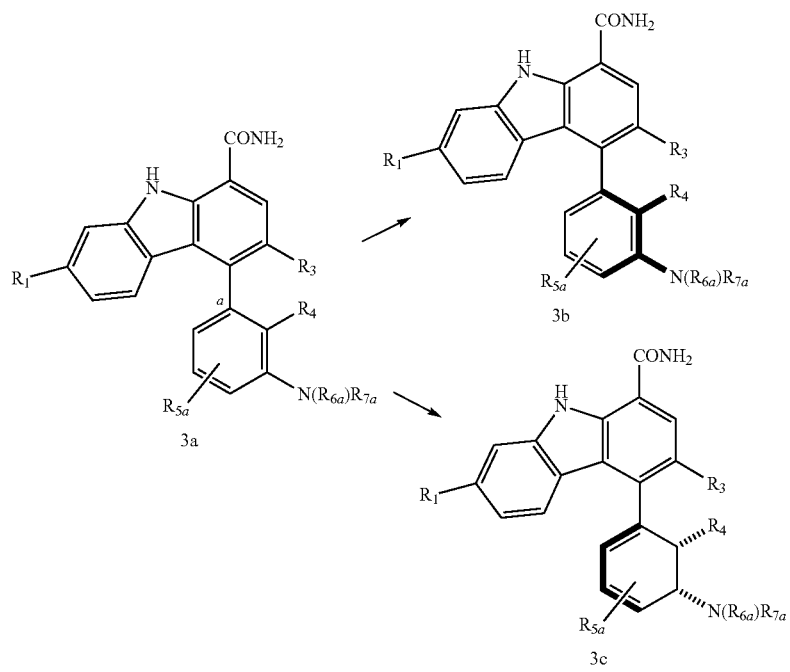

In certain cases of compounds 3, $R_3$ is not hydrogen; and Ar is a phenyl ring with $R_4$ other than H. In these cases, steric hindrance can cause limited rotation about the bond labeled a, and compound 3a displays chirality, known as atropisomerism, and can exist as two enantiomers 3b and 3c, or as mixtures of two or more diastereomers. Racemic mixtures of pairs of diastereomers (3e and 3h, or 3f and 3g) are possible. As described above, the diastereomers may be separated using methods known in the literature, such as chromatography on a chiral stationary phase.

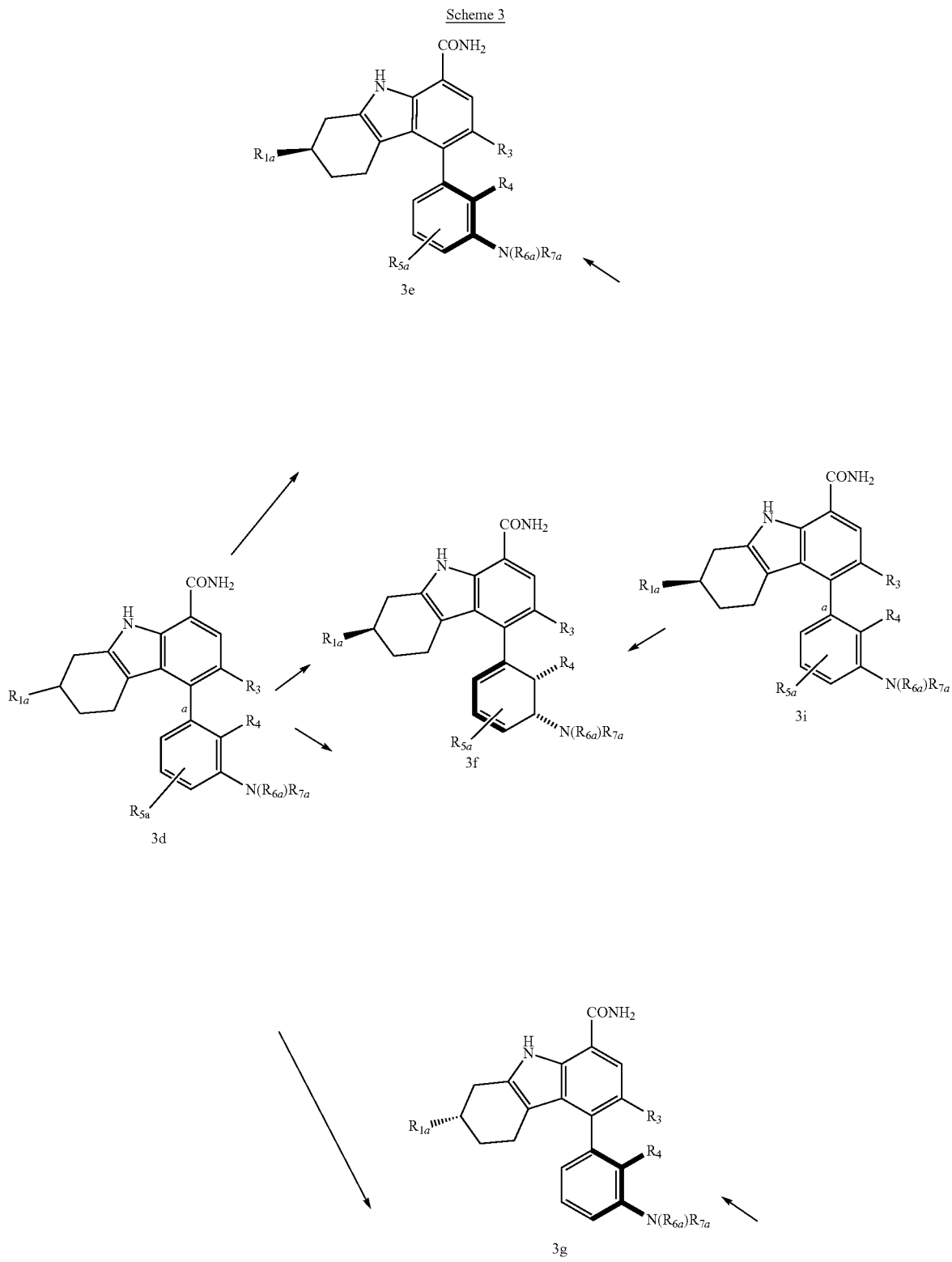

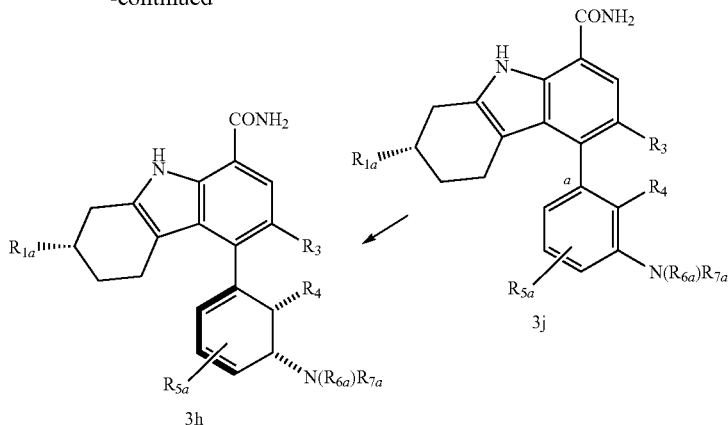

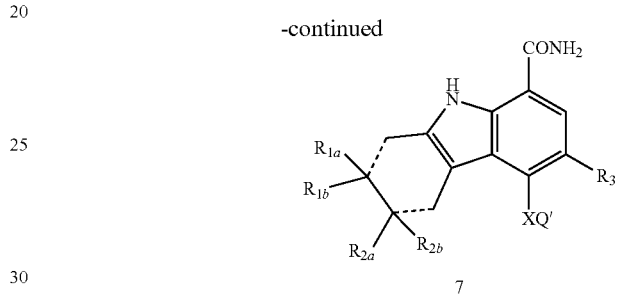

In certain cases, a compound 3 can be prepared from a single enantiomer of a chiral tetrahydrocarbazolecarboxamide 1 or 4 where $R_3$ is not hydrogen. If Ar is a phenyl ring with $R_4$ other than H, then a mixture of two diastereomers can result from the Suzuki-Miyaura reaction which gives the compound 3. Example are 3i and 3j, shown in Scheme 3, where $R_1$, $R_3$ and $R_4$ are all other than hydrogen. Compound 3i, formed from one enantiomer of the appropriate compound 1 or 4, will be a mixture of diastereomers 3e and 3f, while compound 3j, formed from the other enantiomer of the appropriate compound 1 or 4, will be a mixture of diastereomers 3g and 3h. As described above, these diastereomers may be separated using methods known in the literature, such as chromatography or selective crystallization.

In some cases where 1 or 4 is a chiral tetrahydrocarbazolecarboxamide, chiral induction can occur during the Suzuki-Miyaura coupling reaction to provide a compound 3 where $R_3$ is other than H, and Ar is a phenyl ring with $R_4$ other than H. In these cases, mixtures of diastereomers can be obtained which are not equimolar mixtures; that is, the compound 3 can be a mixture of diastereomers in which one or more of the diastereomers, having bond a with one absolute configuration, is present to a greater extent than one or more diastereomers having bond a with the opposite absolute configuration.

Certain compounds of Formula (I), represented by 7, can be prepared using methods illustrated in Scheme 4.

Scheme 4

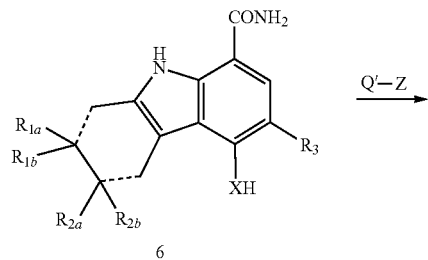

These methods involve reacting a compound 6 bearing a primary or secondary amine (that is, where XH represents a group Q of Formula (I) wherein $R_{7a}$, $R_{7b}$, $R_{7c}$ or $R_{7d}$, as appropriate, is replaced by H) with an appropriate reagent Q'-Z, where Q' represents $R_{7a}$, $R_{7b}$, $R_{7c}$ or $R_{7d}$, as appropriate, or a precursor to such a group, and Z represents a leaving group such as Cl or OH, to provide a compound 7, where XQ' represents one of the groups Q of Formula (I) resulting from such a reaction. Such reactions of amines are known in the literature. One example of such a reaction is acylation of the amine of a compound 6 with a carboxylic acid chloride or a carboxylic acid anhydride, usually performed in a suitable solvent such as tetrahydrofuran, ethyl acetate, acetonitrile, or dichloromethane, usually in the presence of a base such as triethylamine, diisopropylethylamine, pyridine, or an aqueous solution of an inorganic base such as sodium hydroxide or potassium carbonate. Alternatively, a solvent such as pyridine can be used, in which case the solvent can also serve as a base.

Another example of a reaction shown in Scheme 4 is acylation of the amine of a compound 6 with a carboxylic acid using any of a number of amide coupling reagents known in the literature, for example, (benzotriazol-1-yloxy)tris(dimethylamino) phosphonium hexafluorophosphate (also known as BOP or Castro's reagent), O-(7-azabenzotriazol-1-yl)-N,N,N',N'-tetramethyluronium hexafluorophosphate (also known as HATU), or a combination of N,N'-dicyclohexylcarbodiimide or 1-ethyl-3-(3-dimethylaminopropyl)carbodiimide hydrochloride (also known as EDC) and a reagent such as 1-hydroxybenzotriazole (also known as HOBT) or 1-hydroxy-7-azabenzotriazole (also known as HOAT). Such reactions are usually performed in a suitable solvent such as ethyl acetate, dichloromethane, tetrahydrofuran, N,N-dimethylformamide or N-methylpyrrolidin-2-one, in the presence of a suitable base such as triethylamine or diisopropylethylamine.

Another example of a reaction shown in Scheme 4, which can be used to prepare a compound 7 where Q' is $SO_2CH=CH_2$, is treatment of the amine of a compound 6 with 2-chloroethanesulfonyl chloride, in a suitable solvent such as dichloromethane or tetrahydrofuran, in the presence of a base such as triethylamine or diisopropylethylamine. In this case, an intermediate 2-chloroethanesulfonamide can be formed, which in the presence of base can undergo elimination of HCl to provide the desired ethenesulfonamide.

Certain compounds 6 of Scheme 4, where XH represents a suitable substituted 3-aminophenyl group, a suitable 1,2,3,4-tetrahydroisoquinolinyl group, a suitable indolinyl group, a suitable isoindolinyl group, or a suitable 1,2,5,6-tetrahydropyridin-3-yl group, can be prepared as shown in Scheme 5.

compound 6 after the removal of the protecting group P if necessary. If P in the compound 8 represents H, the compound 6 can be obtained directly.

By analogy to the methods illustrated in Scheme 1, an alternative method to prepare a compound 6 of Scheme 4, where XH represents a suitable 2-substituted-3-aminophenyl group, a suitable 1,2,3,4-tetrahydroisoquinolinyl group, a suitable indolinyl group, a suitable isoindolinyl group, or a suitable 1,2,5,6-tetrahydropyridin-3-yl group, is also shown in Scheme 5. Reaction of a boronic acid or boronic acid ester 4 (where R is, for example, H, alkyl, or taken together form an optionally substituted 1,3,2-dioxaboralane or 1,3,2-dioxaborinane) of Scheme 1 with a compound 9, where Y is a suitable leaving group such as Br, Cl or trifluorosulfonyloxy, using the Suzuki-Miyaura coupling as described above, can also provide a compound 6. As

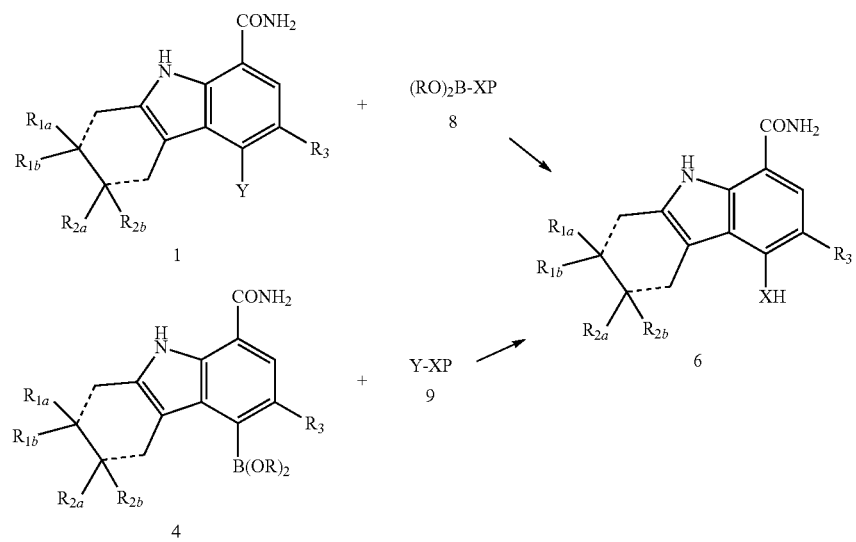

Scheme 5

Reaction of a compound 1 with a boronic acid or boronic acid ester 8 (where XP is analogous to XH in Scheme 4; P can be either H or a suitable amine protecting group such as, for example, tert-butyloxycarbonyl (Boc) or benzyloxycarbonyl (Cbz), which are known in the literature as protecting groups for amines), using the Suzuki-Miyaura coupling as described above (Scheme 1), can provide a corresponding described above, P can be H, or P can be a suitable protecting group in which case deprotection can provide the compound 6.

Also, a compound 8 can be prepared from a compound 9 using the same method described for the preparation of a compound 4 from a compound 1 (Scheme 1).

Compounds 13, representing certain compounds 6 of Scheme 4, can be prepared as shown in Scheme 6.

Scheme 6

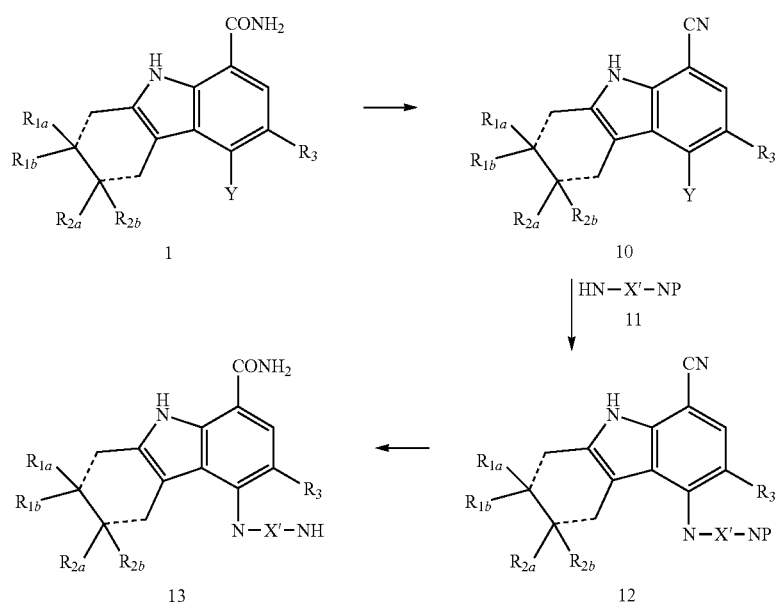

Reaction of a compound 1 with a dehydrating agent such as phosphorus oxychloride, using a method known in the literature, can provide a nitrile 10. Treatment of a compound 10 with a suitable mono-protected diamine such as an aminopyrrolidine or an aminopiperidine (represented by HN-X'-NP, 11, where P can represent a suitable protecting group such as Cbz or Boc) can provide the corresponding compound 12. The conversion of a compound 10 to a compound 12 can be achieved using a suitable palladium catalyst such as, for example, tris(dibenzylideneacetone) dipalladium, a ligand such as, for example, 2,2'-bis(diphenylphosphino)-1,1'-binaphthalene (also known as BINAP) or 4,5-bis(diphenylphosphino)-9,9-dimethylxanthene (also known as Xantphos), and a base such as cesium carbonate or sodium tert-butoxide, in a suitable solvent such as 1,4-dioxane, toluene, N,N-dimethylacetamide or N-methylpyrrolidin-2-one. This reaction, commonly referred to as the Buchwald coupling, is well known in the literature (see, for example, Surry, D. et al., $Angew.$ $Chem.$, 47:6338 (2008), and references cited therein). The nitrile moiety of a compound 12 can be hydrolyzed to the corresponding amide by treatment under suitable conditions, for example, by heating with aqueous sulfuric acid, to provide a compound 13, which is an example of a compound 6 of Scheme 4. A protecting group P, if present in a compound 12, can be removed during this reaction, or alternatively can be removed before or after the nitrile hydrolysis step using methods known in the chemical literature.

It will be noted that compounds 12 and 13 contain a chiral center arising from the 3-aminopyrrolidine or 3-aminopiperidine of 11. Therefore, compounds 12 and 13 may exist as racemic mixtures, single enantiomers or non-racemic mixtures of enantiomers if the compound 1 is non-chiral. In cases where the compound 1 is a chiral tetrahydrocarbazolecarboxamide, compounds 12 and 13 may exist as mixtures of diastereomers or single diastereomers. If compound 1 is non-chiral and 11 is a single enantiomer, a single enantiomer of compound 12 can be formed. If compound 1 is non-chiral and 11 is racemic or a non-racemic mixture of enantiomers, two enantiomers of compound 12 will result, which can be separated, for example, by chromatography on a chiral stationary phase. If compound 1 is chiral and a single enantiomer and 11 is a single enantiomer, a single diastereomer of compound 12 can be formed, but if 11 is racemic or a non-racemic mixture of enantiomers, a mixture of two diastereomers of compound 12 will be formed. If compound 1 is chiral and either racemic or a non-racemic mixture of enantiomers, and 11 is a single enantiomer, a mixture of two diastereomers of compound 12 will be formed, but if 11 is racemic or a non-racemic mixture of enantiomers, a mixture of four diastereomers of compound 12 will be formed. Mixtures of diastereomers can be separated, for example, by chromatography on a chiral or non-chiral stationary phase.

Compounds 14, which are examples of compounds of Formula (I), can be prepared by a method shown in Scheme 7. A compound 15 (which can be prepared by installing a suitable protecting group such as trimethylsilylethoxymethyl on a compound 10; see Scheme 6) can be reacted with a suitable organozinc compound such as 16, in the presence of a catalyst such as tetrakis(triphenylphosphine)palladium, to provide a compound 17. Such a palladium-catalyzed coupling of organozinc compounds, commonly known as the Negishi coupling, is well known in the chemical literature (see, for example, Negishi, E. et al. in De Meijere, A. et al., eds., $Metal$-$Catalyzed$ $Cross$-$Coupling$ $Reactions$, Second Edition, p. 815, Wiley-VCH (2004)). Removal of the protecting group of a compound 17 and reaction with an appropriate organostannane such as tri-n-butyl(vinyl)stannane in the presence of a catalyst such as tetrakis(triphenylphosphine)palladium, can provide a compound 18. Such a palladium-catalyzed coupling of organotin compounds, commonly known as the Stille coupling, is well known in the chemical literature (see, for example, Stille, J., $Angew.$ $Chem.$, $Int.$ $Ed.$ $Engl.$, 25:508 (1986)). Conversion of the nitrile of a compound 18 to the carboxamide by hydrolysis, using methods described in Scheme 6 or related methods, can provide a compound 14.

Scheme 7
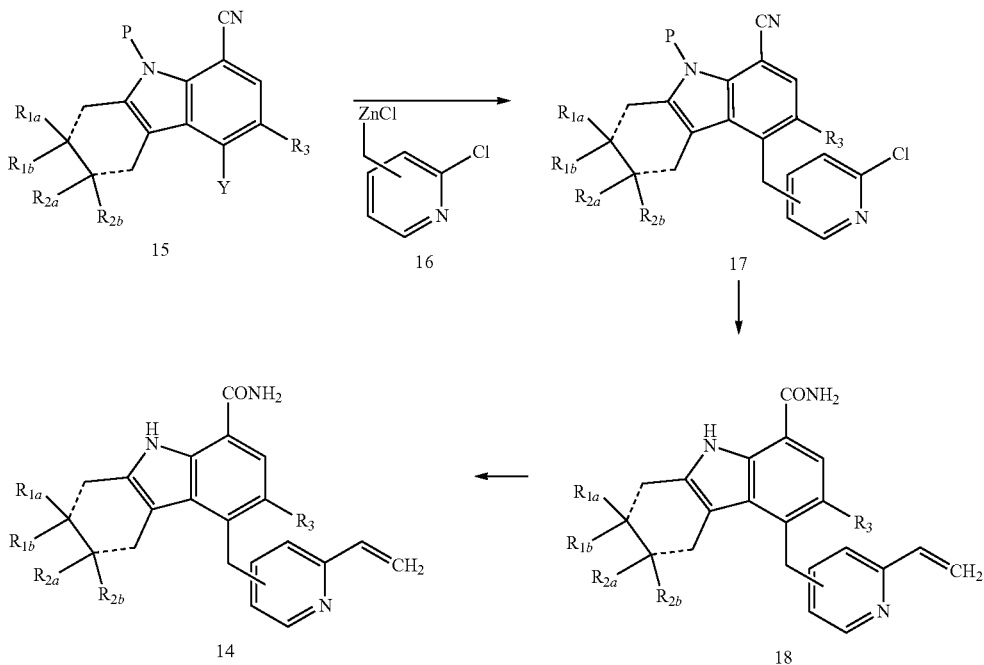
Compounds 1 (see Scheme 1) used in the preparation of compounds of Formula (I), can be prepared using procedures shown in Scheme 8.
Scheme 8
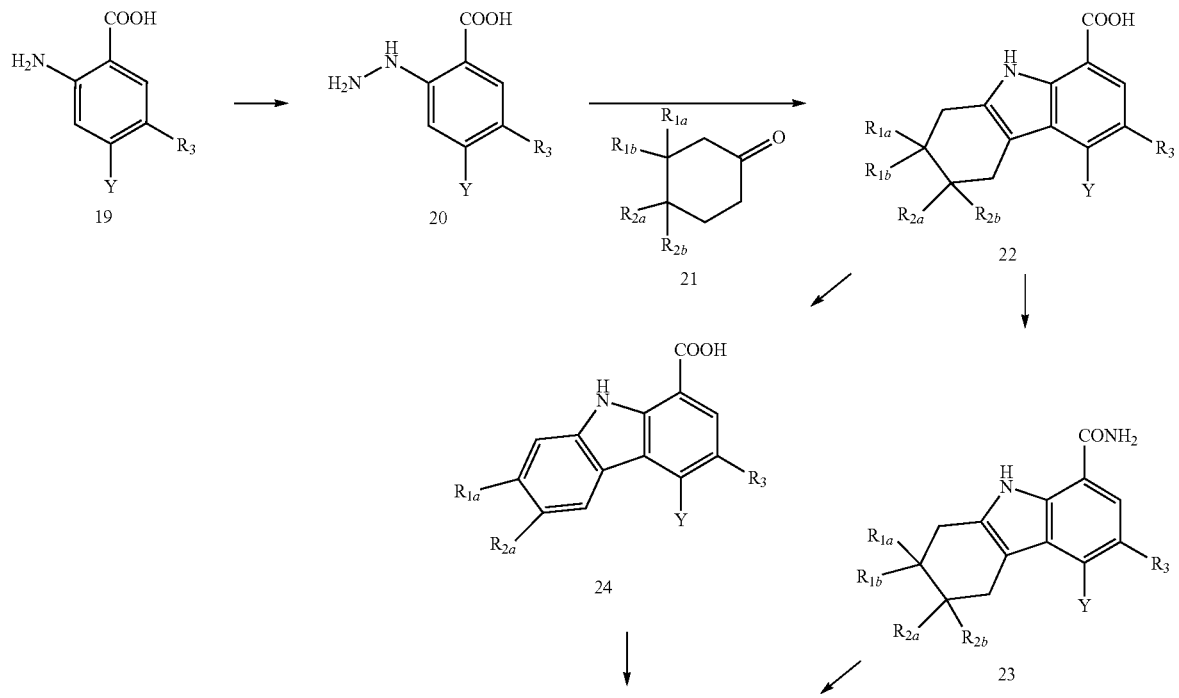

-continued

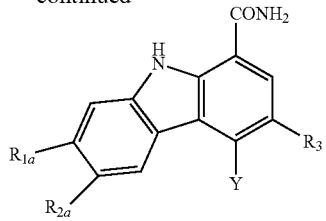

25

A substituted 2-aminobenzoic acid 19 (known in the literature, or prepared using procedures known in the literature) can be converted to the corresponding 2-hydrazinylbenzoic acid 20 as the hydrochloric acid salt using methods known in the literature, for example, by conversion to the corresponding diazonium salt by treatment with sodium nitrite in aqueous hydrochloric acid, followed by reduction with tin(II) chloride. Reaction of 20 with a suitable cyclohexanone 21 in a suitable solvent with an appropriate catalyst, for example, ethanol with hydrochloric acid, toluene with p-toluenesulfonic acid or trifluoroacetic acid, or acetic acid (in which case the solvent also can serve as the catalyst), can provide the corresponding substituted tetrahydrocarbazole 22. This reaction is commonly known as the Fischer indole synthesis, and is known in the chemical literature (for example, see Kamata, J. et al., Chem. Pharm. Bull., 52:1071 (2004)). Alternatively, the Fischer indole synthesis can be carried out in two consecutive steps: 20 can react with 21 under suitable conditions (such as in an appropriate solvent such as ethanol or toluene, optionally with a suitable catalyst such as p-toluenesulfonic acid) to form an intermediate hydrazone, which can be isolated and then reacted further under suitable conditions (for example, ethanol with hydrochloric acid, acetic acid with zinc chloride, or toluene with trifluoroacetic acid) to provide a compound 22.

The carboxylic acid of a compound 22 can be converted to the corresponding carboxamide of compound 23 (which is an example of a compound 1 shown in Scheme 1) using methods known in the chemical literature, for example, by conversion of a compound 22 to the corresponding acid chloride by treatment with oxalyl chloride or thionyl chloride, followed by treatment with ammonia; or by treatment of a compound 22 with ammonia or ammonium chloride in the presence of a coupling reagent such as carbodiimide, or a mixture of EDC and HOAT. In cases of a compound 23 where $R_{1b}$ and $R_{2b}$ are both H, conversion of the compound 23 to the corresponding carbazole 25 (which is another example of a compound 1 shown in Scheme 1) can be performed using methods known in the chemical literature, for example, by treatment of the compound 23 with an oxidizing agent such as DDQ in a suitable solvent.

Alternatively, the order of the amide formation and oxidation steps can be reversed to convert a compound 22 (where both $R_{1b}$ and $R_{2b}$ are both H) to a compound 25. Thus, a compound 22 (where both $R_{1b}$ and $R_{2b}$ are both H) can be oxidized using the procedure described above, or a similar procedure, to give the corresponding compound 24. The carboxylic acid of the compound 24 can then be converted into the primary amide, again using a procedure described above or a similar procedure, to give the corresponding compound 25.

Compounds 22 and 23, where $R_{1a}$ and $R_{1b}$ are different from each other, contain a chiral center, and thus exist as two enantiomers. Preparation of compounds 22 and 23 as shown in Scheme 8 can provide racemic products, which may be used to prepare compounds of Formula (I) as shown in Schemes 1 and 6. Alternatively, compounds 22 and 23 may be resolved into separated enantiomers, using well-known methods such as chromatography on a chiral stationary phase.

It will be recognized by one skilled in the art of organic synthesis that some substituents $R_{1a}$ may be incompatible with reaction conditions used to prepare compounds of Formula (I) or intermediate compounds as shown in Schemes 1, 4, 5, 6, 7, and 8. In these cases, a different substituent may take the place of $R_{1a}$ during certain synthetic steps, and be converted into $R_{1a}$ at an appropriate stage of the synthesis using methods known in the chemical literature. Alternatively, in some cases a suitable protecting group may be used to protect $R_{1a}$ during certain synthetic steps, and removed at an appropriate stage of the synthesis. Such cases will be apparent to one skilled in the art. Some examples of such synthetic transformations are shown in Scheme 9.

A compound 1 shown in Scheme 1 bearing certain substituents $R_{1a}$ and $R_{1b}$ can be prepared from a precursor compound 26. A compound 26 can be prepared using the methods shown in Scheme 8 but substituting ethyl 3-oxo-cyclohexanecarboxylate for compound 21 in Scheme 8. (Some examples of compounds 26 are described in the literature, for example, Intermediates 47-2 and 48-1 and Example 73-1 in U.S. Pat. No. 8,084,620.) Some transformations of the carboxylic acid ester of a compound 26 into $R_{1a}$ and $R_{1b}$ are shown in Scheme 9; some of these as well as others are also illustrated in the examples of U.S. Pat. No. 8,084,620. Compounds 27, 29 and 31 in Scheme 9 are examples of Compound 1 shown in Scheme 1.

Scheme 9

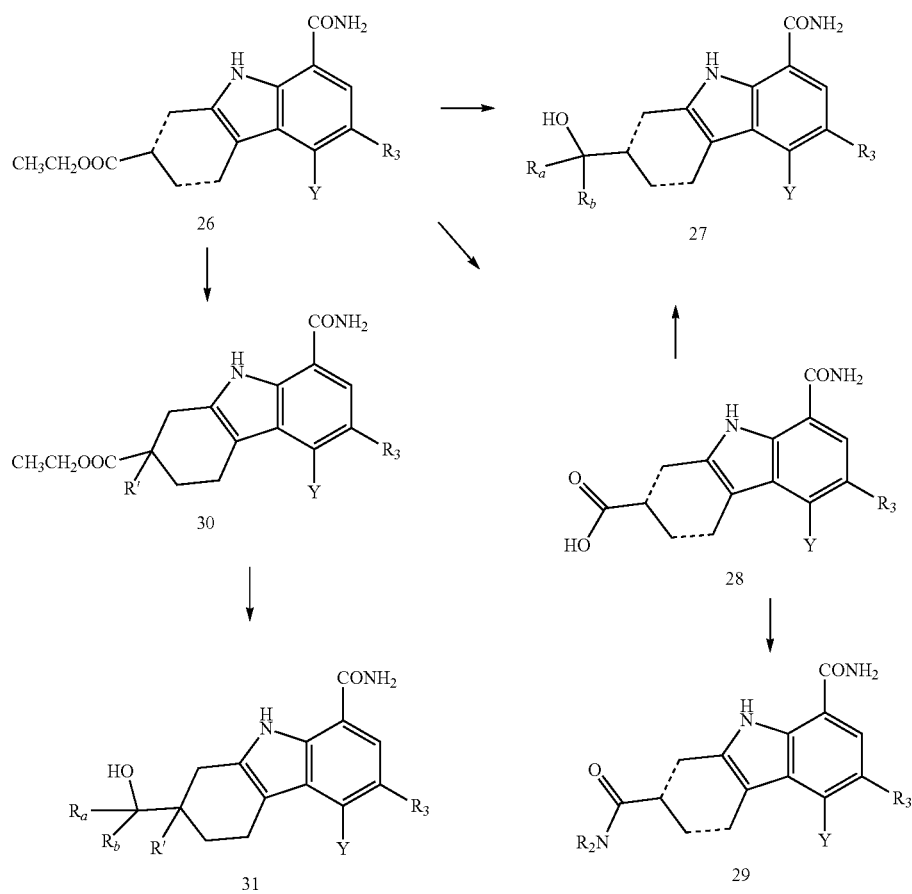

The ester moiety of a compound 26 can be reduced to the corresponding primary carbinol of a compound 27 ($R_a$ and $R_b$ are both H) by treatment with a suitable reducing agent such as lithium aluminum hydride in a suitable solvent such as tetrahydrofuran. Alternatively, the ester moiety of a compound 26 can be converted to the corresponding tertiary carbinol of a compound 27 ($R_a$ and $R_b$ are both methyl) by treatment with a suitable reagent such as methylmagnesium chloride or methyllithium in a suitable solvent such as tetrahydrofuran.

The ester moiety of a compound 26 can be hydrolyzed to the corresponding carboxylic acid of a compound 28, for example, by treatment with aqueous lithium hydroxide or sodium hydroxide in a suitable co-solvent such as methanol, ethanol or tetrahydrofuran. The carboxylic acid moiety of a compound 28 can be converted to the secondary carbinol moiety of a compound 27 (one of $R_a$ and $R_b$ is H, and the other is methyl), for example, by conversion to the N,O-dimethylhydroxamate (commonly called a Weinreb amide) followed by treatment with a reagent such as methylmagnesium chloride or methyllithium and subsequent reduction of the thus-formed ketone with a suitable reducing agent such as sodium borohydride. Alternatively, the carboxylic acid moiety of a compound 28 can be converted to the amide of a compound 29 using any of a variety of methods, such as conversion to the acid chloride followed by treatment with ammonia or a primary or secondary amine, or by treatment with ammonia or ammonium chloride or a primary or secondary amine in the presence of suitable coupling reagents such as HATU, BOP, or a combination of EDC with HOBT or HOAT.

In cases where the dotted lines of a compound 26 represent single bonds, the carbon atom bearing the ester moiety can be alkylated by treatment of the compound 26 with a base such as lithium bis(trimethylsilyl)amide or lithium diisopropylamide in a suitable solvent such as tetrahydrofuran, and treatment of the resulting anion with an alkylating agent such as iodomethane to give a compound 30 where R' is methyl. The ester moiety of the compound 30 can then be converted to the carbinol moiety of a compound 31 (where $R_a$ and $R_b$ are both H, both methyl or one is H and the other is methyl) by the same methods used to prepare a compound 27 as described above.

Certain compounds 1 of Scheme 1, used to prepare compounds of Formula (I), may also be prepared using procedures shown in Scheme 10.

Scheme 10

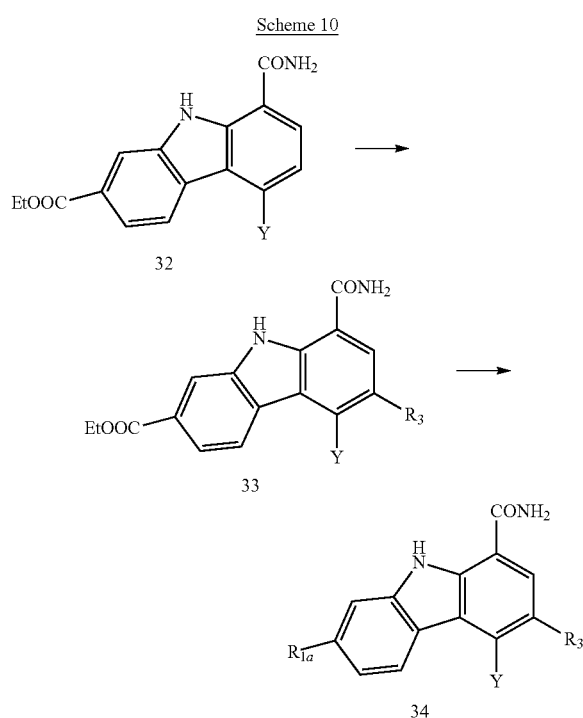

A compound 32, prepared from the appropriate 2-hydrazinylbenzoic acid as shown in Scheme 8 (see, for example, U.S. Pat. No. 8,084,620, Intermediate 48-1) can be treated with an appropriate halogenating reagent to give a compound 33, where $R_3$ is a halogen atom. For example, treatment of a compound 32 with a chlorinating reagent such as N-chlorosuccinimide can give the compound 33 where $R_3$ is Cl, and treatment of a compound 32 with a fluorinating reagent such as 1-(chloromethyl)-4-fluoro-1,4-diazoniabicyclo[2.2.2]octane-bis (tetrafluoroborate) [SELECT-FLUOR®] can give the compound 33 where $R_3$ is F. Conversion of a compound 33 to a corresponding compound 34 (which is an example of a compound 1 of Scheme 1) can be achieved using methods known in the literature, some of which are described in the discussion of Scheme 9.

As shown in Scheme 11, a compound 35 can be converted to a compound 36, which is an example of a compound 5 of Scheme 1. Analogously, a compound 37 can be converted to a compound 38, which is an example of a compound 2 of Scheme 1.

Scheme 11

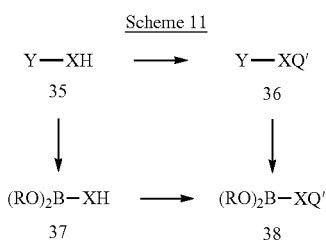

In Scheme 11, Y represents a suitable group such as Br, Cl or trifluoromethanesulfonyloxy; $(RO)_2B$ represents a boronic acid or boronic acid ester; and XH represents a group Q of Formula (I) attached to the carbazole or tetrahydrocarbazole moiety of Formula (I) via a bond to a benzene ring of Q but where $R_{7a}$, $R_{7b}$, $R_{7c}$ or $R_{7d}$, as appropriate, is replaced by H; and Q' represents $R_{7a}$, $R_{7b}$, $R_{7c}$ or $R_{7d}$. Conversion of a compound 35 to a compound 36, and conversion of a compound 37 to a compound 38, can be accomplished using the same methods described for the analogous transformations of a compound 6 to a compound 7 in Scheme 4. Also, conversion of a compound 35 to a compound 37, and conversion of a compound 36 to a compound 38, can be accomplished using the methods described for the transformation of a compound 1 to a compound 4 in Scheme 1.

In some cases, when the conversion of an intermediate compound into another intermediate compound or a compound of Formula (I) requires more than one synthetic reaction, the order of the individual steps can be changed. Such cases will be recognized by one skilled in the art of organic synthesis. One example is shown in Scheme 11. Conversion of a compound 35 to a compound 38 can be done by (1) conversion of the amine of a compound 35 to the substituted amine of a compound 36, followed by (2) conversion of the group Y of the compound 36 to the boronic acid or boronic acid ester of the compound 38. Alternatively, the same conversion of a compound 35 to a compound 38 can be done by (1) conversion of the group Y of a compound 35 to the boronic acid or boronic acid ester of a compound 37, followed by (2) conversion of the amine of the compound 37 to the substituted amine of the compound 38. Another example is shown in Scheme 8. Conversion of a compound 22 to a compound 25 can be done by (1) conversion of the carboxylic acid of a compound 22 to the carboxamide of a compound 23, followed by (2) oxidation of the compound 23 to the carbazole 25. Alternatively, the same conversion of a compound 22 to a compound 25 can be done by (1) oxidation of a compound 22 to the carbazole 24, followed by (2) conversion of the carboxylic acid of the compound 24 to the carboxamide of the compound 25.

EXAMPLES

Compounds of the current invention, and intermediates used in the preparation of compounds of the current invention, can be prepared using procedures shown in the following Examples and related procedures. The methods and conditions used in these Examples, and the actual compounds prepared in these Examples, are not meant to be limiting, but are meant to demonstrate how the compounds of the current invention can be prepared. Starting materials and reagents used in these Examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative Examples set forth herein below, but rather defined by the claims appended hereto.

In the Examples given, the phrase "dried and concentrated" generally refers to removal of most residual water from a solution in an organic solvent using either anhydrous sodium sulfate or magnesium sulfate, followed by filtration and removal of the solvent from the filtrate (generally under reduced pressure and at a temperature suitable to the stability of the material being prepared). Column chromatography was generally performed using the flash chromatography technique (Still, W. et al., *J. Org. Chem.*, 43:2923 (1978)), or with pre-packed silica gel cartridges using an Isco medium pressure chromatography apparatus (Teledyne Corporation), eluting with the solvent or solvent mixture indicated. Preparative high pressure liquid chromatography (HPLC) was performed using a reverse phase column (Waters SunFire $C_{18}$, Waters XBridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Supercritical fluid chromatography (SFC), a form of normal phase HPLC using a mobile phase containing super- or subcritical fluid $CO_2$ and polar organic modifiers such as alcohols, was used to separate chiral compounds. (White, C. et al., *J. Chromatography A*, 1074:175 (2005)). Chiral SFC separation of enantiomers or diastereomers was performed using conditions described for the individual cases. Mass spectral data were obtained by liquid chromatography-mass spectrometry using electrospray ionization.

Single crystal x-ray diffraction data were collected on a Bruker-AXS APEX2 CCD system using Cu Kα radiation (λ=1.5418 Å). Indexing and processing of the measured intensity data were carried out with the APEX2 software package/program suite (see the APEX2 User Manual, v1.27; Bruker AXS, Inc., WI 53711 USA). When indicated, crystals were cooled in the cold stream of an Oxford Cryosystems cryostream cooler (Cosier, J. et al., *J. Appl. Cryst.*, 19:105 (1986)) during data collection. The structures were solved by direct methods and refined on the basis of observed reflections using the crystallographic package SHELXTL (see the APEX2 User Manual, v1.27; Bruker AXS, Inc., WI 53711 USA). The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied. Unit cell parameters were obtained according to the procedure described in Stout et al., *X-Ray Structure Determination: A Practical Guide*, MacMillan (1968).

Chemical names were determined using ChemBioDraw Ultra, version 12.0 (CambridgeSoft).

ABBREVIATIONS

Ac acetyl
ACN acetonitrile
AcOH acetic acid
aq. aqueous
anhyd. anhydrous
Boc tert-butyloxycarbonyl
BOP benzotriazol-1-yloxy)tris(dimethylamino)phosphonium hexafluorophosphate
Cbz benzyloxycarbonyl
Conc. concentration
DCM dichloromethane
DDQ 2,3-dichloro-5,6-dicyano-1,4-benzoquinone
DIEA diisopropylethylamine
DMF N,N-dimethylformamide
DMSO dimethyl sulfoxide
dppf 1,1'-bis(diphenylphosphino)ferrocene
EDC 1-[3-(dimethylamino)propyl]-3-ethyl-carbodiimide hydrochloride
eq. or Eq. or equiv. equivalent(s)
EtOAc ethyl acetate
h or hr hour(s)
HATU O-(7-azabenzotriazol-1-yl)-1,1,3,3-tetramethyluronium hexafluorophosphate
HOAT 1-hydroxy-7-azabenzotriazole
HOBT 1-hydroxybenzotriazole
LC liquid chromatography
LCMS or LC/MS liquid chromatograph mass spectrometry
Me methyl
MeOH methanol
MHz megahertz
min. minute(s)
$M^+$ $(M+H)^+$
$M^{+1}$ $(M+H)^+$
MS mass spectrometry
m/z mass to charge ratio
N Normal
NMP N-methylpyrrolidinone
NMR nuclear magnetic resonance
ppm parts per million
Ret Time or Rt retention time
sat. or sat'd. saturated
sec second(s)
TFA trifluoroacetic acid
THF tetrahydrofuran Intermediate 1

5-Bromo-2,3,4,9-tetrahydro-1H-carbazole-8-carboxamide

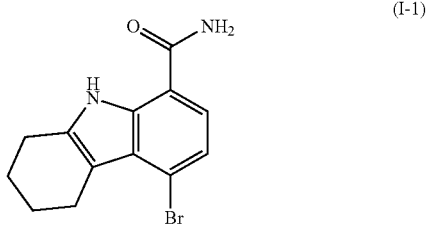 [SMILES: NC(=O)c1ccc(Br)c2c3c([nH]c12)CCCC3]

(I-1)

Intermediate 1A: 5-Bromo-2,3,4,9-tetrahydro-1H-carbazole-8-carboxylic acid

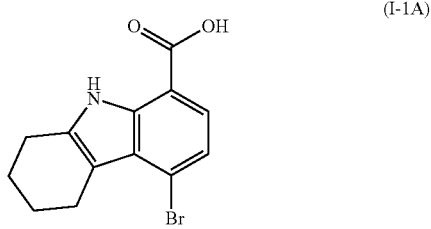 [SMILES: O=C(O)c1ccc(Br)c2c3c([nH]c12)CCCC3]

(I-1A)

A suspension of 4-bromo-2-hydrazinylbenzoic acid hydrochloride [prepared according to U.S. Pat. No. 8,084,620, Intermediate 46-1, Step 1] (5.00 g, 18.69 mmol) in acetic acid (80 mL) was treated with cyclohexanone (2.32 mL, 22.4 mmol) and the mixture was heated at 100-105° C. for 3.5 h. The mixture was cooled to room temperature and concentrated. The residue was triturated with EtOAc, and the precipitate was collected by filtration, rinsed with EtOAc and air-dried. The solid was sonicated in water, and the precipitate was again collected by filtration, washed with water and dried to provide 5-bromo-2,3,4,9-tetrahydro-1H-carbazole-8-carboxylic acid as a dull yellow powder (3.05 g, 56% yield). Mass spectrum m/z 294, 296 (M+H)$^+$. $^1$H NMR (400 MHz, DMSO-d$_6$) δ 12.94 (1H, br. s.), 10.80 (1H, s), 7.34 (1H, d, J=8.1 Hz), 7.04 (1H, d, J=8.1 Hz), 2.84 (2H, br. s.), 2.60 (2H, br. s.), 1.63 (4H, br. s.).

Intermediate 1

A mixture of 5-bromo-2,3,4,9-tetrahydro-1H-carbazole-8-carboxylic acid (1.50 g, 5.10 mmol) in THF (40 mL) was treated with HOAT (0.833 g, 6.12 mmol) and EDC (1.173 g, 6.12 mmol) and the suspension was stirred at room temperature. After 2.25 h, the mixture was bubbled with anhydrous ammonia for about 2 min, forming a thick slurry. The mixture was stirred for 30 min, then was bubbled again with ammonia for about 1 min. After stirring for another 2 h, the mixture was diluted with water and EtOAc. The layers were separated and the aqueous phase was extracted again with EtOAc. The combined organic layers were washed twice with 0.1 M aqueous NaOH, then sequentially with 1 M aqueous HCl and saturated brine, dried and concentrated to provide 5-bromo-2,3,4,9-tetrahydro-1H-carbazole-8-carboxamide as a light brown solid (1.105 g, 67% yield, purity about 90%) which was used without further purification. Mass spectrum m/z 293, 295 (M+H)$^+$. $^1$H NMR (400 MHz, DMSO-d$_6$) δ 10.95 (1H, s), 8.02 (1H, br. s.), 7.44 (1H, d, J=7.9 Hz), 7.38 (1H, br. s.), 7.14 (1H, d, J=8.1 Hz), 2.99 (2H, br. s.), 2.75 (2H, br. s.), 1.78 (4H, br. s.).

Intermediate 2

(RS)-5-Bromo-2-methyl-2,3,4,9-tetrahydro-1H-carbazole-8-carboxamide

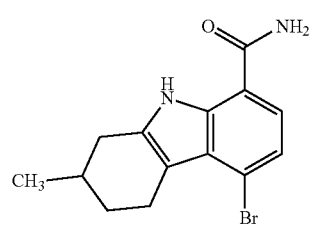

(I-2)

Following the procedures used to prepare Intermediate 1, (RS)-3-methylcyclohexanone was converted into (RS)-5-bromo-2-methyl-2,3,4,9-tetrahydro-1H-carbazole-8-carboxamide. Mass spectrum m/z 307, 309 (M+H)$^+$. $^1$H NMR (400 MHz, DMSO-d$_6$) δ 10.93 (s, 1H), 8.02 (br. s., 1H), 7.44 (d, J=8.1 Hz, 1H), 7.42-7.31 (m, 1H), 7.14 (d, J=8.1 Hz, 1H), 3.22-3.10 (m, 1H), 2.97-2.79 (m, 2H), 2.32 (dd, J=16.7, 9.5 Hz, 1H), 1.98-1.81 (m, 2H), 1.50-1.33 (m, 1H), 1.07 (d, J=6.6 Hz, 3H).

Intermediate 3

5-Bromo-2,2-dimethyl-2,3,4,9-tetrahydro-1H-carbazole-8-carboxamide

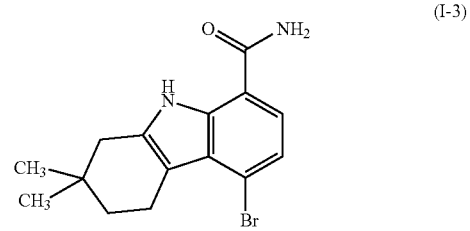 [SMILES: CC1(C)CCc2c([nH]c3c(C(N)=O)ccc(Br)c23)C1]

(I-3)

Following the procedures used to prepare Intermediate 1, 3,3-dimethylcyclohexanone was converted into 5-bromo-2,2-dimethyl-2,3,4,9-tetrahydro-1H-carbazole-8-carboxamide. Mass spectrum m/z 321, 323 (M+H)$^+$. $^1$H NMR (400 MHz, DMSO-d$_6$) δ 10.92 (s, 1H), 8.02 (br. s., 1H), 7.44 (d, J=8.1 Hz, 1H), 7.38 (br. s., 1H), 7.15 (d, J=8.1 Hz, 1H), 2.98 (t, J=6.2 Hz, 2H), 2.55 (s, 2H), 1.57 (t, J=6.4 Hz, 2H), 1.00 (s, 6H).

Intermediate 4

(RS)-5-Bromo-2-(trifluoromethyl)-2,3,4,9-tetrahydro-1H-carbazole-8-carboxamide

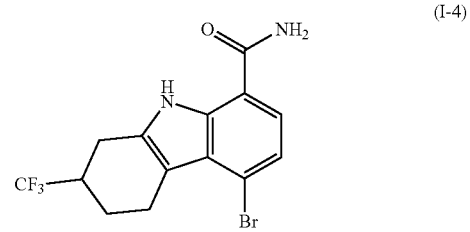 [SMILES: NC(=O)c1ccc(Br)c2c3c([nH]c12)CC(C(F)(F)F)CC3]

(I-4)

Following the procedures used to prepare Intermediate 1, (RS)-3-trifluoromethylcyclohexanone was converted into (RS)-5-bromo-2-(trifluoromethyl)-2,3,4,9-tetrahydro-1H-carbazole-8-carboxamide. Mass spectrum m/z 361, 363 (M+H)$^+$. $^1$H NMR (400 MHz, DMSO-d$_6$) δ 11.19 (s, 1H), 8.05 (br. s., 1H), 7.49 (d, J=7.9 Hz, 1H), 7.41 (br. s., 1H), 7.18 (d, J=7.9 Hz, 1H), 3.39-3.24 (m, 1H), 3.13 (dd, J=16.0, 4.3 Hz, 1H), 3.00-2.65 (m, 3H), 2.19 (d, J=12.8 Hz, 1H), 1.74-1.58 (m, 1H).

Intermediate 5

(RS)-5-Bromo-6-fluoro-2-(trifluoromethyl)-2,3,4,9-tetrahydro-1H-carbazole-8-carboxamide

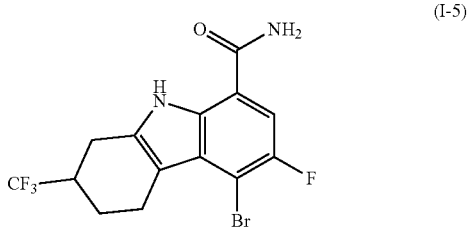 [SMILES: NC(=O)c1cc(F)c(Br)c2c3c([nH]c12)CC(C(F)(F)F)CC3]

(I-5)

Intermediate 5A: 4-Bromo-2,5-difluorobenzoic acid

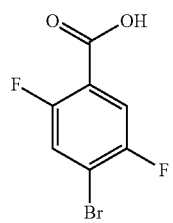

(I-5A)

A solution of 1,4-dibromo-2,5-difluorobenzene (640 mg, 2.35 mmol) in dry diethyl ether (10 mL) cooled in a dry ice-acetone bath was treated dropwise with 2.5 M n-butyllithium in hexanes (1.04 mL, 2.59 mmol). The solution was stirred at −78° C. for 30 min, then was treated with a piece of dry ice. The cooling bath was removed after 5 min and the mixture was stirred for another 30 min while warming to room temperature. The mixture was diluted with EtOAc and water. The organic phase was separated and washed twice with saturated aqueous $NaHCO_3$. The combined aqueous phases were acidified with 1 M aqueous HCl, extracted twice with DCM, and the combined organic phases were dried and concentrated to give 4-bromo-2,5-difluorobenzoic acid as a white solid (297 mg, 53% yield).

Intermediate 5B: 4-Bromo-5-fluoro-2-hydrazinylbenzoic acid hydrochloride

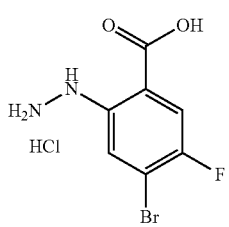

(I-5B)

A mixture of 4-bromo-2,5-difluorobenzoic acid (2.50 g, 10.6 mmol) and hydrazine (3.81 mL, 121 mmol) in N-methyl-2-pyrrolidinone (2 mL) was heated at 95° C. for 4 h. The cooled mixture was poured into vigorously stirred 6 M aqueous HCl (400 mL) which was cooled in a NaCl-ice bath. The resulting precipitate was collected by filtration, washed with 6 M aqueous HCl (200 mL) and dried under vacuum to give 4-bromo-5-fluoro-2-hydrazinylbenzoic acid hydrochloride as a yellow solid (1.88 g, 71% purity, 44% yield), used without further purification.

Alternative Synthesis of Intermediate 5B

A suspension of 2-amino-4-bromo-5-fluorobenzoic acid (10.0 g, 42.7 mmol) in a mixture of 37% aqueous HCl (42.7 mL) and water (14.3 mL), stirred on a NaCl-ice bath, was treated dropwise with a solution of sodium nitrite (3.24 g, 47.0 mmol) in water (15.7 mL). When addition was complete, the mixture was stirred for 30 min more. A solution of tin(II) chloride dihydrate (28.9 g, 128 mmol) in 37% aqueous HCl (27.5 mL) was added dropwise. The cooling bath was removed and the mixture was stirred at room temperature for 45 min. The thick suspension was filtered and the collected precipitate was washed thoroughly with water and dried overnight under reduced pressure. The solid was triturated with MeOH with sonication, and the precipitate was collected by filtration, washed with MeOH and dried. The filtrate was concentrated, and the residue was triturated with DCM. The resulting solid was collected by filtration and dried, and the two solids were combined to give 4-bromo-5-fluoro-2-hydrazinylbenzoic acid hydrochloride (5.37 g, 44% yield) as a white solid. Mass spectrum m/z 249, 251 $(M+H)^+$.

Intermediate 5C: 5-Bromo-6-fluoro-2-(trifluoromethyl)-2,3,4,9-tetrahydro-1H-carbazole-8-carboxylic acid

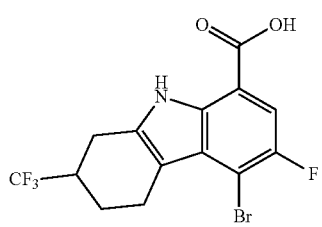

(I-5C)

A mixture of 4-bromo-5-fluoro-2-hydrazinylbenzoic acid hydrochloride (5.00 g, 17.5 mmol), and (RS)-3-trifluoromethylcyclohexanone (4.07 g, 24.5 mmol) in acetic acid (8.0 mL) was stirred at 78° C. for 18 h. The mixture was cooled to room temperature and concentrated. The residue was suspended in EtOAc and the precipitate was collected by filtration and dried. The filtrate was concentrated and the residue was suspended in DCM. The precipitate was collected by filtration and dried, and the two precipitates were combined to provide 5-bromo-6-fluoro-2-(trifluoromethyl)-2,3,4,9-tetrahydro-1H-carbazole-8-carboxylic acid as light orange solid (4.10 g, 55% yield). Mass spectrum m/z 380, 382 $(M+H)^+$.

Intermediate 5

A solution of 5-bromo-6-fluoro-2-(trifluoromethyl)-2,3,4,9-tetrahydro-1H-carbazole-8-carboxylic acid (2.00 g, 5.26 mmol), $NH_4Cl$ (2.81 g, 52.6 mmol) and HATU (2.20 g, 5.79 mmol) in DMF (25 mL) was treated with triethylamine (3.67 mL, 26.3 mmol) and the mixture was stirred at room temperature for 90 min. Ice water (30 mL) was added and the mixture was stirred for 30 min. The precipitate was collected by filtration and washed with water (60 mL). The collected solid was twice suspended in toluene (30 mL) and concentrated under vacuum, then dried. The residue was subjected to column chromatography on silica gel, eluting with 10% MeOH/EtOAc-hexanes (gradient from 0-100%), to provide 5-bromo-6-fluoro-2-(trifluoromethyl)-2,3,4,9-tetrahydro-1H-carbazole-8-carboxamide as a light yellow solid (1.55 g, 74% yield). Mass spectrum m/z 379, 381 $(M+H)^+$. $^1H$ NMR (400 MHz, MeOH-$d_4$) δ 7.46 (d, J=9.9 Hz, 1H), 3.46 (dd, J=16.1, 4.4 Hz, 1H), 3.11 (dd, J=16.4, 5.3 Hz, 1H), 3.06-2.93 (m, 1H), 2.92-2.80 (m, 1H), 2.79-2.59 (m, 1H), 2.37-2.23 (m, 1H), 1.86-1.65 (m, 1H).

Intermediate 6

5-Bromo-3,3,6-trifluoro-2,3,4,9-tetrahydro-1H-carbazole-8-carboxamide

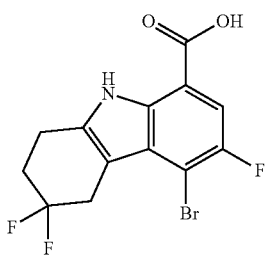
(I-6)

Following the procedures used to convert Intermediate 5B into Intermediate 5, 4,4-difluorocyclohexanone was converted into 5-bromo-3,3,6-trifluoro-2,3,4,9-tetrahydro-1H-carbazole-8-carboxamide. Mass spectrum m/z 347, 349 (M+H)$^+$. $^1$H NMR (400 MHz, DMSO-d$_6$) δ 11.34 (s, 1H), 8.12 (br. s., 1H), 7.64 (d, J=10.1 Hz, 1H), 7.57 (br. s., 1H), 3.54 (t, J=14.4 Hz, 2H), 2.97 (t, J=6.6 Hz, 2H), 2.31 (tt, J=13.9, 6.7 Hz, 2H).

Intermediate 7

4-Bromo-7-cyano-9H-carbazole-1-carboxamide

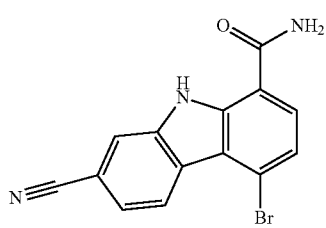
(I-7)

Intermediate 7A: (RS)-5-Bromo-2-cyano-2,3,4,9-tetrahydro-1H-carbazole-8-carboxylic acid

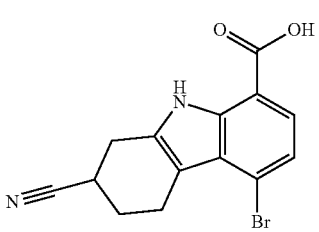
(I-7A)

A mixture of (RS)-3-oxocyclohexanecarbonitrile (0.200 g, 1.62 mmol) and 4-bromo-2-hydrazinylbenzoic acid hydrochloride [prepared according to U.S. Pat. No. 8,084, 620, Intermediate 46-1, Step 1] (0.434 g, 1.62 mmol) in acetic acid (4.3 mL) was heated at 110° C. for 3 h. The mixture was cooled to room temperature, diluted with diethyl ether (8 mL) and stirred for 5 min. The precipitate was collected by filtration, washed with ether and dried to provide (RS)-5-bromo-2-cyano-2,3,4,9-tetrahydro-1H-carbazole-8-carboxylic acid as a solid (403 mg, 78% yield). Mass spectrum m/z 319, 321 (M+H)$^+$. $^1$H NMR (400 MHz, DMSO-d$_6$) δ 13.15 (br. s., 1H), 11.16 (s, 1H), 7.55 (d, J=7.9 Hz, 1H), 7.25 (d, J=8.1 Hz, 1H), 3.47-3.36 (m, 1H), 3.24-2.99 (m, 4H), 2.09 (q, J=5.9 Hz, 2H).

Intermediate 7B: 4-Bromo-7-cyano-9H-carbazole-1-carboxylic acid

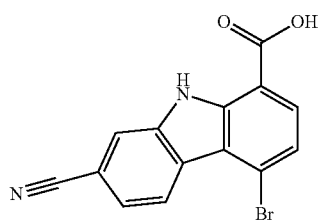
(I-7B)

A solution of (RS)-5-bromo-2-cyano-2,3,4,9-tetrahydro-1H-carbazole-8-carboxylic acid (346 mg, 1.08 mmol) in THF (7 mL) was treated with DDQ (541 mg, 2.39 mmol) and the mixture was heated at 60° C. for 2 h. The mixture was cooled to room temperature, combined with the mixture from an identical reaction of 5-bromo-2-cyano-2,3,4,9-tetrahydro-1H-carbazole-8-carboxylic acid (50.0 mg, 0.157 mmol) and DDQ (78.0 mg, 0.345 mmol), and the combined mixture was diluted with diethyl ether (20 mL) and stirred. The resulting precipitate was collected by filtration, washed with ether and dried to provide 4-bromo-7-cyano-9H-carbazole-1-carboxylic acid (346 mg, 89% yield). Mass spectrum m/z 315, 317 (M+H)$^+$.

Intermediate 7

A mixture of 4-bromo-7-cyano-9H-carbazole-1-carboxylic acid (340 mg, 1.08 mmol), EDC (248 mg, 1.30 mmol) and HOBT (198 mg, 1.30 mmol) in THF (10 mL) was treated with 28% aqueous ammonia (0.21 mL) and DIEA (0.30 mL, 1.72 mmol), and the mixture was stirred overnight at room temperature. Water was added, and the mixture was extracted twice with EtOAc. The insoluble material was collected by filtration, washed with EtOAc and dried to provide 4-bromo-7-cyano-9H-carbazole-1-carboxamide as a white solid (196 mg, 58% yield). Mass spectrum m/z 314, 316 (M+H)$^+$.

Intermediate 8

4-Bromo-3-fluoro-9H-carbazole-1-carboxamide

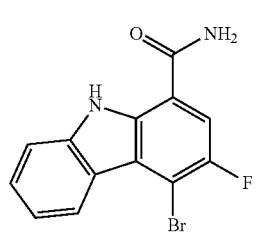
(I-8)

Following the procedures used to prepare Intermediate 7, cyclohexanone and 4-bromo-5-fluoro-2-hydrazinylbenzoic acid hydrochloride [Intermediate 5B] were converted into 4-bromo-3-fluoro-9H-carbazole-1-carboxamide. Mass spectrum m/z 307, 309 (M+H)+, 290, 292 (M+H−NH$_3$)+. $^1$H NMR (400 MHz, MeOH-d$_4$) δ 8.73 (dd, J=8.1, 0.9 Hz, 1H), 7.83 (d, J=9.9 Hz, 1H), 7.69-7.63 (m, 1H), 7.54 (ddd, J=8.2, 7.1, 1.2 Hz, 1H), 7.29 (ddd, J=8.1, 7.1, 1.0 Hz, 1H).

Intermediate 9

4-Bromo-3-fluoro-7-(trifluoromethyl)-9H-carbazole-1-carboxamide

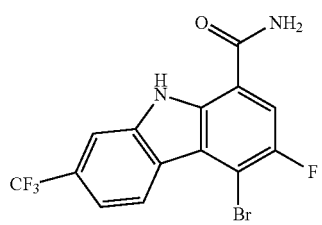

(I-9)

Following the procedures used to convert Intermediate 7A into Intermediate 7, 5-bromo-6-fluoro-2-(trifluoromethyl)-2,3,4,9-tetrahydro-1H-carbazole-8-carboxylic acid [Intermediate 5C] was converted into 4-bromo-3-fluoro-7-(trifluoromethyl)-9H-carbazole-1-carboxamide. Mass spectrum m/z 416, 418 (M+H+CH$_3$CN)+. $^1$H NMR (400 MHz, MeOH-d$_4$) δ 8.83 (d, J=8.6 Hz, 1H), 8.00 (d, J=0.7 Hz, 1H), 7.89 (d, J=9.8 Hz, 1H), 7.52 (dd, J=8.4, 1.1 Hz, 1H).

Intermediate 10

4-Bromo-3-chloro-7-(2-hydroxypropan-2-yl)-9H-carbazole-1-carboxamide

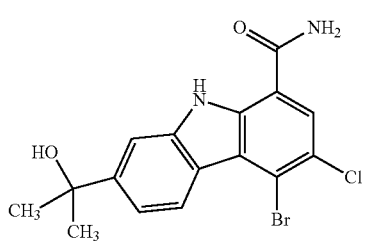

(I-10)

Intermediate 10A: Ethyl 5-bromo-8-carbamoyl-6-chloro-9H-carbazole-2-carboxylate

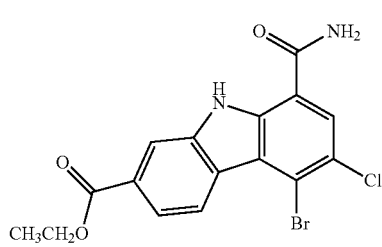

(I-10A)

A mixture of ethyl 5-bromo-8-carbamoyl-9H-carbazole-2-carboxylate [synthesized according to the procedure described in U.S. Pat. No. 8,084,620, Intermediate 48-1] (0.100 g, 0.277 mmol) and N-chlorosuccinimide (recrystallized from toluene; 0.037 g, 0.277 mmol) in CCl$_4$ (10 mL) and DMF (2 mL) was stirred at room temperature for 112 h. The mixture was filtered, and the collected precipitate was washed with CCl$_4$ and dried overnight under vacuum. The residue was purified by column chromatography on silica gel (40 g), eluting with hexanes, then with EtOAc-hexanes (30%, then 50%), to give ethyl 5-bromo-8-carbamoyl-6-chloro-9H-carbazole-2-carboxylate as a fluffy white solid (0.071 g, 65% yield). Mass spectrum m/z 395, 397 (M+H)+. $^1$H NMR (400 MHz, DMSO-d$_6$) δ 12.13 (s, 1H), 8.77 (d, J=8.6 Hz, 1H), 8.53 (d, J=1.1 Hz, 1H), 8.36 (br. s., 1H), 8.29 (s, 1H), 7.89 (dd, J=8.4, 1.5 Hz, 1H), 7.74 (br. s., 1H), 4.38 (q, J=7.0 Hz, 2H), 1.38 (t, J=7.0 Hz, 3H).

Alternative Preparation of Intermediate 10A

To a mixture of ethyl 5-bromo-8-carbamoyl-9H-carbazole-2-carboxylate (90 g, 249 mmol), CCl$_4$ (2900 mL), and NMP (600 mL) was added N-chlorosuccinimide (36.1 g, 271 mmol). The reaction mixture was stirred at 45° C. for 2 h. After cooling to room temperature, the solid was collected by vacuum filtration. The solid was stirred in MeOH (1 L) at 60° C. for 2 h and the suspension was cooled to room temperature. The solid was collected by filtration and dried to give ethyl 5-bromo-8-carbamoyl-6-chloro-9H-carbazole-2-carboxylate (69.5 g, 167 mmol, 67% yield, 95% purity). The filtrate was concentrated under reduced pressure to remove CCl$_4$. The residual NMP solution was diluted with water (2 L). The resulting precipitate was collected by filtration and dried to give an additional ethyl 5-bromo-8-carbamoyl-6-chloro-9H-carbazole-2-carboxylate (13.7 g, 25% yield, 75% purity).

Intermediate 10

A solution of ethyl 5-bromo-8-carbamoyl-6-chloro-9H-carbazole-2-carboxylate (4.14 g, 10.5 mmol) in THF (200 mL) was cooled in a dry ice-acetone bath and treated portionwise over 30 min with 1.6 M methyllithium in hexanes (45.8 mL, 73.2 mmol). The mixture was stirred at −78° C. for 60 min, then was treated portionwise with saturated aqueous NH$_4$Cl. Water was added and the mixture was extracted twice with EtOAc. The combined organic phases were washed twice with water. All aqueous phases were combined and extracted with DCM, and this organic phase was washed with water. All organic phases were combined, dried and concentrated. The residue was crystallized from EtOAc to give a solid. The residue from concentration of the mother liquor was purified by column chromatography on silica gel (330 g), eluting with EtOAc-hexanes (gradient from 0-100%), to give additional solid. The two solids were combined to give 4-bromo-3-chloro-7-(2-hydroxypropan-2-yl)-9H-carbazole-1-carboxamide as a light yellow solid (3.13 g, 78% yield). Mass spectrum m/z 363, 365, (M+H−H$_2$O)+. $^1$H NMR (400 MHz, DMSO-d$_6$) δ 11.71 (s, 1H), 8.56 (d, J=8.6 Hz, 1H), 8.29 (br. s., 1H), 8.17 (s, 1H), 7.97 (d, J=1.3 Hz, 1H), 7.66 (br. s., 1H), 7.42 (dd, J=8.6, 1.8 Hz, 1H), 1.52 (s, 6H).

Alternative Preparation of Intermediate 10

A suspension of ethyl 5-bromo-8-carbamoyl-6-chloro-9H-carbazole-2-carboxylate (58.56 g, 148 mmol) in THF (700 mL) under nitrogen was cooled to −15° C. in an acetone-dry ice bath. The mixture was treated dropwise with 3 M methylmagnesium chloride in THF (395 mL, 1.19 mol) at a rate such that the internal temperature remained between −15° C. and −10° C. After 5 h the mixture was poured into 3 vessels, each containing about 1.5 L of crushed ice and 500 mL of saturated aqueous NH₄Cl. The resulting mixtures were extracted with EtOAc, and the combined organic phases were dried and concentrated. The residue was combined with material from 2 additional batches, one starting from 146 mmol of ethyl 5-bromo-8-carbamoyl-6-chloro-9H-carbazole-2-carboxylate and the other starting from 142 mmol of ethyl 5-bromo-8-carbamoyl-6-chloro-9H-carbazole-2-carboxylate, and stirred for 1 h in acetone (250 mL). The precipitate was collected by filtration, washed with hexane and dried to provide 4-bromo-3-chloro-7-(2-hydroxypropan-2-yl)-9H-carbazole-1-carboxamide as a solid (134.56 g). The filtrate was concentrated and the residue was again stirred for 1 h in acetone, forming a precipitate which was collected by filtration, washed with hexane and dried to give additional 4-bromo-3-chloro-7-(2-hydroxypropan-2-yl)-9H-carbazole-1-carboxamide as a solid (7.36 g) for a total of 141.92 g (88% yield). The filtrate from the second filtration was combined with impure material from other batches and subjected to column chromatography on silica gel, eluting with EtOAc-hexanes (gradient from 40-100%), to provide additional 4-bromo-3-chloro-7-(2-hydroxypropan-2-yl)-9H-carbazole-1-carboxamide.

Intermediate 11

(RS)-5-Bromo-6-chloro-2-(2-hydroxypropan-2-yl)-2,3,4,9-tetrahydro-1H-carbazole-8-carboxamide

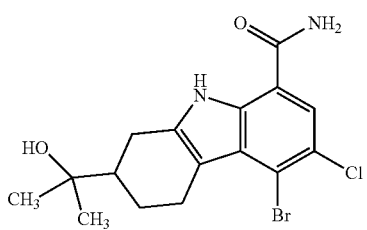

(I-11)

Intermediate 11A:
4-Bromo-5-chloro-2-hydrazinylbenzoic acid hydrochloride

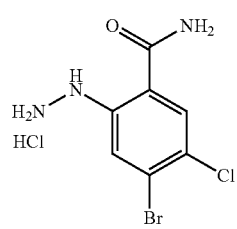

(I-11A)

A solution of sodium nitrite (3.03 g, 43.9 mmol) in water (14.8 mL) was added dropwise to a suspension of 2-amino-4-bromo-5-chlorobenzoic acid (10.0 g, 39.9 mmol) in 37% aqueous HCl (39.9 mL) and water (13.3 mL) which was stirred at −10° C. on a NaCl-ice bath, at such rate that the temperature did not exceed 0° C. The resulting suspension was stirred at 0° C. for 15 min, then was treated with a solution of tin(II) chloride hydrate (22.7 g, 120 mmol) in 37% aqueous HCl (17 mL). The resulting mixture was warmed to room temperature and stirred for 60 min. The precipitate was collected by filtration, washed with water and air-dried overnight to give 4-bromo-5-chloro-2-hydrazinylbenzoic acid hydrochloride as an off-white solid (12.86 g, 96% yield). Mass spectrum m/z 365, 267 (M+H)⁺. ¹H NMR (400 MHz, DMSO-d₆) δ 9.05 (br. s., 1H), 7.95 (s, 1H), 7.55 (s, 1H).

Intermediate 11B: (RS)-5-Bromo-6-chloro-2-(ethoxycarbonyl)-2,3,4,9-tetrahydro-1H-carbazole-8-carboxylic acid

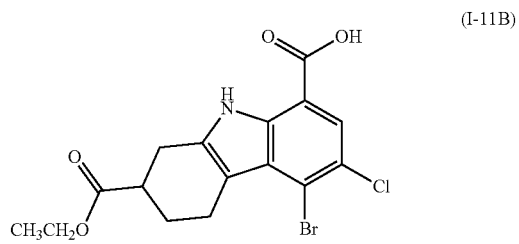

(I-11B)

A suspension of 4-bromo-5-chloro-2-hydrazinylbenzoic acid hydrochloride (12.89 g, 37.6 mmol), ethyl (RS)-3-oxocyclohexanecarboxylate (7.03 g, 41.3 mmol) and acetic acid (6.45 mL, 113 mmol) in toluene (188 mL) was heated at 105° C. overnight. After 16 h, more acetic acid (6 mL) and ethyl 3-(RS)-oxocyclohexanecarboxylate (2.00 g) were added and the mixture was heated at 110° C. for 4.5 h. The mixture was concentrated, and the residue was combined with toluene (100 mL) and TFA (20 mL). The suspension was heated at 90° C. overnight. The cooled mixture was concentrated and the residue was suspended in EtOAc. The resulting solid was collected by filtration, washed with EtOAc and air-dried to give (RS)-5-bromo-6-chloro-2-(ethoxycarbonyl)-2,3,4,9-tetrahydro-1H-carbazole-8-carboxylic acid as a yellow solid (11.0 g, 73% yield). Mass spectrum m/z 400, 402 (M+H)⁺. ¹H NMR (400 MHz, DMSO-d₆) δ 13.44 (br. s., 1H), 11.24 (s, 1H), 7.69 (s, 1H), 4.12 (qd, J=7.1, 2.3 Hz, 2H), 3.23-2.81 (m, 5H), 2.23-2.09 (m, 1H), 1.91-1.75 (m, 1H), 1.22 (t, J=7.0 Hz, 3H).

Intermediate 11C: Ethyl (RS)-5-bromo-8-carbamoyl-6-chloro-2,3,4,9-tetrahydro-1H-carbazole-2-carboxylate

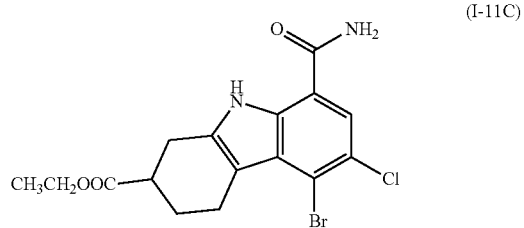

(I-11C)

Following the procedure used to prepare Intermediate 7, (RS)-5-bromo-6-chloro-2-(ethoxycarbonyl)-2,3,4,9-tetrahydro-1H-carbazole-8-carboxylic acid was converted into ethyl (RS)-5-bromo-8-carbamoyl-6-chloro-2,3,4,9-tetrahydro-1H-carbazole-2-carboxylate as a light brown solid (8.54 g, 78% yield). Mass spectrum m/z 399, 401 (M+H)$^+$. $^1$H NMR (400 MHz, DMSO-d$_6$) δ 13.44 (br. s., 1H), 11.24 (s, 1H), 7.69 (s, 1H), 4.12 (qd, J=7.1, 2.3 Hz, 2H), 3.23-2.81 (m, 5H), 2.23-2.09 (m, 1H), 1.91-1.75 (m, 1H), 1.22 (t, J=7.0 Hz, 3H). This material was contaminated (10-15%) with (RS)-5-bromo-6-chloro-2,3,4,9-tetrahydro-1H-carbazole-2,8-dicarboxamide. Mass spectrum m/z 370, 372, 374 (M+H)$^+$. The impure material was used in subsequent reactions.

Intermediate 11

A solution of impure ethyl (RS)-5-bromo-8-carbamoyl-6-chloro-2,3,4,9-tetrahydro-1H-carbazole-2-carboxylate (7.03 g, 17.6 mmol) in THF (200 mL) was cooled in a dry ice-acetone bath and treated portionwise over 40 min with 1.6 M methyllithium in THF (66.0 mL, 106 mmol). After 60 min, the mixture was treated slowly at −78° C. with saturated aqueous NH$_4$Cl and stirred for 10 min while warming to room temperature. The mixture was extracted 3 times with DCM, and the combined organic phases were washed sequentially with water and brine, and dried and concentrated. The residue was purified by column chromatography on silica gel (120 g), eluting with EtOAc-hexanes (gradient from 0-100%), to give (RS)-5-bromo-6-chloro-2-(2-hydroxypropan-2-yl)-2,3,4,9-tetrahydro-1H-carbazole-8-carboxamide as a yellow solid (4.66 g). Mass spectrum m/z 385, 387 (M+H)$^+$. $^1$H NMR (400 MHz, DMSO-d$_6$) δ 11.08 (s, 1H), 8.13 (br. s., 1H), 7.76 (s, 1H), 7.50 (br. s., 1H), 3.28 (d, J=5.5 Hz, 1H), 2.94 (dd, J=17.1, 4.7 Hz, 1H), 2.79-2.66 (m, 1H), 2.49-2.39 (m, 1H), 2.14 (d, J=9.5 Hz, 1H), 1.66 (td, J=11.4, 4.1 Hz, 1H), 1.33 (qd, J=12.4, 5.2 Hz, 1H), 1.15 (s, 6H).

Intermediate 12

(RS)-5-Bromo-6-fluoro-2-(2-hydroxypropan-2-yl)-2,3,4,9-tetrahydro-1H-carbazole-8-carboxamide

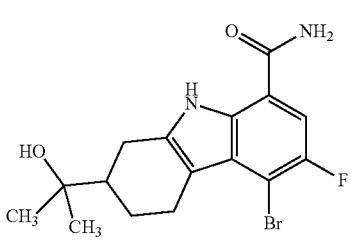

(I-12)

Intermediate 12A: (RS)-5-Bromo-2-(ethoxycarbonyl)-6-fluoro-2,3,4,9-tetrahydro-1H-carbazole-8-carboxylic acid

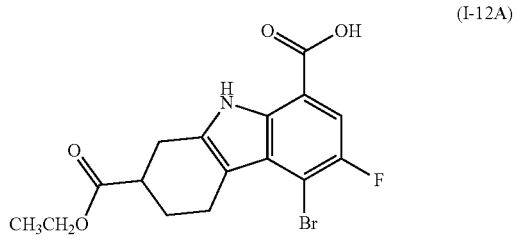

(I-12A)

A mixture of 4-bromo-5-fluoro-2-hydrazinylbenzoic acid hydrochloride [Intermediate 5B] (5.37 g, 18.8 mmol), ethyl (RS)-3-oxocyclohexanecarboxylate (3.52 g, 20.7 mmol) and acetic acid (3.23 mL, 56.4 mmol) in toluene (90 mL) was heated at 110° C. for 20 h. The solvent was removed under reduced pressure, and the residue was diluted with toluene (43 mL) and TFA (11 mL). The mixture was stirred at 90-94° C. overnight. The cooled mixture was diluted with EtOAc, sonicated, and the precipitate was collected by filtration. The filtrate was concentrated and the residue was suspended in EtOAc with sonication, resulting in another precipitate which was also collected by filtration and washed with EtOAc. The combined solids were triturated twice with MeOH to give a solid. The combined filtrates were concentrated and the residue was triturated with MeOH to give additional solid. The solids were combined to give (RS)-5-bromo-2-ethoxycarbonyl-6-fluoro-2,3,4,9-tetrahydro-1H-carbazole-8-carboxylic acid as a pale yellow solid (3.38 g). Mass spectrum m/z 384, 386 (M+H)$^+$.

Intermediate 12B: Ethyl (RS)-5-bromo-8-carbamoyl-6-fluoro-2,3,4,9-tetrahydro-1H-carbazole-2-carboxylate

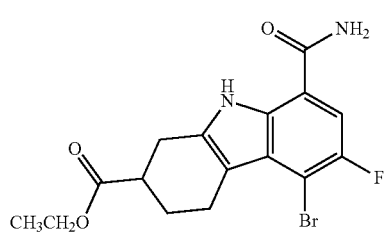

(I-12B)

A mixture of (RS)-5-bromo-2-(ethoxy carbonyl)-6-fluoro-2,3,4,9-tetrahydro-1H-carbazole-8-carboxylic acid (0.513 g, 1.34 mmol), EDC (0.384 g, 2.00 mmol), and HOBT (0.307 g, 2.00 mmol) in THF (10 mL) and DCM (1.7 mL) was stirred at room temperature for 20 min. Aqueous NH$_4$OH (28%, 0.078 mL, 2.00 mmol) was added, and the mixture was stirred at room temperature for 60 min. The mixture was diluted with EtOAc and washed twice with saturated aqueous NaHCO$_3$, then with brine. The aqueous layers were extracted with EtOAc, and the combined organic layers were dried and concentrated. The residue was triturated in MeOH with sonication to provide ethyl (RS)-5-bromo-8-carbamoyl-6-fluoro-2,3,4,9-tetrahydro-1H-carbazole-2-carboxylate as a yellow solid (0.432 g, 84% yield). Mass spectrum m/z 383, 385 (M+H)+.

Intermediate 12

A solution of ethyl (RS)-5-bromo-8-carbamoyl-6-fluoro-2,3,4,9-tetrahydro-1H-carbazole-2-carboxylate (10.0 g, 26.1 mmol) in THF (200 mL) at −78° C. was treated dropwise over 30 min with 1.6 M methyllithium in ether (49 mL, 78 mmol). The mixture was stirred at −78° C. for 45 min, then was treated with additional methyllithium solution (33 mL) over 25 min. The mixture was stirred at −78° C. for an additional 90 min, then was treated with saturated aqueous NH4Cl and warmed to room temperature. The mixture was diluted with EtOAc and washed sequentially with water and brine. The aqueous layers were extracted with EtOAc. The combined organic layers were dried and concentrated. The residue was dissolved in EtOAc (about 100 mL) and filtered through a pad of CELITE® topped with a pad of silica gel. The CELITE® and silica gel were washed further with EtOAc (about 1000 mL). Concentration of the combined filtrates gave (RS)-5-bromo-6-fluoro-2-(2-hydroxypropan-2-yl)-2,3,4,9-tetrahydro-1H-carbazole-8-carboxamide as a pale yellow solid (9.24 g, 96% yield). Mass spectrum m/z 369, 371 (M+H)+.

Intermediates 13 and 14

(R)-5-Bromo-6-chloro-2-(2-hydroxypropan-2-yl)-2,3,4,9-tetrahydro-1H-carbazole-8-carboxamide (I-13), and (S)-5-Bromo-6-chloro-2-(2-hydroxypropan-2-yl)-2,3,4,9-tetrahydro-1H-carbazole-8-carboxamide (I-14)

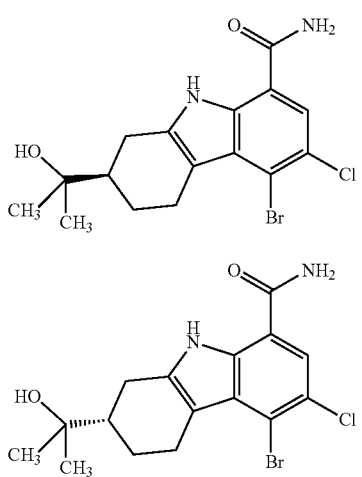

A sample of (RS)-5-bromo-6-chloro-2-(2-hydroxypropan-2-yl)-2,3,4,9-tetrahydro-1H-carbazole-8-carboxamide [Intermediate 11] (2.35 g) was separated by chiral supercritical fluid chromatography (Column: CHIRALPAK® IA (3×25 cm, 5 μm); Mobile Phase: CO2-MeOH (50:50) at 124 mL/min, 100 bar, 45° C.; sample preparation: 39 mg/mL in MeOH-DMSO (4:1); injection: 2.33 mL). The first peak eluting from the column provided (R)-5-bromo-6-chloro-2-(2-hydroxypropan-2-yl)-2,3,4,9-tetrahydro-1H-carbazole-8-carboxamide [Intermediate 13] as a yellow solid (1.15 g). Mass spectrum m/z 385, 387 (M+H)+. 1H NMR (500 MHz, DMSO-d6) δ 11.07 (s, 1H), 8.12 (br. s., 1H), 7.75 (s, 1H), 7.57-7.45 (m, 1H), 4.23 (s, 1H), 3.27 (d, J=4.7 Hz, 1H), 2.93 (dd, J=17.2, 4.7 Hz, 1H), 2.78-2.67 (m, 1H), 2.48-2.39 (m, 1H), 2.16-2.08 (m, 1H), 1.69-1.59 (m, 1H), 1.37-1.26 (m, 1H), 1.14 (s, 6H). The second peak eluting from the column provided (S)-5-bromo-6-chloro-2-(2-hydroxypropan-2-yl)-2,3,4,9-tetrahydro-1H-carbazole-8-carboxamide [Intermediate 14] as an off-white solid (0.92 g). Mass spectrum m/z 385, 387 (M+H)+. 1H NMR (500 MHz, DMSO-d6) δ 11.06 (s, 1H), 8.12 (br. s., 1H), 7.74 (s, 1H), 7.49 (br. s., 1H), 4.23 (s, 1H), 3.27 (d, J=5.0 Hz, 1H), 2.93 (dd, J=17.1, 4.6 Hz, 1H), 2.72 (t, J=11.8 Hz, 1H), 2.48-2.37 (m, 1H), 2.12 (d, J=9.2 Hz, 1H), 1.69-1.59 (m, 1H), 1.38-1.24 (m, 1H), 1.14 (s, 6H).

The absolute configuration of Intermediate 13 was confirmed by single crystal x-ray analysis of crystals prepared by dissolving the compound in excess 1,2-dichloroethane-EtOAc-acetic acid and slowly evaporating the solvent at room temperature to provide a di-acetic acid solvate. Unit cell dimensions: a=11.690(2) Å, b=7.0901(9) Å, c=14.427(3) Å, α=90°, β3=110.607(5°), γ=90°; volume=1119.2(3) Å³; volume/number of molecules in the unit cell=560 Å³; space group: P2₁; molecules of Intermediate 30/asymmetric unit (Z'): 1; density (calculated) 1.501 g/cm⁻³. Fractional atomic coordinates at room temperature are given in Table 1, and a depiction of the structure is given in FIG. 1.

TABLE 1

Fractional Atomic Coordinates for the Di-acetic Acid Solvate of Intermediate 13 at Room Temperature

| Atom | X | Y | Z |
|---|---|---|---|
| Br1 | 0.7129 | 0.3740 | 0.6642 |
| Cl1 | 0.7740 | 0.3738 | 0.4607 |
| N1 | 0.2665 | 0.3652 | 0.4430 |
| O1 | 0.2004 | 0.3636 | 0.2416 |
| C1 | 0.1772 | 0.3609 | 0.5790 |
| C2 | 0.5901 | 0.3791 | 0.5379 |
| C3 | 0.2812 | 0.3738 | 0.5418 |
| C4 | 0.3773 | 0.3661 | 0.4329 |
| C5 | 0.4669 | 0.3740 | 0.5291 |
| C6 | 0.3082 | 0.3690 | 0.2482 |
| C7 | 0.5312 | 0.3740 | 0.3598 |
| C8 | 0.4074 | 0.3753 | 0.3462 |
| C9 | 0.4036 | 0.3762 | 0.5976 |
| C10 | 0.4463 | 0.3870 | 0.7085 |
| C11 | 0.6203 | 0.3747 | 0.4534 |
| C12 | 0.2289 | 0.3165 | 0.6913 |
| N2 | 0.3387 | 0.3721 | 0.1672 |
| O2 | 0.1932 | 0.2852 | 0.8423 |
| C13 | 0.1290 | 0.3293 | 0.7384 |
| C14 | 0.0723 | 0.5210 | 0.7302 |
| C15 | 0.0325 | 0.1757 | 0.6967 |
| C16 | 0.3389 | 0.4360 | 0.7413 |
| O3 | 0.0996 | 0.3570 | −0.0085 |
| C17 | 0.0053 | 0.3621 | 0.0046 |
| O4 | −0.0020 | 0.3642 | 0.0929 |
| C18 | −0.1174 | 0.3580 | −0.0772 |
| C19 | 0.6259 | 0.3810 | 0.0872 |
| O5 | 0.5910 | 0.4309 | 0.1503 |
| O6 | 0.7118 | 0.4731 | 0.0663 |
| C20 | 0.5791 | 0.2200 | 0.0206 |
| H1 | 0.1973 | 0.3602 | 0.3950 |
| H2 | 0.1212 | 0.2621 | 0.5441 |
| H3 | 0.1327 | 0.4793 | 0.5676 |
| H4 | 0.5548 | 0.3721 | 0.3046 |
| H5 | 0.5091 | 0.4833 | 0.7321 |
| H6 | 0.4813 | 0.2674 | 0.7370 |
| H7 | 0.2569 | 0.1852 | 0.6979 |
| H8 | 0.2826 | 0.3705 | 0.1095 |
| H9 | 0.4142 | 0.3755 | 0.1729 |
| H10 | 0.1460 | 0.2951 | 0.8728 |
| H11 | 0.0219 | 0.5258 | 0.7703 |

TABLE 1-continued

Fractional Atomic Coordinates for the Di-acetic Acid Solvate of Intermediate 13 at Room Temperature

| Atom | X | Y | Z |
|---|---|---|---|
| H12 | 0.0232 | 0.5455 | 0.6624 |
| H13 | 0.1355 | 0.6145 | 0.7528 |
| H14 | 0.0720 | 0.0559 | 0.7005 |
| H15 | −0.0148 | 0.2037 | 0.6289 |
| H16 | −0.0205 | 0.1714 | 0.7347 |
| H17 | 0.3637 | 0.4190 | 0.8124 |
| H18 | 0.3175 | 0.5675 | 0.7267 |
| H19 | 0.0671 | 0.3654 | 0.1347 |
| H20 | −0.1430 | 0.4843 | −0.0980 |
| H21 | −0.1761 | 0.2992 | −0.0536 |
| H22 | −0.1116 | 0.2873 | −0.1321 |
| H23 | 0.7379 | 0.5591 | 0.1062 |
| H24 | 0.6424 | 0.1271 | 0.0321 |
| H25 | 0.5538 | 0.2622 | −0.0469 |
| H26 | 0.5107 | 0.1656 | 0.0330 |

Intermediates 15 and 16

(S)-5-Bromo-2-(2-hydroxypropan-2-yl)-2,3,4,9-tetrahydro-1H-carbazole-8-carboxamide (I-15), and (R)-5-Bromo-2-(2-hydroxypropan-2-yl)-2,3,4,9-tetrahydro-1H-carbazole-8-carboxamide (I-16)

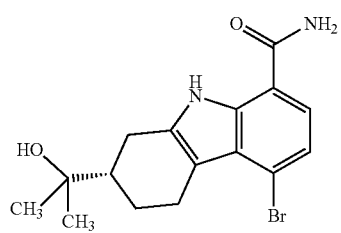

(I-15)

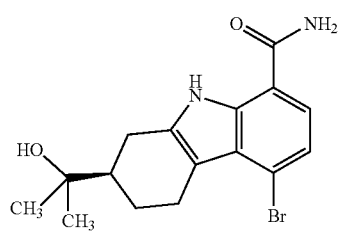

(I-16)

A sample of (RS)-5-bromo-2-(2-hydroxypropan-2-yl)-2,3,4,9-tetrahydro-1H-carbazole-8-carboxamide [synthesized according to the procedure described in U.S. Pat. No. 8,084,620, Example 73-1] (4.03 g) was separated by chiral super-critical fluid chromatography (Column: OD-H (3×25 cm, 5 μm); Mobile Phase: $CO_2$-MeOH (65:35) at 150 mL/min, 100 bar, 40° C.; sample preparation: 66.5 mg/mL in MeOH; injection: 1.2 mL). The first peak eluting from the column provided (S)-5-bromo-2-(2-hydroxypropan-2-yl)-2,3,4,9-tetrahydro-1H-carbazole-8-carboxamide [Intermediate 15] as a light yellow solid (1.79 g). The second peak eluting from the column provided (R)-5-bromo-2-(2-hydroxypropan-2-yl)-2,3,4,9-tetrahydro-1H-carbazole-8-carboxamide [Intermediate 16] as a light yellow solid (1.82 g).

Intermediates 17 and 18

(R)-5-Bromo-6-fluoro-2-(2-hydroxypropan-2-yl)-2,3,4,9-tetrahydro-1H-carbazole-8-carboxamide (I-17), and (S)-5-Bromo-6-fluoro-2-(2-hydroxypropan-2-yl)-2,3,4,9-tetrahydro-1H-carbazole-8-carboxamide (I-18)

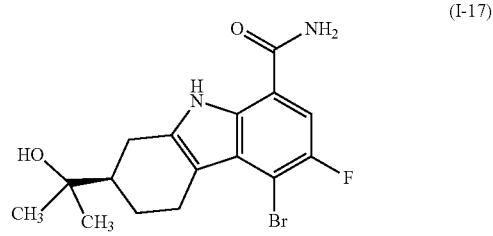

(I-17)

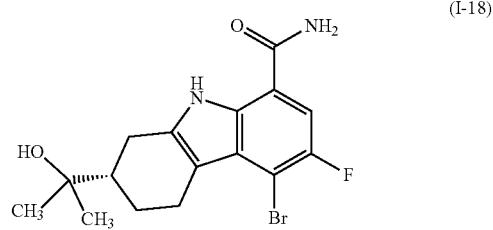 [SMILES: CC(C)(O)c1ccc2c(c1)[nH]c1c(C(N)=O)cc(F)c(Br)c12]

(I-18)

A sample of (RS)-5-bromo-6-fluoro-2-(2-hydroxypropan-2-yl)-2,3,4,9-tetrahydro-1H-carbazole-8-carboxamide [Intermediate 12] was separated by chiral super-critical fluid chromatography (Column: CHIRALPAK® OD-H (3×25 cm, 5 μm); Mobile Phase: $CO_2$-MeOH (70:30) at 150 mL/min, 40° C.). The first peak eluting from the column provided (R)-5-bromo-6-fluoro-2-(2-hydroxypropan-2-yl)-2,3,4,9-tetrahydro-1H-carbazole-8-carboxamide [Intermediate 17]. The second peak eluting from the column provided (S)-5-bromo-6-fluoro-2-(2-hydroxypropan-2-yl)-2,3,4,9-tetrahydro-1H-carbazole-8-carboxamide [Intermediate 18]. The mass spectra and $^1$H NMR spectra of the two enantiomers were the same. Mass spectrum m/z 369, 371 (M+H)$^+$. $^1$H NMR (500 MHz, DMSO-$d_6$) δ 10.96 (s, 1H), 8.07 (br. s., 1H), 7.55 (d, J=10.3 Hz, 1H), 7.50 (br. s., 1H), 4.24 (s, 1H), 3.26 (dd, J=15.8, 4.4 Hz, 1H), 2.93 (dd, J=17.1, 4.6 Hz, 1H), 2.72 (t, J=11.7 Hz, 1H), 2.48-2.40 (m, 1H), 2.12 (d, J=9.2 Hz, 1H), 1.70-1.62 (m, 1H), and 1.32 (qd, J=12.4, 5.3 Hz, 1H).

Alternative Super-Critical Fluid Chromatography Separation

A sample of (RS)-5-bromo-6-fluoro-2-(2-hydroxypropan-2-yl)-2,3,4,9-tetrahydro-1H-carbazole-8-carboxamide [Intermediate 12] was separated by chiral super-critical fluid chromatography (Column: CHIRALPAK® AD-H (3×25 cm, 5 μm); Mobile Phase: $CO_2$-MeOH (55:45) at 150 mL/min, 40° C.). The first peak eluting from the column provided (S)-5-bromo-6-fluoro-2-(2-hydroxypropan-2-yl)-2,3,4,9-tetrahydro-1H-carbazole-8-carboxamide [Intermediate 18]. The second peak eluting from the column provided (R)-5-bromo-6-fluoro-2-(2-hydroxypropan-2-yl)-2,3,4,9-tetrahydro-1H-carbazole-8-carboxamide [Intermediate 17].

Intermediate 19

4-Bromo-3-fluoro-7-(2-hydroxypropan-2-yl)-9H-carbazole-1-carboxamide

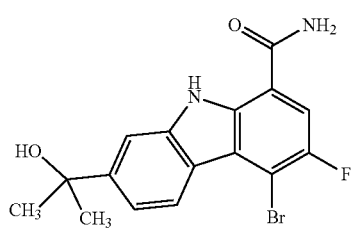
(I-19)

Intermediate 19A: 4-Bromo-7-ethoxycarbonyl-3-fluoro-9H-carbazole-1-carboxylic acid

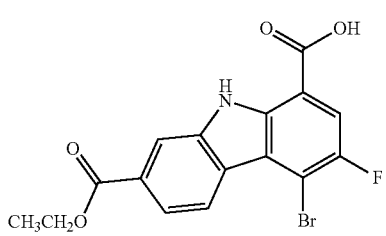
(I-19A)

A solution of (RS)-5-bromo-2-(ethoxycarbonyl)-6-fluoro-2,3,4,9-tetrahydro-1H-carbazole-8-carboxylic acid [Intermediate 12A] (2.87 g, 7.47 mmol) and DDQ (3.73 g, 16.4 mmol) in THF (45 mL) was heated at 60° C. for 90 min. The cooled mixture was diluted with EtOAc (about 50 mL) and stirred for 60 min. The resulting precipitate was collected by filtration, washed with EtOAc and dried. The filtrate was concentrated and the residue was triturated in MeOH with sonication, filtered, and the precipitate was washed with MeOH and dried. The two precipitates were combined to give 4-bromo-7-ethoxycarbonyl-3-fluoro-9H-carbazole-1-carboxylic acid as a pale yellow solid (2.39 g, 84% yield). Mass spectrum m/z 380, 382 (M+H)+.

Intermediate 19B: Ethyl 5-bromo-8-carbamoyl-6-fluoro-9H-carbazole-2-carboxylate

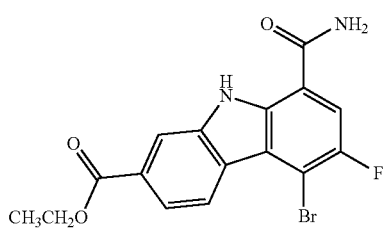
(I-19B)

A mixture of 4-bromo-7-(ethoxycarbonyl)-3-fluoro-9H-carbazole-1-carboxylic acid (2.39 g, 6.29 mmol), EDC (1.81 g, 9.43 mmol) and HOBT (1.44 g, 9.43 mmol) in THF (30 mL) and DCM (5 mL) was stirred at room temperature for 20 min. Aqueous NH$_4$OH (28%, 0.367 mL, 9.43 mmol) was added, and the mixture was stirred at room temperature for 4 h. The mixture was diluted with EtOAc, washed twice with saturated aqueous NaHCO$_3$, then with brine. The aqueous layers were extracted with EtOAc, and the combined organic layers were dried and concentrated. The residue was triturated in MeOH with sonication to provide ethyl 5-bromo-8-carbamoyl-6-fluoro-9H-carbazole-2-carboxylate as a pale yellow solid (2.26 g, 95% yield). Mass spectrum m/z 379, 381 (M+H)+. $^1$H NMR (500 MHz, DMSO-d$_6$) δ 12.02 (s, 1H), 8.70 (d, J=8.3 Hz, 1H), 8.51 (d, J=1.1 Hz, 1H), 8.29 (br. s., 1H), 8.10 (d, J=10.3 Hz, 1H), 7.87 (dd, J=8.5, 1.5 Hz, 1H), 7.74 (br. s., 1H), 4.37 (q, J=6.9 Hz, 2H), and 1.37 (t, J=7.1 Hz, 3H). $^1$H NMR (500 MHz, MeOH-d$_4$) δ 8.77 (d, J=8.2 Hz, 1H), 8.36 (d, J=0.9 Hz, 1H), 7.83 (d, J=8.2 Hz, 1H), 7.46 (d, J=8.2 Hz, 1H), 4.12 (q, J=7.0 Hz, 2H), 1.58-1.36 (m, 4H), and 1.26 (t, J=7.2 Hz, 3H).

Alternative Synthesis of Intermediate 19B

A mixture of ethyl 5-bromo-8-carbamoyl-9H-carbazole-2-carboxylate [synthesized according to the procedure described in U.S. Pat. No. 8,084,620, Intermediate 48-1] (0.100 g, 0.277 mmol) and 1-(chloromethyl)-4-fluoro-1,4-diazoniabicyclo[2.2.2] octane bis(tetrafluoroborate) [SELECTFLUOR®] (0.100 g, 0.554 mmol) in THF (2 mL) and acetonitrile (2 mL) was heated at 60° C. overnight. The cooled mixture was filtered and the filtrate was concentrated. The residue was purified using preparative reverse-phase HPLC to give ethyl 5-bromo-8-carbamoyl-3-fluoro-9H-carbazole-2-carboxylate as a tan solid (0.035 g).

Intermediate 19

A solution of ethyl 5-bromo-8-carbamoyl-6-fluoro-9H-carbazole-2-carboxylate (0.500 g, 1.32 mmol) in THF (9.0 mL) at −78° C. was treated dropwise over 10 min with 1.6 M methyllithium in ether (2.47 mL, 3.96 mmol). The mixture was stirred at −78° C. for 30 min, then was treated with additional methyllithium solution (1.65 mL, 2.64 mmol) and the mixture was stirred at −78° C. for 45 min more. The mixture was treated with saturated aqueous NH$_4$Cl and allowed to warm to room temperature. The mixture was diluted with EtOAc and washed sequentially with water and brine. The aqueous layers were extracted with EtOAc and the combined organic layers were dried and concentrated to provide a pale yellow solid which was purified by preparative reverse-phase HPLC. The appropriate fractions were neutralized with saturated aqueous NaHCO$_3$ and concentrated. The residue was partitioned between EtOAc and water, and the organic layer was washed with brine. The aqueous layers were extracted with EtOAc, and the combined organic layers were dried and concentrated to provide 4-bromo-3-fluoro-7-(2-hydroxypropan-2-yl)-9H-carbazole-1-carboxamide as a pale yellow solid (0.240 g, 50% yield). Mass spectrum m/z 347, 349 (M+H−H$_2$O)+. $^1$H NMR (500 MHz, DMSO-d$_6$) δ 11.58 (s, 1H), 8.50 (d, J=8.6 Hz, 1H), 8.22 (br. s., 1H), 7.96 (d, J=10.3 Hz, 1H), 7.94 (d, J=1.1 Hz, 1H), 7.65 (br. s., 1H), 7.39 (dd, J=8.5, 1.5 Hz, 1H), 5.09 (s, 1H), and 1.51 (s, 6H).

Alternative Synthesis of Intermediate 19

A solution of ethyl 5-bromo-8-carbamoyl-6-fluoro-9H-carbazole-2-carboxylate (10.0 g, 26.4 mmol) in THF (300 mL) was cooled in an ice-water bath and treated dropwise with 3.0 M methylmagnesium chloride in THF (70.3 mL, 211 mmol). The solution was stirred at 0° C. for 18 h, then was poured into 1000 mL of well-stirred saturated aqueous NH$_4$Cl cooled in an ice-water bath. The resulting mixture was diluted with water and extracted twice with EtOAc. The combined organic phases were washed twice with water, then with brine, and dried and concentrated. The residue was purified by column chromatography on silica gel (330 g), eluting with EtOAc-DCM (gradient from 20-100%), to give 4-bromo-3-fluoro-7-(2-hydroxypropan-2-yl)-9H-carbazole-1-carboxamide (6.36 g, 65% yield).

Intermediate 20

(RS)-5-Bromo-6-chloro-2-(hydroxymethyl)-2,3,4,9-tetrahydro-1H-carbazole-8-carboxamide

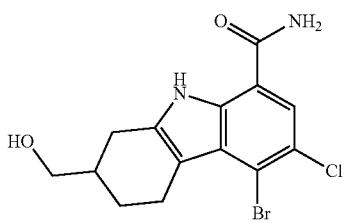

(I-20)

A solution of impure (RS)-ethyl 5-bromo-8-carbamoyl-6-chloro-2,3,4,9-tetrahydro-1H-carbazole-2-carboxylate [Intermediate 11C] (0.600 g, 1.50 mmol) in THF (18.8 mL) was cooled in a NaCl/ice bath and treated with 1 M lithium aluminum hydride in THF (4.05 mL, 4.05 mmol). The resulting thick suspension was stirred at room temperature for 1 h, then was treated with saturated aqueous NH$_4$Cl. The mixture was extracted with EtOAc, and the organic phase was washed with brine, dried and concentrated. The residue was suspended in EtOAc and the precipitate was collected by filtration and dried, and subjected to column chromatography on silica gel (40 g), eluting with EtOAc-hexanes (gradient from 80-100%), to provide (RS)-5-bromo-6-chloro-2-(hydroxymethyl)-2,3,4,9-tetrahydro-1H-carbazole-8-carboxamide as a solid (378 mg, 66% yield). Mass spectrum m/z 357, 359 (M+H)$^+$. $^1$H NMR (400 MHz, DMSO-d$_6$) δ 11.11 (s, 1H), 8.13 (br. s., 1H), 7.75 (s, 1H), 7.50 (br. s., 1H), 4.58 (t, J=5.2 Hz, 1H), 3.42 (t, J=5.9 Hz, 2H), 3.19 (d, J=15.4 Hz, 1H), 2.93-2.77 (m, 2H), 2.39 (dd, J=16.9, 9.9 Hz, 1H), 2.02-1.93 (m, 1H), 1.86 (br. s., 1H), 1.47-1.37 (m, 1H).

Intermediate 21

(RS)-5-Bromo-6-chloro-2-(hydroxymethyl)-2-methyl-2,3,4,9-tetrahydro-1H-carbazole-8-carboxamide

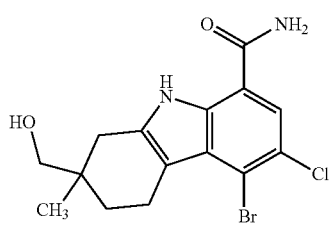

(I-21)

Intermediate 21A: (RS)-5-Bromo-6-chloro-2-(ethoxycarbonyl)-2-methyl-2,3,4,9-tetrahydro-1H-carbazole-8-carboxylic acid

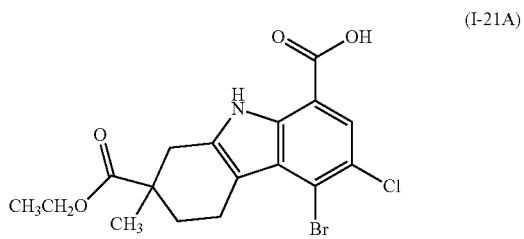

(I-21A)

A suspension of 4-bromo-5-chloro-2-hydrazinylbenzoic acid hydrochloride [Intermediate 11A] (3.28 g, 10.86 mmol) and ethyl (RS)-1-methyl-3-oxocyclohexanecarboxylate [which can be prepared using the procedures of PCT Publication No. WO 2009/153720, Preparation 43; or of PCT Publication No. WO 2013/106535, Example 254] (2.00 g, 10.86 mmol) in acetic acid (24 mL) was heated at 115° C. The resulting thick suspension was diluted with additional acetic acid (12 mL), heated at for 6 h more, cooled to room temperature and concentrated. The residue was triturated with ether, and the precipitate was collected by filtration and dried under vacuum to provide (RS)-5-bromo-6-chloro-2-(ethoxycarbonyl)-2-methyl-2,3,4,9-tetrahydro-1H-carbazole-8-carboxylic acid as a yellow solid (3.01 g, 67% yield). Mass spectrum m/z 414, 416, 418 (M+H)$^+$. $^1$H NMR (400 MHz, DMSO-d$_6$) δ 11.22 (s, 1H), 7.69 (s, 1H), 4.07 (qd, J=7.1, 3.5 Hz, 2H), 3.22-2.92 (m, 3H), 2.68 (s, 1H), 2.18-2.07 (m, 1H), 1.87-1.76 (m, 1H), 1.28 (s, 3H), 1.15 (t, J=7.0 Hz, 3H).

Intermediate 21B: Ethyl (RS)-5-bromo-8-carbamoyl-6-chloro-2-methyl-2,3,4,9-tetrahydro-1H-carbazole-2-carboxylate

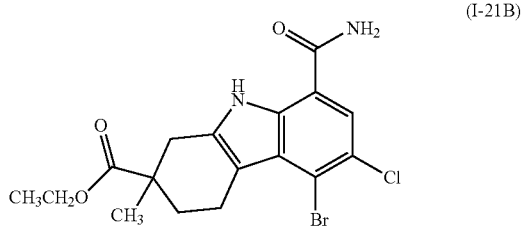

(I-21B)

A solution of (RS)-5-bromo-6-chloro-2-(ethoxycarbonyl)-2-methyl-2,3,4,9-tetrahydro-1H-carbazole-8-carboxylic acid (3.01 g, 7.26 mmol) in DMF (10 mL) was treated with EDC (1.531 g, 7.98 mmol) and HOBT (1.223 g, 7.98 mmol), and stirred at room temperature for 1.5 h. The mixture was treated with 0.5 M NH$_3$ in 1,4-dioxane (29.0 mL, 14.5 mmol) and stirred for 35 min. The mixture was diluted with water, and the resulting precipitate was collected by filtration, washed with water and dried. The solid was triturated in MeOH, collected by filtration and dried to provide ethyl (RS)-5-bromo-8-carbamoyl-6-chloro-2-methyl-2,3,4,9-tetrahydro-1H-carbazole-2-carboxylate as a yellow solid (1.91 g, 64% yield). Mass spectrum m/z 413, 415, 417 (M+H)$^+$. $^1$H NMR (400 MHz, DMSO-d$_6$) δ 11.21

(s, 1H), 8.14 (br. s., 1H), 7.77 (s, 1H), 7.52 (br. s., 1H), 4.14-3.99 (m, 2H), 3.27 (d, J=17.4 Hz, 1H), 3.13-2.92 (m, 2H), 2.65 (d, J=17.2 Hz, 1H), 2.20-2.05 (m, 1H), 1.79 (dt, J=13.6, 6.7 Hz, 1H), 1.27 (s, 3H), 1.14 (t, J=7.0 Hz, 3H).

Intermediate 21

A suspension of ethyl (RS)-5-bromo-8-carbamoyl-6-chloro-2-methyl-2,3,4,9-tetrahydro-1H-carbazole-2-carboxylate (587 mg, 1.42 mmol) in THF (5 mL) was stirred on an ice-water bath and treated portionwise with lithium aluminum hydride (188 mg, 4.97 mmol). The mixture was stirred at 0° C. for 1 h. The mixture was treated with saturated aqueous $NH_4Cl$ and extracted 3 times with DCM. The combined organic phases were washed with water, dried and concentrated. The residue was subjected to column chromatography on silica gel (40 g), eluting with EtOAc-hexanes (gradient from 20-100%), to provide (RS)-5-bromo-6-chloro-2-(hydroxymethyl)-2-methyl-2,3,4,9-tetrahydro-1H-carbazole-8-carboxamide as a yellow solid (380 mg, 61% yield). Mass spectrum m/z 371, 373, 375 $(M+H)^+$. $^1H$ NMR (400 MHz, DMSO-$d_6$) δ 11.09 (s, 1H), 8.13 (br. s., 1H), 7.75 (s, 1H), 7.51 (br. s., 1H), 4.67-4.60 (m, 1H), 3.30-3.20 (m, 2H), 3.13-3.00 (m, 1H), 2.97-2.85 (m, 1H), 2.66 (d, J=17.4 Hz, 1H), 2.44 (d, J=17.4 Hz, 1H), 1.72-1.61 (m, 1H), 1.58-1.47 (m, 1H), 0.97-0.88 (m, 3H).

Intermediates 22 and 23

(RS)-5-Bromo-6-chloro-$N^2$,$N^2$-dimethyl-2,3,4,9-tetrahydro-1H-carbazole-2,8-dicarboxamide (I-22), and (RS)-5-Bromo-6-chloro-2,3,4,9-tetrahydro-1H-carbazole-2,8-dicarboxamide (I-23)

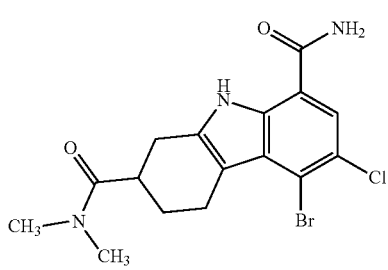

(I-22)

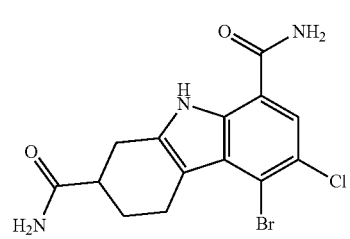

(I-23)

Intermediate 22A: (RS)-5-Bromo-8-carbamoyl-6-chloro-2,3,4,9-tetrahydro-1H-carbazole-2-carboxylic acid

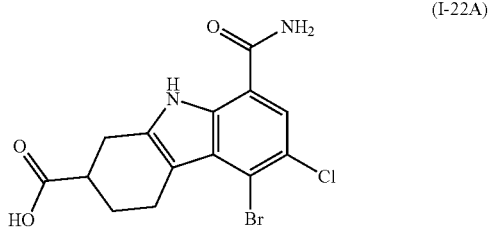 [SMILES: NC(=O)c1cc(Cl)c(Br)c2c3c([nH]c12)CC(C(=O)O)CC3]

(I-22A)

A suspension of impure ethyl (RS)-5-bromo-8-carbamoyl-6-chloro-2,3,4,9-tetrahydro-1H-carbazole-2-carboxylate [contaminated with (RS)-5-bromo-6-chloro-2,3,4,9-tetrahydro-1H-carbazole-2,8-dicarboxamide, Intermediate 11C] (1.00 g, 2.50 mmol) and lithium hydroxide monohydrate (0.250 g, 6.26 mmol) in a mixture of THF-EtOH-water (3:1:1, 29.4 mL) was stirred at room temperature. After 15 h, the mixture was concentrated. The residue was suspended in water and acidified (pH 1-2) with 1 M aqueous HCl. The precipitate was collected by filtration, washed with water, and air-dried to provide (RS)-5-bromo-8-carbamoyl-6-chloro-2,3,4,9-tetrahydro-1H-carbazole-2-carboxylic acid as a solid (1.19 g, 78% yield). Mass spectrum m/z 371, 373, 375 $(M+H)^+$. $^1H$ NMR (400 MHz, DMSO-$d_6$) δ 12.34 (br. s., 1H), 11.27-11.13 (m, 1H), 8.14 (br. s., 1H), 7.77 (d, J=1.8 Hz, 1H), 7.52 (br. s., 1H), 3.23-3.11 (m, 1H), 3.06-2.65 (m, 4H), 2.20-2.01 (m, 1H), 1.87-1.63 (m, 1H). This material was contaminated (about 30%) with (RS)-5-bromo-6-chloro-2,3,4,9-tetrahydro-1H-carbazole-2,8-dicarboxamide, which was present in the starting material. Mass spectrum m/z 370, 372, 374 $(M+H)^+$. The impure material was used in the subsequent reaction.

Intermediates 22 and 23

A mixture of impure (RS)-5-bromo-8-carbamoyl-6-chloro-2,3,4,9-tetrahydro-1H-carbazole-2-carboxylic acid [contaminated with (RS)-5-bromo-6-chloro-2,3,4,9-tetrahydro-1H-carbazole-2,8-dicarboxamide] (1.19 g, 3.20 mmol), EDC (0.921 g, 4.80 mmol), HOBT (0.736 g, 4.80 mmol), and dimethylamine (4.80 mL, 9.61 mmol) in THF (47.4 mL) and DCM (23.7 mL) was stirred at room temperature. After 17 h, the mixture was partitioned between EtOAc and saturated aqueous $NaHCO_3$. The organic phase was washed with saturated brine, dried and concentrated. The residue was subjected to column chromatography on silica gel (80 g), eluting with MeOH-EtOAc (4:96), to provide (RS)-5-bromo-6-chloro-$N^2$,$N^2$-dimethyl-2,3,4,9-tetrahydro-1H-carbazole-2,8-dicarboxamide [Intermediate 22] as a solid (0.585 g, 44% yield). Mass spectrum m/z 398, 400, 402 $(M+H)^+$. $^1H$ NMR (400 MHz, DMSO-$d_6$) δ 11.18 (s, 1H), 8.13 (br. s., 1H), 7.76 (s, 1H), 7.51 (br. s., 1H), 3.26-3.18 (m, 1H), 3.10-2.82 (m, 10H), 2.06-1.96 (m, 1H), 1.70-1.56 (m, 1H). Also isolated was (RS)-5-bromo-6-chloro-2,3,4,9-tetrahydro-1H-carbazole-2,8-dicarboxamide [Intermediate 23], present in the starting material, as a solid (0.300 g). Mass spectrum m/z 370, 372, 374 $(M+H)^+$.

Intermediate 24

(RS)-5-Bromo-N²,N²-dimethyl-2,3,4,9-tetrahydro-1H-carbazole-2,8-dicarboxamide

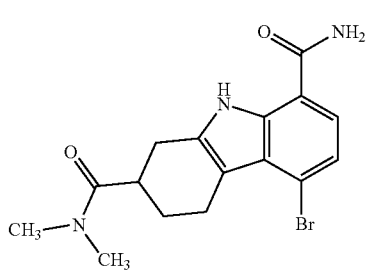

(I-24)

Following the procedure used to prepare Intermediate 22, (RS)-5-bromo-8-carbamoyl-2,3,4,9-tetrahydro-1H-carbazole-2-carboxylic acid [prepared according to U.S. Pat. No. 8,084,620, Intermediate 49-3] was converted into (RS)-5-bromo-N²,N²-dimethyl-2,3,4,9-tetrahydro-1H-carbazole-2,8-dicarboxamide in 99% yield. Mass spectrum m/z 364, 366 (M+H)⁺. $^1$H NMR (400 MHz, DMSO-$d_6$) δ 11.03 (s, 1H), 8.02 (br. s., 1H), 7.45 (d, J=8.1 Hz, 1H), 7.38 (br. s., 1H), 7.15 (d, J=8.1 Hz, 1H), 3.21 (dd, J=16.2, 3.4 Hz, 1H), 3.10-3.00 (m, 4H), 2.98-2.81 (m, 6H), 2.05-1.98 (m, 1H), 1.71-1.57 (m, 1H).

Intermediate 25

(RS)-5-Bromo-2,3,4,9-tetrahydro-1H-carbazole-2,8-dicarboxamide

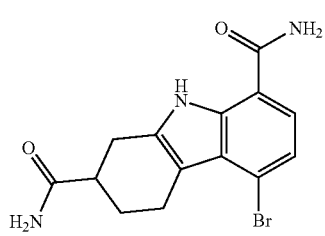

(I-25)

A mixture of (RS)-5-bromo-8-carbamoyl-2,3,4,9-tetrahydro-1H-carbazole-2-carboxylic acid [prepared according to U.S. Pat. No. 8,084,620, Intermediate 49-3] (0.3 g, 0.890 mmol), HOBT (0.164 g, 1.07 mmol), DIEA (0.622 mL, 3.56 mmol), EDC (0.205 g, 1.07 mmol), and NH₄Cl (0.095 g, 1.78 mmol) in DMF (5 mL) was stirred at room temperature overnight. The mixture was concentrated and the residue was diluted with water and EtOAc. The mixture was filtered to collect a precipitate, which was washed with water and EtOAc, and air-dried to provide a solid. The layers of the filtrate were separated, and the organic phase was dried and concentrated. The residue was combined with the solid to provide (RS)-5-bromo-2,3,4,9-tetrahydro-1H-carbazole-2,8-dicarboxamide as an off-white solid, used without further purification. Mass spectrum m/z 336, 338 (M+H)⁺.

Intermediate 26

(RS)-5-Bromo-6-chloro-2-(2-hydroxypropan-2-yl)-2-methyl-2,3,4,9-tetrahydro-1H-carbazole-8-carboxamide

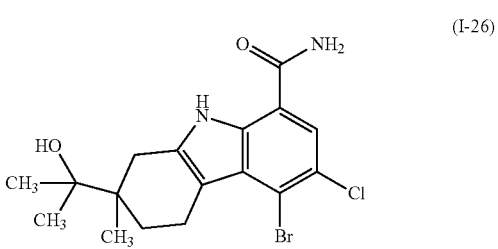 [SMILES: CC(C)(O)C1(C)CCc2c([nH]c3c(C(N)=O)cc(Cl)c(Br)c23)C1]

(I-26)

A suspension of ethyl (RS)-5-bromo-8-carbamoyl-6-chloro-2-methyl-2,3,4,9-tetrahydro-1H-carbazole-2-carboxylate [Intermediate 21B] (635 mg, 1.54 mmol) in THF (10 mL) was stirred on a dry ice-acetone bath and treated dropwise with 1.6 M methyllithium in ether (6.71 mL, 10.7 mmol). The mixture was stirred at −78° C. for 30 min. The mixture was treated with saturated aqueous NH₄Cl, extracted 3 times with DCM, and the combined organic phases were washed with water, dried and concentrated. The residue was subjected to column chromatography on silica gel (40 g), eluting with EtOAc-hexanes (gradient from 20-100%), to provide impure material which was again subjected to column chromatography on silica gel, eluting with methanolic ammonia-DCM (gradient from 3-10%), to provide (RS)-5-bromo-6-chloro-2-(2-hydroxypropan-2-yl)-2-methyl-2,3,4,9-tetrahydro-1H-carbazole-8-carboxamide as a yellow solid (650 mg, greater than quantitative yield, containing residual solvents), used without further purification. Mass spectrum m/z 399, 401, 403 (M+H)⁺. $^1$H NMR (400 MHz, DMSO-$d_6$) δ 11.04 (s, 1H), 8.13 (br. s., 1H), 7.75 (s, 1H), 7.50 (br. s., 1H), 4.20 (s, 1H), 3.28-3.19 (m, 1H), 2.84 (d, J=17.6 Hz, 1H), 2.78-2.65 (m, 1H), 1.76-1.61 (m, 2H), 1.17 (d, J=5.3 Hz, 6H), 0.84 (s, 3H).

Intermediate 27

7-(2-Hydroxypropan-2-yl)-4-(4,4,5,5-tetramethyl-1,3,2-dioxaborolan-2-yl)-9H-carbazole-1-carboxamide

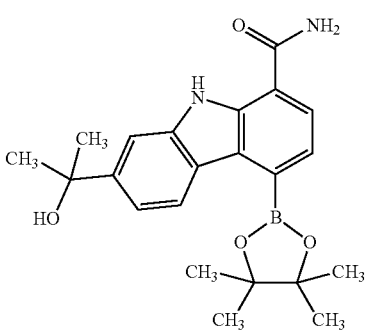

(I-27)

A mixture 4-bromo-7-(2-hydroxypropan-2-yl)-9H-carbazole-1-carboxamide [synthesized according to the procedure described in U.S. Pat. No. 8,084,620, Example 73-2] (3.00 g, 8.64 mmol), 4,4,4',4',5,5,5',5'-octamethyl-2,2'-bi(1,3,2-dioxaborolane) (2.19 g, 8.64 mmol) and potassium acetate (2.12 g, 21.6 mmol) in 1,4-dioxane (30 mL) was bubbled with nitrogen for 5 min. PdCl₂(dppf) DCM adduct (0.353 g, 0.432 mmol) was added and the mixture was bubbled with nitrogen for another 5 min. The reaction vessel was sealed and heated at 90° C. overnight. The cooled mixture was diluted with DCM, washed twice with water, dried and concentrated. The residue was purified by column chromatography on silica gel (40 g+12 g, stacked columns), eluting with EtOAc-hexanes, to provide 7-(2-hydroxypropan-2-yl)-4-(4,4,5,5-tetramethyl-1,3,2-dioxaborolan-2-yl)-9H-carbazole-1-carboxamide as a light yellow solid (2.79 g, 82% yield). Mass spectrum m/z 377 (M+H−H₂O)⁺.

Intermediate 28

(RS)-2-(2-Hydroxypropan-2-yl)-5-(4,4,5,5-tetramethyl-1,3,2-dioxaborolan-2-yl)-2,3,4,9-tetrahydro-1H-carbazole-8-carboxamide

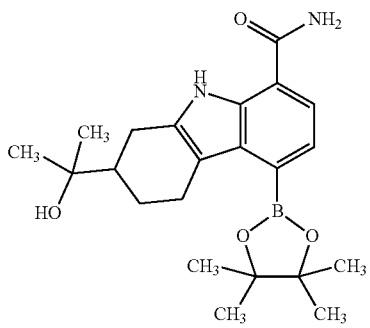

(I-28)

Following the procedure used to prepare Intermediate 27, (RS)-5-bromo-2-(2-hydroxypropan-2-yl)-2,3,4,9-tetrahydro-1H-carbazole-8-carboxamide [synthesized according to the procedure described in U.S. Pat. No. 8,084,620, Example 73-1] was converted into (RS)-2-(2-hydroxypropan-2-yl)-5-(4,4,5,5-tetramethyl-1,3,2-dioxaborolan-2-yl)-2,3,4,9-tetrahydro-1H-carbazole-8-carboxamide in 79% yield. Mass spectrum m/z 399 (M+H)⁺. ¹H NMR (400 MHz, DMSO-d₆) δ 10.65 (s, 1H), 8.00 (br. s., 1H), 7.50 (d, J=7.5 Hz, 1H), 7.33 (br. s., 1H), 7.26 (d, J=7.5 Hz, 1H), 4.20 (s, 1H), 3.09-3.00 (m, 1H), 2.92 (dd, J=16.8, 4.5 Hz, 1H), 2.65-2.55 (m, 1H), 2.47-2.43 (m, 1H), 2.15-2.06 (m, 1H), 1.74-1.64 (m, 1H), 1.37-1.26 (m, 13H), 1.15 (m, 6H).

Intermediate 29

5-(3-(S)-Aminopiperidin-1-yl)-2-(RS)-methyl-2,3,4,9-tetrahydro-1H-carbazole-8-carboxamide (mixture of diastereomers)

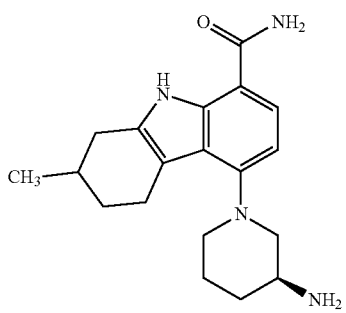

(I-29)

Intermediate 29A: (RS)-5-Bromo-2-methyl-2,3,4,9-tetrahydro-1H-carbazole-8-carbonitrile

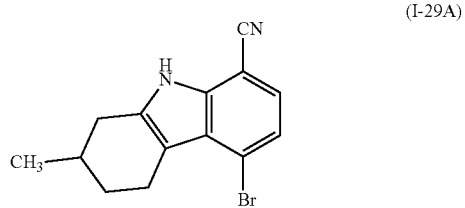 [SMILES: CC1CCc2c([nH]c3c(C#N)ccc(Br)c23)C1]

(I-29A)

A solution of (RS)-5-bromo-2-methyl-2,3,4,9-tetrahydro-1H-carbazole-8-carboxamide [Intermediate 2] (325 mg, 1.06 mmol) in THF (7.5 mL) was treated with phosphorus oxychloride (0.789 mL, 8.46 mmol) and the mixture was stirred at room temperature. After 42 h, the mixture was concentrated and the residue was stirred in EtOAc. A precipitate was removed by filtration, and the filtrate was washed sequentially with water, saturated aqueous NaHCO₃ and saturated brine, dried and concentrated. The residue was partitioned between EtOAc and saturated aqueous NaHCO₃, and the organic phase was dried and concentrated. The residue was subjected to column chromatography on silica gel (40 g), eluting with EtOAc-hexanes (gradient from 5-50%), to provide (RS)-5-bromo-2-methyl-2,3,4,9-tetrahydro-1H-carbazole-8-carbonitrile as an off-white solid (202 mg, 66% yield). Mass spectrum m/z 289, 291 (M+H)⁺ and 599, 601, 603 (2M+Na)⁺. ¹H NMR (400 MHz, DMSO-d₆) δ 11.89 (s, 1H), 7.37 (d, J=8.1 Hz, 1H), 7.26 (d, J=8.1 Hz, 1H), 3.15 (d, J=15.6 Hz, 1H), 2.94-2.76 (m, 2H), 2.33 (dd, J=16.6, 9.8 Hz, 1H), 1.98-1.84 (m, 2H), 1.43 (dtd, J=13.1, 10.9, 5.6 Hz, 1H), 1.09 (d, J=6.6 Hz, 3H).

Intermediate 29B: Benzyl (1-(8-cyano-2-(RS)-methyl-2,3,4,9-tetrahydro-1H-carbazol-5-yl)piperidin-3-(S)-yl)carbamate

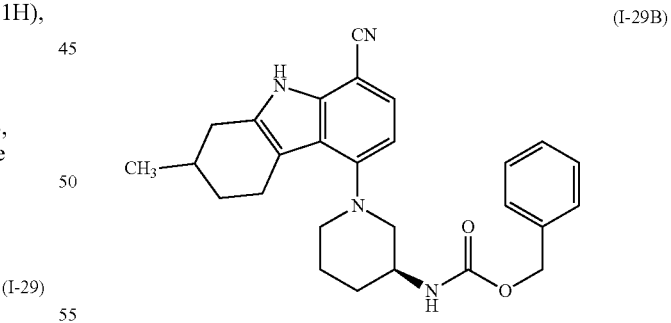

(I-29B)

A mixture of (RS)-5-bromo-2-methyl-2,3,4,9-tetrahydro-1H-carbazole-8-carbonitrile (0.19 g, 0.657 mmol), benzyl (S)-piperidin-3-ylcarbamate (0.162 g, 0.690 mmol), 2,2'-bis (diphenylphosphino)-1,1'-binaphthalene (0.020 g, 0.033 mmol), tris(dibenzylideneacetone)dipalladium (0.030 g, 0.033 mmol) and Cs₂CO₃ (0.300 g, 0.920 mmol) in 1,4-dioxane (7.30 mL) was bubbled with nitrogen, then was heated at 100° C. under nitrogen in a sealed vessel. After 16 h, the mixture was cooled to room temperature, diluted with THF and filtered through CELITE®. The solids were washed with THF, and the combined filtrates were concentrated. The residue was subjected to column chromatography on silica gel (12 g), eluting with EtOAc-hexanes (gradient from 10-20%) to provide benzyl (1-(8-cyano-2-(RS)-methyl-2,3,4,9-tetrahydro-1H-carbazol-5-yl)piperidin-3-(S)-yl)carbamate, a mixture of diastereomers, as a light yellow solid (0.179 g, 62% yield). Mass spectrum m/z 443 (M+H)+.

Intermediate 29

A suspension of benzyl (1-(8-cyano-2-(RS)-methyl-2,3,4,9-tetrahydro-1H-carbazol-5-yl)piperidin-3-(S)-yl)carbamate (0.179 g, 0.337 mmol) in 80% aqueous $H_2SO_4$ (1.12 mL) was heated at 60° C. After 3 h, the resulting solution was cooled to room temperature and poured onto crushed ice. The pH of the mixture was adjusted to 9-10 with aqueous KOH and solid $Na_2CO_3$, and extracted with 3:1 chloroform-isopropanol. The organic phase was dried and concentrated to provide 5-(3-(S)-aminopiperidin-1-yl)-2-(RS)-methyl-2,3,4,9-tetrahydro-1H-carbazole-8-carboxamide, a mixture of two diastereomers, as a light brown solid (0.173 g, 99% yield), which was used without further purification. Mass spectrum m/z 327 (M+H)+.

Intermediate 30

(S)-4-(3-Aminopiperidin-1-yl)-3-fluoro-9H-carbazole-1-carboxamide hydrochloride

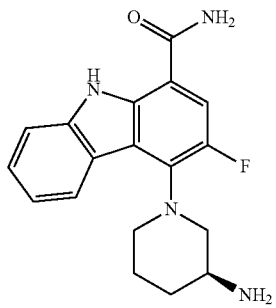

(I-30)

Intermediate 30A: (S)-Benzyl (1-(1-cyano-3-fluoro-9H-carbazol-4-yl)piperidin-3-yl) Carbamate

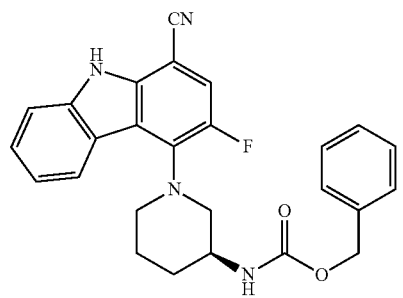

(I-30A)

Following the procedures used to prepare Intermediate 29B, 4-bromo-3-fluoro-9H-carbazole-1-carboxamide [Intermediate 8] was converted into (S)-benzyl (1-(1-cyano-3-fluoro-9H-carbazol-4-yl)piperidin-3-yl)carbamate. Mass spectrum m/z 443 (M+H)+.

Intermediate 30

A mixture of (S)-benzyl (1-(1-cyano-3-fluoro-9H-carbazol-4-yl)piperidin-3-yl) carbamate (100 mg, 0.226 mmol), chlorotrimethylsilane (2.0 mL, 15.7 mmol) and water (1.0 mL, 55.5 mmol) was stirred at room temperature for 3 days. Additional chlorotrimethylsilane (1.0 mL) was added and stirring was continued for another day. The aqueous layer of the mixture was separated and concentrated to provide (S)-4-(3-aminopiperidin-1-yl)-3-fluoro-9H-carbazole-1-carboxamide hydrochloride as a yellow-green solid (78 mg, 95% yield). Mass spectrum m/z 327 (M+H)+.

Intermediate 31

(S)-3-Fluoro-4-(3-(methylamino)piperidin-1-yl)-9H-carbazole-1-carboxamide

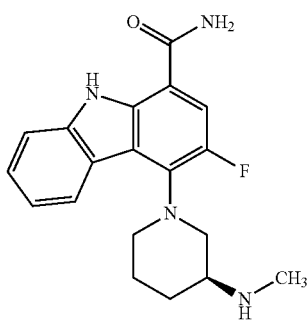

(I-31)

Following the procedures used to prepare Intermediate 30 but substituting (S)-tert-butyl methyl(piperidin-3-yl)carbamate for benzyl (S)-piperidine-3-ylcarbamate, 4-bromo-3-fluoro-9H-carbazole-1-carboxamide [Intermediate 8] was converted into (S)-3-fluoro-4-(3-(methylamino)piperidin-1-yl)-9H-carbazole-1-carboxamide hydrochloride. This material was partitioned between saturated aqueous $NaHCO_3$ and EtOAc, and the organic phase was dried and concentrated to provide (S)-3-fluoro-4-(3-(methylamino) piperidin-1-yl)-9H-carbazole-1-carboxamide as a yellow solid. Mass spectrum m/z 341 (M+H)+.

Intermediate 32

(S)-5-(3-Aminopiperidin-1-yl)-3,3,6-trifluoro-2,3,4,9-tetrahydro-1H-carbazole-8-carboxamide

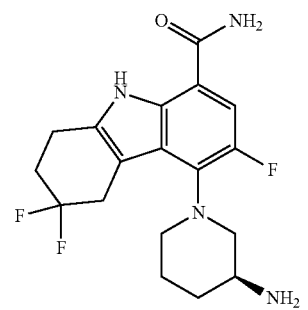

(I-32)

Following the procedures used to prepare Intermediate 29, 5-bromo-3,3,6-trifluoro-2,3,4,9-tetrahydro-1H-carbazole-8-carboxamide [Intermediate 6] was converted into (S)-5-(3-aminopiperidin-1-yl)-3,3,6-trifluoro-2,3,4,9-tetrahydro-1H-carbazole-8-carboxamide. Mass spectrum m/z 367 (M+H)⁺.

Intermediate 33

(S)-5-(Pyrrolidin-3-ylamino)-2,3,4,9-tetrahydro-1H-carbazole-8-carboxamide

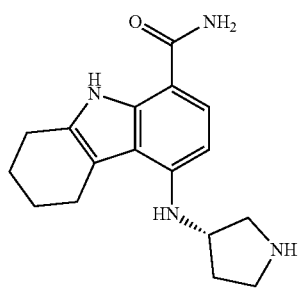

(I-33)

Intermediate 33A: 5-Bromo-2,3,4,9-tetrahydro-1H-carbazole-8-carbonitrile

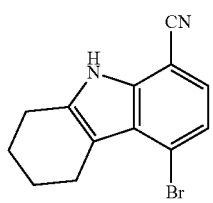

(I-33A)

A mixture of 5-bromo-2,3,4,9-tetrahydro-1H-carbazole-8-carboxamide [Intermediate 1] (355 mg, 1.21 mmol) and THF (9 mL) was treated with phosphorus oxychloride (1.01 mL, 10.9 mmol), and the mixture was heated at 45° C. After 4 h, the mixture was concentrated, and the residue was treated with water. The resulting precipitate was collected by filtration, washed sequentially with water, saturated aqueous NaHCO₃ and water, and dried under vacuum. The residual solid was suspended in toluene and concentrated under vacuum twice, then dried further under vacuum to provide 5-bromo-2,3,4,9-tetrahydro-1H-carbazole-8-carbonitrile as a brown solid (322 mg, 87% yield). Mass spectrum m/z 275, 277 (M+H)⁺. ¹H NMR (400 MHz, DMSO-d₆) δ 11.92 (s, 1H), 7.37 (d, J=8.1 Hz, 1H), 7.26 (d, J=8.1 Hz, 1H), 2.98 (br. s., 2H), 2.73 (br. s., 2H), 1.80 (br. s., 4H).

Intermediate 33B: tert-Butyl (S)-3-((8-cyano-2,3,4,9-tetrahydro-1H-carbazol-5-yl)amino) pyrrolidine-1-carboxylate

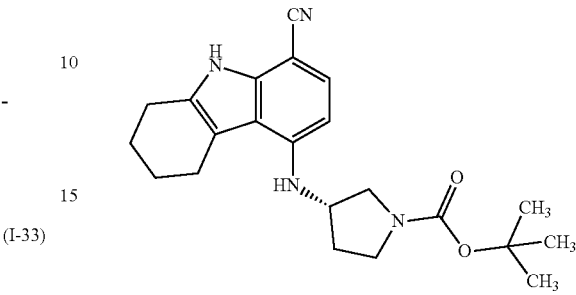

(I-33B)

Following the procedure used to prepare Intermediate 29B but substituting tert-butyl (S)-3-aminopyrrolidine-1-carboxylate for benzyl (S)-piperidin-3-ylcarbamate, 5-bromo-2,3,4,9-tetrahydro-1H-carbazole-8-carbonitrile was converted into tert-butyl (S)-3-((8-cyano-2,3,4,9-tetrahydro-1H-carbazol-5-yl)amino)pyrrolidine-1-carboxylate in 77% yield. Mass spectrum m/z 381 (M+H)⁺, 325 (M+H–C₄H₈)⁺. ¹H NMR (400 MHz, DMSO-d₆) δ 11.19 (s, 1H), 7.25 (d, J=8.1 Hz, 1H), 6.25 (d, J=8.4 Hz, 1H), 5.19 (br. s., 1H), 4.17 (br. s., 1H), 3.72-3.52 (m, 1H), 3.48-3.33 (m, 2H), 3.23 (d, J=10.8 Hz, 1H), 2.91 (br. s., 2H), 2.65 (br. s., 2H), 2.20 (br. s., 1H), 2.03-1.89 (m, 1H), 1.77 (br. s., 4H), 1.40 (2s, 9H).

Intermediate 33C: (S)-5-(Pyrrolidin-3-ylamino)-2,3,4,9-tetrahydro-1H-carbazole-8-carbonitrile TFA Salt

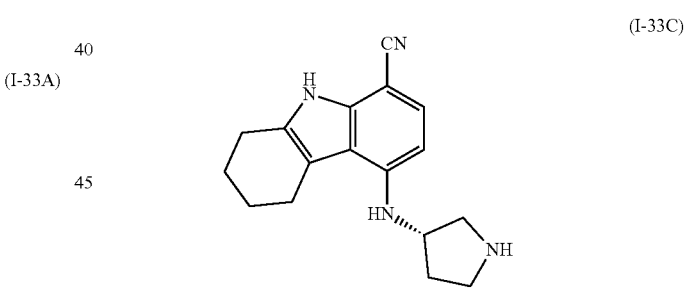

(I-33C)

A solution of tert-butyl (S)-3-((8-cyano-2,3,4,9-tetrahydro-1H-carbazol-5-yl)amino)pyrrolidine-1-carboxylate (317 mg, 0.833 mmol) in DCM (5 mL) was cooled to 0° C. and treated with TFA (4 mL). The mixture was stirred at 0° C. for 1 h, then was concentrated and dried under vacuum to provide (S)-5-(pyrrolidin-3-ylamino)-2,3,4,9-tetrahydro-1H-carbazole-8-carbonitrile as the TFA salt (325 mg), which was used without further purification. Mass spectrum m/z 281 (M+H)⁺. ¹H NMR (400 MHz, MeOH-d₄) δ 7.27 (d, J=8.2 Hz, 1H), 6.27 (d, J=8.3 Hz, 1H), 4.53-4.32 (m, 1H), 3.66-3.36 (m, 4H), 3.02 (br. s., 2H), 2.75 (br. s., 2H), 2.51 (td, J=14.2, 8.1 Hz, 1H), 2.30-2.10 (m, 1H), 1.91 (br. s., 4H).

Intermediate 33

A mixture of (S)-5-(pyrrolidin-3-ylamino)-2,3,4,9-tetrahydro-1H-carbazole-8-carbonitrile TFA salt (325 mg, 0.824 mmol) and 80% aqueous H₂SO₄ (2.5 mL, 37.5 mmol) was heated at 60° C. for 3 h. The cooled mixture was added to aqueous NaOH at 0° C. (final pH about 9), and the mixture was extracted four times with EtOAc. The combined organic layers were dried and concentrated to provide (S)-5-(pyrrolidin-3-ylamino)-2,3,4,9-tetrahydro-1H-carbazole-8-carboxamide as a yellow solid (250 mg, 92% yield). Mass spectrum m/z 299 (M+H)$^+$.

Intermediate 34

5-(Pyrrolidin-3-(S)-ylamino)-2-(RS)-(trifluoromethyl)-2,3,4,9-tetrahydro-1H-carbazole-8-carboxamide (mixture of diastereomers)

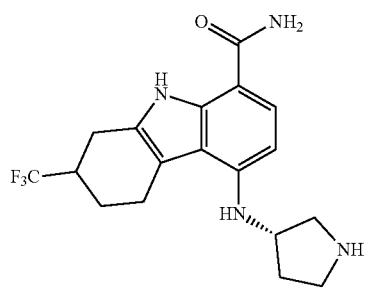

(I-34)

Intermediate 34A: tert-Butyl 3-(S)-((8-cyano-2-(RS)-(trifluoromethyl)-2,3,4,9-tetrahydro-1H-carbazol-5-yl)amino)pyrrolidine-1-carboxylate (Mixture of Diastereomers)

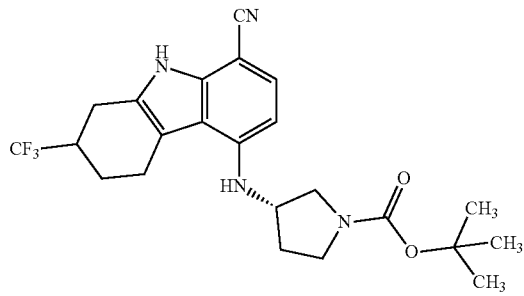

(I-34A)

Following the procedures used to prepare Intermediate 33A and 33B, (RS)-5-bromo-2-(trifluoromethyl)-2,3,4,9-tetrahydro-1H-carbazole-8-carboxamide [Intermediate 4] was converted into tert-butyl 3-(S)-((8-cyano-2-(RS)-(trifluoromethyl)-2,3,4,9-tetrahydro-1H-carbazol-5-yl)amino)pyrrolidine-1-carboxylate, a mixture of diastereomers. Mass spectrum m/z 449 (M+H)$^+$, 393 (M+H–C₄H₈)$^+$.

Intermediate 34

Following the procedures used to convert Intermediate 33B into Intermediate 33, tert-butyl 3-(S)-((8-cyano-2-(RS)-(trifluoromethyl)-2,3,4,9-tetrahydro-1H-carbazol-5-yl)amino)pyrrolidine-1-carboxylate was converted into 5-(pyrrolidin-3-(S)-ylamino)-2-(RS)-(trifluoromethyl)-2,3,4,9-tetrahydro-1H-carbazole-8-carboxamide as a mixture of diastereomers. Mass spectrum m/z 367 (M+H)$^+$.

Intermediate 44

N-(5-Bromo-2-methoxyphenyl)acrylamide

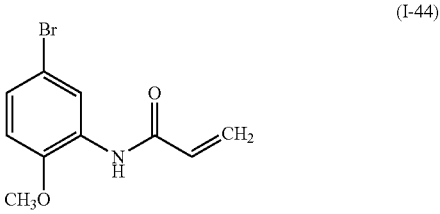

(I-44)

A solution of 5-bromo-2-methoxyaniline (500 mg, 2.48 mmol) in DCM (12 mL) was treated sequentially with DIEA (0.562 mL, 3.22 mmol) and acryloyl chloride (0.211 mL, 2.60 mmol), and the resulting solution was stirred at room temperature. After 16.25 h, the solution was concentrated under vacuum to provide a light brown syrup. The material was subjected to column chromatography on silica gel (40 g), eluting with EtOAc-hexanes (gradient from 20-100%), to provide N-(5-bromo-2-methoxyphenyl) acrylamide as a white solid (570 mg, 90% yield). Mass spectrum m/z 256, 258 (M+H)$^+$. $^1$H NMR (400 MHz, CDCl₃) δ 8.70 (d, J=2.0 Hz, 1H), 7.86 (br. s., 1H), 7.18 (dd, J=8.8, 2.4 Hz, 1H), 6.77 (d, J=8.6 Hz, 1H), 6.52-6.37 (m, 1H), 6.36-6.21 (m, 1H), 5.80 (dd, J=10.1, 1.3 Hz, 1H), 3.91 (s, 3H).

Intermediate 45

N-(3-Bromo-2-methylphenyl)acrylamide

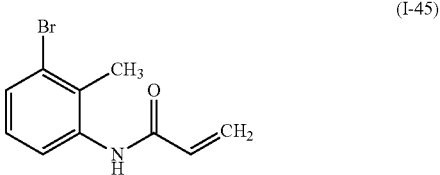

(I-45)

A solution of 3-bromo-2-methylaniline (500 mg, 2.69 mmol) and DIEA (0.563 mL, 3.22 mmol) in DCM (13.4 mL) was treated with acryloyl chloride (0.218 mL, 2.69 mmol) and the resulting mixture was stirred at room temperature. After 2 h, the mixture was diluted with EtOAc and washed sequentially with 1 M aqueous HCl, saturated aqueous NaHCO₃ and saturated brine. The organic phase was dried and concentrated to provide N-(3-Bromo-2-methylphenyl) acrylamide as a solid (580 mg, 90% yield, 85% purity), used without further purification. Mass spectrum m/z 240, 242 (M+H)$^+$. $^1$H NMR (400 MHz, DMSO-d₆) δ 9.77 (s, 1H), 7.48 (d, J=7.9 Hz, 1H), 7.42 (d, J=7.9 Hz, 1H), 7.15 (t, J=8.0 Hz, 1H), 6.51 (dd, J=17.1, 10.2 Hz, 1H), 6.26 (dd, J=17.2, 2.0 Hz, 1H), 5.82-5.74 (m, 1H), 2.27 (s, 3H).

Intermediate 46

N-(5-Bromo-2-(trifluoromethoxy)phenyl)acrylamide

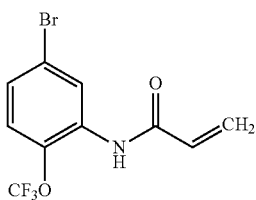

(I-46)

Following the procedure used to prepare Intermediate 44, 5-bromo-2-trifluoromethoxyaniline was converted into N-(5-bromo-2-(trifluoromethoxy)phenyl) acrylamide as a white solid in 75% yield. Mass spectrum m/z 310, 312 (M+H)$^+$. $^1$H NMR (400 MHz, CDCl$_3$) δ 8.79 (d, J=2.4 Hz, 1H), 7.50 (br. s., 1H), 7.33-7.24 (m, 1H), 7.21-7.10 (m, 1H), 6.54-6.43 (m, 1H), 6.37-6.22 (m, 1H), 5.89 (dd, J=10.1, 1.1 Hz, 1H).

Intermediate 47

N-(5-Bromo-2-fluorophenyl)acrylamide

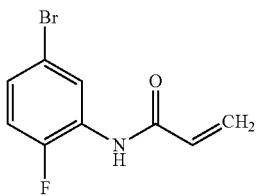

(I-47)

Following the procedure used to prepare Intermediate 44, 5-bromo-2-fluoroaniline was converted into N-(5-bromo-2-fluorophenyl)acrylamide as a tan solid in 93% yield. Mass spectrum m/z 244, 246 (M+H)$^+$. $^1$H NMR (400 MHz, CDCl$_3$) δ 8.69 (dd, J=7.0, 2.2 Hz, 1H), 7.43 (br. s., 1H), 7.21 (ddd, J=8.6, 4.6, 2.4 Hz, 1H), 7.01 (dd, J=10.8, 8.8 Hz, 1H), 6.56-6.43 (m, 1H), 6.36-6.21 (m, 1H), 5.87 (dd, J=10.3, 1.1 Hz, 1H).

Intermediate 48

N-(3-Bromophenyl)ethenesulfonamide

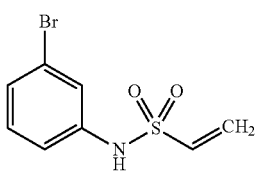

(I-48)

A solution of 3-bromoaniline (1.00 mL, 9.18 mmol) in DCM (77 mL) was stirred on an ice-water bath and treated with DIEA (2.41 mL, 13.8 mmol), then was treated dropwise with 2-chloroethanesulfonyl chloride (1.15 mL, 11.0 mmol). The mixture was stirred at room temperature for 2 h, then was treated with more 2-chloroethanesulfonyl chloride (0.48 mL) and stirred at room temperature for 18 h more. The mixture was washed sequentially with 1 M aqueous HCl and saturated brine, dried and concentrated. The residue was subjected to column chromatography on silica gel (40 g), eluting with EtOAc-hexanes (gradient from 10-30%). The crude product was again subjected to column chromatography on silica gel (24 g), eluting with DCM, to provide N-(3-bromophenyl)ethenesulfonamide as a light yellow syrup (400 mg, 17% yield). $^1$H NMR (400 MHz, CDCl$_3$) δ 7.35-7.29 (m, 2H), 7.20 (t, J=7.9 Hz, 1H), 7.13-7.09 (m, 1H), 6.57 (dd, J=16.4, 9.8 Hz, 1H), 6.37-6.31 (m, 2H), 6.02 (d, J=9.9 Hz, 1H).

Intermediate 49

N-(3-(4,4,5,5-Tetramethyl-1,3,2-dioxaborolan-2-yl)phenyl)acrylamide

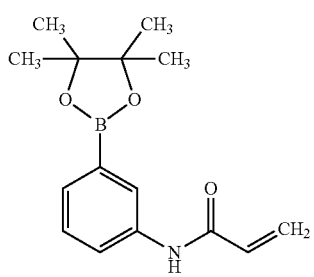

(I-49)

Intermediate 49A: 3-(4,4,5,5-Tetramethyl-1,3,2-dioxaborolan-2-yl)aniline

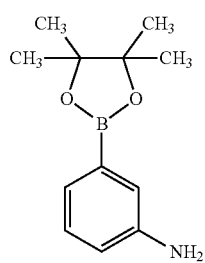

(I-49A)

A mixture of 3-bromoaniline (1.00 g, 5.81 mmol), 4,4,4',4',5,5,5',5'-octamethyl-2,2'-bi(1,3,2-dioxaborolane) (1.55 g, 6.10 mmol) and potassium acetate (1.14 g, 11.6 mmol) in 1,4-dioxane (14.5 mL) was bubbled with nitrogen for 10 min. The mixture was treated with PdCl$_2$(dppf) DCM adduct (0.114 g, 0.140 mmol) and bubbled with nitrogen for 5 min more. The mixture was heated to reflux for 2.75 h, then cooled to room temperature and filtered through CELITE®. The solids were washed with EtOAc and THF. The combined filtrates were concentrated and the residue was subjected to column chromatography on silica gel (40 g), eluting with EtOAc-hexanes (gradient from 10-25%), to provide 3-(4,4,5,5-tetramethyl-1,3,2-dioxaborolan-2-yl)aniline as an off-white solid (1.27 g, quantitative yield). Mass spectrum m/z 220 (M+H)⁺. ¹H NMR (400 MHz, CDCl₃) δ 7.24-7.13 (m, 3H), 6.82-6.77 (m, 1H), 3.64 (br. s., 2H), 1.35 (s, 12H).

Intermediate 49

A solution of 3-(4,4,5,5-tetramethyl-1,3,2-dioxaborolan-2-yl)aniline (0.300 g, 1.37 mmol) and DIEA (0.311 mL, 1.78 mmol) in DCM (9.1 mL) was cooled in an ice-bath and treated with acryloyl chloride (0.117 mL, 1.44 mmol). The mixture was stirred at room temperature for 40 min, then was concentrated and the residue was subjected to column chromatography on silica gel (24 g), eluting with EtOAc-hexanes (gradient from 15-40%), to provide N-(3-(4,4,5,5-tetramethyl-1,3,2-dioxaborolan-2-yl)phenyl) acrylamide as a white solid (0.292 g, 78% yield). Mass spectrum m/z 270 (M+H)⁺.

Intermediate 50

N-(2-Methyl-3-(4,4,5,5-tetramethyl-1,3,2-dioxaborolan-2-yl)phenyl)acrylamide

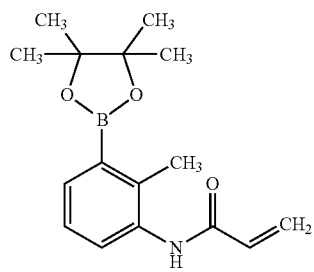

(I-50)

Following the procedure used to prepare Intermediate 49, 2-methyl-3-(4,4,5,5-tetramethyl-1,3,2-dioxaborolan-2-yl)aniline [prepared according to U.S. Pat. No. 8,084,620, Intermediate 50-1] was converted into N-(2-methyl-3-(4,4,5,5-tetramethyl-1,3,2-dioxaborolan-2-yl)phenyl)acrylamide in 80% yield. Mass spectrum m/z 288 (M+H)⁺. ¹H NMR (400 MHz, CDCl₃) δ 8.01 (br. s., 1H), 7.64 (d, J=5.9 Hz, 1H), 7.23 (t, J=7.7 Hz, 1H), 7.07 (br. s., 1H), 6.48-6.40 (m, 1H), 6.32 (br. s., 1H), 5.78 (d, J=9.5 Hz, 1H), 2.49 (s, 3H), 1.36 (s, 12H).

Intermediate 51

(E)-N-(2-Methyl-3-(4,4,5,5-tetramethyl-1,3,2-dioxaborolan-2-yl)phenyl)but-2-enamide

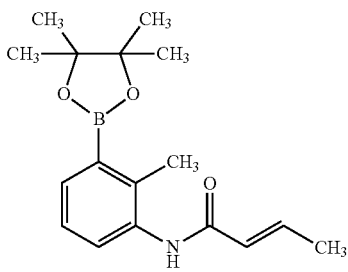

(I-51)

Following the procedure used to prepare Intermediate 49 but substituting (E)-but-2-enoyl chloride for acryloyl chloride, 2-methyl-3-(4,4,5,5-tetramethyl-1,3,2-dioxaborolan-2-yl)aniline [prepared according to U.S. Pat. No. 8,084,620, Intermediate 50-1] was converted into (E)-N-(2-methyl-3-(4,4,5,5-tetramethyl-1,3,2-dioxaborolan-2-yl) phenyl)but-2-enamide in 85% yield. Mass spectrum m/z 302 (M+H)⁺. ¹H NMR (400 MHz, DMSO-d₆) δ 9.28 (s, 1H), 7.46 (d, J=7.5 Hz, 2H), 7.15 (t, J=7.7 Hz, 1H), 6.83-6.66 (m, 1H), 6.21 (d, J=14.7 Hz, 1H), 2.34 (s, 3H), 1.86 (dd, J=6.9, 1.2 Hz, 3H), 1.30 (s, 12H).

Intermediate 52

N-Methyl-N-(2-methyl-3-(4,4,5,5-tetramethyl-1,3,2-dioxaborolan-2-yl)phenyl) acrylamide

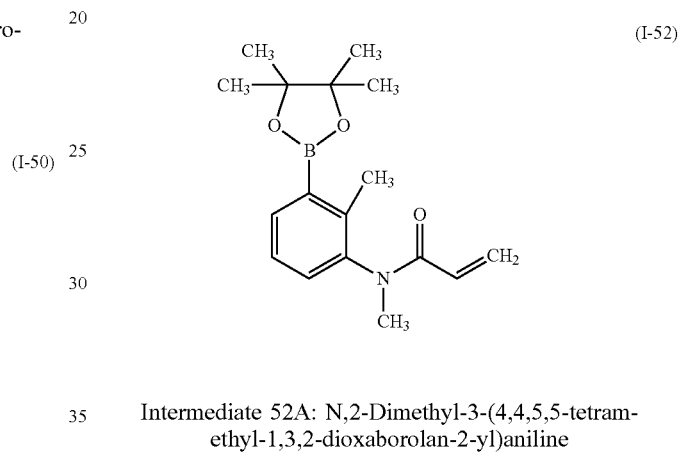

(I-52)

Intermediate 52A: N,2-Dimethyl-3-(4,4,5,5-tetramethyl-1,3,2-dioxaborolan-2-yl)aniline

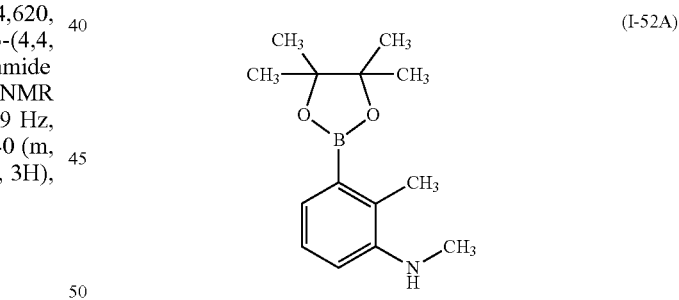

(I-52A)

A mixture of 3-bromo-N,2-dimethylaniline (1.90 g, 9.50 mmol), 4,4,4',4',5,5,5',5'-octamethyl-2,2'-bi(1,3,2-dioxaborolane) (2.53 g, 9.97 mmol) and potassium acetate (1.86 g, 19.0 mmol) in 1,4-dioxane (23.7 mL) was bubbled with nitrogen for 10 min. The mixture was treated with PdCl₂(dppf) DCM adduct (0.194 g, 0.237 mmol) and the mixture was bubbled with nitrogen for another 5 min, then was heated at reflux. After 2.75 h, the mixture was cooled to room temperature, filtered through CELITE®, and the solids were washed with EtOAc. The combined filtrates were concentrated and the residue was subjected to column chromatography on silica gel (40 g), eluting with EtOAc-hexanes (gradient from 5-15%), to provide N,2-dimethyl-3-(4,4,5,5-tetramethyl-1,3,2-dioxaborolan-2-yl)aniline as an off-white waxy solid (2.26 g, 96% yield). Mass spectrum m/z 249 (M+H)⁺. ¹H NMR (400 MHz, CDCl₃) δ 7.21-7.12

(m, 2H), 6.72 (dd, J=6.5, 2.8 Hz, 1H), 3.63 (br. s., 1H), 2.90 (s, 3H), 2.36 (s, 3H), 1.35 (s, 12H).

Intermediate 52

A solution of N,2-dimethyl-3-(4,4,5,5-tetramethyl-1,3,2-dioxaborolan-2-yl)aniline (0.71 g, 2.87 mmol) and DIEA (0.652 mL, 3.73 mmol) in DCM (14.4 mL), cooled in an ice-bath, was treated with acryloyl chloride (0.245 mL, 3.02 mmol) and the mixture was stirred at room temperature. After 2 h, the mixture was concentrated and the residue was subjected to column chromatography on silica gel (24 g), eluting with EtOAc-hexanes (gradient from 15-35%), to provide N-methyl-N-(2-methyl-3-(4,4,5,5-tetramethyl-1,3,2-dioxaborolan-2-yl)phenyl)acrylamide as a white solid (0.845 g, 98% yield). Mass spectrum m/z 302 (M+H)$^+$. $^1$H NMR (400 MHz, CDCl$_3$) δ 7.77 (dd, J=7.3, 1.3 Hz, 1H), 7.25-7.16 (m, 2H), 6.37 (dd, J=16.8, 2.1 Hz, 1H), 5.90 (dd, J=16.9, 10.3 Hz, 1H), 5.47 (dd, J=10.3, 2.2 Hz, 1H), 3.25 (s, 3H), 2.38 (s, 3H), 1.37 (s, 12H).

Intermediate 53

N-Methyl-N-(3-(4,4,5,5-tetramethyl-1,3,2-dioxaborolan-2-yl)phenyl)acrylamide

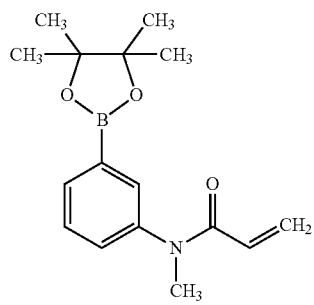

(I-53)

Intermediate 53A: N-Methyl-3-(4,4,5,5-tetramethyl-1,3,2-dioxaborolan-2-yl)aniline

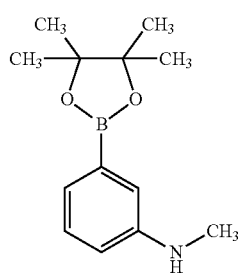

(I-53A)

Following the procedure used in the preparation of Intermediate 52A, 3-bromo-N-methylaniline was converted into N-methyl-3-(4,4,5,5-tetramethyl-1,3,2-dioxaborolan-2-yl)aniline in quantitative yield. Mass spectrum m/z 234 (M+H)$^+$. $^1$H NMR (400 MHz, CDCl$_3$) δ 7.25-7.15 (m, 2H), 7.07 (d, J=2.4 Hz, 1H), 6.73 (ddd, J=7.7, 2.6, 1.3 Hz, 1H), 4.02-3.43 (b, 1H), 2.87 (s, 3H), 1.35 (s, 12H).

Intermediate 53

Following the procedure used in the conversion of Intermediate 52A into Intermediate 52, N-methyl-3-(4,4,5,5-tetramethyl-1,3,2-dioxaborolan-2-yl)aniline was converted into N-methyl-N-(3-(4,4,5,5-tetramethyl-1,3,2-dioxaborolan-2-yl)phenyl) acrylamide in 88% yield. Mass spectrum m/z 288 (M+H)$^+$. $^1$H NMR (400 MHz, CDCl$_3$) δ 7.77 (d, J=7.3 Hz, 1H), 7.62 (d, J=1.5 Hz, 1H), 7.42 (t, J=7.7 Hz, 1H), 7.26-7.23 (m, 1H), 6.37 (dd, J=16.7, 2.0 Hz, 1H), 6.06 (dd, J=16.7, 10.6 Hz, 1H), 5.51 (dd, J=10.3, 2.0 Hz, 1H), 3.36 (s, 3H), 1.36 (s, 12H).

Intermediate 54

N-(2-Fluoro-3-(4,4,5,5-tetramethyl-1,3,2-dioxaborolan-2-yl)phenyl)-N-methylacrylamide

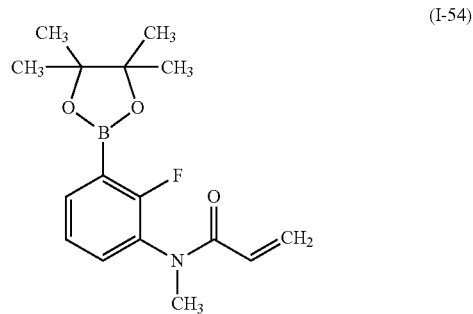 [SMILES: C=CC(=O)N(C)c1cccc(B2OC(C)(C)C(C)(C)O2)c1F]

(I-54)

Intermediate 54A: 2 N-(3-Bromo-2-fluorophenyl)formamide

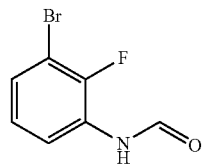

(I-54A)

A solution of 3-bromo-2-fluoroaniline (1.00 g, 5.26 mmol) in formic acid (1.99 mL, 52.6 mmol) was heated at 90° C. for 16 h. The mixture was cooled to room temperature and partitioned between EtOAc and water. The organic phase was washed sequentially with saturated aqueous NaHCO$_3$ and brine, dried and concentrated to provide N-(3-bromo-2-fluorophenyl)formamide as a beige solid (1.02 g, 89% yield). Mass spectrum m/z 218, 220 (M+H)$^+$. $^1$H NMR (400 MHz, CDCl$_3$) δ 8.50 (s, 1H), 8.40-8.17 (m, 1H), 7.53-7.41 (m, 1H), 7.31 (ddd, J=8.0, 6.6, 1.4 Hz, 1H), 7.05 (td, J=8.2, 1.4 Hz, 1H).

Intermediate 54B: 3-Bromo-2-fluoro-N-methylaniline

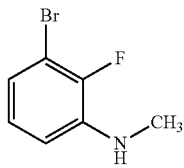

(I-54B)

A solution of N-(3-bromo-2-fluorophenyl)formamide (1.00 g, 4.59 mmol) in THF (15 mL) was cooled to 0° C., treated dropwise with borane-methyl sulfide complex (6.88 mL, 13.8 mmol) and heated at 70° C. for 2 h. The mixture was cooled to room temperature and treated with MeOH. The mixture was stirred at room temperature for 30 min, then was treated slowly with 1 M aqueous HCl. The mixture was heated to 70° C. for 1 h, then was cooled to room temperature, treated with 1 M aqueous NaOH and extracted with EtOAc. The organic extract was washed with brine, dried and concentrated. The residue was subjected to column chromatography on silica gel, eluting with EtOAc-hexanes, to provide 3-bromo-2-fluoro-N-methylaniline as a colorless oil (0.800 g, 85% yield). Mass spectrum m/z 204, 206 (M+H)$^+$. $^1$H NMR (400 MHz, CDCl$_3$) δ 6.92-6.86 (m, 1H), 6.84-6.78 (m, 1H), 6.63-6.56 (m, 1H), 4.03 (br. s., 1H), 2.88 (d, J=4.6 Hz, 3H).

Intermediate 54C: 2-Fluoro-N-methyl-3-(4,4,5,5-tetramethyl-1,3,2-dioxaborolan-2-yl) aniline

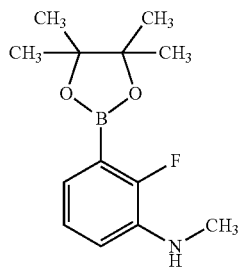

(I-54C)

Following the procedure used in the preparation of Intermediate 52A, 3-bromo-2-fluoro-N-methylaniline was converted into 2-fluoro-N-methyl-3-(4,4,5,5-tetramethyl-1,3,2-dioxaborolan-2-yl)aniline in 71% yield. Mass spectrum m/z 252 (M+H)$^+$. $^1$H NMR (400 MHz, CDCl$_3$) δ 7.02 (d, J=7.3 Hz, 2H), 6.85-6.73 (m, 1H), 4.07-3.85 (m, 1H), 2.86 (s, 3H), 1.38-1.32 (m, 12H).

Intermediate 54

Following the procedure used in the conversion of Intermediate 52A into Intermediate 52, 2-fluoro-N-methyl-3-(4,4,5,5-tetramethyl-1,3,2-dioxaborolan-2-yl) aniline was converted into N-(2-fluoro-3-(4,4,5,5-tetramethyl-1,3,2-dioxaborolan-2-yl) phenyl)-N-methylacrylamide in 56% yield. $^1$H NMR (400 MHz, CDCl$_3$) δ 7.74 (s, 1H), 7.33-7.27 (m, 1H), 7.22-7.06 (m, 1H), 6.37 (d, J=16.7 Hz, 1H), 6.16-5.87 (m, 1H), 5.52 (d, J=10.1 Hz, 1H), 3.30 (s, 3H), 1.38 (s, 12H).

Intermediate 55

N-Methyl-N-(2-methyl-3-(4,4,5,5-tetramethyl-1,3,2-dioxaborolan-2-yl)phenyl)ethenesulfonamide

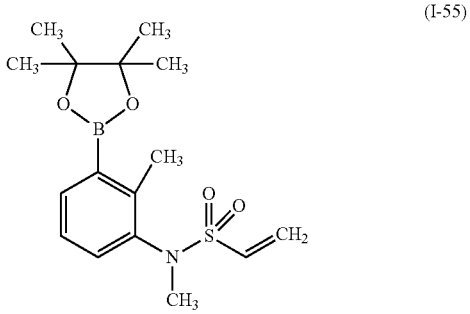 [SMILES: C=CS(=O)(=O)N(C)c1cccc(B2OC(C)(C)C(C)(C)O2)c1C]

(I-55)

A solution of N,2-dimethyl-3-(4,4,5,5-tetramethyl-1,3,2-dioxaborolan-2-yl)aniline [Intermediate 52A] (0.500 g, 2.02 mmol) in DCM (10.1 mL), cooled to 0° C., was treated with DIEA (0.530 mL, 3.03 mmol), then 2-chloroethanesulfonyl chloride (0.254 mL, 2.43 mmol) was added dropwise. The mixture was stirred at room temperature for 3 h, then was concentrated. The residue was subjected to column chromatography on silica gel (24 g), eluting with EtOAc-hexanes (gradient from 10-20%), to provide N-methyl-N-(2-methyl-3-(4,4,5,5-tetramethyl-1,3,2-dioxaborolan-2-yl)phenyl) ethenesulfonamide as a white waxy solid (0.432 g, 63% yield). Mass spectrum m/z 338 (M+H)$^+$. $^1$H NMR (400 MHz, CDCl$_3$) δ 7.75 (dd, J=7.3, 1.3 Hz, 1H), 7.27-7.23 (m, 1H), 7.21-7.15 (m, 1H), 6.62 (dd, J=16.5, 9.9 Hz, 1H), 6.23 (d, J=16.7 Hz, 1H), 6.02 (d, J=9.9 Hz, 1H), 3.15 (s, 3H), 2.61 (s, 3H), 1.35 (s, 12H).

Intermediate 56

N-Methyl-N-(3-(4,4,5,5-tetramethyl-1,3,2-dioxaborolan-2-yl)phenyl)ethenesulfonamide

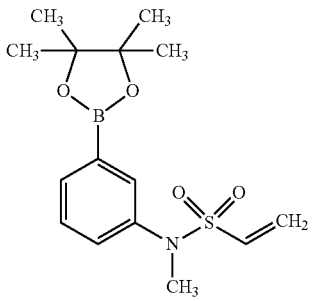

(I-56)

Following the procedure used to prepare Intermediate 55, N-methyl-3-(4,4,5,5-tetramethyl-1,3,2-dioxaborolan-2-yl) aniline [Intermediate 53A] was converted into N-methyl-N-(3-(4,4,5,5-tetramethyl-1,3,2-dioxaborolan-2-yl)phenyl) ethenesulfonamide in 61% yield. Mass spectrum m/z 324 (M+H)$^+$. $^1$H NMR (400 MHz, DMSO-d$_6$) δ 7.62-7.54 (m, 2H), 7.51-7.37 (m, 2H), 6.86 (dd, J=16.4, 10.0 Hz, 1H), 6.14 (d, J=10.1 Hz, 1H), 6.02 (d, J=16.5 Hz, 1H), 3.18 (s, 3H), 1.30 (s, 12H).

Intermediate 57

N-(2-Methyl-3-(4,4,5,5-tetramethyl-1,3,2-dioxaborolan-2-yl)phenyl)ethenesulfonamide

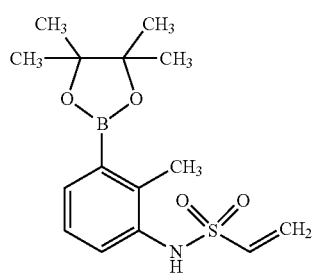

(I-57)

Following the procedure used to prepare Intermediate 55, 2-methyl-3-(4,4,5,5-tetramethyl-1,3,2-dioxaborolan-2-yl)aniline [prepared according to the procedure of U.S. Pat. No. 8,084,620, Intermediate 46-1, Step 1] was converted into N-(2-methyl-3-(4,4,5,5-tetramethyl-1,3,2-dioxaborolan-2-yl)phenyl)ethenesulfonamide in 49% yield. Mass spectrum m/z 324 (M+H)$^+$. $^1$H NMR (400 MHz, DMSO-d$_6$) δ 9.24 (s, 1H), 7.52-7.47 (m, 1H), 7.27 (d, J=6.6 Hz, 1H), 7.19-7.13 (m, 1H), 6.83 (dd, J=16.5, 9.9 Hz, 1H), 5.99-5.89 (m, 2H), 2.44 (s, 3H), 1.30 (s, 12H).

Intermediate 58

N-(3-(4,4,5,5-Tetramethyl-1,3,2-dioxaborolan-2-yl)phenyl)ethenesulfonamide

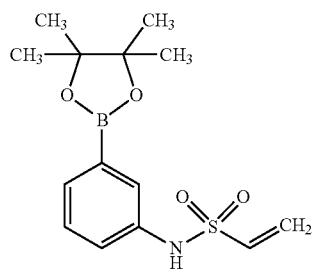

(I-58)

Following the procedure used to prepare Intermediate 55, 3-(4,4,5,5-tetramethyl-1,3,2-dioxaborolan-2-yl)aniline [Intermediate 49A] was converted into N-(3-(4,4,5,5-tetramethyl-1,3,2-dioxaborolan-2-yl)phenyl)ethenesulfonamide in 40% yield. Mass spectrum m/z 310 (M+H)$^+$. $^1$H NMR (400 MHz, CDCl$_3$) δ 7.63 (d, J=7.0 Hz, 1H), 7.47 (d, J=2.2 Hz, 1H), 7.44-7.40 (m, 1H), 7.40-7.34 (m, 1H), 6.57 (dd, J=16.5, 9.9 Hz, 1H), 6.34-6.26 (m, 2H), 5.97 (d, J=9.9 Hz, 1H), 1.36 (s, 12H).

Intermediate 59

N-(2-Fluoro-3-(4,4,5,5-tetramethyl-1,3,2-dioxaborolan-2-yl)phenyl)-N-methylethenesulfonamide

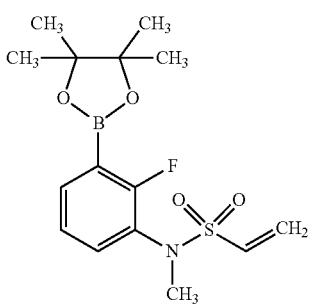

(I-59)

Following the procedure used to prepare Intermediate 55, 2-fluoro-N-methyl-3-(4,4,5,5-tetramethyl-1,3,2-dioxaborolan-2-yl)aniline [Intermediate 54C] was converted into N-(2-fluoro-3-(4,4,5,5-tetramethyl-1,3,2-dioxaborolan-2-yl)phenyl)-N-methylethenesulfonamide.

Intermediate 60

N-(2-Chloro-3-(4,4,5,5-tetramethyl-1,3,2-dioxaborolan-2-yl)phenyl)-N-methylethenesulfonamide

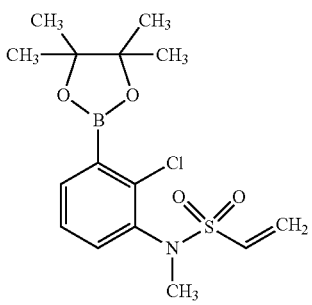

(I-60)

Intermediate 60A:
N-(3-Bromo-2-chlorophenyl)formamide

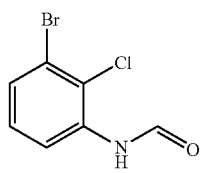

(I-60A)

Following the procedure used to prepare Intermediate 54A, 3-bromo-2-chloroaniline was converted into N-(3-bromo-2-chlorophenyl)formamide in 97% yield. Mass spectrum m/z 234, 236, 238 (M+H)$^+$. $^1$H NMR (400 MHz, CDCl$_3$) δ 8.53 (s, 1H), 8.44 (d, J=8.4 Hz, 1H), 7.76 (br. s., 1H), 7.44 (d, J=8.1 Hz, 1H), 7.19 (t, J=8.1 Hz, 1H).

Intermediate 60B:
3-Bromo-2-chloro-N-methylaniline

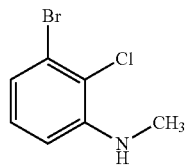
(I-60B)

Following the procedure used to prepare Intermediate 54B, N-(3-bromo-2-chlorophenyl)formamide was converted into 3-bromo-2-chloro-N-methylaniline in 97% yield. Mass spectrum m/z 220, 222, 224 (M+H)+. $^1$H NMR (400 MHz, CDCl$_3$) δ 7.09-7.01 (m, 1H), 7.00-6.94 (m, 1H), 6.60 (dd, J=8.1, 1.3 Hz, 1H), 4.54 (br. s., 1H), 2.93 (d, J=5.1 Hz, 3H).

Intermediate 60C: 2-Chloro-N-methyl-3-(4,4,5,5-tetramethyl-1,3,2-dioxaborolan-2-yl) aniline

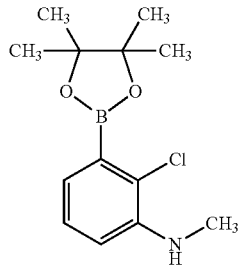
(I-60C)

Following the procedure used in the preparation of Intermediate 52A, 3-bromo-2-chloro-N-methylaniline was converted into 2-chloro-N-methyl-3-(4,4,5,5-tetramethyl-1,3,2-dioxaborolan-2-yl)aniline in 72% yield. Mass spectrum m/z 268, 270 (M+H)+. $^1$H NMR (400 MHz, CDCl$_3$) δ 7.21-7.15 (m, 1H), 7.02 (dd, J=7.3, 1.5 Hz, 1H), 6.73 (dd, J=8.0, 1.4 Hz, 1H), 4.50 (br. s., 1H), 2.91 (d, J=5.1 Hz, 3H), 1.39 (s, 12H).

Intermediate 60

Following the procedure used to convert Intermediate 55A into Intermediate 55, 2-chloro-N-methyl-3-(4,4,5,5-tetramethyl-1,3,2-dioxaborolan-2-yl)aniline was converted into N-(2-fluoro-3-(4,4,5,5-tetramethyl-1,3,2-dioxaborolan-2-yl)phenyl)-N-methylethenesulfonamide in 54% yield. Mass spectrum m/z 358, 360 (M+H)+. $^1$H NMR (400 MHz, CDCl$_3$) δ 7.78-7.62 (m, 1H), 7.60-7.45 (m, 1H), 7.28 (s, 1H), 6.74-6.55 (m, 1H), 6.23 (d, J=16.5 Hz, 1H), 5.97 (d, J=9.9 Hz, 1H), 3.21 (s, 3H), 1.38 (s, 12H).

Intermediate 61

(RS)-3-Fluoro-4-(isoindolin-4-yl)-9H-carbazole-1-carboxamide TFA Salt

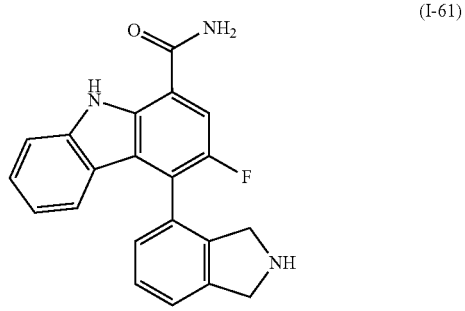 [SMILES: NC(=O)c1cc(F)c(-c2cccc3c2CNC3)c2c1[nH]c1ccccc12]
(I-61)

Intermediate 61A: tert-Butyl 4-bromoisoindoline-2-carboxylate

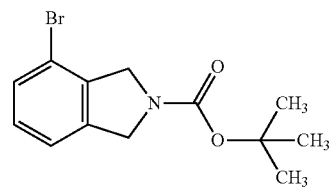
(I-61A)

A solution of 4-bromoisoindoline hydrochloride (1.40 g, 5.97 mmol) in DMF (30 mL) was treated with triethylamine (2.50 mL, 17.9 mmol) and di-tert-butyl dicarbonate (2.08 mL, 8.95 mmol), and the mixture was stirred at room temperature for 18 h. The mixture was diluted with EtOAc (65 mL) and washed three times with saturated aqueous NaHCO$_3$. The organic phase was dried and concentrated. The residue was subjected to column chromatography on silica gel, eluting with EtOAc-hexanes (gradient from 0-30%), to provide tert-butyl 4-bromoisoindoline-2-carboxylate as a white solid (1.70 g, 91% yield).

Intermediate 61B: tert-Butyl 4-(4,4,5,5-tetramethyl-1,3,2-dioxaborolan-2-yl)isoindoline-2-carboxylate

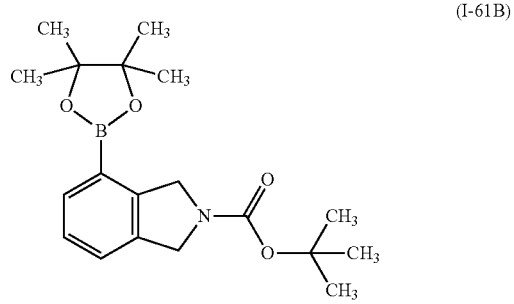 [SMILES: CC(C)(C)OC(=O)N1Cc2cccc(B3OC(C)(C)C(C)(C)O3)c2C1]
(I-61B)

A mixture of tert-butyl 4-bromoisoindoline-2-carboxylate (1.70 g, 5.70 mmol), 4,4,4',4',5,5,5',5'-octamethyl-2,2'-bi(1, 3,2-dioxaborolane) (1.74 g, 6.84 mmol), potassium acetate (1.68 g, 17.1 mmol), and PdCl$_2$(dppf) DCM adduct (0.466 g, 0.570 mmol) in 1,4-dioxane (25 mL) was bubbled with nitrogen and stirred at 80° C. overnight. The mixture was cooled to room temperature, diluted with EtOAc, washed with water, dried and concentrated. The residue was subjected to column chromatography on silica gel, eluting with EtOAc-hexanes (gradient from 0-30%), to provide tert-butyl 4-(4,4,5,5-tetramethyl-1,3,2-dioxaborolan-2-yl)isoindoline-2-carboxylate as a white solid (1.50 g, 76% yield).

Intermediate 61C: tert-Butyl 4-(1-carbamoyl-3-fluoro-9H-carbazol-4-yl)isoindoline-2-carboxylate

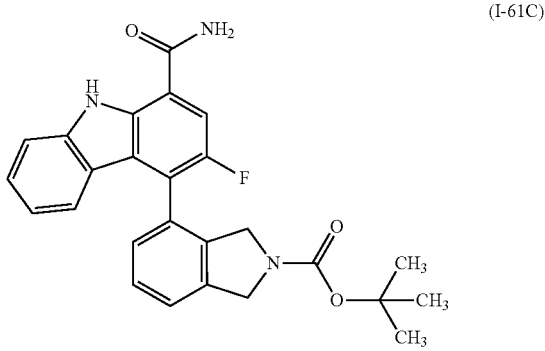 [SMILES: CC(C)(C)OC(=O)N1Cc2cccc(-c3c(F)cc(C(N)=O)c4[nH]c5ccccc5c34)c2C1]

(I-61C)

A mixture of 4-bromo-3-fluoro-9H-carbazole-1-carboxamide [Intermediate 8] (40 mg, 0.130 mmol), tert-butyl 4-(4,4,5,5-tetramethyl-1,3,2-dioxaborolan-2-yl)isoindoline-2-carboxylate (47.2 mg, 0.137 mmol), K$_2$HPO$_4$ (68.1 mg, 0.391 mmol), and 1,1'-bis(di-tert-butylphosphino)ferrocene palladium dichloride (4.24 mg, 6.51 μmol) in THF (1.00 mL) and water (0.250 mL) was bubbled with nitrogen and stirred at 60° C. for 3 h. The mixture was diluted with EtOAc, washed with water, dried and concentrated. The residue was subjected to column chromatography on silica gel, eluting with EtOAc-hexanes (gradient from 0-100%), to provide tert-butyl 4-(1-carbamoyl-3-fluoro-9H-carbazol-4-yl)isoindoline-2-carboxylate as a light yellow oil (41 mg, 71% yield).

Intermediate 61

A solution of tert-butyl 4-(1-carbamoyl-3-fluoro-9H-carbazol-4-yl)isoindoline-2-carboxylate (41 mg, 0.092 mmol) and TFA (0.500 mL, 6.49 mmol) in DCM (1 mL) was stirred at room temperature for 15 min. The mixture was concentrated to provide 3-fluoro-4-(isoindolin-4-yl)-9H-carbazole-1-carboxamide TFA salt as a yellow solid (38.9 mg, 92% yield). Mass spectrum m/z 346 (M+H)$^+$. $^1$H NMR (400 MHz, MeOH-d$_4$) δ 7.86 (d, J=10.5 Hz, 1H), 7.71-7.66 (m, 2H), 7.64-7.60 (m, 1H), 7.60-7.56 (m, 1H), 7.39 (ddd, J=8.3, 6.7, 1.7 Hz, 1H), 6.98-6.90 (m, 2H), 4.82-4.79 (m, 2H), 4.43 (d, J=14.7 Hz, 1H), 4.23 (d, J=14.7 Hz, 1H).

Intermediate 62

3-Fluoro-4-(1,2,3,4-tetrahydroisoquinolin-7-yl)-9H-carbazole-1-carboxamide TFA Salt

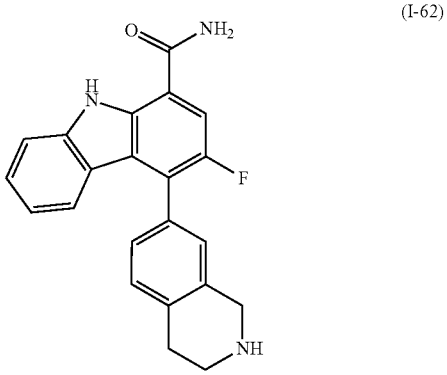 [SMILES: NC(=O)c1cc(F)c(-c2ccc3c(c2)CNCC3)c2c1[nH]c1ccccc12]

(I-62)

Following the procedures used to prepare Intermediate 61, tert-butyl 7-bromo-3,4-dihydroisoquinoline-2(1H)-carboxylate was converted into 3-fluoro-4-(1,2,3,4-tetrahydroisoquinolin-7-yl)-9H-carbazole-1-carboxamide TFA salt. Mass spectrum m/z 360 (M+H)$^+$. $^1$H NMR (400 MHz, MeOH-d$_4$) δ 7.82 (d, J=10.6 Hz, 1H), 7.61 (d, J=8.2 Hz, 1H), 7.57-7.50 (m, 2H), 7.46 (s, 1H), 7.38 (ddd, J=8.2, 7.1, 1.2 Hz, 1H), 7.18-7.12 (m, 1H), 6.89 (ddd, J=8.1, 7.1, 1.0 Hz, 1H), 4.50 (s, 2H), 3.76-3.57 (m, 2H), 3.48-3.20 (m, 2H) [hidden under residual MeOH peak].

Intermediate 63

3-Fluoro-4-(1,2,3,4-tetrahydroisoquinolin-6-yl)-9H-carbazole-1-carboxamide TFA Salt

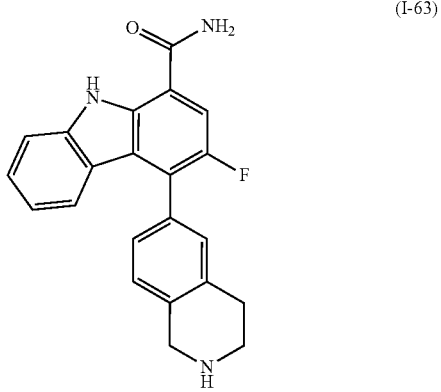 [SMILES: NC(=O)c1cc(F)c(-c2ccc3c(c2)CCNC3)c2c1[nH]c1ccccc12]

(I-63)

Following the procedures used to prepare Intermediate 61, 6-bromo-1,2,3,4-tetrahydroisoquinoline hydrochloride was converted into 3-fluoro-4-(1,2,3,4-tetrahydroisoquinolin-6-yl)-9H-carbazole-1-carboxamide TFA salt. Mass spectrum m/z 360 (M+H)$^+$. $^1$H NMR (400 MHz, MeOH-d$_4$) δ 7.80 (d, J=10.6 Hz, 1H), 7.59 (d, J=8.2 Hz, 1H), 7.48 (s, 3H), 7.36 (ddd, J=8.3, 7.2, 1.1 Hz, 1H), 7.12 (d, J=8.1 Hz, 1H), 6.86 (td, J=7.6, 1.0 Hz, 1H), 4.54 (ABq, J=17.1 Hz, 2H), 3.72-3.55 (m, 2H), 3.28-3.21 (m, 2H).

Intermediate 64

3-Fluoro-4-(indolin-4-yl)-9H-carbazole-1-carboxamide TFA Salt

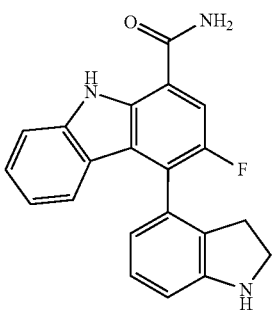

(I-64)

Following the procedures used to prepare Intermediate 61, 4-bromoindoline was converted into 3-fluoro-4-(indolin-4-yl)-9H-carbazole-1-carboxamide TFA salt. Mass spectrum m/z 346 (M+H)$^+$. $^1$H NMR (400 MHz, MeOH-d$_4$) δ 7.88 (d, J=10.6 Hz, 1H), 7.78-7.61 (m, 4H), 7.40 (ddd, J=8.3, 5.3, 3.0 Hz, 1H), 6.95-6.90 (m, 2H), 3.93-3.76 (m, 2H), 3.20-3.07 (m, 1H), 3.04-2.91 (m, 1H).

Intermediate 67

3-Fluoro-4-(indolin-6-yl)-9H-carbazole-1-carboxamide TFA Salt

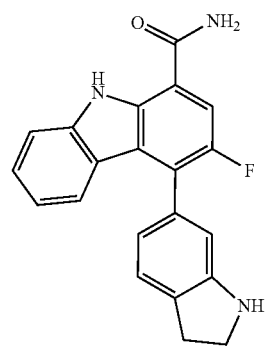

(I-67)

Following the procedures used to prepare Intermediate 61, 6-bromoindoline [prepared according to the procedure of PCT Publication No. WO 2010/093949, Example 82, Step 1] was converted into 3-fluoro-4-(indolin-6-yl)-9H-carbazole-1-carboxamide TFA salt. Mass spectrum m/z 346 (M+H)$^+$. $^1$H NMR (400 MHz, MeOH-d$_4$) δ 7.85 (d, J=10.6 Hz, 1H), 7.77 (d, J=7.5 Hz, 1H), 7.71-7.65 (m, 2H), 7.63 (d, J=8.1 Hz, 1H), 7.40 (t, J=7.6 Hz, 1H), 7.14 (d, J=7.9 Hz, 1H), 6.93 (t, J=7.2 Hz, 1H), 4.06-3.95 (m, 2H), 3.59-3.51 (m, 2H).

Intermediate 68

3-Fluoro-4-(1,2,5,6-tetrahydropyridin-3-yl)-9H-carbazole-1-carboxamide TFA Salt

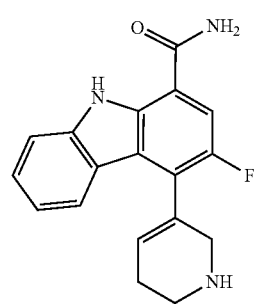

(I-68)

Intermediate 68A: tert-Butyl 3-(1-carbamoyl-3-fluoro-9H-carbazol-4-yl)-5,6-dihydropyridine-1(2H)-carboxylate

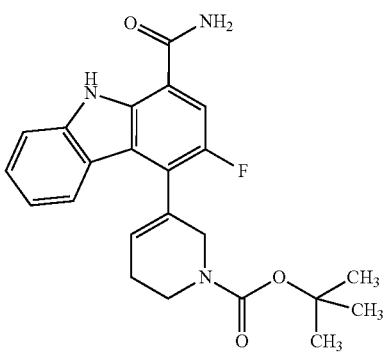

(I-68A)

A mixture of 4-bromo-3-fluoro-9H-carbazole-1-carboxamide [Intermediate 8] (120 mg, 0.391 mmol), tert-butyl 3-(4,4,5,5-tetramethyl-1,3,2-dioxaborolan-2-yl)-5,6-dihydropyridine-1(2H)-carboxylate (169 mg, 0.547 mmol), 2 M aqueous K$_3$PO$_4$ (0.391 mL, 0.781 mmol) and 1,1'-bis(di-tert-butylphosphino)ferrocene palladium dichloride (20 mg, 0.031 mmol) in THF (1.5 mL) was purged with nitrogen and stirred at 60° C. for 4 h. The mixture was cooled to room temperature, diluted with EtOAc, washed with water, dried and concentrated. The residue was subjected to column chromatography on silica gel, eluting with EtOAc-hexanes (gradient from 0-50%), to provide tert-butyl 3-(1-carbamoyl-3-fluoro-9H-carbazol-4-yl)-5,6-dihydropyridine-1(2H)-carboxylate as a light yellow solid (73 mg, 46% yield). Mass spectrum m/z 354 (M+H−C$_4$H$_8$)$^+$.

Intermediate 68

Following the procedure used to convert Intermediate 33B into Intermediate 33C, tert-butyl 3-(1-carbamoyl-3-fluoro-9H-carbazol-4-yl)-5,6-dihydropyridine-1(2H)-carboxylate was converted into 3-fluoro-4-(1,2,5,6-tetrahydropyridin-3-yl)-9H-carbazole-1-carboxamide TFA salt. Mass spectrum m/z 310 (M+H)$^+$. $^1$H NMR (400 MHz, MeOH-d$_4$)

δ 8.19-8.09 (m, 1H), 7.76 (d, J=11.0 Hz, 1H), 7.62 (d, J=8.2 Hz, 1H), 7.45 (ddd, J=8.2, 7.2, 1.1 Hz, 1H), 7.19 (ddd, J=8.0, 7.1, 1.0 Hz, 1H), 6.31 (dt, J=3.9, 2.0 Hz, 1H), 4.14-4.01 (m, 2H), 3.64-3.53 (m, 2H), 2.76 (br. s., 2H).

Intermediate 69

(RS)-3-Fluoro-4-(piperidin-3-yl)-9H-carbazole-1-carboxamide TFA Salt

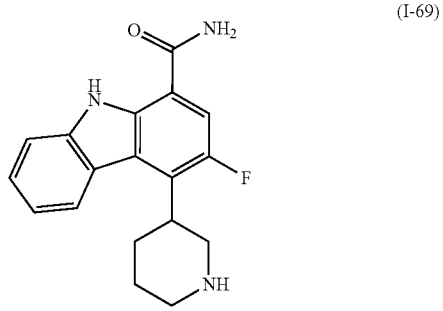 [SMILES: NC(=O)c1cc(F)c(C2CCCNC2)c2c1[nH]c1ccccc12]

(I-69)

A mixture of tert-butyl 3-(1-carbamoyl-3-fluoro-9H-carbazol-4-yl)-5,6-dihydropyridine-1(2H)-carboxylate [Intermediate 68A] (88 mg, 0.215 mmol) and 5% Pd on charcoal (46 mg, 0.021 mmol) in MeOH (6 mL) was stirred overnight at room temperature under a hydrogen atmosphere (50 psi). The mixture was filtered and concentrated, and the residue was dissolved in DCM (1 mL), treated with TFA (0.5 mL, 6.49 mmol) and stirred for 30 min at room temperature. The mixture was concentrated and the residue was subjected to preparative reverse phase HPLC (PHENOMENEX® Luna Axia $C_{18}$ column, 5 m, 30×100 mm, eluting with methanol-water containing 0.1% TFA, gradient from 20-100%, 40 mL/min) to provide (RS)-3-fluoro-4-(piperidin-3-yl)-9H-carbazole-1-carboxamide TFA salt as a white solid (44 mg, 49% yield). Mass spectrum m/z 312 (M+H)+. $^1$H NMR (400 MHz, MeOH-$d_4$) δ 8.30-8.24 (m, 1H), 7.78-7.72 (m, 1H), 7.70-7.65 (m, 1H), 7.54-7.46 (m, 1H), 7.35-7.23 (m, 1H), 4.41-4.30 (m, 1H), 3.80-3.71 (m, 1H), 3.70-3.63 (m, 1H), 3.62-3.51 (m, 1H), 3.24-3.12 (m, 1H), 2.30-2.04 (m, 4H).

Intermediate 70

3-Fluoro-4-(isoindolin-5-yl)-9H-carbazole-1-carboxamide, TFA Salt

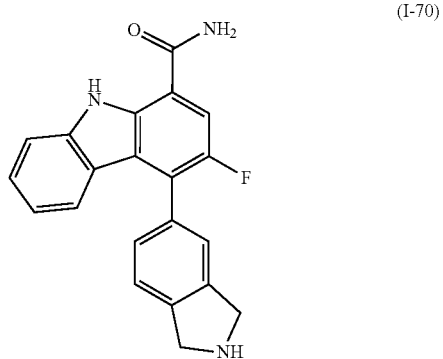 [SMILES: NC(=O)c1cc(F)c(-c2ccc3c(c2)CNC3)c2c1[nH]c1ccccc12]

(I-70)

Following the procedures used to prepare Intermediate 35, tert-butyl 5-(1-carbamoyl-3-fluoro-9H-carbazol-4-yl)isoindoline-2-carboxylate was converted into 3-fluoro-4-(isoindolin-5-yl)-9H-carbazole-1-carboxamide TFA salt. Mass spectrum m/z 346 (M+H)+. $^1$H NMR (400 MHz, methanol-$d_4$) δ 7.81 (d, J=10.6 Hz, 1H), 7.67 (d, J=8.1 Hz, 1H), 7.63-7.57 (m, 3H), 7.36 (ddd, J=8.2, 7.1, 1.1 Hz, 1H), 7.08 (d, J=8.1 Hz, 1H), 6.86 (td, J=7.6, 0.9 Hz, 1H), 4.81 (s, 4H).

Intermediate 71

4-(2,5-Dihydro-1H-pyrrol-3-yl)-3-fluoro-9H-carbazole-1-carboxamide, TFA Salt

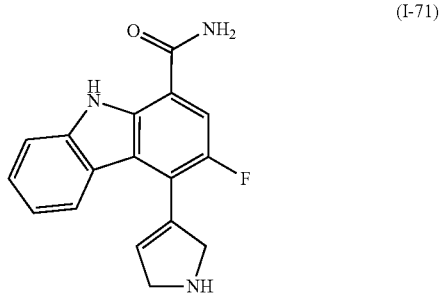 [SMILES: NC(=O)c1cc(F)c(C2=CCNC2)c2c1[nH]c1ccccc12]

(I-71)

Intermediate 71A: tert-Butyl 3-(((trifluoromethyl)sulfonyl)oxy)-2,5-dihydro-1H-pyrrole-1-carboxylate

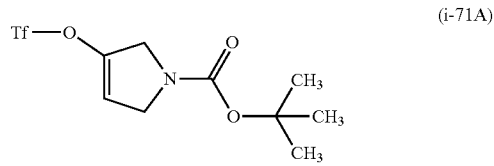

(i-71A)

1M LHMDS in toluene (30.9 mL, 30.9 mmol) was added to a stirred solution of tert-butyl 3-oxopyrrolidine-1-carboxylate (5.2 g, 28.1 mmol) in THF (75 mL) at −60° C., stirred for 15 min, then added a solution of N,N-bis(trifluoromethylsulfonyl)aniline (11.03 g, 30.9 mmol) in THF (25 mL). The mixture was allowed to come to room temperature and stirred for 15 minutes. The reaction mixture was diluted with methylene chloride and washed with saturated sodium bicarbonate solution. The organic phase was dried (MgSO$_4$) and concentrated to afford crude product. The crude product was subjected to ISCO flash chromatography (silica gel/hexane-DCM 100:0 to 0:100 gradient) to afford tert-butyl 3-(((trifluoromethyl)sulfonyl)oxy)-2,5-dihydro-1H-pyrrole-1-carboxylate (3.1 g, 34.8% yield). $^1$H NMR (400 MHz, chloroform-d) δ 5.96-5.60 (m, 1H), 4.44-4.05 (m, 4H), 1.48 (s, 9H).

Intermediate 71B: tert-Butyl 3-(4,4,5,5-tetramethyl-1,3,2-dioxaborolan-2-yl)-2,5-dihydro-1H-pyrrole-1-carboxylate

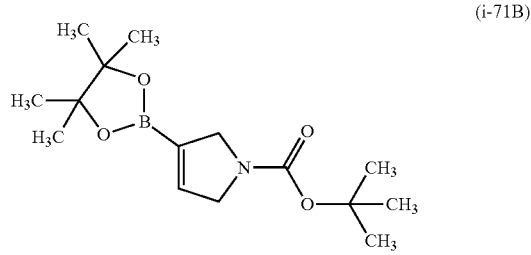 [SMILES: CC(C)(C)OC(=O)N1CC=C(B2OC(C)(C)C(C)(C)O2)C1]

(i-71B)

A mixture of PdCl₂(dppf)-CH₂Cl₂ adduct (0.399 g, 0.489 mmol), 4,4,4',4',5,5,5',5'-octamethyl-2,2'-bi(1,3,2-dioxaborolane) (2.48 g, 9.77 mmol), tert-butyl 3-(((trifluoromethyl)sulfonyl)oxy)-2,5-dihydro-1H-pyrrole-1-carboxylate (3.1 g, 9.77 mmol) and potassium acetate (1.92 g, 19.5 mmol) in dioxane (50 mL) was purged with nitrogen and heated at 80° C. for 3 hours. The reaction mixture was diluted with EtOAc, washed with saturated sodium bicarbonate, dried (MgSO₂) and concentrated. The crude product was subjected to ISCO flash chromatography (silica gel/hexane-EtOAc 100:0 to 0:100 gradient) to afford tert-butyl 3-(4,4,5,5-tetramethyl-1,3,2-dioxaborolan-2-yl)-2,5-dihydro-1H-pyrrole-1-carboxylate (1.3 g, 45.1% yield) as a yellow oil. ¹H NMR (400 MHz, chloroform-d) δ 6.54-6.36 (m, 1H), 4.36-4.02 (m, 4H), 1.47 (s, 9H), 1.32-1.17 (m, 12H).

Intermediate 71

Following the procedures used to prepare Intermediate 68, tert-butyl 3-(1-carbamoyl-3-fluoro-9H-carbazol-4-yl)-2,5-dihydro-1H-pyrrole-1-carboxylate was converted into 4-(2,5-dihydro-1H-pyrrol-3-yl)-3-fluoro-9H-carbazole-1-carboxamide TFA salt. Mass spectrum m/z 295 (M+H)⁺. ¹H NMR (400 MHz, methanol-d₄) δ 8.13-8.07 (m, 1H), 7.78 (d, J=11.1 Hz, 1H), 7.65 (d, J=8.2 Hz, 1H), 7.47 (ddd, J=8.3, 7.2, 1.1 Hz, 1H), 7.19 (ddd, J=8.1, 7.1, 1.0 Hz, 1H), 6.35 (t, J=2.1 Hz, 1H), 4.56-4.46 (m, 4H).

Intermediates 72 and 73

(RS)-3-Fluoro-4-(pyrrolidin-3-yl)-9H-carbazole-1-carboxamide TFA Salt, and (RS)-6-Fluoro-5-(pyrrolidin-3-yl)-2,3,4,9-tetrahydro-1H-carbazole-8-carboxamide TFA Salt

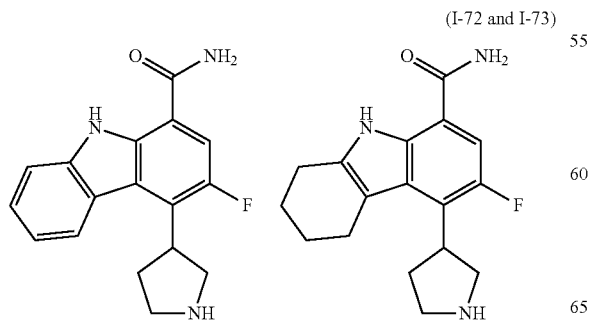

(I-72 and I-73)

A mixture of tert-butyl 3-(1-carbamoyl-3-fluoro-9H-carbazol-4-yl)-2,5-dihydro-1H-pyrrole-1-carboxylate (54 mg, 0.14 mmol) and 20% Pd(OH)₂ (47.9 mg, 0.068 mmol) in MeOH (10 mL) and DMF (0.5 mL) was stirred overnight at room temperature under a hydrogen atmosphere (50 psi). The mixture was filtered and concentrated. The residue was dissolved in DCM (1 mL), treated with TFA (0.5 mL, 6.49 mmol) and stirred for 30 minutes at room temperature. The mixture was concentrated and the residue was subjected to preparative reverse phase HPLC (YMC ODS 5μ 30×250 mm column, eluting with methanol-water containing 0.1% TFA, gradient from 10-100%, 40 mL/min) to provide (RS)-3-fluoro-4-(pyrrolidin-3-yl)-9H-carbazole-1-carboxamide TFA salt [Intermediate 72] (32 mg, 61% yield). Mass spectrum m/z 298 (M+H)⁺. ¹H NMR (400 MHz, methanol-d₄) δ 8.29 (d, J=8.2 Hz, 1H), 7.79 (d, J=13.3 Hz, 1H), 7.67 (d, J=8.2 Hz, 1H), 7.49 (td, J=7.7, 1.0 Hz, 1H), 7.26 (ddd, J=8.1, 7.2, 1.1 Hz, 1H), 4.90-4.86 (m, 1H), 3.91-3.73 (m, 2H), 3.72-3.53 (m, 2H), 2.79-2.63 (m, 1H), 2.58-2.42 (m, 1H). And (RS)-6-fluoro-5-(pyrrolidin-3-yl)-2,3,4,9-tetrahydro-1H-carbazole-8-carboxamide TFA salt [Intermediate 73] (15 mg, 28.7% yield). Mass spectrum m/z 302 (M+H)⁺. ¹H NMR (400 MHz, methanol-d₄) δ 7.41 (d, J=13.4 Hz, 1H), 4.40 (t, J=9.0 Hz, 1H), 3.77-3.57 (m, 3H), 3.55-3.43 (m, 1H), 2.97 (br. s., 2H), 2.82 (t, J=4.6 Hz, 2H), 2.60-2.34 (m, 2H), 2.03-1.86 (m, 4H).

Intermediate 74

(R)-4-(3-Aminopiperidin-1-yl)-3-fluoro-9H-carbazole-1-carboxamide

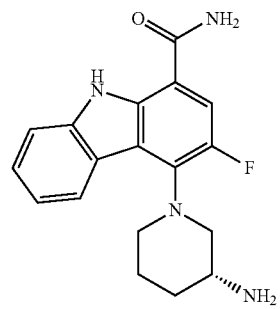

(I-74)

Intermediate 74A: tert-Butyl (R)-(1-(1-cyano-3-fluoro-9H-carbazol-4-yl)piperidin-3-yl) Carbamate

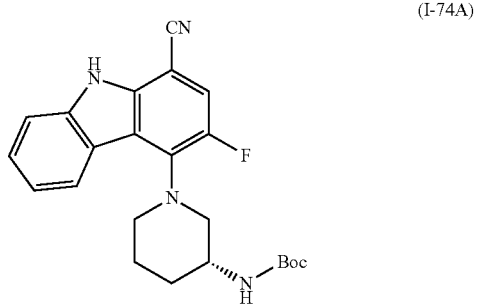 [SMILES: CC(C)(C)OC(=O)N[C@@H]1CCCN(c2c(F)cc(C#N)c3[nH]c4ccccc4c23)C1]

(I-74A)

Following the procedures used to prepare Intermediate 29B, 4-bromo-3-fluoro-9H-carbazole-1-carbonitrile was converted into tert-butyl (R)-(1-(1-cyano-3-fluoro-9H-carbazol-4-yl)piperidin-3-yl)carbamate. Mass spectrum m/z 409 (M+H)+.

Intermediate 74

Following the procedures used to prepare Intermediate 30, tert-butyl (R)-(1-(1-cyano-3-fluoro-9H-carbazol-4-yl)piperidin-3-yl)carbamate was converted into (R)-4-(3-aminopiperidin-1-yl)-3-fluoro-9H-carbazole-1-carboxamide. Mass spectrum m/z 327 (M+H)+.

Intermediate 75

(RS)-Cis-3-fluoro-4-(octahydro-6H-pyrrolo[3,4-b]pyridin-6-yl)-9H-carbazole-1-carboxamide TFA Salt

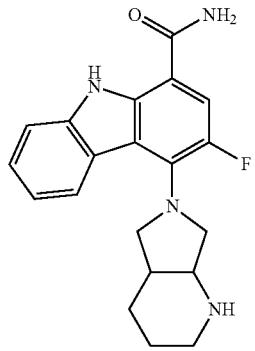

(I-75)

Intermediate 75A: (RS)-Cis-tert-butyl 6-(1-cyano-3-fluoro-9H-carbazol-4-yl)octahydro-1H-pyrrolo[3,4-b]pyridine-1-carboxylate

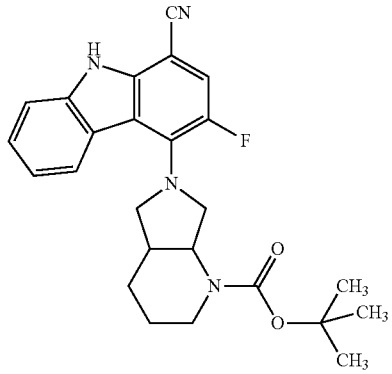

(I-75A)

Following the procedures used to prepare Intermediate 29B, 4-bromo-3-fluoro-9H-carbazole-1-carbonitrile was converted into (RS)-cis-tert-butyl 6-(1-cyano-3-fluoro-9H-carbazol-4-yl)octahydro-1H-pyrrolo[3,4-b]pyridine-1-carboxylate. Mass spectrum m/z 435 (M+H)+.

Intermediate 75

Aqueous H$_2$O$_2$ (35%, 0.13 mL, 1.49 mmol) was added dropwise to a solution of (RS)-cis-tert-butyl 6-(1-cyano-3-fluoro-9H-carbazol-4-yl)octahydro-1H-pyrrolo[3,4-b]pyridine-1-carboxylate (65 mg, 0.15 mmol) and 30% aqueous KOH (0.140 mL, 0.75 mmol) in DMSO (1.5 mL) and stirred for 15 min. The mixture was extracted with EtOAc, washed with water, dried (MgSO$_4$), and concentrated. The residue was stirred in TFA (1 mL, 12.98 mmol) and DCM (1 mL) for 30 min and concentrated. The crude material was purified using preparative HPLC (PHENOMENEX® Luna Axia C18 5μ; 30×100 mm column, eluting with methanol-water containing 0.1% TFA, gradient from 30-100%, 40 mL/min) to provide (RS)-cis-3-fluoro-4-(octahydro-6H-pyrrolo[3,4-b]pyridin-6-yl)-9H-carbazole-1-carboxamide TFA salt (46.3, 66.4% yield) as a light brown solid. Mass spectrum m/z 353 (M+H)+. $^1$H NMR (400 MHz, methanol-d$_4$) δ 8.20 (d, J=7.9 Hz, 1H), 7.77 (d, J=14.1 Hz, 1H), 7.60 (d, J=8.2 Hz, 1H), 7.45 (ddd, J=8.2, 7.2, 1.2 Hz, 1H), 7.25 (td, J=7.5, 1.0 Hz, 1H), 4.16-4.06 (m, 1H), 3.99-3.89 (m, 1H), 3.83-3.71 (m, 2H), 3.55 (t, J=8.9 Hz, 1H), 3.49-3.38 (m, 1H), 3.23-3.12 (m, 1H), 2.97 (d, J=4.9 Hz, 1H), 2.13-1.96 (m, 3H), 1.92-1.81 (m, 1H).

Intermediate 76

(RS)-Cis-3-fluoro-4-(hexahydropyrrolo[3,4-b]pyrrol-5(1H)-yl)-9H-carbazole-1-carboxamide TFA Salt

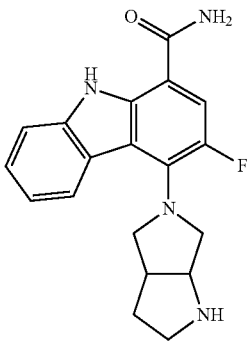

(I-76)

Intermediate 76A: (RS)-Cis-tert-butyl 5-(1-cyano-3-fluoro-9H-carbazol-4-yl) hexahydropyrrolo[3,4-b]pyrrole-1(2H)-carboxylate

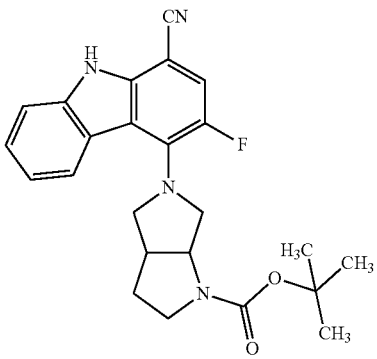

(I-76A)

A mixture of 4-bromo-3-fluoro-9H-carbazole-1-carbonitrile (100 mg, 0.34 mmol), hexahydropyrrolo[3,4-b]pyrrole-1-carboxylic acid tert-butyl ester (81 mg, 0.380 mmol), cesium carbonate (282 mg, 0.87 mmol), BINAP (10.77 mg, 0.017 mmol), and Pd$_2$(dba)$_3$ (15.84 mg, 0.017 mmol) in dioxane (2 mL) was purged with nitrogen and stirred at 105° C. for 24 hours. The mixture was cooled to room temperature, filtered and concentrated. The crude material was purified using ISCO flash chromatography (silica gel/hexanes/ethyl acetate 100:0 to 50:50 gradient) to afford tert-butyl 5-(1-cyano-3-fluoro-9H-carbazol-4-yl)hexahydropyrrolo[3,4-b]pyrrole-1(2H)-carboxylate (65 mg, 44.7% yield) as a light yellow solid. Mass spectrum m/z 421 (M+H)$^+$.

Intermediate 76: (RS)-Cis-3-fluoro-4-(hexahydropyrrolo[3,4-b]pyrrol-5(1H)-yl)-9H-carbazole-1-carboxamide, TFA Salt Aqueous H$_2$O$_2$ (35% 0.135 mL, 1.546 mmol) was added dropwise to a solution of (RS)-cis-tert-butyl 5-(1-cyano-3-fluoro-9H-carbazol-4-yl)hexahydropyrrolo[3,4-b] pyrrole-1 (2H)-carboxylate (65 mg, 0.155 mmol) and 30% aqueous KOH (0.145 mL, 0.773 mmol) in DMSO (1.5 mL) and stirred at room temperature for 15 minutes. The mixture was diluted with water, extracted with EtOAc, washed with water, dried (MgSO$_4$), and concentrated. The crude material was stirred in TFA (1 mL, 12.98 mmol) and DCM (1 mL) for 30 minutes and concentrated to afford the crude (RS)-cis-3-fluoro-4-(hexahydropyrrolo[3,4-b]pyrrol-5(1H)-yl)-9H-carbazole-1-carboxamide, TFA (62 mg, 89% yield) as a brown solid. Mass spectrum m/z 339 (M+H)$^+$. $^1$H NMR (400 MHz, methanol-d$_4$) δ 8.14 (d, J=7.9 Hz, 1H), 7.71 (d, J=14.4 Hz, 1H), 7.59 (d, J=8.2 Hz, 1H), 7.47-7.41 (m, 1H), 7.27-7.21 (m, 1H), 4.60-4.49 (m, 1H), 4.12 (dd, J=10.6, 7.5 Hz, 1H), 3.76-3.67 (m, 1H), 3.64-3.34 (m, 5H), 2.41-2.28 (m, 1H), 2.25-2.14 (m, 1H).

Intermediate 77

3-Fluoro-4-(1,4,5,6-tetrahydropyridin-3-yl)-9H-carbazole-1-carboxamide TFA Salt

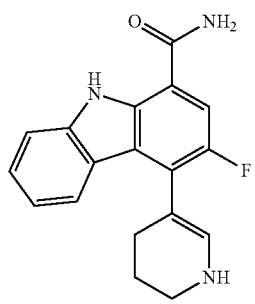

(I-77)

Following the procedures used to prepare Intermediate 68, tert-butyl 5-(1-carbamoyl-3-fluoro-9H-carbazol-4-yl)-3,4-dihydropyridine-1(2H)-carboxylate was converted into 3-fluoro-4-(1,4,5,6-tetrahydropyridin-3-yl)-9H-carbazole-1-carboxamide TFA salt. Mass spectrum m/z 310 (M+H)$^+$.

Intermediate 78

3-Fluoro-4-(2,7-diazaspiro[4.4]nonan-2-yl)-9H-carbazole-1-carboxamide TFA Salt

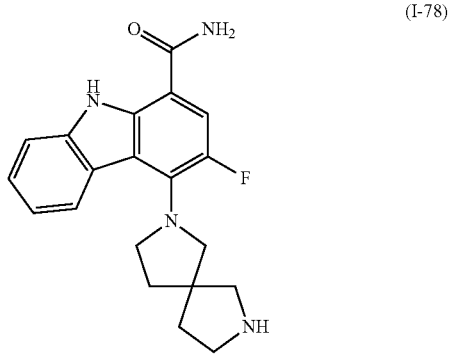 [SMILES: NC(=O)c1cc(F)c(N2CCC3(CCNC3)C2)c2c1[nH]c1ccccc12]

(I-78)

Following the procedures used to prepare Intermediate 75, tert-butyl 7-(1-carbamoyl-3-fluoro-9H-carbazol-4-yl)-2,7-diazaspiro[4.4]nonane-2-carboxylate was converted into 3-fluoro-4-(2,7-diazaspiro[4.4]nonan-2-yl)-9H-carbazole-1-carboxamide TFA salt. Mass spectrum m/z 353 (M+H)$^+$. $^1$H NMR (400 MHz, methanol-d$_4$) δ 8.11 (d, J=7.8 Hz, 1H), 7.73 (d, J=14.2 Hz, 1H), 7.59 (d, J=8.1 Hz, 1H), 7.43 (t, J=7.4 Hz, 1H), 7.23 (t, J=7.5 Hz, 1H), 3.67-3.39 (m, 8H), 2.37-2.16 (m, 4H).

Intermediate 79

(RS)-3-Fluoro-4-(octahydro-5H-pyrrolo[3,2-c]pyridin-5-yl)-9H-carbazole-1-carboxamide TFA Salt

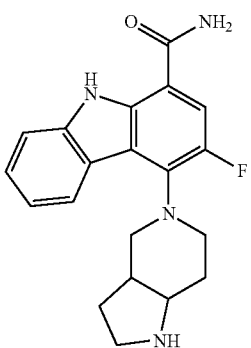

(I-79)

Following the procedures used to prepare Intermediate 75, (RS)-tert-butyl 5-(1-carbamoyl-3-fluoro-9H-carbazol-4-yl)octahydro-1H-pyrrolo[3,2-c]pyridine-1-carboxylate was converted into (RS)-3-fluoro-4-(octahydro-5H-pyrrolo[3,2-c]pyridin-5-yl)-9H-carbazole-1-carboxamide TFA salt. Mass spectrum m/z 353 (M+H)$^+$.

Intermediate 80

5-Bromo-6-chloro-2,3,4,9-tetrahydro-1H-carbazole-8-carboxylic acid

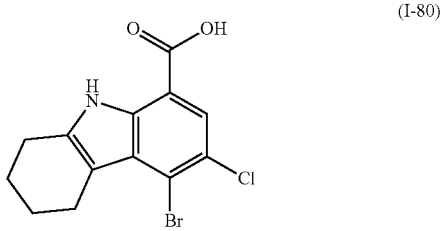 [SMILES: O=C(O)c1cc(Cl)c(Br)c2c3c([nH]c12)CCCC3]
(I-80)

To a suspension of 2-amino-4 bromo-5-chlorobenzoic acid (1.0 g, 3.99 mmol) in concentrated HCl (20 mL) at −10° C. was added dropwise a solution of sodium nitrite (0.289 g, 4.19 mmol) in water (2.0 mL) at a rate such that the reaction temperature remained below 0° C. The mixture was stirred at 0° C. for 15 min. A solution of tin(II) chloride (1.590 g, 8.38 mmol) in concentrated HCl (5.0 mL) was added to the mixture at a rate that the reaction temperature remained below −5° C. The reaction mixture was stirred at room temperature for 60 min. The precipitate was filtered, washed with water and air dried. Yield 4-bromo-5-chloro-2-hydrazinylbenzoic acid, HCl (752 mg, 1.868 mmol, 46.8% yield) as white solid.

A mixture of 4-bromo-5-chloro-2-hydrazinylbenzoic acid, HCl (1.0 g, 3.31 mmol) and cyclohexanone (0.650 g, 6.62 mmol) in HOAc (20 mL) was stirred at 110° C. for 18 hour. Precipitate was filtered and washed with HOAc and DCM. Crude yield 5-bromo-6-chloro-2,3,4,9-tetrahydro-1H-carbazole-8-carboxylic acid (893 g, 2582 mmol, 7.80E+04% yield) as light green solid. $^1$H NMR (400 MHz, DMSO-$d_6$) δ 11.12 (s, 1H), 7.67 (s, 1H), 3.01 (br. s., 2H), 2.76 (br. s., 2H), 1.78 (br. s., 4H). LCMS: 1.21 min, M+H 329.

Intermediate 81

5-Bromo-6-chloro-2,3,4,9-tetrahydro-1H-carbazole-8-carboxamide

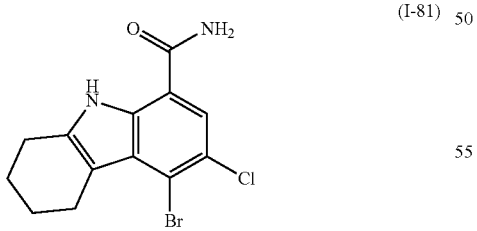
(I-81)

A mixture of 5-bromo-6-chloro-2,3,4,9-tetrahydro-1H-carbazole-8-carboxylic acid (100 mg, 0.304 mmol, 1-80), ammonium chloride (81 mg, 1.522 mmol), BOP (148 mg, 0.335 mmol) and TEA (0.297 mL, 2.130 mmol) in DMF (5.0 mL) was stirred at room temperature for 2 hours. The mixture was diluted with EtOAc (15 mL) and was washed with a solution of aqueous saturated sodium bicarbonate (2×15 mL) and aqueous 1.0 M HCl (15 mL). The ethyl acetate layer was dried over sodium sulfate and concentrated to afford 5-bromo-6-chloro-2,3,4,9-tetrahydro-1H-carbazole-8-carboxamide (106 mg, 0.291 mmol, 96% yield) as light gray solid. LCMS: 1.18 min, M+H 328.

Intermediate 82

Ethyl 4-bromo-3-chloro-9H-carbazole-1-carboxylate

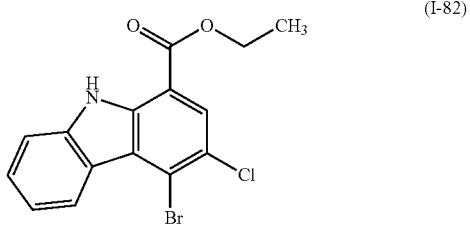
(I-82)

To a solution of 5-bromo-6-chloro-2,3,4,9-tetrahydro-1H-carbazole-8-carboxylic acid (2.27 g, 6.91 mmol, 1-80) in THF (80 mL) was added DDQ (3.14 g, 13.82 mmol), the mixture was stirred at 60° C. for 18 hour. The mixture was concentrated to give 4-bromo-3-chloro-9H-carbazole-1-carboxylic acid. A mixture of 4-bromo-3-chloro-9H-carbazole-1-carboxylic acid and sulfuric acid (0.736 mL, 13.82 mmol) in EtOH (100 mL) was stirred at reflux for 18 hour. The mixture was concentrated. The crude product was subjected to ISCO flash chromatography (silica gel/hexane-EtOAc 100:0 to 50:50 gradient). Yield ethyl 4-bromo-3-chloro-9H-carbazole-1-carboxylate (760 mg, 2.048 mmol, 29.6% yield) as light brown solid. $^1$H NMR (400 MHz, chloroform-d) δ 10.12 (br. s., 1H), 8.82 (dd, J=8.1, 0.9 Hz, 1H), 8.23-8.08 (m, 1H), 7.65-7.48 (m, 2H), 7.37 (ddd, J=8.1, 6.6, 1.6 Hz, 1H), 4.52 (q, J=7.1 Hz, 2H), 1.55-1.47 (m, 3H).

Intermediate 83

Ethyl 4-bromo-3,6-dichloro-9H-carbazole-1-carboxylate

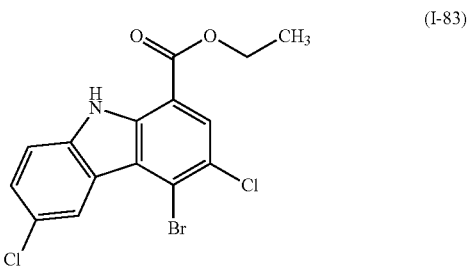 [SMILES: CCOC(=O)c1cc(Cl)c(Br)c2c1[nH]c1ccc(Cl)cc12]
(I-83)

Prepared following the procedures used to prepare Intermediate 82. $^1$H NMR (400 MHz, DMSO-$d_6$) δ 11.87 (s, 1H), 8.59 (d, J=2.1 Hz, 1H), 7.97-7.90 (m, 1H), 7.84 (d, J=8.8 Hz, 1H), 7.61 (dd, J=8.8, 2.1 Hz, 1H), 4.48 (q, J=7.1 Hz, 2H), 1.46-1.38 (m, 3H).

Intermediate 84

Ethyl 4-bromo-3-fluoro-9H-carbazole-1-carboxylate

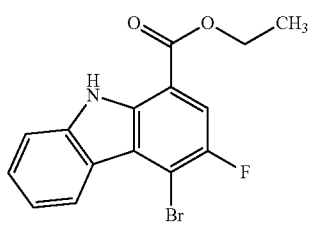

(I-84)

Prepared following the procedures used to prepare Intermediate 82. $^1$H NMR (400 MHz, chloroform-d) δ 10.04 (br. s., 1H), 8.76 (d, J=7.9 Hz, 1H), 7.85 (d, J=9.3 Hz, 1H), 7.64-7.48 (m, 2H), 7.35 (ddd, J=8.1, 6.5, 1.7 Hz, 1H), 4.51 (q, J=7.1 Hz, 2H), 1.50 (t, J=7.2 Hz, 3H).

Intermediate 85

(S)-4-(3-Aminopiperidin-1-yl)-3-fluoro-9H-carbazole-1-carboxamide

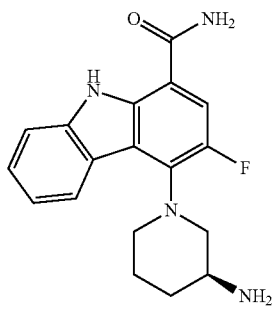

(I-85)

Intermediate 85A: tert-Butyl (S)-(1-(1-cyano-3-fluoro-9H-carbazol-4-yl)piperidin-3-yl) Carbamate

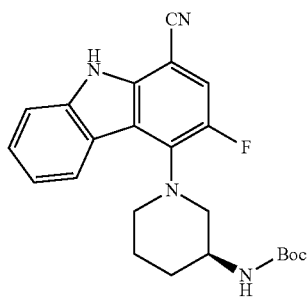

(I-85A)

A mixture of 4-bromo-3-fluoro-9H-carbazole-1-carbonitrile (2.8 g, 9.69 mmol), (S)-tert-butyl piperidin-3-ylcarbamate (2.328 g, 11.62 mmol), cesium carbonate (7.89 g, 24.21 mmol), BINAP (0.302 g, 0.484 mmol), and Pd$_2$(dba)$_3$ (0.443 g, 0.484 mmol) in 1,4-dioxane (80 mL) was degassed with nitrogen and stirred at 105° C. for 19 hours. LC/MS indicated 90% conversion. Additional Pd$_2$(dba)$_3$ (0.443 g, 0.484 mmol) and BINAP (0.030 g, 0.048 mmol) were added. The reaction mixture was stirred at 110° C. for 9 hours. The mixture was cooled to room temperature and filtered through CELITE® and concentrated. The crude material was dissolved in DCM and stirred overnight. The solids were collected by vacuum filtration and washed with DCM to afford (S)-tert-butyl (1-(1-cyano-3-fluoro-9H-carbazol-4-yl)piperidin-3-yl)carbamate (3.24 g, 82% yield) as an off-white solid. Mass spectrum m/z 409 (M+H)$^+$.

Intermediate 85B: tert-Butyl (S)-(1-(1-cyano-3-fluoro-9H-carbazol-4-yl)piperidin-3-yl) Carbamate

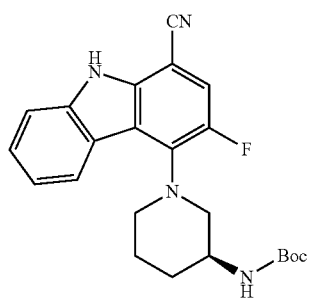

(I-85B)

Aqueous H$_2$O$_2$ (30%, 5.95 ml, 58.3 mmol) was added dropwise over 30 minutes to a solution of (S)-tert-butyl (1-(1-cyano-3-fluoro-9H-carbazol-4-yl)piperidin-3-yl) carbamate (2.38 g, 5.83 mmol) and 30% aqueous KOH (5.45 ml, 29.1 mmol) in DMSO and stirred at room temperature for 1.5 hours. The conversion was 95%. Added additional 30% aqueous H$_2$O$_2$ (1 mL) was added and the reaction mixture was stirred for 30 minutes. The mixture was diluted with water and stirred for 30 minutes. The solids were collected by vacuum filtration and washed with water. Then, the product was triturated with DCM to afford the crude (S)-tert-butyl (1-(1-carbamoyl-3-fluoro-9H-carbazol-4-yl)piperidin-3-yl)carbamate (2.56 g, 103% yield) as a light yellow solid. Mass spectrum m/z 427 (M+H)$^+$.

Intermediate 85

A solution of (S)-tert-butyl (1-(1-carbamoyl-3-fluoro-9H-carbazol-4-yl)piperidin-3-yl)carbamate (3.09 g, 7.25 mmol) and TFA (8 mL, 104 mmol) in DCM (8 mL) was stirred at room temperature for 30 min. The mixture was concentrated, neutralized using saturated NaHCO$_3$, extracted with EtOAc (3×), washed with water, dried (MgSO$_4$), and concentrated to afford the crude (S)-4-(3-aminopiperidin-1-yl)-3-fluoro-9H-carbazole-1-carboxamide (2.43 g, 103% yield) as a light yellow foam. Mass spectrum m/z 327 (M+H)$^+$.

Example 1

(RS)-5-(3-Acrylamidophenyl)-2-(2-hydroxypropan-2-yl)-2,3,4,9-tetrahydro-1H-carbazole-8-carboxamide

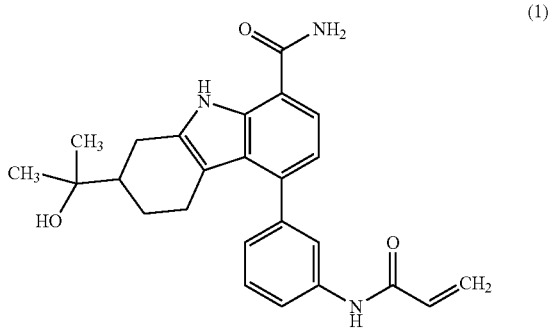 [SMILES: C=CC(=O)Nc1cccc(-c2ccc(C(N)=O)c3[nH]c4c(c23)CCC(C(C)(C)O)C4)c1]
(1)

A mixture of (RS)-5-bromo-2-(2-hydroxypropan-2-yl)-2,3,4,9-tetrahydro-1H-carbazole-8-carboxamide [prepared according to U.S. Pat. No. 8,084,620, Example 73-1] (35 mg, 0.100 mmol), N-(3-(4,4,5,5-tetramethyl-1,3,2-dioxaborolan-2-yl)phenyl) acrylamide [Intermediate 49] (28.6 mg, 0.105 mmol), and tetrakis(triphenylphosphine) palladium (5.76 mg, 4.98 µmol) in toluene (1.87 mL) and ethanol (623 µL) was bubbled with nitrogen for 2-5 min. The mixture was treated with 2 M aqueous $Na_2CO_3$ (126 µL, 0.252 mmol), bubbled again with nitrogen, and sealed in a glass tube. The mixture was heated at 90° C. for 16 h. The mixture was concentrated and the residue was subjected to preparative reverse-phase HPLC (Waters XBridge $C_{18}$ column, 5 µm, 19×150 mm, eluting with acetonitrile-10 mM aqueous ammonium acetate, gradient from 5-95%, 20 mL/min). Concentration of the appropriate effluent fractions under high vacuum provided (RS)-5-(3-acrylamidophenyl)-2-(2-hydroxypropan-2-yl)-2,3,4,9-tetrahydro-1H-carbazole-8-carboxamide (28.4 mg, 68% yield). Mass spectrum m/z 418 (M+H)$^+$. $^1$H NMR (500 MHz, DMSO-d$_6$) δ 10.80 (s, 1H), 10.22 (s, 1H), 8.02 (br. s., 1H), 7.75-7.68 (m, 2H), 7.60 (d, J=7.4 Hz, 1H), 7.39 (t, J=7.7 Hz, 1H), 7.33 (br. s., 1H), 7.10 (d, J=7.4 Hz, 1H), 6.82 (d, J=7.9 Hz, 1H), 6.45 (dd, J=17.1, 10.2 Hz, 1H), 6.26 (dd, J=16.8, 1.5 Hz, 1H), 5.79-5.72 (m, 1H), 4.21 (s, 1H), 2.93 (dd, J=16.8, 5.0 Hz, 1H), 2.47-2.41 (m, 1H), 2.28 (t, J=12.4 Hz, 1H), 2.00 (d, J=12.9 Hz, 1H), 1.89 (d, J=8.9 Hz, 1H), 1.72-1.61 (m, 1H), 1.10 (d, J=2.0 Hz, 7H).

Example 2

(RS)-2-(2-Hydroxypropan-2-yl)-5-(2-methyl-3-(N-methylvinylsulfonamido)phenyl)-2,3,4,9-tetrahydro-1H-carbazole-8-carboxamide

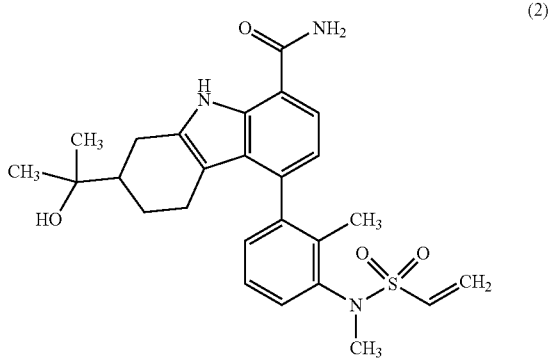 [SMILES: C=CS(=O)(=O)N(C)c1cccc(-c2ccc(C(N)=O)c3[nH]c4c(c23)CCC(C(C)(C)O)C4)c1C]
(2)

A mixture of (RS)-5-bromo-2-(2-hydroxypropan-2-yl)-2,3,4,9-tetrahydro-1H-carbazole-8-carboxamide [prepared according to U.S. Pat. No. 8,084,620, Example 73-1] (35 mg, 0.100 mmol), N-methyl-N-(2-methyl-3-(4,4,5,5-tetramethyl-1,3,2-dioxaborolan-2-yl)phenyl)ethenesulfonamide [Intermediate 55] (33.6 mg, 0.100 mmol), and $Cs_2CO_3$ (81 mg, 0.249 mmol) in 4:1 THF-water (3.32 mL) was bubbled with nitrogen, then treated with $PdCl_2$(dppf) DCM adduct (4.1 mg, 5.0 µmol). The mixture was bubbled further with nitrogen, sealed in a tube under nitrogen and heated at 50° C. After 16 h, the mixture was cooled and concentrated. The residue was subjected to preparative reverse-phase HPLC (Waters XBridge Cis column, 5 µm, 19×250 mm, eluting with acetonitrile-10 mM aqueous ammonium acetate, gradient from 5-95%, 20 mL/min). Concentration of the appropriate effluent fractions under high vacuum provided (RS)-2-(2-hydroxypropan-2-yl)-5-(2-methyl-3-(N-methylvinylsulfonamido) phenyl)-2,3,4,9-tetrahydro-1H-carbazole-8-carboxamide (24.6 mg, 51% yield). Mass spectrum m/z 482 (M+H)$^+$. $^1$H NMR (500 MHz, DMSO-d$_6$) δ 10.75 (d, J=19.8 Hz, 1H), 8.02 (br. s., 1H), 7.59 (d, J=7.4 Hz, 1H), 7.39-7.24 (m, 3H), 7.21-7.12 (m, 1H), 7.10-7.00 (m, 1H), 6.79-6.67 (m, 1H), 6.24-5.99 (m, 2H), 4.20-4.13 (m, 1H), 3.19-3.05 (m, 3H), 2.95-2.82 (m, 1H), 2.47-2.31 (m, 1H), 2.11-1.47 (m, 7H), 1.22-0.97 (m, 7H).

Example 3

5-(3-Acrylamido-2-methylphenyl)-2,2-dimethyl-2,3,4,9-tetrahydro-1H-carbazole-8-carboxamide

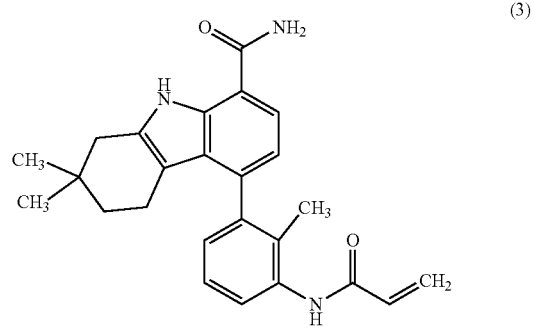 [SMILES: C=CC(=O)Nc1cccc(-c2ccc(C(N)=O)c3[nH]c4c(c23)CCC(C)(C)C4)c1C]
(3)

A mixture of 5-bromo-2,2-dimethyl-2,3,4,9-tetrahydro-1H-carbazole-8-carboxamide [Intermediate 3] (35 mg, 0.109 mmol), N-(2-methyl-3-(4,4,5,5-tetramethyl-1,3,2-dioxaborolan-2-yl)phenyl)acrylamide [Intermediate 50] (37.5 mg, 0.131 mmol) and 2.0 M aqueous $K_3PO_4$ (0.20 mL, 0.400 mmol) in THF (0.80 mL) was bubbled with argon for 1 min with sonication. The mixture was treated with $PdCl_2$ (dppf) DCM adduct (6.67 mg, 8.17 µmol). The reaction vessel was sealed and subjected to 5 evacuate-fill cycles with argon. The mixture was stirred at 50° C. for 16.75 h, cooled to room temperature, diluted with MeOH and concentrated. The residue was purified by preparative reverse-phase HPLC (PHENOMENEX® Axia Cis column, 5 µm, 30×100 mm, eluting with acetonitrile-water containing 0.1% TFA, gradient from 10-100%, 30 mL/min). The appropriate fractions were combined, treated with saturated aqueous $NaHCO_3$ (3-4 mL) and concentrated to an aqueous suspension. This was extracted twice with EtOAc, and the combined organic phases were dried and concentrated to provide 5-(3-acrylamido-2-methylphenyl)-2,2-dimethyl-2,3,4,9-tetrahydro-1H-carbazole-8-carboxamide as a light brown solid (16.7 mg, 36% yield). Mass spectrum m/z 402 (M+H)$^+$. $^1$H NMR (400 MHz, DMSO-d$_6$) δ 10.73 (s, 1H), 9.58 (s, 1H), 8.00 (br. s., 1H), 7.61 (d, J=7.5 Hz, 1H), 7.52 (d, J=7.9 Hz, 1H), 7.30 (br. s., 1H), 7.24 (t, J=7.7 Hz, 1H), 7.04 (d, J=7.5 Hz, 1H), 6.72 (d, J=7.7 Hz, 1H), 6.56 (dd, J=17.2, 10.1 Hz, 1H), 6.26 (dd, J=17.2, 2.0 Hz, 1H), 5.75 (dd, J=10.2, 1.9 Hz, 1H), 2.53 (br. s., 3H), 1.98-1.72 (m, 4H), 1.30 (t, J=2.0 Hz, 2H), 0.94 (d, J=4.2 Hz, 6H).

Example 4

4-(3-Acrylamido-2-methylphenyl)-7-(2-hydroxypropan-2-yl)-9H-carbazole-1-carboxamide

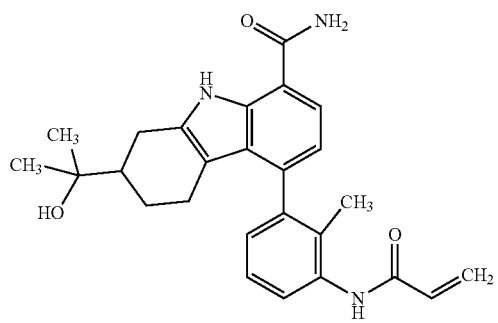

(4)

A mixture of 7-(2-hydroxypropan-2-yl)-4-(4,4,5,5-tetramethyl-1,3,2-dioxaborolan-2-yl)-9H-carbazole-1-carboxamide [Intermediate 27] (35 mg, 0.089 mmol), N-(3-bromo-2-methylphenyl)acrylamide [Intermediate 45] (30.1 mg, 0.107 mmol), and 2 M aqueous $Na_2CO_3$ (89 µl, 0.178 mmol) in toluene (1.33 mL) and ethanol (0.44 mL) was bubbled with argon for 5-10 min. The mixture was treated with tetrakis (triphenylphosphine)palladium (5.1 mg, 4.44 µmol) and the vessel was sealed and heated at 90° C. for 16 h. The mixture was cooled to room temperature, diluted with MeOH and DMSO and filtered. The filtrate was concentrated and purified by preparative reverse-phase HPLC (Waters XBridge $C_{18}$ column, 5 µm, 19×250 mm, eluting with acetonitrile-10 mM aqueous ammonium acetate, gradient from 5-95%, 20 mL/min). Concentration of the appropriate effluent fractions under high vacuum provided 4-(3-acrylamido-2-methylphenyl)-7-(2-hydroxypropan-2-yl)-9H-carbazole-1-carboxamide (5.9 mg, 16% yield). Mass spectrum m/z 410 $(M+H-H_2O)^+$. $^1H$ NMR (500 MHz, MeOH-$d_4$) δ 7.87 (d, J=7.4 Hz, 1H), 7.68 (d, J=1.0 Hz, 1H), 7.64 (d, J=7.9 Hz, 1H), 7.37 (t, J=7.9 Hz, 1H), 7.22 (d, J=7.4 Hz, 1H), 7.06 (dd, J=8.4, 2.0 Hz, 1H), 7.02 (d, J=7.4 Hz, 1H), 6.94 (d, J=8.4 Hz, 1H), 6.57-6.47 (m, 1H), 6.45-6.37 (m, 1H), 5.83-5.74 (m, 1H), 1.97 (s, 3H), 1.58 (s, 6H).

Example 5

(RS)-2-(2-Hydroxypropan-2-yl)-5-(3-(vinylsulfonamido)phenyl)-2,3,4,9-tetrahydro-1H-carbazole-8-carboxamide

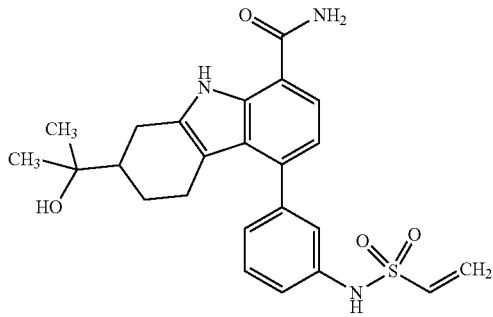

(5)

A mixture of (RS)-2-(2-hydroxypropan-2-yl)-5-(4,4,5,5-tetramethyl-1,3,2-dioxaborolan-2-yl)-2,3,4,9-tetrahydro-1H-carbazole-8-carboxamide [Intermediate 28] (40 mg, 0.100 mmol), N-(3-bromophenyl)ethenesulfonamide [Intermediate 48] (29 mg, 0.110 mmol), and $Cs_2CO_3$ (82 mg, 0.251 mmol) in 4:1 THF-water (3.35 mL) was bubbled with nitrogen, then treated with $PdCl_2$(dppf) DCM adduct (4.10 mg, 5.02 µmol). The mixture was bubbled further with nitrogen, the reaction vessel was sealed under a nitrogen atmosphere, and the mixture was heated at 50° C. for 19 h. The mixture was cooled to room temperature and concentrated. The residue was purified by preparative reverse-phase HPLC (Waters XBridge $C_{18}$ column, 5 µm, 19×250 mm, eluting with acetonitrile-10 mM aqueous ammonium acetate, gradient from 5-95%, 20 mL/min). Concentration of the appropriate effluent fractions under high vacuum provided (RS)-2-(2-hydroxypropan-2-yl)-5-(3-(vinylsulfonamido)phenyl)-2,3,4,9-tetrahydro-1H-carbazole-8-carboxamide (22.8 mg, 50% yield). Mass spectrum m/z 454 $(M+H-H_2O)^+$. $^1H$ NMR (500 MHz, DMSO-$d_6$) δ 10.81 (s, 1H), 10.09 (s, 1H), 8.01 (br. s., 1H), 7.59 (d, J=7.4 Hz, 1H), 7.39-7.29 (m, 2H), 7.19 (dd, J=8.2, 1.2 Hz, 1H), 7.16-7.13 (m, 1H), 7.11 (d, J=7.4 Hz, 1H), 6.85-6.76 (m, 2H), 6.13-6.00 (m, 2H), 4.22 (s, 1H), 2.92 (dd, J=17.1, 4.7 Hz, 1H), 2.44 (d, J=15.9 Hz, 1H), 2.30-2.20 (m, 1H), 1.98-1.84 (m, 2H), 1.65 (td, J=11.9, 4.0 Hz, 1H), 1.11 (s, 7H).

Additional Examples which were prepared by procedures described in Examples 1 through 5 or similar procedures, using the indicated starting materials, are shown in Table 2.

TABLE 2

| Example, Description | Structure | Starting Materials | Mass Spectrum |
|---|---|---|---|
| 6 (racemate) | ![structure] | Intermediates 10, 50 | m/z 404, 446 $(M + H - H_2O)^+$ |

TABLE 2-continued

| Example, Description | Structure | Starting Materials | Mass Spectrum |
|---|---|---|---|
| 7 (racemate) | 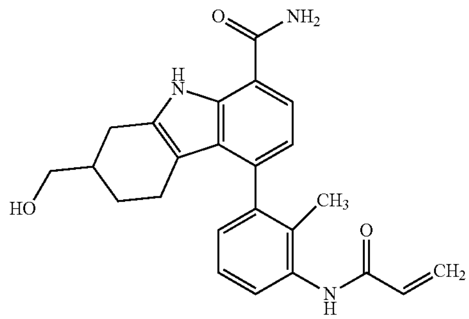 [SMILES: C=CC(=O)Nc1cccc(-c2ccc(C(N)=O)c3[nH]c4c(c23)CCC(CO)C4)c1C] | Intermediate 50; (b) | m/z 404 (M + H)+ |
| 8 (mixture of diastereomers) | 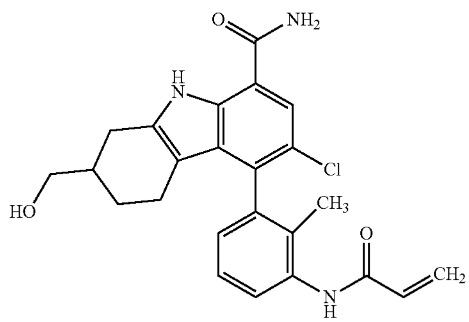 [SMILES: C=CC(=O)Nc1cccc(-c2c(Cl)cc(C(N)=O)c3[nH]c4c(c23)CCC(CO)C4)c1C] | Intermediates 20, 50 | m/z 438, 440 (M + H)+ |
| 9 (mixture of diastereomers) | 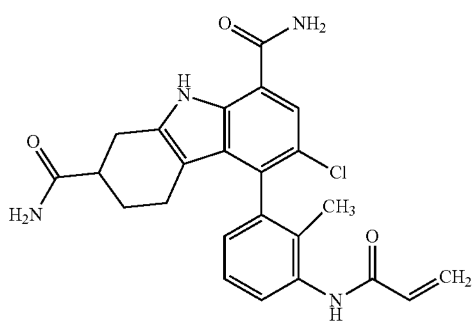 [SMILES: C=CC(=O)Nc1cccc(-c2c(Cl)cc(C(N)=O)c3[nH]c4c(c23)CCC(C(N)=O)C4)c1C] | Intermediates 23, 50 | m/z 451, 453 (M + H)+ |
| 10 (racemate) | 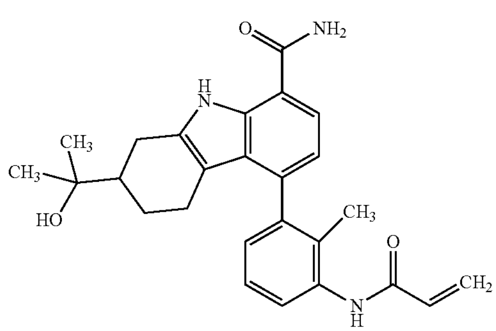 [SMILES: C=CC(=O)Nc1cccc(-c2ccc(C(N)=O)c3[nH]c4c(c23)CCC(C(C)(C)O)C4)c1C] | Intermediate 50; (c) | m/z 432 (M + H)+ |

TABLE 2-continued
| Example, Description | Structure | Starting Materials | Mass Spectrum |
|---|---|---|---|
| 11 (racemate) | 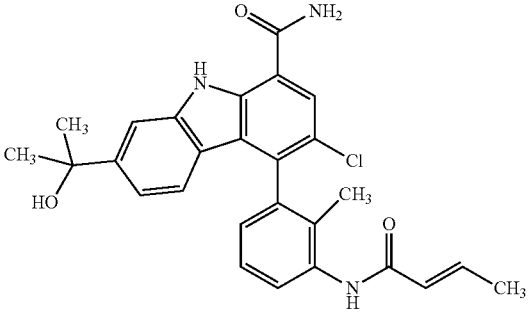 [SMILES: C/C=C/C(=O)Nc1cccc(-c2c(Cl)cc(C(N)=O)c3[nH]c4cc(C(C)(C)O)ccc4c23)c1C] | Intermediates 10, 51 | m/z 458 (M + H − H₂O)⁺ |
| 12 (achiral) | 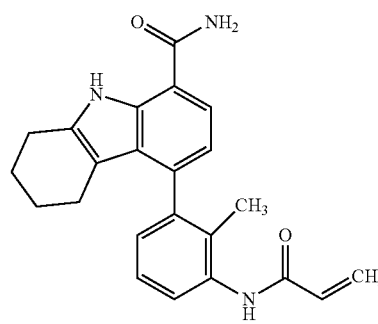 | Intermediates 1, 50 | m/z 374 (M + H)⁺ |
| 13 (racemate) | 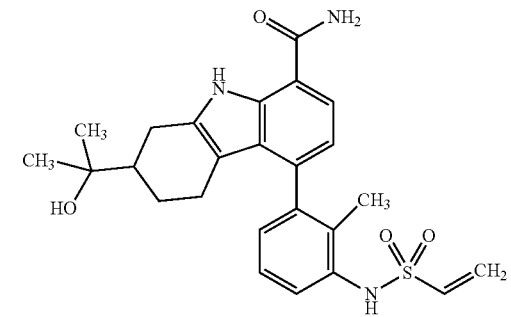 [SMILES: C=CS(=O)(=O)Nc1cccc(-c2ccc(C(N)=O)c3[nH]c4c(c23)CCC(C(C)(C)O)C4)c1C] | Intermediate 57; (c) | m/z 468 (M + H)⁺ |
| 14 (racemate) | 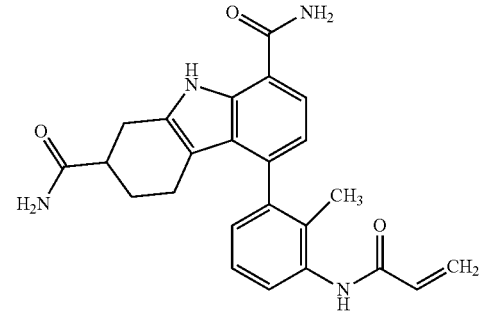 [SMILES: C=CC(=O)Nc1cccc(-c2ccc(C(N)=O)c3[nH]c4c(c23)CCC(C(N)=O)C4)c1C] | Intermediates 25, 50 | m/z 417 (M + H)⁺ |
| 15 (achiral) | 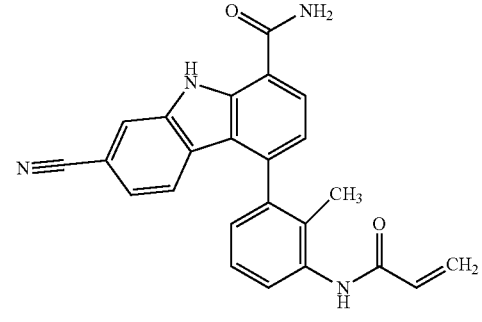 [SMILES: C=CC(=O)Nc1cccc(-c2ccc(C(N)=O)c3[nH]c4cc(C#N)ccc4c23)c1C] | Intermediates 7, 50 | m/z 395 (M + H)⁺ |

TABLE 2-continued
| Example, Description | Structure | Starting Materials | Mass Spectrum |
|---|---|---|---|
| 16 (racemate) | 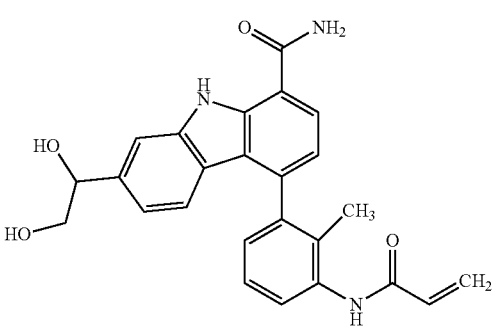 [SMILES: C=CC(=O)Nc1cccc(-c2ccc(C(N)=O)c3[nH]c4cc(C(O)CO)ccc4c23)c1C] | Intermediate 50; (e) | m/z 429 (M + H − H₂O)⁺ |
| 17 (achiral) | 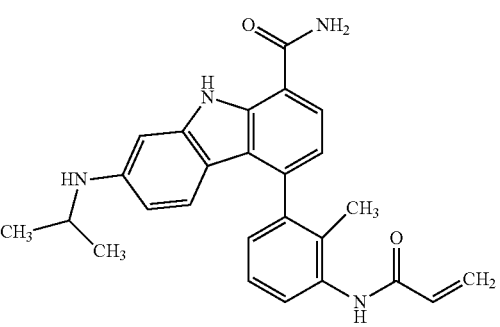 [SMILES: C=CC(=O)Nc1cccc(-c2ccc(C(N)=O)c3[nH]c4cc(NC(C)C)ccc4c23)c1C] | Intermediate 50; (f) | m/z 427 (M + H)⁺ |
| 18 (racemate) | 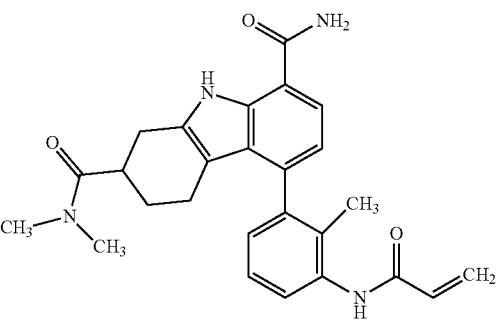 [SMILES: C=CC(=O)Nc1cccc(-c2ccc(C(N)=O)c3[nH]c4c(c23)CCC(C(=O)N(C)C)C4)c1C] | Intermediates 24, 50 | m/z 445 (M + H)⁺ |
| 19 (racemate) | 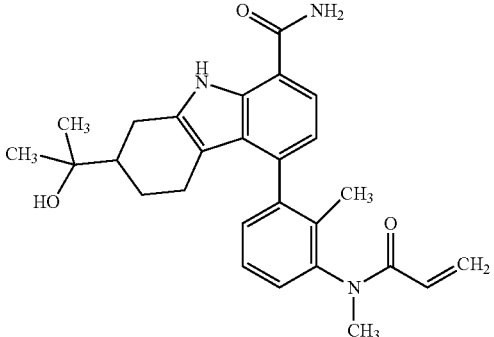 | Intermediate 52; (c) | m/z 446 (M + H)⁺ |

TABLE 2-continued
| Example, Description | Structure | Starting Materials | Mass Spectrum |
|---|---|---|---|
| 20 (racemate) | 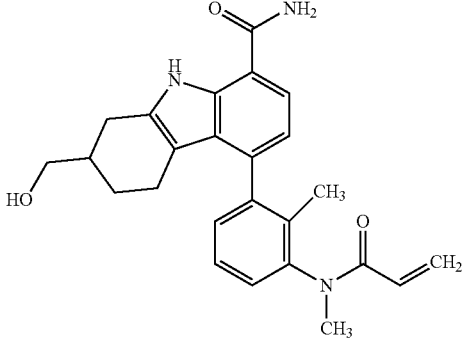 [SMILES: C=CC(=O)N(C)c1cccc(-c2ccc(C(N)=O)c3[nH]c4c(c23)CCC(CO)C4)c1C] | Intermediate 52; (b) | m/z 418 (M + H)+ |
| 21 (racemate) | 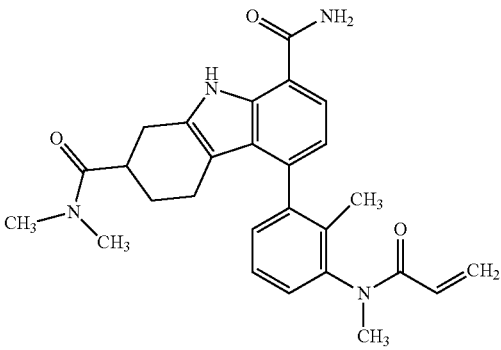 [SMILES: C=CC(=O)N(C)c1cccc(-c2ccc(C(N)=O)c3[nH]c4c(c23)CCC(C(=O)N(C)C)C4)c1C] | Intermediates 24, 52 | m/z 459 (M + H)+ |
| 22 (mixture of diastereomers) | 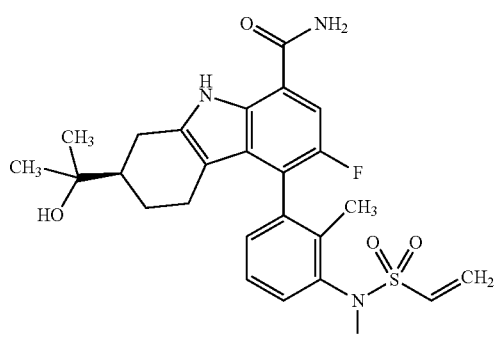 | Intermediates 17, 55 | m/z 500 (M + H)+ |
| 23 (mixture of diastereomers) | 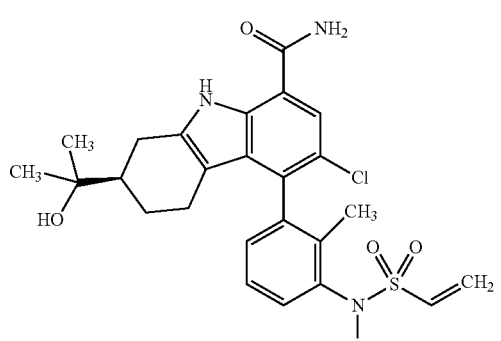 | Intermediates 13, 55 | m/z 516, 518 (M + H)+ |

TABLE 2-continued

| Example, Description | Structure | Starting Materials | Mass Spectrum |
|---|---|---|---|
| 24 (single enantiomer) | 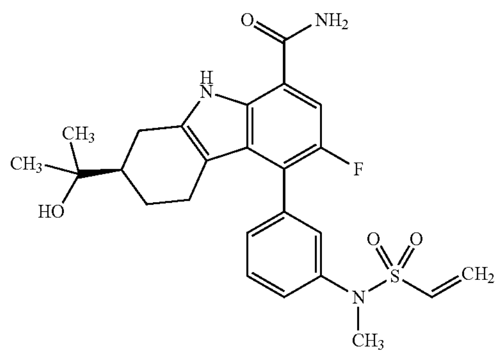 | Intermediates 17, 56 | m/z 486 (M + H)+ |
| 25 (single enantiomer) | 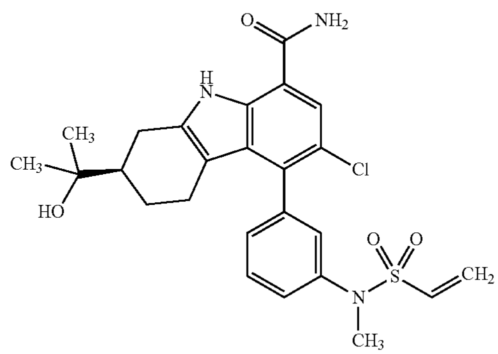 [SMILES: C=CS(=O)(=O)N(C)c1cccc(-c2c(Cl)cc(C(N)=O)c3[nH]c4c(c23)CC[C@@H](C(C)(C)O)C4)c1] | Intermediates 13, 56 | m/z 502, 504 (M + H)+ |
| 26 (racemate) | 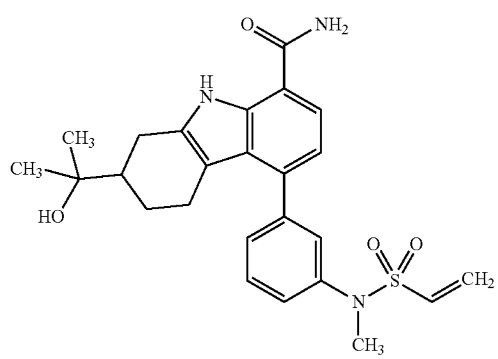 [SMILES: C=CS(=O)(=O)N(C)c1cccc(-c2ccc(C(N)=O)c3[nH]c4c(c23)CCC(C(C)(C)O)C4)c1] | Intermediate 56; (c) | m/z 468 (M + H)+ |
| 27 (achiral) | 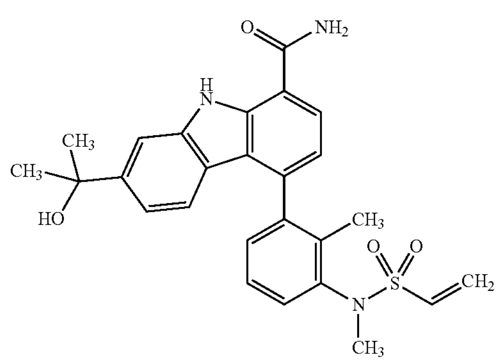 [SMILES: C=CS(=O)(=O)N(C)c1cccc(-c2ccc(C(N)=O)c3[nH]c4cc(C(C)(C)O)ccc4c23)c1C] | Intermediate 55; (a) | m/z 478 (M + H)+ |

TABLE 2-continued

| Example, Description | Structure | Starting Materials | Mass Spectrum |
|---|---|---|---|
| 28 (achiral) | (carbazole structure with 7-(2-hydroxypropan-2-yl) group, 1-carboxamide, 4-[3-(N-methyl-N-vinylsulfonylamino)phenyl]) | Intermediate 56; (a) | m/z 446 (M + H − H₂O)⁺ |
| 29 (racemate) | (carbazole structure with 7-(2-hydroxypropan-2-yl), 1-carboxamide, 3-fluoro, 4-[2-methyl-3-(vinylsulfonylamino)phenyl]) | Intermediates 19, 57 | m/z 464 (M + H − H₂O)⁺ |
| 30 (racemate) | (carbazole structure with 7-(2-hydroxypropan-2-yl), 1-carboxamide, 3-fluoro, 4-[2-methyl-3-(N-methyl-N-vinylsulfonylamino)phenyl]) | Intermediates 19, 55 | m/z 478 (M + H − H₂O)⁺ |
| 31 (achiral) | (carbazole structure with 7-(2-hydroxypropan-2-yl), 1-carboxamide, 3-fluoro, 4-[3-(N-methyl-N-vinylsulfonylamino)phenyl]) | Intermediates 19, 56 | m/z 464 (M + H − H₂O)⁺ |

TABLE 2-continued

| Example, Description | Structure | Starting Materials | Mass Spectrum |
|---|---|---|---|
| 32 (achiral) | 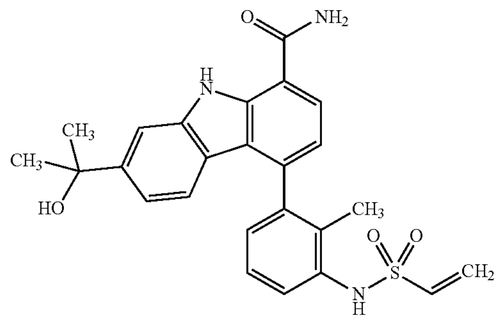 [SMILES: C=CS(=O)(=O)Nc1cccc(-c2ccc(C(N)=O)c3[nH]c4cc(C(C)(C)O)ccc4c23)c1C] | Intermediate 57; (a) | m/z 446 (M + H − H₂O)⁺ |
| 33 (achiral) | 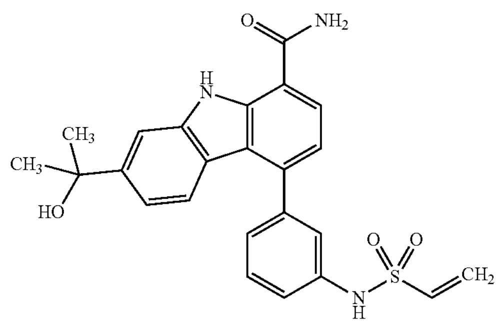 [SMILES: C=CS(=O)(=O)Nc1cccc(-c2ccc(C(N)=O)c3[nH]c4cc(C(C)(C)O)ccc4c23)c1] | Intermediate 58; (a) | m/z 432 (M + H − H₂O)⁺ |
| 34 (achiral) | 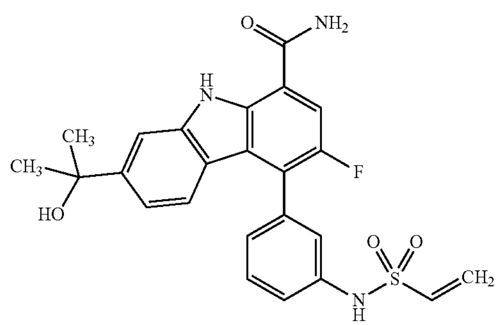 [SMILES: C=CS(=O)(=O)Nc1cccc(-c2c(F)cc(C(N)=O)c3[nH]c4cc(C(C)(C)O)ccc4c23)c1] | Intermediates 19, 58 | m/z 450 (M + H − H₂O)⁺ |
| 35 (racemate) | 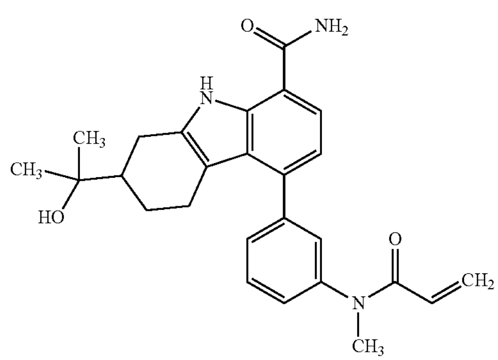 [SMILES: C=CC(=O)N(C)c1cccc(-c2ccc(C(N)=O)c3[nH]c4c(c23)CCC(C(C)(C)O)C4)c1] | Intermediates 53; (c) | m/z 432 (M + H)⁺ |

TABLE 2-continued

| Example, Description | Structure | Starting Materials | Mass Spectrum |
|---|---|---|---|
| 36 (single enantiomer) | (structure) | Intermediates 17, 53 | m/z 450 (M + H)+ |
| 37 (achiral) | (structure) | Intermediate 53; (a) | m/z 410 (M + H − H2O)+ |
| 38 (achiral) | (structure) | Intermediates 19, 53 | m/z 428 (M + H − H2O)+ |
| 39 (single enantiomer) | (structure) | Intermediates 13, 53 | m/z 466, 468 (M + H)+ |

TABLE 2-continued

| Example, Description | Structure | Starting Materials | Mass Spectrum |
|---|---|---|---|
| 40 (single enantiomer) | [structure] | Intermediates 15, 58 | m/z 454 (M + H)+ |
| 41 (single enantiomer) | [structure] | Intermediates 16, 58 | m/z 454 (M + H)+ |
| 42 (racemate) | [structure] | Intermediates 54;(c) | m/z 450 (M + H)+ |
| 43 (single diastereomer) | [structure] | Intermediates 17, 58 | m/z 472 (M + H)+ |

TABLE 2-continued

| Example, Description | Structure | Starting Materials | Mass Spectrum |
|---|---|---|---|
| 44 (mixture of diastereomers) | 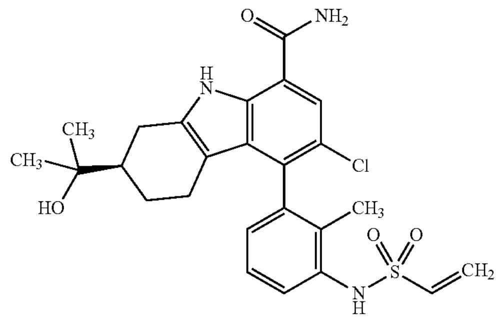 [SMILES: C=CS(=O)(=O)Nc1cccc(-c2c(Cl)cc(C(N)=O)c3[nH]c4c(c23)CC[C@@H](C(C)(C)O)C4)c1C] | Intermediates 13, 57 | m/z 502, 504 (M + H)+ |
| 45 (racemate) | 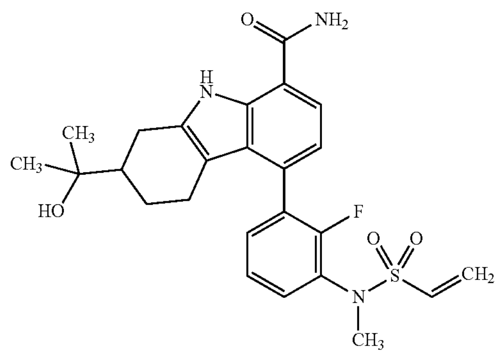 [SMILES: C=CS(=O)(=O)N(C)c1cccc(-c2ccc(C(N)=O)c3[nH]c4c(c23)CCC(C(C)(C)O)C4)c1F] | Intermediates 59; (c) | m/z 486 (M + H)+ |
| 46 (racemate) | 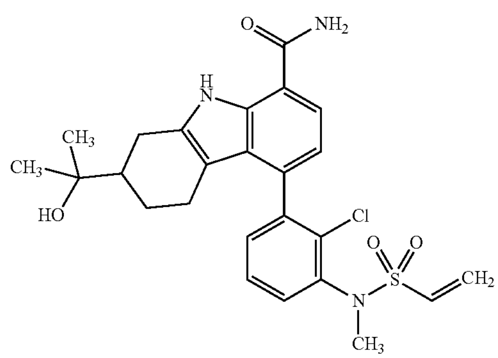 [SMILES: C=CS(=O)(=O)N(C)c1cccc(-c2ccc(C(N)=O)c3[nH]c4c(c23)CCC(C(C)(C)O)C4)c1Cl] | Intermediates 60; (c) | m/z 502, 504 (M + H)+ |
| 47 (mixture of diastereomers) | 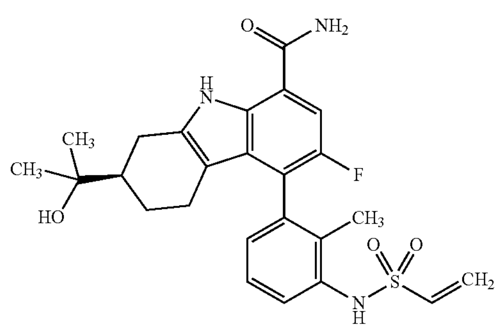 | Intermediates 17, 57 | m/z 486 (M + H)+ |

TABLE 2-continued

| Example, Description | Structure | Starting Materials | Mass Spectrum |
|---|---|---|---|
| 48 (achiral) | 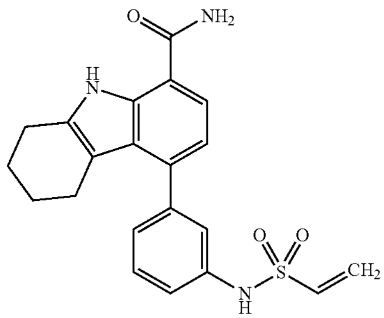 [SMILES: C=CS(=O)(=O)Nc1cccc(-c2ccc(C(N)=O)c3[nH]c4c(c23)CCCC4)c1] | Intermediates 1, 58 | m/z 396 (M + H)+ |
| 49 (achiral) | 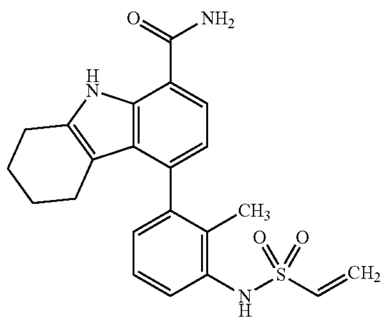 [SMILES: C=CS(=O)(=O)Nc1cccc(-c2ccc(C(N)=O)c3[nH]c4c(c23)CCCC4)c1C] | Intermediates 1, 57 | m/z 410 (M + H)+ |
| 50 (racemate) | 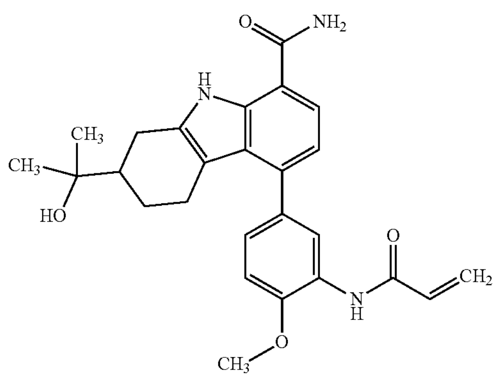 | Intermediates 28, 44 | m/z 448 (M + H)+ |
| 51 (racemate) | 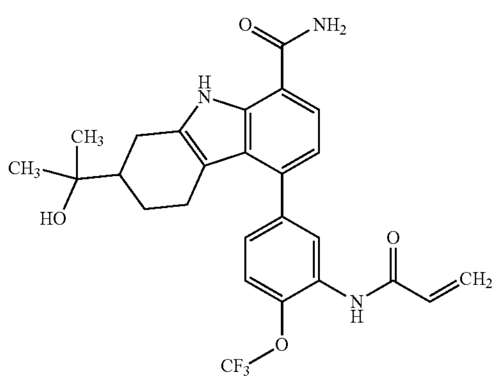 [SMILES: C=CC(=O)Nc1cc(-c2ccc(C(N)=O)c3[nH]c4c(c23)CCC(C(C)(C)O)C4)ccc1OC(F)(F)F] | Intermediates 28, 46 | m/z 502 (M + H)+ |

TABLE 2-continued

| Example, Description | Structure | Starting Materials | Mass Spectrum |
|---|---|---|---|
| 52 (racemate) | 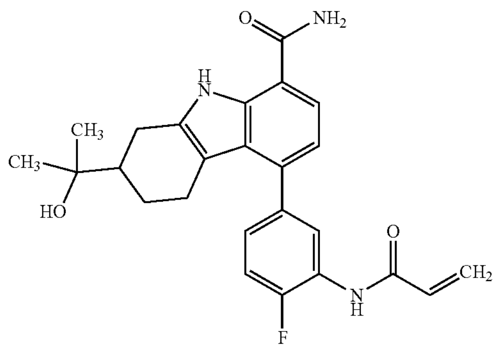 [SMILES: C=CC(=O)Nc1cc(-c2ccc(C(N)=O)c3[nH]c4c(c23)CCC(C(C)(C)O)C4)ccc1F] | Intermediates 28, 47 | m/z 436 (M + H)+ |
| 53 (racemate) | 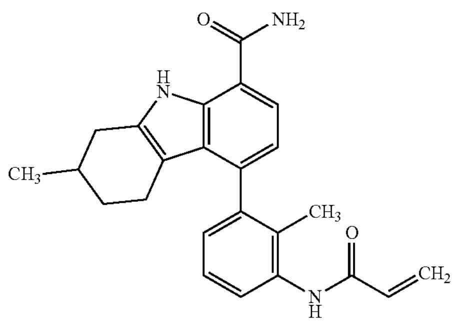 [SMILES: C=CC(=O)Nc1cccc(-c2ccc(C(N)=O)c3[nH]c4c(c23)CCC(C)C4)c1C] | Intermediates 2, 50 | m/z 388 (M + H)+ |
| 54 (racemate) | 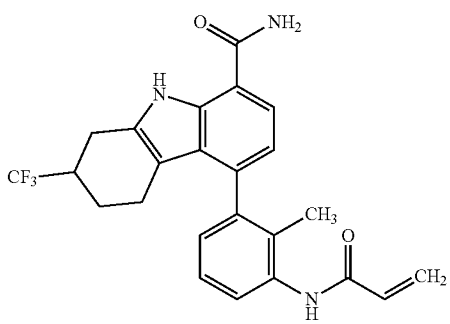 [SMILES: C=CC(=O)Nc1cccc(-c2ccc(C(N)=O)c3[nH]c4c(c23)CCC(C(F)(F)F)C4)c1C] | Intermediates 4, 50 | m/z 442 (M + H)+ |
| 4* (achiral) | 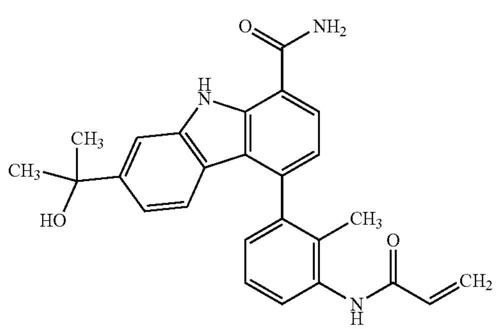 [SMILES: C=CC(=O)Nc1cccc(-c2ccc(C(N)=O)c3[nH]c4cc(C(C)(C)O)ccc4c23)c1C] | Intermediate 50; (a) | m/z 410 (M + H − H$_2$O)+ |

(a) Example 73-2 of U.S. Patent No. 8,084,620;
(b) Example 30-3 of U.S. Patent No. 8,084,620;
(c) Example 73-1 of U.S. Patent No. 8,084,620;
(d) Example 1-3 of U.S. Patent No. 8,084,620;
(e) Example 68-1 of U.S. Patent No. 8,084,620;
(f) Example 61-5 of U.S. Patent No. 8,084,620.
*alternative preparation of Example 4

Examples 55 and 56

5-(3-Acrylamido-2-methylphenyl)-6-chloro-2-(hydroxymethyl)-2-methyl-2,3,4,9-tetrahydro-1H-carbazole-8-carboxamide (two diastereomeric racemates)

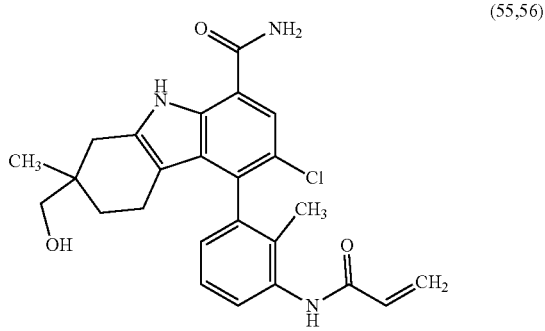 [SMILES: C=CC(=O)Nc1cccc(-c2c(Cl)cc(C(N)=O)c3[nH]c4c(c23)CCC(C)(CO)C4)c1C]

(55,56)

A mixture of (RS)-5-bromo-6-chloro-2-(hydroxymethyl)-2-methyl-2,3,4,9-tetrahydro-1H-carbazole-8-carboxamide [Intermediate 21] (35 mg, 0.094 mmol), N-(2-methyl-3-(4,4,5,5-tetramethyl-1,3,2-dioxaborolan-2-yl)phenyl)acrylamide [Intermediate 50] (29.7 mg, 0.104 mmol), and tetrakis(triphenylphosphine)palladium (5.44 mg, 4.71 μmol) in toluene (1.77 mL) and ethanol (0.59 mL) was bubbled with argon for about 2-5 min. The mixture was treated with 2 M aqueous $Na_2CO_3$ (0.12 mL, 0.24 mmol) bubbled again with argon, and the reaction vessel was sealed under an argon atmosphere and heated at 90° C. After 16 h, the mixture was cooled to room temperature and purified by preparative reverse-phase HPLC (Waters XBridge $C_{18}$ column, 5 μm, 19×250 mm, eluting with acetonitrile-10 mM aqueous ammonium acetate, gradient from 5-95%, 20 mL/min) to provide two products, which were diastereomeric racemates of 5-(3-acrylamido-2-methylphenyl)-6-chloro-2-(hydroxymethyl)-2-methyl-2,3,4,9-tetrahydro-1H-carbazole-8-carboxamide.

Example 55 (7.8 mg, 18% yield): Mass spectrum m/z 452, 454 (M+H)$^+$. $^1$H NMR (500 MHz, DMSO-$d_6$) δ 10.90 (s, 1H), 9.61 (s, 1H), 8.13 (br. s., 1H), 7.73 (s, 1H), 7.57 (d, J=7.9 Hz, 1H), 7.46 (br. s., 1H), 7.26 (t, J=7.7 Hz, 1H), 6.97 (d, J=6.9 Hz, 1H), 6.55 (dd, J=16.8, 10.4 Hz, 1H), 6.26 (dd, J=17.3, 2.0 Hz, 1H), 5.75 (dd, J=10.2, 1.7 Hz, 1H), 4.55 (t, J=5.2 Hz, 1H), 3.20-3.09 (m, 2H), 2.61 (d, J=17.3 Hz, 1H), 2.39 (d, J=16.8 Hz, 1H), 1.81 (s, 3H), 1.76-1.62 (m, 2H), 1.40-1.31 (m, 1H), 1.22-1.13 (m, 1H), 0.82 (s, 3H).

Example 56 (8.9 mg, 21% yield): Mass spectrum m/z 452, 454 (M+H)$^+$. $^1$H NMR (500 MHz, DMSO-$d_6$) δ 10.90 (s, 1H), 9.61 (s, 1H), 8.13 (br. s., 1H), 7.72 (s, 1H), 7.56 (d, J=7.9 Hz, 1H), 7.45 (br. s., 1H), 7.26 (t, J=7.9 Hz, 1H), 6.96 (d, J=7.4 Hz, 1H), 6.54 (dd, J=17.1, 10.2 Hz, 1H), 6.25 (dd, J=16.8, 2.0 Hz, 1H), 5.75 (dd, J=10.2, 1.7 Hz, 1H), 4.56 (t, J=5.4 Hz, 1H), 3.20-3.07 (m, 2H), 2.64 (d, J=17.3 Hz, 1H), 2.37 (d, J=16.8 Hz, 1H), 1.82 (s, 3H), 1.69 (d, J=5.0 Hz, 2H), 1.33 (dt, J=13.9, 6.9 Hz, 1H), 1.24-1.14 (m, 1H), 0.80 (s, 3H).

The relative configurations at C2 and the atropisomeric bond for Examples 55 and 56 have not been assigned.

Additional Examples which were prepared by procedures described for Examples 55 and 56 or similar procedures, using the indicated starting materials, are shown in Table 3. The relative configurations at C2 and the atropisomeric bond for the pairs of racemic diastereomers have not been assigned.

TABLE 3

| Example, Description | Structure | Starting Materials | Mass Spectrum |
|---|---|---|---|
| 57 (single racemic diastereomer) | 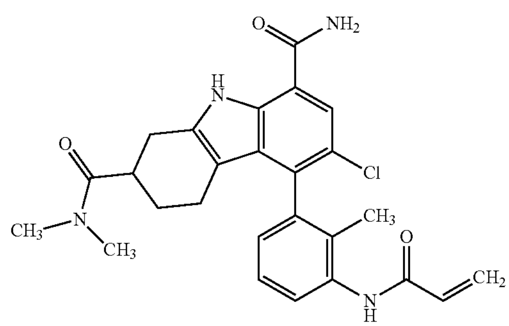 [SMILES: C=CC(=O)Nc1cccc(-c2c(Cl)cc(C(N)=O)c3[nH]c4c(c23)CCC(C(=O)N(C)C)C4)c1C] | Intermediates 22, 50 | m/z 479, 481 (M + H)$^+$ |
| 58 (single racemic diastereomer) | 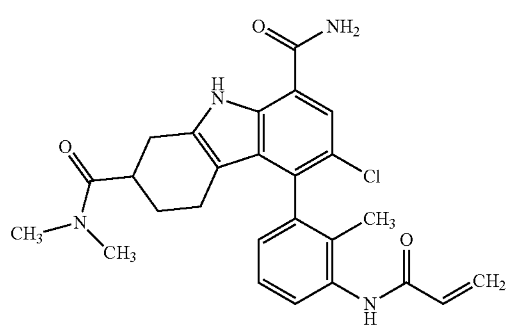 [SMILES: C=CC(=O)Nc1cccc(-c2c(Cl)cc(C(N)=O)c3[nH]c4c(c23)CCC(C(=O)N(C)C)C4)c1C] | Intermediates 22, 50 | m/z 479, 481 (M + H)$^+$ |

TABLE 3-continued
| Example, Description | Structure | Starting Materials | Mass Spectrum |
|---|---|---|---|
| 59 (single racemic diastereomer) | 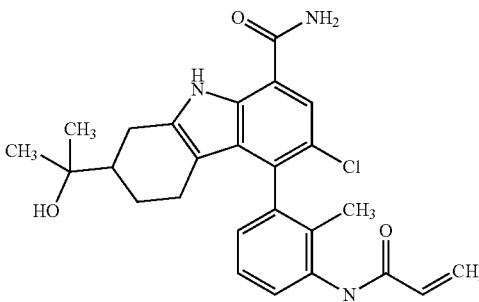 | Intermediates 11, 50 | m/z 466, 468 (M + H)+ |
| 60 (single racemic diastereomer) | 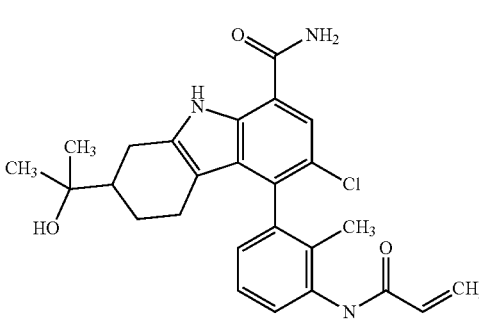 | Intermediates 11, 50 | m/z 466, 468 (M + H)+ |
| 61 (single racemic diastereomer) | 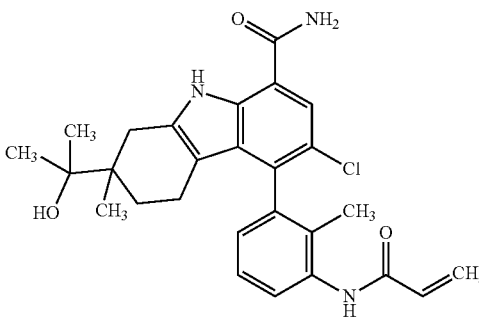 | Intermediates 26, 50 | m/z 480, 482 (M + H)+ |
| 62 (single racemic diastereomer) | 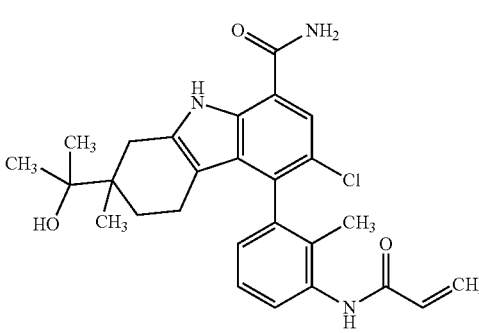 | Intermediates 26, 50 | m/z 480, 482 (M + H)+ |

Example 63

(S)-5-((1-Acryloylpyrrolidin-3-yl)amino)-2,3,4,9-tetrahydro-1H-carbazole-8-carboxamide

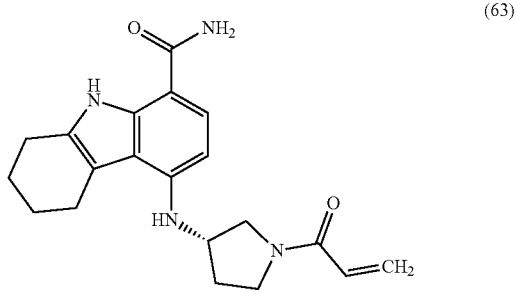 [SMILES: C=CC(=O)N1CC[C@H](Nc2ccc(C(N)=O)c3[nH]c4c(c23)CCCC4)C1]
(63)

A solution of (S)-5-(pyrrolidin-3-ylamino)-2,3,4,9-tetrahydro-1H-carbazole-8-carboxamide [Intermediate 33] (120 mg, 0.362 mmol) in THF (9 mL) and DCM (2 mL) was treated with DIEA (0.190 mL, 1.09 mmol). The solution was cooled to 0° C. and treated dropwise over 3 min with a solution of acryloyl chloride (0.024 mL, 0.290 mmol) in THF (1 mL). The mixture was stirred at 0° C. for 1.5 h, then was concentrated. The residue was purified by column chromatography on silica gel (24 g), eluting with EtOAc-hexanes, then with MeOH-DCM, to provide (S)-5-((1-acryloylpyrrolidin-3-yl)amino)-2,3,4,9-tetrahydro-1H-carbazole-8-carboxamide as a white solid (35 mg, 27% yield). Mass spectrum m/z 353 (M+H)$^+$. $^1$H NMR (400 MHz, DMSO-$d_6$) δ 10.47 (s, 1H), 7.58 (br. s., 1H), 7.46 (dd, J=8.1, 1.3 Hz, 1H), 6.88 (br. s., 1H), 6.69-6.51 (m, 1H), 6.23-6.09 (m, 2H), 5.67 (ddd, J=13.4, 10.6, 2.4 Hz, 1H), 5.01 (dd, J=8.6, 6.8 Hz, 1H), 4.34-4.12 (m, 1H), 3.82-3.39 (m, 4H), 2.92 (br. s., 2H), 2.69 (d, J=3.7 Hz, 2H), 2.39-2.17 (m, 1H), 2.15-1.89 (m, 1H), 1.76 (br. s., 4H).

Additional Examples which were prepared by procedures described for Example 63 or similar procedures, using the indicated starting material and the appropriate carboxylic acid chloride, are shown in Table 4.

TABLE 4

| Example, Description | Structure | Starting Material | Mass Spectrum |
|---|---|---|---|
| 64 (achiral) | 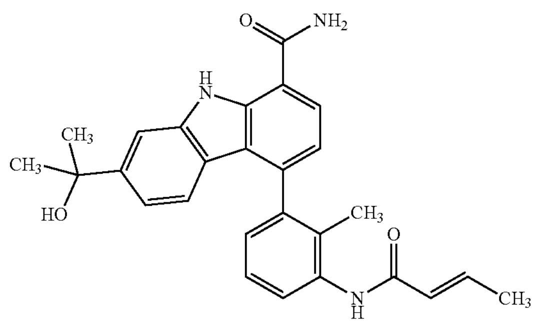 [SMILES: C/C=C/C(=O)Nc1cccc(-c2ccc(C(N)=O)c3[nH]c4cc(C(C)(C)O)ccc4c23)c1C] | (a) | m/z 424 (M + H − H$_2$O)$^+$ |
| 65 (diastereomer mixture) | 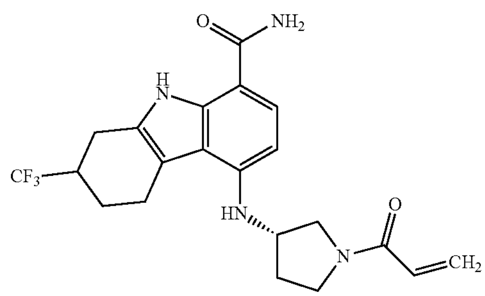 [SMILES: C=CC(=O)N1CC[C@H](Nc2ccc(C(N)=O)c3[nH]c4c(c23)CCC(C(F)(F)F)C4)C1] | Intermediate 34 | m/z 421 (M + H)$^+$ |
| 66 (homochiral) | 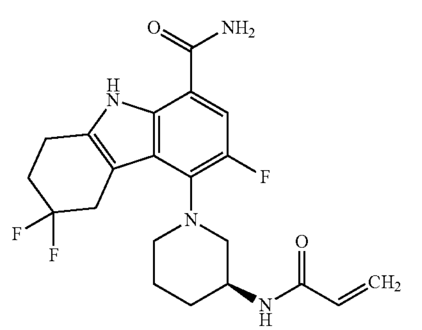 [SMILES: C=CC(=O)N[C@H]1CCCN(c2c(F)cc(C(N)=O)c3[nH]c4c(c23)CC(F)(F)CC4)C1] | Intermediate 32 | m/z 421 (M + H)$^+$ |

TABLE 4-continued

| Example, Description | Structure | Starting Material | Mass Spectrum |
|---|---|---|---|
| 69 (homochiral) | 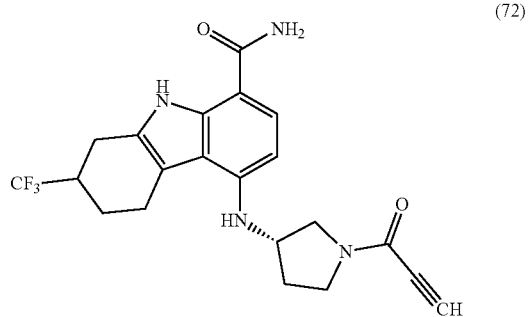 | Intermediate 30 | m/z 381 (M + H)+ |

(a) Example 76-36 in U.S. Pat. No. 8,084,620.

Example 72

5-(((S)-1-Propioloylpyrrolidin-3-yl)amino)-2-(RS)-(trifluoromethyl)-2,3,4,9-tetrahydro-1H-carbazole-8-carboxamide (mixture of diastereomers)

(72)

A solution of propiolic acid (16.8 mg, 0.240 mmol) and HATU (108 mg, 0.285 mmol) in DMF (3 mL) was treated with a solution of 5-((S)-pyrrolidin-3-ylamino)-2-(RS)-(trifluoromethyl)-2,3,4,9-tetrahydro-1H-carbazole-8-carbox- amide, a mixture of diastereomers, [Intermediate 34] (55 mg, 0.150 mmol) and DIEA (0.131 mL, 0.751 mmol) in DMF (1 mL). The mixture was stirred at room temperature for 2 h, then was treated with 1 M aqueous HCl (1 mL), diluted with 10% aqueous LiCl and extracted twice with EtOAc. The combined organic layers were dried and concentrated. The residue was purified by preparative reverse-phase HPLC (Waters XBridge C18 column, 5 μm, 19×200 mm, eluting with acetonitrile-water containing 0.1% TFA, gradient from 15-55%, 20 mL/min) to provide 5-(((S)-1-propioloylpyrrolidin-3-yl)amino)-2-(RS)-(trifluoromethyl)-2,3,4,9-tetrahydro-1H-carbazole-8-carboxamide, a mixture of diastereomers (4.0 mg, 5.9% yield). Mass spectrum m/z 419 (M+H)+. $^1$H NMR (500 MHz, DMSO-$d_6$) δ 10.72 (br. s., 1H), 7.94 (s, 1H), 7.48 (d, J=8.1 Hz, 1H), 7.30-6.97 (m, 2H), 6.18 (dd, J=18.7, 8.2 Hz, 1H), 4.52-4.39 (m, 1H), 4.23 (d, J=19.9 Hz, 1H), 3.82-3.68 (m, 1H), 3.57 (br. s., 1H), 3.47-3.29 (m, 1H), 3.15 (d, J=10.1 Hz, 1H), 3.05 (d, J=12.5 Hz, 1H), 2.96 (br. s., 1H), 2.73 (s, 1H), 2.70-2.65 (m, 2H), 2.28 (d, J=6.1 Hz, 1H), 2.12 (br. s., 1H), 2.03 (br. s., 1H), 1.64 (d, J=6.4 Hz, 1H).

Additional Examples which were prepared by procedures described for Example 72 or similar procedures, using the indicated starting material and the appropriate carboxylic acid, are shown in Table 5.

TABLE 5

| Example, Description | Structure | Starting Material | Mass Spectrum |
|---|---|---|---|
| 73 (homochiral) | 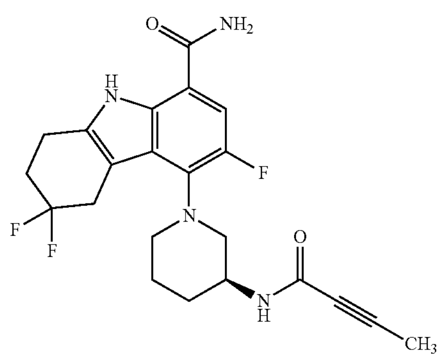 [SMILES: CC#CC(=O)N[C@H]1CCCN(c2c(F)cc(C(N)=O)c3[nH]c4c(c23)CC(F)(F)CC4)C1] | Intermediate 32 | m/z 433 (M + H)+ |

TABLE 5-continued

| Example, Description | Structure | Starting Material | Mass Spectrum |
|---|---|---|---|
| 74 (homochiral) | 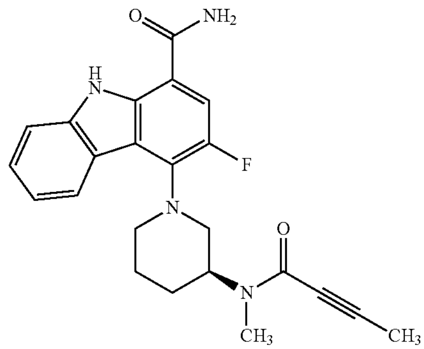 [SMILES: CC#CC(=O)N(C)[C@H]1CCCN(c2c(F)cc(C(N)=O)c3[nH]c4ccccc4c23)C1] | Intermediate 31 | m/z 407 (M + H)+ |
| 75 (homochiral) | 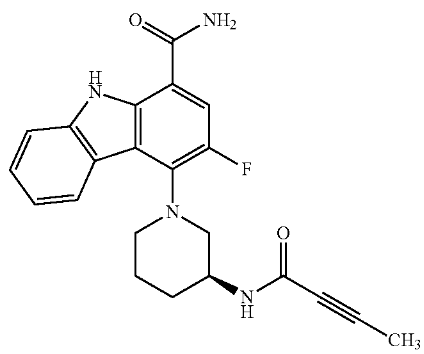 [SMILES: CC#CC(=O)N[C@H]1CCCN(c2c(F)cc(C(N)=O)c3[nH]c4ccccc4c23)C1] | Intermediate 30 | m/z 393 (M + H)+ |
| 76 (homochiral) | 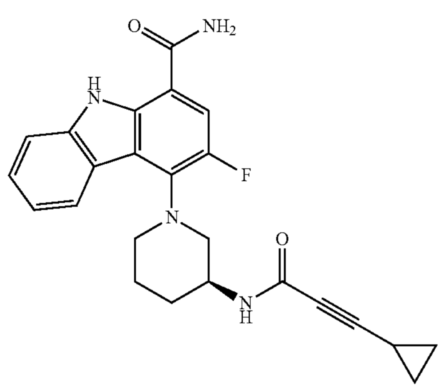 [SMILES: NC(=O)c1cc(F)c(N2CCC[C@H](NC(=O)C#CC3CC3)C2)c2c1[nH]c1ccccc12] | Intermediate 30 | m/z 419 (M + H)+ |

Examples 77 and 78

5-((((S)-1-Acryloylpyrrolidin-3-yl)amino)-2-(trifluoromethyl)-2,3,4,9-tetrahydro-1H-carbazole-8-carboxamide (single diastereomers)

(77, 78)

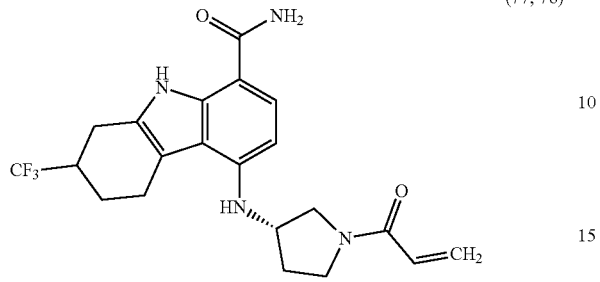

A sample of 5-(((S)-1-acryloylpyrrolidin-3-yl)amino)-2-(trifluoromethyl)-2,3,4,9-tetrahydro-1H-carbazole-8-carboxamide (mixture of two diastereomers) [Example 65] (40 mg) was separated by chiral super-critical fluid chromatography (Column: CHIRALCEL® OD-H (3×25 cm, 5 µm); Mobile Phase: CO$_2$-MeOH (60:40) at 85 mL/min; sample preparation: 4 mg/mL in MeOH-acetonitrile; injection: 3 mL). The first peak eluting from the column provided one diastereomer of 5-(((S)-1-acryloylpyrrolidin-3-yl)amino)-2-(trifluoromethyl)-2,3,4,9-tetrahydro-1H-carbazole-8-carboxamide [Example 77] (11.5 mg). Mass spectrum m/z 421 (M+H)$^+$. $^1$H NMR (400 MHz, DMSO-d$_6$) δ 10.72 (s, 1H), 7.49 (dd, J=8.3, 1.3 Hz, 1H), 6.67-6.51 (m, 1H), 6.24-6.12 (m, 2H), 5.69 (ddd, J=12.8, 10.3, 2.4 Hz, 1H), 5.07 (m, 1H), 4.1-4.3 (m, 1H), 3.79-3.62 (m, 2H), 3.62-3.39 (m, 2H), 3.17-2.92 (m, 3H), 2.69 (d, J=14.2 Hz, 2H), 2.33-2.11 (m, 3H).

The second peak eluting from the column provided the other diastereomer of 5-(((S)-1-acryloylpyrrolidin-3-yl)amino)-2-(trifluoromethyl)-2,3,4,9-tetrahydro-1H-carbazole-8-carboxamide [Example 78] (13.0 mg). Mass spectrum m/z 421 (M+H)$^+$. $^1$H NMR (400 MHz, DMSO-d$_6$) δ 10.72 (s, 1H), 7.49 (dd, J=8.3, 1.3 Hz, 1H), 6.67-6.51 (m, 1H), 6.24-6.12 (m, 2H), 5.69 (ddd, J=12.8, 10.3, 2.4 Hz, 1H), 5.07 (m, 1H), 4.1-4.3 (m, 1H), 3.79-3.62 (m, 2H), 3.62-3.39 (m, 2H), 3.17-3.01 (m, 3H), 2.69 (d, J=14.2 Hz, 2H), 2.33-2.11 (m, 3H).

The absolute stereochemistries at the tetrahydrocarbazole ring 2-position of Examples 77 and 78 have not been assigned.

Example 87

3-Fluoro-4-((6-vinylpyridin-3-yl)methyl)-9H-carbazole-1-carboxamide (87)

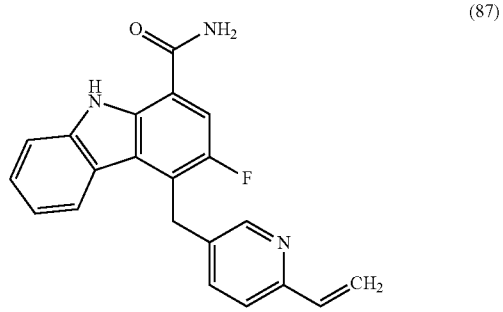 [SMILES: C=Cc1ccc(Cc2c(F)cc(C(N)=O)c3[nH]c4ccccc4c23)cn1]

Intermediate 87A: 4-((6-Chloropyridin-3-yl)methyl)-3-fluoro-9H-carbazole-1-carboxamide TFA Salt (87A)

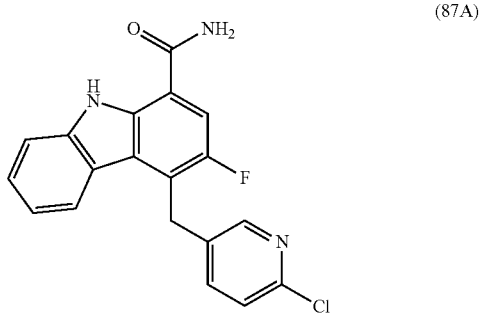 [SMILES: NC(=O)c1cc(F)c(Cc2ccc(Cl)nc2)c2c1[nH]c1ccccc12]

A solution of 4-bromo-3-fluoro-9H-carbazole-1-carboxamide [Intermediate 8] (100 mg, 0.326 mmol) and tetrakis(triphenylphosphine)palladium (75 mg, 0.065 mmol) in THF (1 mL) was stirred at 65° C. for 5 min, then was treated dropwise with ((6-chloropyridin-3-yl)methyl)zinc(II) chloride (0.5 M in THF; 1.95 mL, 0.977 mmol). Heating was continued overnight. The mixture was cooled to room temperature and diluted with EtOAc, washed with saturated aqueous NaHCO$_3$, dried and concentrated. The residue was subjected to preparative HPLC (Column: PHENOMENEX® Axia C$_{18}$, 5µ; 30×100 mm), eluting with MeOH-water containing 0.1% TFA (gradient from 10-90%), to provide 4-((6-chloropyridin-3-yl)methyl)-3-fluoro-9H-carbazole-1-carboxamide TFA salt, as a yellow solid (33 mg, 22% yield). Mass spectrum m/z 354, 356 (M+H)$^+$. $^1$H NMR (400 MHz, MeOH-d$_4$) δ 8.32 (d, J=2.3 Hz, 1H), 8.04 (d, J=8.1 Hz, 1H), 7.81 (d, J=10.9 Hz, 1H), 7.72-7.59 (m, 2H), 7.46 (td, J=7.7, 1.0 Hz, 1H), 7.33 (d, J=8.3 Hz, 1H), 7.17 (ddd, J=8.1, 7.2, 1.0 Hz, 1H), 4.76-4.73 (m, 2H).

Example 87

A mixture of 4-((6-chloropyridin-3-yl)methyl)-3-fluoro-9H-carbazole-1-carboxamide TFA salt (33 mg, 0.071 mmol), tri-n-butyl(vinyl)stannane (67.1 mg, 0.212 mmol), LiCl (9.0 mg, 0.212 mmol), and tetrakis(triphenylphosphine)palladium (4.1 mg, 3.53 µmol) in DMF (1 mL) was bubbled with nitrogen, then was stirred at 90° C. overnight. The cooled mixture was diluted with EtOAc, washed 3 times with saturated aqueous NaHCO$_3$, dried and concentrated. The residue was subjected to column chromatography on silica gel, eluting with MeOH-DCM (gradient from 0-5%) to provide 3-fluoro-4-((6-vinylpyridin-3-yl)methyl)-9H-carbazole-1-carboxamide as a white solid (14.3 mg, 57% yield). Mass spectrum m/z 346 (M+H)$^+$. $^1$H NMR (400 MHz, MeOH-d$_4$) δ 8.42 (d, J=2.0 Hz, 1H), 8.04 (d, J=8.1 Hz, 1H), 7.80 (d, J=11.0 Hz, 1H), 7.65-7.57 (m, 2H), 7.46-7.39 (m, 2H), 7.14 (ddd, J=8.1, 7.2, 1.0 Hz, 1H), 6.75 (dd, J=17.6, 11.0 Hz, 1H), 6.07 (dd, J=17.7, 1.0 Hz, 1H), 5.44 (dd, J=11.0, 1.0 Hz, 1H), 4.56 (s, 2H).

Example 88

N[1]-(4-((5-(3-Acrylamido-2-methylphenyl)-8-carbamoyl-2,3,4,9-tetrahydro-1H-carbazol-2-(RS)-yl)methyl)(methyl)amino)butyl)-N[5]-(15-oxo-19-((3aS,4S,6aR)-2-oxohexahydro-1H-thieno[3,4-d]imidazol-4-yl)-4,7,10-trioxa-14-azanonadecyl)glutaramide TFA Salt, Mixture of Diastereomers

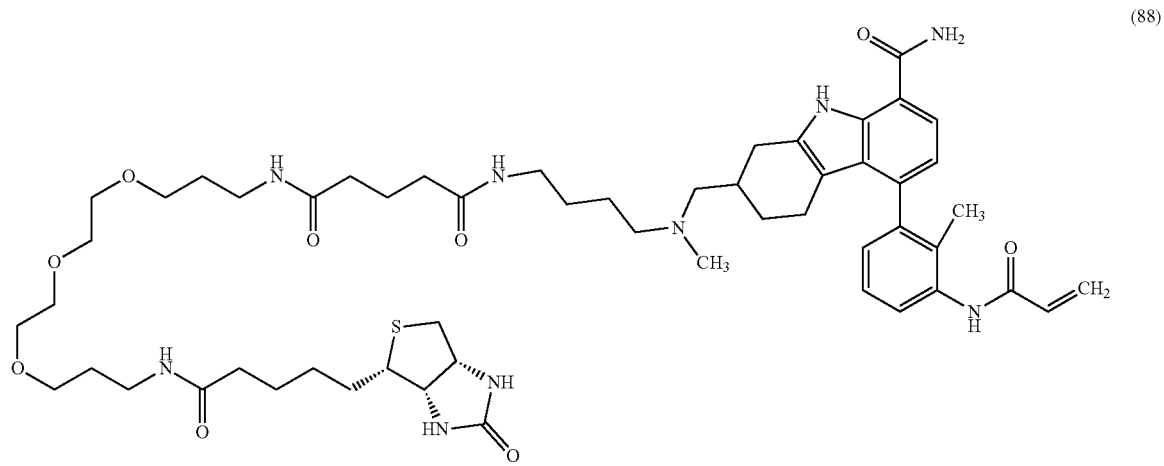 [SMILES: C=CC(=O)Nc1cccc(-c2ccc(C(N)=O)c3[nH]c4c(c23)CCC(CN(C)CCCCNC(=O)CCCC(=O)NCCCOCCOCCOCCCNC(=O)CCCC[C@@H]2SC[C@@H]3NC(=O)N[C@@H]32)C4)c1C]
(88)

Intermediate 88A: (RS)-(5-Bromo-8-carbamoyl-2,3,4,9-tetrahydro-1H-carbazol-2-yl) methyl methanesulfonate

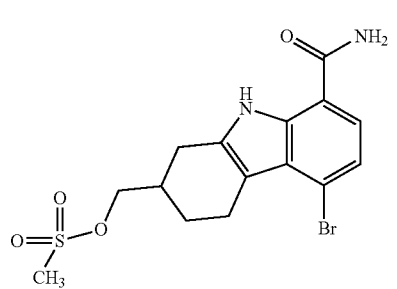
(88A)

A suspension of (RS)-5-bromo-2-(hydroxymethyl)-2,3,4,9-tetrahydro-1H-carbazole-8-carboxamide [prepared according to the procedure of U.S. Pat. No. 8,084,620, Example 73-2] (250 mg, 0.774 mmol) in THF (10 mL), stirred on an ice-water bath, was treated with triethylamine (0.270 mL, 1.93 mmol), then with methanesulfonyl chloride (0.072 mL, 0.928 mmol). The mixture was stirred at room temperature for 90 min. Additional triethylamine (0.270 mL, 1.93 mmol) and methanesulfonyl chloride (0.072 mL, 0.928 mmol) were added and stirring was continued for another 90 min. The mixture was diluted with EtOAc and washed sequentially with water, saturated aqueous NaHCO$_3$ and saturated brine, dried and concentrated to provide crude (RS)-(5-bromo-8-carbamoyl-2,3,4,9-tetrahydro-1H-carbazol-2-yl)methyl methanesulfonate as an orange-brown gum (332 mg), used without further purification. Mass spectrum m/z 401, 403 (M+H)$^+$.

Intermediate 88B: tert-Butyl (RS)-(4-(((5-bromo-8-carbamoyl-2,3,4,9-tetrahydro-1H-carbazol-2-yl)methyl)(methyl)amino)butyl)carbamate

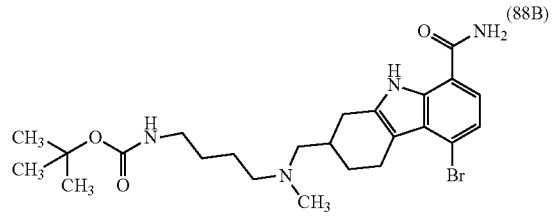 [SMILES: CN(CCCCNC(=O)OC(C)(C)C)CC1CCc2c([nH]c3c(C(N)=O)ccc(Br)c23)C1]
(88B)

A solution of crude (RS)-(5-bromo-8-carbamoyl-2,3,4,9-tetrahydro-1H-carbazol-2-yl)methyl methanesulfonate (310 mg, 0.773 mmol) and tert-butyl (4-(methylamino) butyl) carbamate, methanesulfonic acid salt [prepared according to the procedures of U.S. Pat. No. 7,989,465 Example 45, Steps 1-3] (461 mg, 1.55 mmol) in acetonitrile (10 mL) was treated with DIEA (0.810 mL, 4.64 mmol) and heated on an oil bath at 70° C. for 70 h. The mixture was then heated at reflux for 95 h. The mixture was cooled to room temperature and concentrated, and the residue was subjected to column chromatography on silica gel (40 g), eluting with EtOAc-hexanes (gradient from 25-100%), then eluting further with MeOH-DCM (gradient from 0-20%), then eluting further with MeOH-DCM (20%) containing 5% triethylamine. The product-containing effluent was concentrated and the residue was purified by preparative reverse-phase HPLC (Column: PHENOMENEX® Axia C$_{18}$ 30×100 mm, eluting with acetonitrile-water containing 0.1% TFA, gradient from 10-100%). The appropriate effluent fractions were combined, treated with saturated aqueous NaHCO$_3$ and concentrated to an aqueous residue. This was extracted twice with EtOAc, and the combined organic phases were dried and concentrated to provide tert-butyl (RS)-(4-((5-bromo-8-carbamoyl-2,3,4,9-tetrahydro-1H-carbazol-2-yl)methyl)(methyl)amino)butyl) carbamate as a tan glassy solid (102 mg, 25% yield). Mass spectrum m/z 507, 509 (M+H)$^+$, 451, 453 (M+H-C$_4$H$_8$)$^+$. $^1$H NMR (400 MHz, CDCl$_3$) δ 10.04 (br. s., 1H), 7.21 (d, J=7.9 Hz, 1H), 7.15-7.08 (m, 1H), 5.91 (br. s., 2H), 4.90 (br. s., 1H), 3.37-3.22 (m, 1H), 3.16 (d, J=5.7 Hz, 2H), 3.08-2.81 (m, 2H), 2.54-2.30 (m, 5H), 2.24 (s, 3H), 2.17-2.01 (m, 2H), 1.58-1.40 (m+s, 14H).

Intermediate 88C: (RS)-2-(((4-Aminobutyl)(methyl)amino)methyl)-5-bromo-2,3,4,9-tetrahydro-1H-carbazole-8-carboxamide dihydrochloride

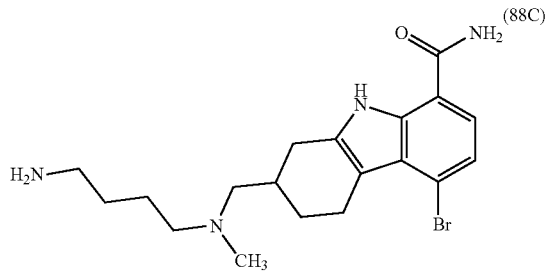 [SMILES: CN(CCCCN)CC1CCc2c([nH]c3c(C(N)=O)ccc(Br)c23)C1]

A solution of tert-butyl (RS)-(4-(((5-bromo-8-carbamoyl-2,3,4,9-tetrahydro-1H-carbazol-2-yl)methyl)(methyl)amino)butyl)carbamate (77 mg, 0.152 mmol) in 1,4-dioxane (2 mL) was treated with 4 M HCl in 1,4-dioxane (1 mL, 4.00 mmol), forming a brown gum. The mixture was sonicated and stirred at room temperature for 100 min. The resulting yellow suspension was diluted with ether, sonicated and stirred at room temperature for 1.5 h. The precipitate was collected by filtration, rinsed with ether and dried to provide (RS)-2-(((4-aminobutyl)(methyl)amino)methyl)-5-bromo-2,3,4,9-tetrahydro-1H-carbazole-8-carboxamide dihydrochloride as a light yellow-tan hygroscopic solid (76.6 mg, quantitative yield). Mass spectrum m/z 407, 409 (M+H)$^+$. $^1$H NMR (400 MHz, DMSO-d$_6$) δ 11.07-10.94 (m, 1H), 10.25 (br. s., 1H), 8.06 (br. s., 4H), 7.49 (dd, J=8.1, 1.5 Hz, 1H), 7.41 (br. s., 1H), 7.17 (d, J=8.1 Hz, 1H), 3.27-2.72 (m, 13H), 2.43-2.07 (m, 2H), 1.89-1.74 (m, 2H), 1.69-1.49 (m, 3H).

Intermediate 88D: N$^1$-(4-(((5-Bromo-8-carbamoyl-2,3,4,9-tetrahydro-1H-carbazol-2-(RS)-yl)methyl)(methyl)amino)butyl)-N$^5$-(15-oxo-19-((3aS,4S,6aR)-2-oxohexahydro-1H-thieno[3,4-d]imidazol-4-yl)-4,7,10-trioxa-14-azanonadecyl)glutaramide TFA Salt, Mixture of Diastereomers A solution of (RS)-2-(((4-aminobutyl)(methyl)amino)methyl)-5-bromo-2,3,4,9-tetrahydro-1H-carbazole-8-carboxamide dihydrochloride (73.2 mg, 0.152 mmol), 5,21-dioxo-25-((3aS,4S,6aR)-2-oxohexahydro-1H-thieno[3,4-d]imidazol-4-yl)-10,13,16-trioxa-6,20-diazapentacosan-1-oate, diisopropylmethylamine salt (103 mg, 0.152 mmol) and HOAT (24.9 mg, 0.183 mmol) in DMF (1 mL) was treated with DIEA (0.093 mL, 0.533 mmol) and EDC (35.1 mg, 0.183 mmol), and the solution was stirred at room temperature for 16 h. The mixture was concentrated and the residue was purified by preparative reverse-phase HPLC (Column: PHENOMENEX® Axia C$_{18}$ 30×100 mm, eluting with acetonitrile-water containing 0.1% TFA, gradient from 10-100%, 30 mL/min). The appropriate fractions were combined and concentrated, and the residue was lyophilized from acetonitrile-water to provide N$^1$-(4-(((5-bromo-8-carbamoyl-2,3,4,9-tetrahydro-1H-carbazol-2-(RS)-yl)methyl)(methyl)amino)butyl)-N$^5$-(15-oxo-19-((3aS,4S,6aR)-2-oxohexahydro-1H-thieno[3,4-d]imidazol-4-yl)-4,7,10-trioxa-14-azanonadecyl) glutaramide TFA salt, mixture of diastereomers, as a tan amorphous solid (121 mg, 75% yield). Mass spectrum m/z 949, 951 (M+H)$^+$. $^1$H NMR (400 MHz, DMSO-d$_6$) complex but with the correct number of NH protons [δ 11.05 (2s, 1H), 9.08 (br. s., 1H), 8.05 (br. s., 1H), 7.83 (d, J=2.9 Hz, 1H), 7.74 (d, J=4.6 Hz, 2H), 7.40 (br. s., 1H), 6.41 (br. s., 2H], aromatic protons [δ 7.48 (d, J=7.9 Hz, 1H), 7.17 (d, J=7.9 Hz, 1H)] and CH$_2$O protons [δ 3.54-3.49 (m, 4H), 3.49-3.44 (m, 4H), 3.39 (td, J=6.4, 2.2 Hz, 4H)].

Example 88

A mixture of N$^1$-(4-((5-bromo-8-carbamoyl-2,3,4,9-tetrahydro-1H-carbazol-2-(RS)-yl)methyl)(methyl)amino)butyl)-N$^5$-(15-oxo-19-((3aS,4S,6aR)-2-oxohexahydro-1H-thieno[3,4-d]imidazol-4-yl)-4,7,10-trioxa-14-azanonadecyl) glutaramide TFA salt, mixture of diastereomers (116.5 mg, 0.109 mmol), N-(2-methyl-3-(4,4,5,5-tetramethyl-1,3,2-dioxaborolan-2-yl)phenyl) acrylamide [Intermediate 50] (47.2 mg, 0.164 mmol), and 2.0 M aqueous K$_3$PO$_4$ (0.274 mL, 0.547 mmol) in THF (1 mL) was bubbled with argon for about 1 minute with sonication. The mixture was treated with 1,1'-bis(di-tert-butylphosphino)ferrocene palladium dichloride (4.47 mg, 5.47 μmol) and the reaction vessel was sealed and heated at 50° C. for 15.75 h. The cooled mixture was concentrated and the residue was purified by preparative reverse-phase HPLC (Column: PHENOMENEX® Axia C$_{18}$ 30×100 mm, eluting with acetonitrile-water containing 0.1%

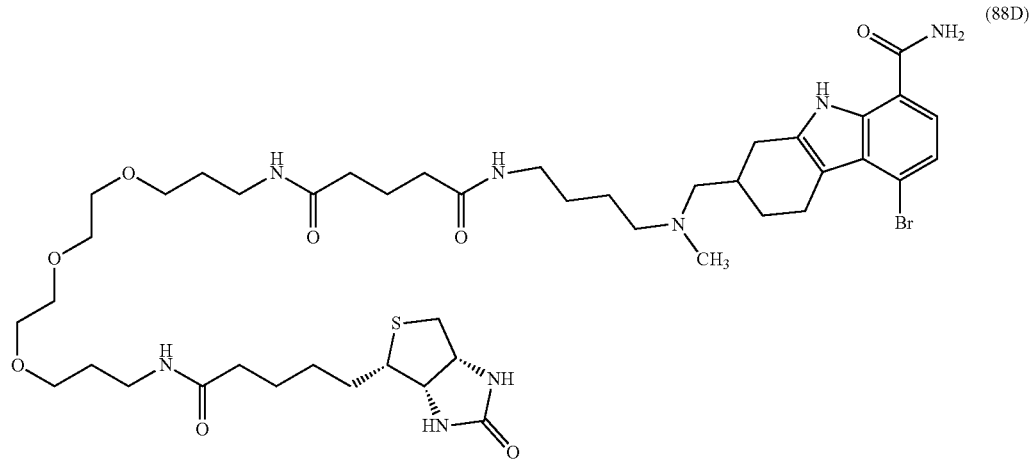 [SMILES: CN(CCCCNC(=O)CCCC(=O)NCCCOCCOCCOCCCNC(=O)CCCC[C@@H]1SC[C@@H]2NC(=O)N[C@@H]21)CC1CCc2c([nH]c3c(C(N)=O)ccc(Br)c23)C1]

TFA, gradient from 10-100%, 10 min, 30 mL/min). The appropriate effluent fractions were combined and concentrated, and the residue was lyophilized from acetonitrile-water to provide $N^1$-(4-((5-(3-acrylamido-2-methylphenyl)-8-carbamoyl-2,3,4,9-tetrahydro-1H-carbazol-2-(RS)-yl)methyl)(methyl)amino)butyl)-$N^5$-(15-oxo-19-((3aS,4S,6aR)-2-oxohexahydro-1H-thieno[3,4-d]imidazol-4-yl)-4,7,10-trioxa-14-azanonadecyl)glutaramide TFA salt, mixture of diastereomers, as a pale yellow amorphous solid (79.9 mg, 59% yield). Mass spectrum m/z 1031 (M+H)$^+$. $^1$H NMR (400 MHz, DMSO-d$_6$) complex but consistent with the expected product. Aromatic, vinyl and NH protons: δ 10.92-10.79 (m, 1H), 9.59 (d, J=10.6 Hz, 1H), 9.08-8.89 (m, 1H), 8.03 (br. s., 1H), 7.81 (t, J=5.4 Hz, 1H), 7.73 (br. s., 2H), 7.64 (dd, J=7.6, 1.9 Hz, 1H), 7.51 (t, J=6.6 Hz, 1H), 7.33 (br. s., 1H), 7.24 (td, J=7.7, 3.7 Hz, 1H), 7.02 (dd, J=10.5, 7.6 Hz, 1H), 6.75 (dd, J=7.6, 2.3 Hz, 1H), 6.56 (dd, J=16.9, 10.3 Hz, 1H), 6.46-6.31 (m, 2H), 6.26 (dd, J=17.1, 2.1 Hz, 1H), 5.76 (dd, J=10.2, 1.9 Hz, 1H). Also CH$_2$O protons: δ 3.56-3.43 (m, 8H), 3.39 (td, J=6.3, 3.0 Hz, 4H). Other proton count about 49, theor. 50.

Additional Examples which were prepared by procedures described above, using the starting material(s) and procedures indicated, are shown in Table 6.

TABLE 6

| Example | Structure | Starting Materials | Procedures | Mass Spectrum |
|---|---|---|---|---|
| 89 | [structure] | Intermediate 61 | (a) | m/z 400 (M + H)$^+$ |
| 90 | [structure] | Intermediate 62 | (a) | m/z 414 (M + H)$^+$ |
| 91 | [structure] | Intermediate 63 | (a) | m/z 414 (M + H)$^+$ |

TABLE 6-continued
| Example | Structure | Starting Materials | Procedures | Mass Spectrum |
|---|---|---|---|---|
| 92 | 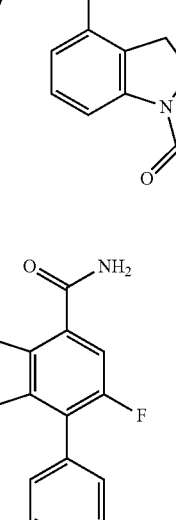 | Intermediate 64 | (a) | m/z 400 (M + H)$^+$ |
| 95 | 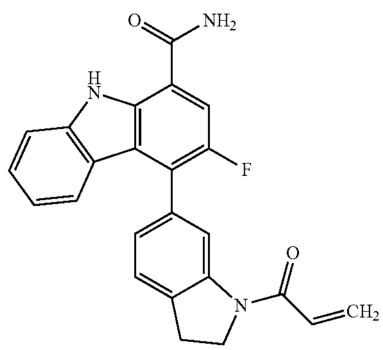 [SMILES: C=CC(=O)N1CCc2ccc(-c3c(F)cc(C(N)=O)c4[nH]c5ccccc5c34)cc21] | Intermediate 67 | (a) | m/z 400 (M + H)$^+$ |
| 96 | 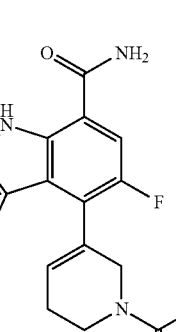 | Intermediate 68 | (a) | m/z 364 (M + H)$^+$ |
| 97 (racemic) | 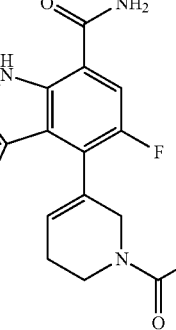 | Intermediate 69 | (a) | m/z 366 (M + H)$^+$ |

TABLE 6-continued

| Example | Structure | Starting Materials | Procedures | Mass Spectrum |
|---|---|---|---|---|
| 98 single enantiomer (peak 1) | 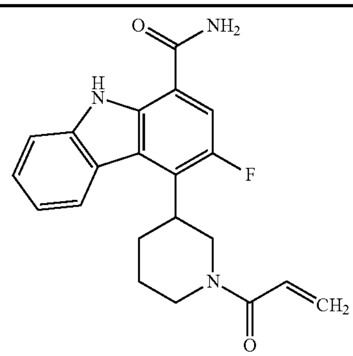 | Example 97 | (b) | m/z 366 (M + H)⁺ |
| 99 single enantiomer (peak 2) | 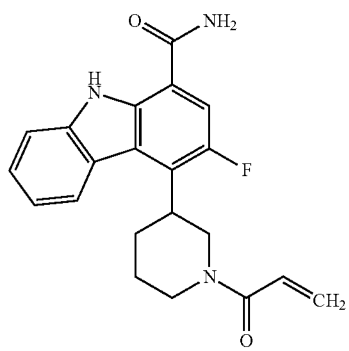 [SMILES: C=CC(=O)N1CCCC(c2c(F)cc(C(N)=O)c3[nH]c4ccccc4c23)C1] | Example 97 | (b) | m/z 366 (M + H)⁺ |

(a) Prepared following the procedure used to prepare Example 63 or similar procedures.
(b) Prepared by super-critical fluid chromatography of the racemic compound. Absolute configuration was not assigned.

Example 100

3-Fluoro-4-((2-vinylpyridin-4-yl)methyl)-9H-carbazole-1-carboxamide

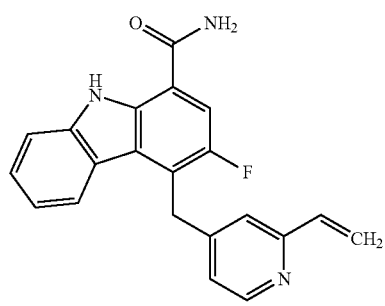

(100)

Intermediate 100A: 4-((2-Chloropyridin-4-yl)methyl)-3-fluoro-9H-carbazole-1-carboxamide

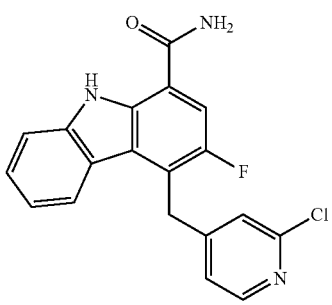

(100A)

A suspension of zinc (55 mg, 0.834 mmol) in THF (2 mL) was treated with chlorotrimethylsilane (2.7 μl, 0.021 mmol) and 1,2-dibromoethane (3.9 mg, 0.021 mmol) and the mixture was stirred at 65° C. for 30 min. The mixture was cooled to 0° C. treated with a solution of 2-chloro-4-(chloromethyl) pyridine (101 mg, 0.625 mmol) in THF (0.5 mL), and stirred for 15 min. The mixture was treated with a solution of 4-bromo-3-fluoro-9H-carbazole-1-carboxamide [Intermediate 8] (64 mg, 0.208 mmol) and bis(tri-tert-butylphosphine) palladium (21.3 mg, 0.042 mmol) in THF (1 mL) and warmed to room temperature, then was stirred at 65° C. overnight. Additional 2-chloro-4-(chloromethyl)pyridine (101 mg, 0.625 mmol) and bis(tri-tert-butylphosphine)palladium (21.3 mg, 0.042 mmol) was added and stirring was continued overnight at 70° C. The mixture was cooled to room temperature and filtered through CELITE®. The filtrate was diluted with EtOAc, washed sequentially with saturated aqueous NaHCO$_3$ and water, dried and concentrated. The residue was subjected to column chromatography on silica gel, eluting with EtOAc-hexanes (gradient from 0-100%), to provide 4-((2-chloropyridin-4-yl)methyl)-3-fluoro-9H-carbazole-1-carboxamide as a yellow solid (27 mg, 37% yield). Mass spectrum m/z 354, 356 (M+H)$^+$.

Example 100

Following the procedure used to convert Intermediate 87A into Example 87, 4-((2-chloropyridin-4-yl)methyl)-3-fluoro-9H-carbazole-1-carboxamide was converted into 3-fluoro-4-((2-vinylpyridin-4-yl)methyl)-9H-carbazole-1-carboxamide as a white solid in 31% yield after purification by preparative reverse-phase chromatography (PHENOMENEX® Luna Axia C$_{18}$ column, 5 μm, eluting with acetonitrile-water containing 0.1% TFA, gradient from 10-90%) and conversion to the free base by partitioning between EtOAc and saturated aqueous NaHCO$_3$. Mass spectrum m/z 346 (M+H)$^+$. $^1$H NMR (400 MHz, MeOH-d$_4$) δ 8.30 (d, J=5.3 Hz, 1H), 7.95 (d, J=8.1 Hz, 1H), 7.80 (d, J=10.8 Hz, 1H), 7.62 (d, J=8.2 Hz, 1H), 7.47-7.38 (m, 2H), 7.17-7.06 (m, 2H), 6.72 (dd, J=17.6, 11.0 Hz, 1H), 6.02 (dd, J=17.6, 1.1 Hz, 1H), 5.43 (dd, J=11.0, 1.0 Hz, 1H), 4.75 (s, 2H).

Comparative Example 101

7-(2-Hydroxypropan-2-yl)-4-(2-methyl-3-propionamidophenyl)-9H-carbazole-1-carboxamide Following the procedure used to prepare Intermediate 49, but substituting propionic anhydride for acryloyl chloride, 2-methyl-3-(4,4,5,5-tetramethyl-1,3,2-dioxaborolan-2-yl) aniline [prepared according to U.S. Pat. No. 8,084,620, Intermediate 50-1] was converted into N-(2-methyl-3-(4,4,5,5-tetramethyl-1,3,2-dioxaborolan-2-yl) phenyl)propionamide in 88% yield. Mass spectrum m/z 290 (M+H)$^+$. $^1$H NMR (400 MHz, DMSO-d$_6$) δ 9.21 (s, 1H), 7.52-7.34 (m, 2H), 7.14 (t, J=7.6 Hz, 1H), 2.37-2.30 (m, 5H), 1.30 (s, 12H), 1.10 (t, J=7.6 Hz, 3H).

Comparative Example 101

Following the procedure used to prepare Example 1, 4-bromo-7-(2-hydroxypropan-2-yl)-9H-carbazole-1-carboxamide [synthesized according to the procedure described in U.S. Pat. No. 8,084,620, Example 73-2] and N-(2-methyl-3-(4,4,5,5-tetramethyl-1,3,2-dioxaborolan-2-yl)phenyl)propionamide were converted into 7-(2-hydroxypropan-2-yl)-4-(2-methyl-3-propionamidophenyl)-9H-carbazole-1-carboxamide in 94% yield. Mass spectrum m/z 412 (M+H−H$_2$O)$^+$. $^1$H NMR (500 MHz, DMSO-d$_6$) δ 11.41 (s, 1H), 9.40 (s, 1H), 8.16 (br. s., 1H), 7.95 (d, J=7.9 Hz, 1H), 7.85 (d, J=1.0 Hz, 1H), 7.54 (d, J=7.9 Hz, 1H), 7.47 (br. s., 1H), 7.33 (t, J=7.7 Hz, 1H), 7.08 (d, J=7.4 Hz, 1H), 6.99 (dd, J=8.4, 1.5 Hz, 1H), 6.93 (d, J=7.4 Hz, 1H), 6.73 (d, J=8.4 Hz, 1H), 4.98 (s, 1H), 2.37 (q, J=7.4 Hz, 2H), 1.86 (s, 3H), 1.44 (s, 6H), 1.11 (t, J=7.7 Hz, 3H).

Comparative Example 102

7-(2-Hydroxypropan-2-yl)-4-(3-(3-ethylureido)-2-methylphenyl)-9H-carbazole-1-carboxamide

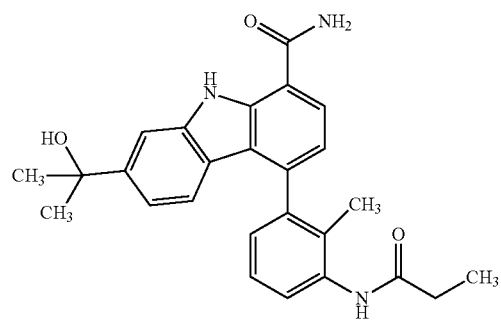

(101)

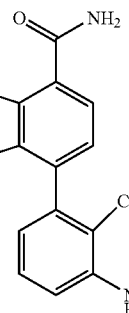

(102)

Comparative Intermediate 101A: N-(2-Methyl-3-(4,4,5,5-tetramethyl-1,3,2-dioxaborolan-2-yl)phenyl) propionamide

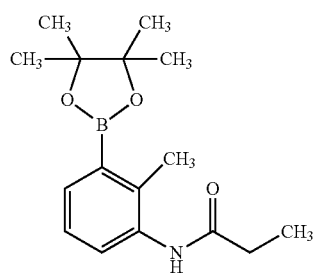

(101A)

Comparative Intermediate 102A: 1-(3-Bromo-2-methylphenyl)-3-ethylurea

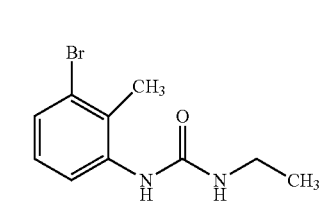

(102A)

A solution of triphosgene (2.249 g, 7.58 mmol) in toluene (26.9 mL) was stirred on an ice-water bath and treated slowly with a solution of 3-bromo-2-methylaniline (3 g, 16.12 mmol) and DIEA (5.63 mL, 32.2 mmol) in toluene (5.37 mL). The resulting suspension was stirred at room temperature for 2 h, filtered, and the precipitate was washed with EtOAc. The combined filtrates were washed quickly with brine, dried and concentrated to provide 1-bromo-3-isocyanato-2-methylbenzene as a brown solid/oil mixture (3.36 g). Treatment of a portion of this crude material with ethanol provided 1-(3-bromo-2-methylphenyl)-3-ethylurea as an off-white solid. Mass spectrum m/z 357, 259 (M+H)$^+$. $^1$H NMR (400 MHz, DMSO-d$_6$) δ 7.80 (s, 1H), 7.75 (d, J=7.5 Hz, 1H), 7.24 (dd, J=7.9, 0.9 Hz, 1H), 7.04 (t, J=8.0 Hz, 1H), 6.50 (t, J=5.4 Hz, 1H), 3.11 (qd, J=7.2, 5.6 Hz, 2H), 1.07 (t, J=7.3 Hz, 3H).

Comparative Example 102

Following the procedure used to prepare Example 4, 7-(2-hydroxypropan-2-yl)-4-(4,4,5,5-tetramethyl-1,3,2-dioxaborolan-2-yl)-9H-carbazole-1-carboxamide [Intermediate 27] and 1-(3-bromo-2-methylphenyl)-3-ethylurea were converted into 7-(2-hydroxypropan-2-yl)-4-(3-(3-ethylureido)-2-methyl phenyl)-9H-carbazol-carboxamide-1 in 33% yield. Mass spectrum m/z 427 (M+H–H$_2$O)$^+$. $^1$H NMR (500 MHz, MeOH-d$_4$) δ 7.86 (d, J=7.9 Hz, 1H), 7.79 (d, J=7.9 Hz, 1H), 7.68 (d, J=1.0 Hz, 1H), 7.31 (t, J=7.7 Hz, 1H), 7.08 (d, J=7.4 Hz, 1H), 7.05 (dd, J=8.4, 1.5 Hz, 1H), 7.00 (d, J=7.9 Hz, 1H), 6.91 (d, J=8.4 Hz, 1H), 3.28 (q, J=6.9 Hz, 2H), 1.94 (s, 3H), 1.58 (s, 6H), 1.18 (t, J=7.2 Hz, 3H).

Comparative Example 103

4-(3-(2-Cyanoacetamido)-2-methylphenyl)-7-(2-hydroxypropan-2-yl)-9H-carbazole-1-carboxamide

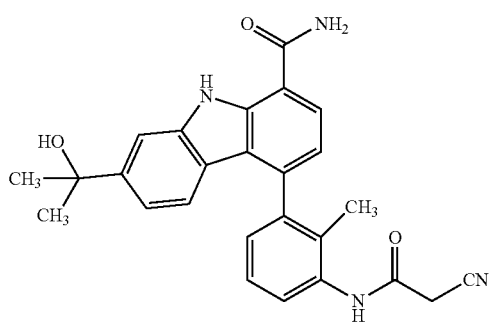

(103)

Comparative Intermediate 103A: 2-Cyano-N-(3-(4,4,5,5-tetramethyl-1,3,2-dioxaborolan-2-yl)phenyl)acetamide

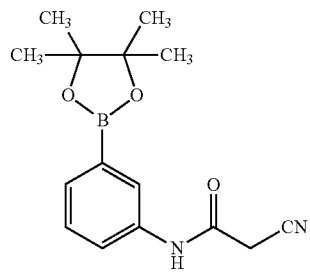

(103A)

A solution of 2-cyanoacetic acid (0.115 g, 1.35 mmol), EDC (0.370 g, 1.93 mmol), HOBT (0.296 g, 1.93 mmol), and DIEA (0.562 mL, 3.22 mmol) in THF (10.7 mL) and DCM (10.7 mL) was stirred at room temperature for 30 min. The mixture was treated with 2-methyl-3-(4,4,5,5-tetramethyl-1,3,2-dioxaborolan-2-yl)aniline [prepared according to U.S. Pat. No. 8,084,620, Intermediate 50-1] (0.300 g, 1.29 mmol) and the mixture was stirred at room temperature for 16 h. Additional cyanoacetic acid (0.115 g) was added, and after 6 h more, additional EDC (0.370 g) and HOBT (0.296 g) were added. After being stirred at room temperature for 2 days, the mixture was partitioned between EtOAc and saturated aqueous NaHCO$_3$. The organic phase was dried and concentrated, and the residue was subjected to column chromatography on silica gel (24 g), eluting with EtOAc-hexanes (gradient from 30-50%), to provide 2-cyano-N-(3-(4,4,5,5-tetramethyl-1,3,2-dioxaborolan-2-yl)phenyl)acetamide as a white solid (344 mg, 89% yield). Mass spectrum m/z 301 (M+H)$^+$. $^1$H NMR (400 MHz, DMSO-d$_6$) δ 9.68 (s, 1H), 7.52-7.47 (m, 1H), 7.43-7.38 (m, 1H), 7.18 (t, J=7.6 Hz, 1H), 3.91 (s, 2H), 2.34 (s, 3H), 1.30 (s, 12H).

Comparative Example 103

Following the procedure used to prepare Example 1, 4-bromo-7-(2-hydroxypropan-2-yl)-9H-carbazole-1-carboxamide [synthesized according to the procedure described in U.S. Pat. No. 8,084,620, Example 73-2] and 2-cyano-N-(3-(4,4,5,5-tetramethyl-1,3,2-dioxaborolan-2-yl)phenyl)acetamide were converted into 4-(3-(2-cyanoacetamido)-2-methylphenyl)-7-(2-hydroxypropan-2-yl)-9H-carbazole-1-carboxamide in 19% yield. Mass spectrum m/z 441 (M+H)$^+$. $^1$H NMR (500 MHz, DMSO-d$_6$) δ 11.42 (s, 1H), 9.86 (s, 1H), 8.16 (br. s., 1H), 7.96 (d, J=7.4 Hz, 1H), 7.86 (d, J=1.0 Hz, 1H), 7.74 (d, J=7.9 Hz, 1H), 7.47 (br. s., 1H), 7.34 (t, J=7.7 Hz, 1H), 7.08 (d, J=7.4 Hz, 1H), 7.00 (dd, J=8.4, 1.5 Hz, 1H), 6.94 (d, J=7.9 Hz, 1H), 6.72 (d, J=8.4 Hz, 1H), 4.98 (s, 1H), 3.31 (s, 2H), 1.89 (s, 3H), 1.43 (s, 6H).

Comparative Example 104

4-(3-Amino-2-methylphenyl)-7-(2-hydroxypropan-2-yl)-9H-carbazole-1-carboxamide

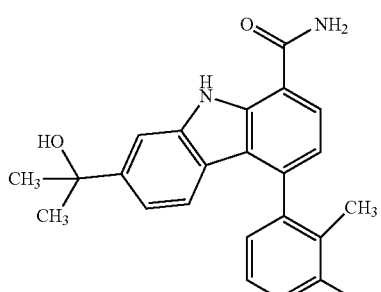

(104)

Comparative Example 104 was prepared according to the procedures described in U.S. Pat. No. 8,084,620, Example 76-36.

Comparative Example 105

4-(3-Benzamido-2-methylphenyl)-7-(2-hydroxypropan-2-yl)-9H-carbazole-1-carboxamide

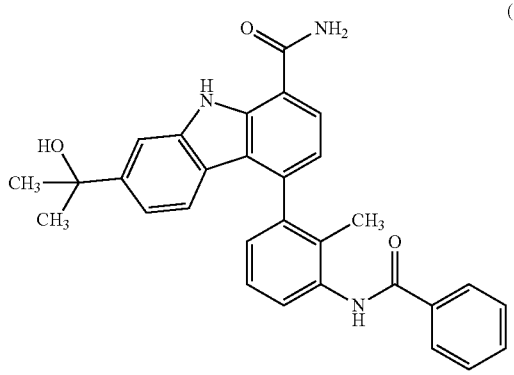
(105)

Following the procedure used to prepare Example 63 but substituting benzoyl chloride for acryloyl chloride, 4-(3-amino-2-methylphenyl)-7-(2-hydroxypropan-2-yl)-9H-carbazole-1-carboxamide [Comparative Example 104] was converted into 4-(3-benzamido-2-methylphenyl)-7-(2-hydroxypropan-2-yl)-9H-carbazole-1-carboxamide in 68% yield. Mass spectrum m/z 460 (M+H–H$_2$O)$^+$. $^1$H NMR (400 MHz, MeOH-d$_4$) δ 8.01 (m, 1H), 7.96-7.90 (m, 1H), 7.78 (s, 1H), 7.64-7.49 (m, 5H), 7.43 (td, J=7.7, 3.5 Hz, 1H), 7.32-7.26 (m, 1H), 7.13-6.98 (m, 3H), 2.07-2.00 (m, 3H), 1.59 (s, 6H).

Comparative Example 106

5-(2-Methyl-3-(1-oxoisoindolin-2-yl)phenyl)-2,3,4,9-tetrahydro-1H-carbazole-8-carboxamide

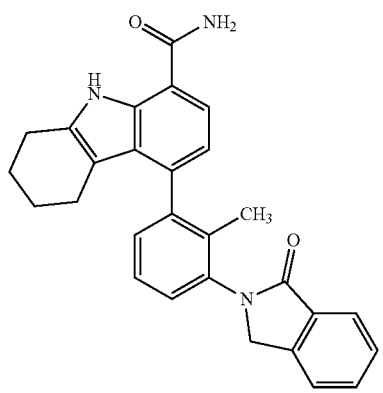
(106)

Comparative Example 106 was prepared according to the procedures described in U.S. Pat. No. 8,084,620, Example 3-99.

Comparative Example 107

4-(3-Acetamido-2-methylphenyl)-7-(4-methylpiperazine-1-carbonyl)-9H-carbazole-1-carboxamide

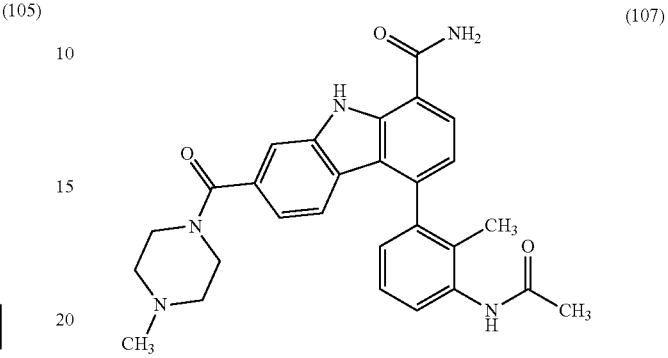
(107)

Comparative Example 107 was prepared according to the procedures described in U.S. Pat. No. 8,084,620, Example 5-2.

Comparative Example 108

4-(3-(Cyclopropanecarboxamido)-2-methylphenyl)-7-(4-methylpiperazine-1-carbonyl)-9H-carbazole-1-carboxamide

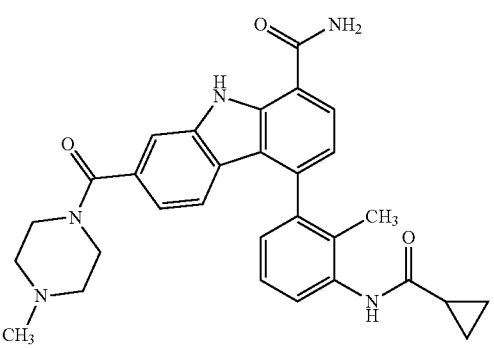
(108)

Comparative Example 108 was prepared according to the procedures described in U.S. Pat. No. 8,084,620, Example 5-49.

Comparative Example 109

(R)-4-(3-Acetamidopiperidin-1-yl)-7-(4-methylpiperazine-1-carbonyl)-9H-carbazole-1-carboxamide

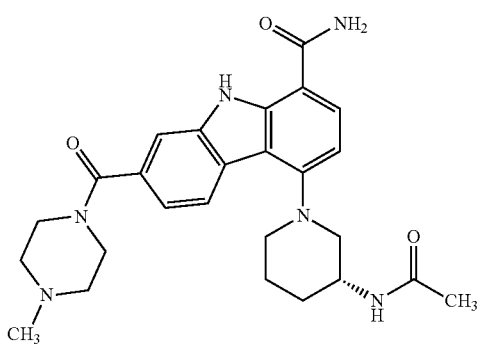
(109)

Comparative Example 109 was prepared according to the procedures described in U.S. Pat. No. 8,084,620, Example 18-1.

Comparative Example 110

(RS)-2-(Hydroxymethyl)-5-(2-methyl-3-(1-oxoisoindolin-2-yl)phenyl)-2,3,4,9-tetrahydro-1H-carbazole-8-carboxamide

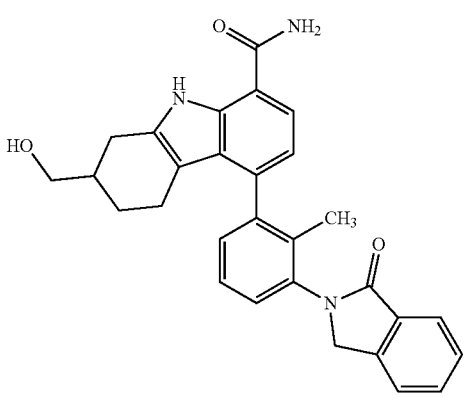
(110)

Comparative Example 110 was prepared according to the procedures described in U.S. Pat. No. 8,084,620, Example 31-1.

Comparative Example 111

7-Acrylamido-4-(2-fluorophenyl)-9H-carbazole-1-carboxamide

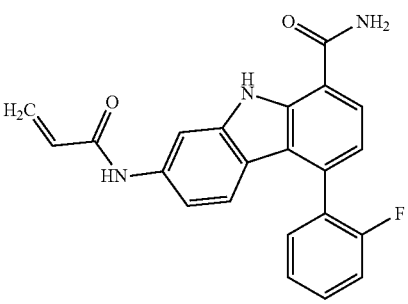
(111)

Comparative Example 111 was prepared according to the procedures described in U.S. Pat. No. 8,084,620, Example 57-10.

Example 112

4-(1-Acryloylpyrrolidin-3-yl)-3-fluoro-9H-carbazole-1-carboxamide (racemic)

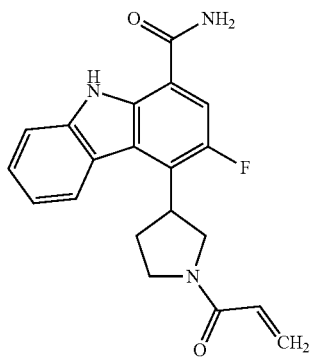
(112)

Acryloyl chloride (4.94 µl, 0.061 mmol) was added to a solution of 3-fluoro-4-(pyrrolidin-3-yl)-9H-carbazole-1-carboxamide, TFA (Intermediate 72) (25 mg, 0.061 mmol) and DIPEA (0.053 mL, 0.304 mmol) in THF (1 mL) and stirred at room temperature for 30 minutes. The mixture was concentrated and the crude material was purified using preparative HPLC (PHENOMENEX® Luna Axia C18 5µ; 30×100 mm column; detection at 220 nM; flow rate=40 mL/min; continuous gradient from 20% B to 100% B over 10 min+5 min hold at 100% B, where A=10:90:0.1 MeOH—H$_2$O-TFA and B=90:10:0.1 MeOH—H$_2$O-TFA) to afford 4-(1-acryloylpyrrolidin-3-yl)-3-fluoro-9H-carbazole-1-carboxamide (11.1 mg, 50.9% yield) as a white solid. Mass spectrum m/z 352 (M+H)$^+$. $^1$H NMR (400 MHz, methanol-d$_4$) δ 8.22 (d, J=7.9 Hz, 1H), 7.74 (dd, J=13.1, 1.7 Hz, 1H), 7.65 (d, J=8.1 Hz, 1H), 7.52-7.43 (m, 1H), 7.23 (tt, J=7.6, 1.5 Hz, 1H), 6.80-6.59 (m, 1H), 6.34 (ddd, J=16.8, 6.1, 2.1 Hz, 1H), 5.86-5.71 (m, 1H), 4.79-4.63 (m, 1H), 4.25-3.70 (m, 4H), 2.71-2.47 (m, 2H).

Examples 113 and 114

4-(1-Acryloylpyrrolidin-3-yl)-3-fluoro-9H-carbazole-1-carboxamide (Single Enantiomers)

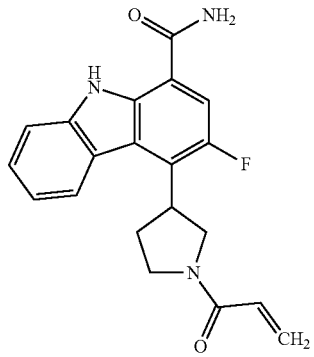

(113 and 114)

A sample of (RS)-4-(1-acryloylpyrrolidin-3-yl)-3-fluoro-9H-carbazole-1-carboxamide (Example 112) (20 mg) was separated by chiral super-critical fluid chromatography (Column: CHIRALCEL® OJ-H (3×25 cm, 5 μm); Mobile Phase: $CO_2$-MeOH (55-45) at 130 mL/min, 100 bars, 35° C.; sample preparation: 10 mg/mL in 25 mL MeOH-DCM-ACN-THF-DMF; injection: 4.5 mL). The first peak eluting from the column provided one enantiomer (Example 113) (2.1 mg). Mass spectrum m/z 352 (M+H)$^+$. $^1$H NMR (400 MHz, methanol-$d_4$) δ 8.22 (d, J=7.9 Hz, 1H), 7.74 (dd, J=13.0, 1.7 Hz, 1H), 7.65 (d, J=7.5 Hz, 1H), 7.52-7.41 (m, 1H), 7.30-7.19 (m, 1H), 6.81-6.59 (m, 1H), 6.34 (ddd, J=16.8, 6.1, 2.1 Hz, 1H), 5.87-5.70 (m, 1H), 4.79-4.58 (m, 1H), 4.18 (d, J=8.4 Hz, 1H), 4.12-3.85 (m, 2H), 3.74 (d, J=12.3 Hz, 1H), 2.80-2.45 (m, 2H). The second peak eluting from the column provided one enantiomer (Example 114) (2.6 mg). Mass spectrum m/z 352 (M+H)$^+$. The absolute configurations of Examples 113 and 114 were not been assigned.

Example 115

Cis-4-(1-(but-2-ynoyl)octahydro-6H-pyrrolo[3,4-b]pyridin-6-yl)-3-fluoro-9H-carbazole-1-carboxamide (racemic)

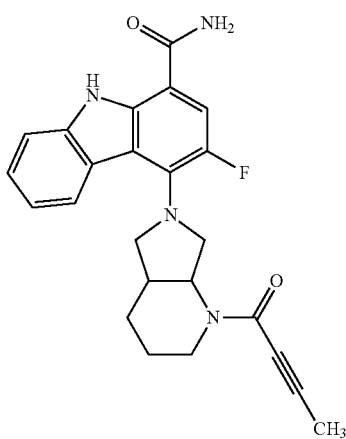

(115)

A solution of 3-fluoro-4-(hexahydro-1H-pyrrolo[3,4-b]pyridin-6(2H)-yl)-9H-carbazole-1-carboxamide, TFA (19 mg, 0.041 mmol) [Intermediate 75], but-2-ynoic acid (3.42 mg, 0.041 mmol), DIPEA (7.11 μl, 0.041 mmol), and HATU (15.49 mg, 0.041 mmol) in DMF (1 mL) was stirred for 30 minutes at room temperature. The mixture was diluted with EtOAc, washed with water, dried (MgSO$_4$), and concentrated. The crude material was purified using preparative HPLC (YMC ODS C18 5μ; 30×100 mm column; detection at 220 nM; flow rate=30 mL/min; continuous gradient from 10% B to 100% B over 40 min+5 min hold at 100% B, where A=05:95:0.1 ACN-H$_2$O-TFA and B=95:05:0.1 ACN-H$_2$O-TFA) to afford (RS)-cis 4-(1-(but-2-ynoyl)hexahydro-1H-pyrrolo[3,4-b]pyridin-6(2H)-yl)-3-fluoro-9H-carbazole-1-carboxamide (12.3 mg, 70.7% yield) as a white solid. Mass spectrum m/z 419 (M+H)$^+$.

Examples 116 and 117

Cis-4-(1-(but-2-ynoyl)octahydro-6H-pyrrolo[3,4-b]pyridin-6-yl)-3-fluoro-9H-carbazole-1-carboxamide (Single Enantiomers)

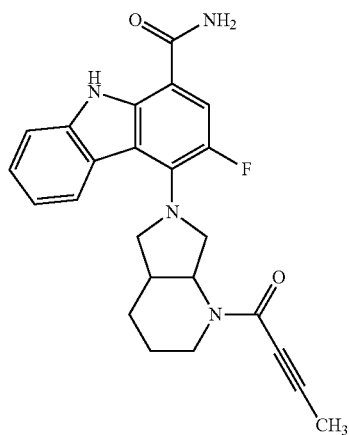

(116 and 117)

A sample of (RS)-cis-4-(1-(but-2-ynoyl)octahydro-6H-pyrrolo[3,4-b]pyridin-6-yl)-3-fluoro-9H-carbazole-1-carboxamide (Example 115) (85 mg) was separated by chiral super-critical fluid chromatography (Column: OD-H (5×25 cm, 5 μm); Mobile Phase: $CO_2$-MeOH (65:35) at 300 mL/min; 100 bar, 35° C.; sample preparation: 85 mg in 18 mL MeOH-DCM (1:1); injection: 4.72 mg/mL). The first peak eluting from the column provided one enantiomer of cis-4-(1-(but-2-ynoyl)octahydro-6H-pyrrolo[3,4-b]pyridin-6-yl)-3-fluoro-9H-carbazole-1-carboxamide (Example 116) as a white solid (31.5 mg). The second peak eluting from the column provided the other enantiomer of 4-(1-(but-2-ynoyl)octahydro-6H-pyrrolo[3,4-b]pyridin-6-yl)-3-fluoro-9H-carbazole-1-carboxamide (Example 117) as an off-white solid (31 mg). Mass spectrum m/z 419 (M+H)$^+$. $^1$H NMR (400 MHz, DMSO-$d_6$) δ 11.39 (d, J=4.4 Hz, 1H), 8.47 (br. s., 1H), 8.18-8.11 (m, J=10.5 Hz, 1H), 8.09 (br. s., 1H), 7.91 (dd, J=14.2, 6.7 Hz, 1H), 7.75 (dd, J=8.1, 2.8 Hz, 1H), 7.49 (br. s., 1H), 7.44-7.38 (m, 1H), 7.22 (t, J=7.6 Hz, 1H), 5.21 (dq, J=16.9, 8.5 Hz, 1H), 4.35-4.24 (m, 1H), 3.74-2.77 (m, 3H), 2.70-2.29 (m, J=15.0 Hz, 1H), 2.08 (d, J=19.0 Hz, 3H), 1.96-1.93 (m, 1H), 1.87 (br. s., 3H), 1.61-1.34 (m, 1H). $^1$H NMR (400 MHz, DMSO-$d_6$) complex due to mixture of

Example 118

(S)-4-(3-(But-2-ynamido)piperidin-1-yl)-3-fluoro-9H-carbazole-1-carboxamide

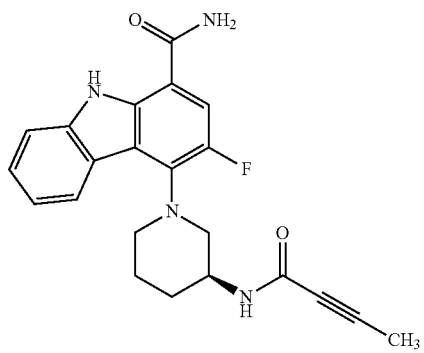

(118)

DIPEA (2.62 mL, 15.01 mmol) was added to a solution of (S)-4-(3-aminopiperidin-1-yl)-3-fluoro-9H-carbazole-1-carboxamide (Intermediate 85) (0.98 g, 3.00 mmol), but-2-ynoic acid (0.265 g, 3.15 mmol), and HATU (1.199 g, 3.15 mmol) in DMF (15 mL) and stirred at room temperature for 45 minutes. The mixture was diluted with EtOAc, washed with saturated NaHCO₃, water (3×), dried (MgSO₄), and concentrated. The crude was purified using ISCO flash chromatography (silica gel/hexanes/ethyl acetate 100:0 to 0:100 gradient) to afford (0.520 g. 51% yield). Mass spectrum m/z 393 (M+H)⁺. ¹H NMR (400 MHz, DMSO-d₆) δ 11.38 (s, 1H), 8.56 (d, J=7.8 Hz, 1H), 8.31 (d, J=8.1 Hz, 1H), 8.07 (br. s., 1H), 7.85 (d, J=14.4 Hz, 1H), 7.73 (d, J=8.1 Hz, 1H), 7.48 (br. s., 1H), 7.43-7.34 (m, 1H), 7.24-7.15 (m, 1H), 4.03 (br. s., 1H), 3.26-3.16 (m, 2H), 2.99 (br. s., 2H), 2.03-1.79 (m, 6H), 1.43 (br. s., 1H).

Example 119

Cis-4-(1-acryloyloctahydro-6H-pyrrolo[3,4-b]pyridin-6-yl)-3-fluoro-9H-carbazole-1-carboxamide (Single Enantiomers)

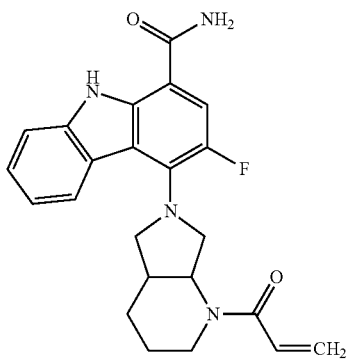

(119)

Acryloyl chloride (3.48 µl, 0.043 mmol) was added to a solution of 3-fluoro-4-(hexahydro-1H-pyrrolo[3,4-b]pyridin-6(2H)-yl)-9H-carbazole-1-carboxamide, TFA (20 mg, 0.043 mmol) (Intermediate 75), and DIPEA (7.49 µl, 0.043 mmol) in THF (1 mL) and stirred at room temperature for 30 minutes. The mixture was concentrated and the crude material was purified using preparative HPLC (YMC ODS C18 5µ; 30×100 mm column; detection at 220 nM; flow rate=30 mL/min; continuous gradient from 10% B to 100% B over 40 min+5 min hold at 100% B, where A=05:95:0.1 ACN-H₂O-TFA and B=95:05:0.1 ACN-H₂O-TFA) to afford (RS)-cis-4-(1-acryloylhexahydro-1H-pyrrolo[3,4-b]pyridin-6(2H)-yl)-3-fluoro-9H-carbazole-1-carboxamide (10.9 mg, 61.3% yield) as a white solid. Mass spectrum m/z 407 (M+H)⁺.

Examples 120 and 121

Cis-4-(1-acryloyloctahydro-6H-pyrrolo[3,4-b]pyridin-6-yl)-3-fluoro-9H-carbazole-1-carboxamide (Single Enantiomers)

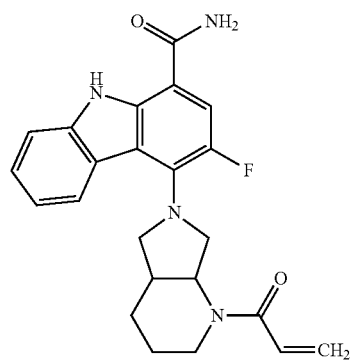

(120 and 121)

A sample of (RS)-cis-4-(1-acryloyloctahydro-6H-pyrrolo[3,4-b]pyridin-6-yl)-3-fluoro-9H-carbazole-1-carboxamide (Example 119) (76 mg) was separated by chiral supercritical fluid chromatography (Column: AS-H (3×25 cm, 5 µm); Mobile Phase: CO₂-MeOH (70:30) at 180 mL/min; 100 bar, 35° C.; sample preparation: 76 mg in 8 mL MeOH; injection: 9.5 mg/mL). The first peak eluting from the column provided one enantiomer of cis-4-(1-acryloyloctahydro-6H-pyrrolo[3,4-b]pyridin-6-yl)-3-fluoro-9H-carbazole-1-carboxamide (Example 120) as a white solid (26.3 mg). The second peak eluting from the column provided the other enantiomer of cis-4-(1-acryloyloctahydro-6H-pyrrolo[3,4-b]pyridin-6-yl)-3-fluoro-9H-carbazole-1-carboxamide (Example 121) as an off-white solid (26.5 mg). Mass spectrum m/z 407 (M+H)⁺. ¹H NMR (400 MHz, DMSO-d₆) δ 11.38 (s, 1H), 8.12 (d, J=7.9 Hz, 1H), 8.07 (br. s., 1H), 7.89 (d, J=14.4 Hz, 1H), 7.73 (d, J=8.1 Hz, 1H), 7.46 (br. s., 1H), 7.43-7.37 (m, 1H), 7.21 (t, J=7.3 Hz, 1H), 6.89 (d, J=12.2 Hz, 1H), 6.10 (dd, J=16.7, 2.4 Hz, 1H), 5.70 (br. s., 1H), 5.33-4.86 (m, 1H), 4.50-3.92 (m, 1H), 3.81-2.71 (m, 5H), 2.46-2.35 (m, 1H), 1.97-1.74 (m, 3H), 1.43 (br. s., 1H). ¹H NMR (400 MHz, DMSO-d₆) complex due to mixture of rotamers. Mass spectra and NMR spectra for both enantiomers were the same. The absolute stereochemistries of Examples 120 and 121 have not been assigned.

Example 122

3-Fluoro-4-((2-vinylpyrimidin-5-yl)methyl)-9H-carbazole-1-carboxamide

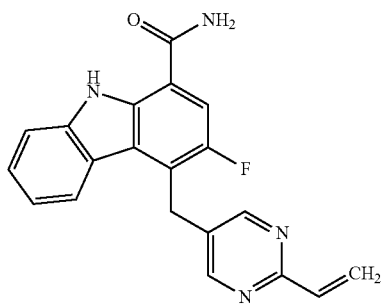

(122)

Intermediate 122A:
3-Fluoro-4-vinyl-9H-carbazole-1-carboxamide

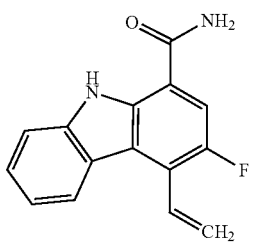

(122A)

A mixture of 4-bromo-3-fluoro-9H-carbazole-1-carboxamide (100 mg, 0.326 mmol), 2,4,6-trivinylcyclotriboroxane pyridine complex (94 mg, 0.39 mmol), 2M potassium phosphate tribasic (0.41 mL, 0.81 mmol), 1,1'-bis(di-tert-butylphosphino) ferrocene palladium dichloride (10.61 mg, 0.016 mmol) in THF (3 mL) was purged with nitrogen and stirred at 60° C. overnight. The mixture was cooled to room temperature and concentrated. The crude was purified using ISCO flash chromatography (silica gel/hexanes/ethyl acetate 100:0 to 0:100 gradient) to afford 3-fluoro-4-vinyl-9H-carbazole-1-carboxamide (70 mg, 85% yield) as a yellow solid. Mass spectrum m/z 255 (M+H)+. 1H NMR (400 MHz, methanol-d4) δ 8.23 (d, J=8.1 Hz, 1H), 7.73 (d, J=12.1 Hz, 1H), 7.61 (d, J=8.2 Hz, 1H), 7.49-7.37 (m, 2H), 7.19 (td, J=7.6, 1.0 Hz, 1H), 6.08 (dt, J=17.9, 1.7 Hz, 1H), 5.90 (dt, J=11.7, 1.7 Hz, 1H).

Intermediate 122B:
3-Fluoro-4-formyl-9H-carbazole-1-carboxamide

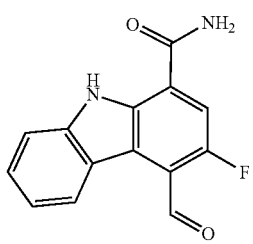

(122B)

A solution of 2% osmium tetraoxide in water (0.35 mL, 0.03 mmol) was added to a solution of 3-fluoro-4-vinyl-9H-carbazole-1-carboxamide (70 mg, 0.26 mmol; Intermediate 8) and 2,6-dimethylpyridine (0.06 mL, 0.55 mmol) in dioxane (0.8 mL). Next, a solution of sodium periodate (236 mg, 1.10 mmol) in water (0.3 mL) was added to the reaction mixture and stirred for 5 hours. The mixture was diluted with EtOAc, washed with water, dried (MgSO4), and concentrated. The crude was purified using ISCO flash chromatography (silica gel/hexanes/ethyl acetate 100:0 to 0:100 gradient) to afford 3-fluoro-4-formyl-9H-carbazole-1-carboxamide (60 mg, 85% yield) as a yellow solid. Mass spectrum m/z 257 (M+H)+.

Intermediate 122C: 4-((2-Chloropyrimidin-5-yl)methyl)-3-fluoro-9H-carbazole-1-carboxamide

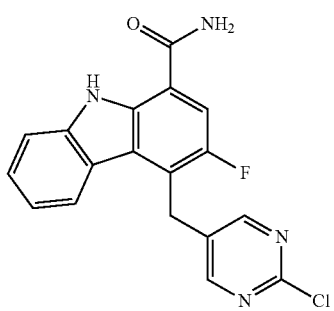

(122C)

A solution of 3-fluoro-4-formyl-9H-carbazole-1-carboxamide (10 mg, 0.04 mmol) and 4-methylbenzenesulfonhydrazide (7.99 mg, 0.04 mmol) in dioxane (1 mL) was stirred at 80° C. for 90 min. LCMS indicated that the formation of tosylhydrazone. 2-Chloropyridine-4-boronic acid (9.21 mg, 0.06 mmol) and potassium carbonate (8.09 mg, 0.06 mmol) were added and stirred at 110° C. for 2 hours (Ref: Nature Chem., Vol. 1 (September 2009), doi: 10.1038/NCHEM.328). The mixture was cooled to room temperature, diluted with EtOAc, washed with water, dried (MgSO4), and concentrated. The crude material was purified using preparative HPLC (PHENOMENEX® Luna Axia C18 5 μm; 30×100 mm column, eluting with methanol-water containing 0.1% TFA, gradient from 20-100%, 40 mL/min) to afford 4-((2-chloropyridin-4-yl)methyl)-3-fluoro-9H-carbazole-1-carboxamide (2.3 mg, 16.66% yield) as a light yellow solid. Mass spectrum m/z 355 (M+H)+. 1H NMR (400 MHz, chloroform-d) δ 10.44 (br. s., 1H), 8.32 (d, J=5.3 Hz, 1H), 7.89 (d, J=7.5 Hz, 1H), 7.61-7.57 (m, 1H), 7.55-7.49 (m, 1H), 7.45 (d, J=10.0 Hz, 1H), 7.25-7.22 (m, 2H), 7.21-7.16 (m, 1H), 6.51 (br. s., 1H), 4.71 (s, 2H).

Example 122

A solution of 4-((2-chloropyrimidin-5-yl)methyl)-3-fluoro-9H-carbazole-1-carboxamide (10 mg, 0.028 mmol), 2,4,6-trivinyl-1,3,5,2,4,6-trioxatriborinane compound with pyridine (1:1) (10.18 mg, 0.042 mmol), 2M potassium carbonate (0.042 mL, 0.085 mmol), and Pd(Ph3P)4 (3.26 mg, 2.82 μmol) in 1,4-dioxane (1 mL) was stirred at 90° C. for 18 hours. The mixture was concentrated and the crude material was purified via preparative LC/MS (XBridge C18, 19×200 mm, 5 μm particles column, eluting with 95 acetonitrile-water containing 10-mM ammonium acetate, gradient from 20-60%, 20 mL/min) to afford 3-fluoro-4-((2-vinylpyrimidin-5-yl)methyl)-9H-carbazole-1-carboxamide. Mass spectrum m/z 347 (M+H)$^+$. $^1$H NMR (400 MHz, chloroform-d) δ 10.44 (br. s., 1H), 8.32 (d, J=5.3 Hz, 1H), 7.89 (d, J=7.5 Hz, 1H), 7.61-7.57 (m, 1H), 7.55-7.49 (m, 1H), 7.45 (d, J=10.0 Hz, 1H), 7.25-7.22 (m, 2H), 7.21-7.16 (m, 1H), 6.51 (br. s., 1H), 4.71 (s, 2H).

Example 123

Cis-4-(1-acryloylhexahydropyrrolo[3,4-b]pyrrol-5 (1H)-yl)-3-fluoro-9H-carbazole-1-carboxamide

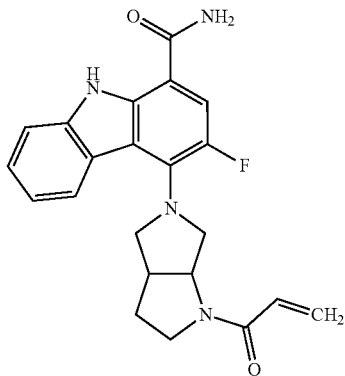

(123)

Acryloyl chloride (4.49 µl, 0.055 mmol) was added to a solution of 3-fluoro-4-(hexahydropyrrolo[3,4-b]pyrrol-5(1H)-yl)-9H-carbazole-1-carboxamide, TFA (Intermediate 76) (25 mg, 0.055 mmol) and DIPEA (9.65 µl, 0.055 mmol) in THF (0.5 mL) and stirred for 30 minutes. The mixture was concentrated and the crude material was purified using preparative HPLC (YMC ODS C18 5µ; 30×100 mm column; detection at 220 nM; flow rate=30 mL/min; continuous gradient from 10% B to 100% B over 40 min+2 min hold at 100% B, where A=05:95:0.1 ACN-H$_2$O-TFA and B=95:05: 0.1 ACN-H$_2$O-TFA) to afford (RS)-cis-4-(1-acryloylhexahydropyrrolo[3,4-b] pyrrol-5(1H)-yl)-3-fluoro-9H-carbazole-1-carboxamide (8.9 mg, 39.8% yield) as a light brown solid. Mass spectrum m/z 393 (M+H)$^+$.

Examples 124 and 125

Cis-4-(1-acryloylhexahydropyrrolo[3,4-b]pyrrol-5 (1H)-yl)-3-fluoro-9H-carbazole-1-carboxamide (Single Enantiomers)

(124 and 125)

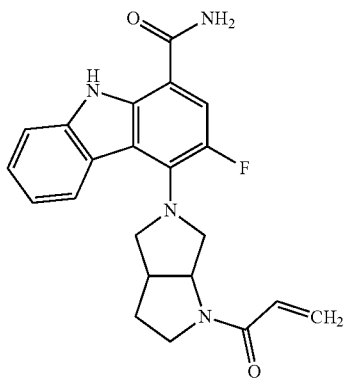

A sample of (RS)-cis-4-(1-acryloylhexahydropyrrolo[3,4-b]pyrrol-5(1H)-yl)-3-fluoro-9H-carbazole-1-carboxamide (Example 123) (108 mg) was separated by chiral supercritical fluid chromatography (Column: AS-H (3×25 cm, 5 µm); Mobile Phase: CO$_2$-MeOH (75:25) at 140 mL/min; 100 bar, 40° C.; sample preparation: 108 mg in MeOH; injection: 1.35 mg/mL). The first peak eluting from the column provided one enantiomer of cis-4-(1-acryloylhexahydropyrrolo[3,4-b]pyrrol-5(1H)-yl)-3-fluoro-9H-carbazole-1-carboxamide (Example 124) as a white solid (42 mg). The second peak eluting from the column provided the other enantiomer of cis-4-(1-acryloylhexahydropyrrolo[3,4-b] pyrrol-5(1H)-yl)-3-fluoro-9H-carbazole-1-carboxamide (Example 125) as an off-white solid (35 mg). Mass spectrum m/z 393 (M+H)$^+$. $^1$H NMR (400 MHz, methanol-d$_4$) δ 8.07-7.98 (m, 1H), 7.73-7.66 (m, 1H), 7.60-7.53 (m, 1H), 7.44-7.34 (m, 1H), 7.22-7.05 (m, 1H), 6.88-6.56 (m, 1H), 6.38-6.25 (m, 1H), 5.90-5.66 (m, 1H), 4.73-4.65 (m, 1H), 4.10-3.74 (m, 4H), 3.64 (d, J=4.5 Hz, 1H), 3.53-3.47 (m, 1H), 3.41-3.18 (m, 1H), 2.41-2.03 (m, 2H). $^1$H NMR (400 MHz, MEOH-d$_4$) complex due to mixture of rotamers. Mass spectra and NMR spectra for both enantiomers were the same. The absolute stereochemistries of Examples 124 and 125 have not been assigned.

Example 126

4-(1-(But-2-ynoyl)octahydro-6H-pyrrolo[3,4-b]pyridin-6-yl)-3-chloro-9H-carbazole-1-carboxamide (Racemic)

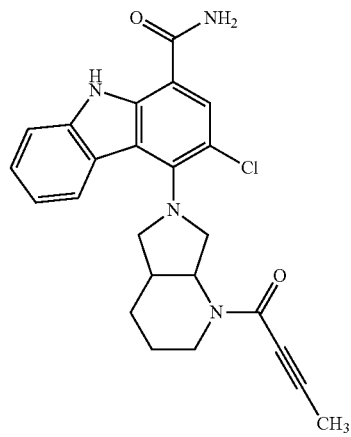

(126)

Intermediate 126A: 5-Bromo-6-chloro-2,3,4,9-tetrahydro-1H-carbazole-8-carboxylic acid

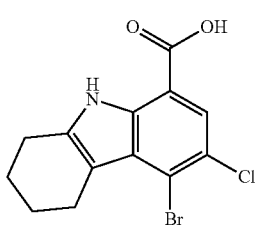

(126A)

To a suspension of 2-amino-4 bromo-5-chlorobenzoic acid (1.0 g, 3.99 mmol) in concentrated HCl (20 mL) at −10° C. was added dropwise a solution of sodium nitrite (0.289 g, 4.19 mmol) in water (2.0 mL) at a rate in which the reaction temperature remained below 0° C. The mixture was stirred at 0° C. for 15 min. A solution of tin(II) chloride (1.590 g, 8.38 mmol) in concentrated HCl (5.0 mL) was added to the mixture at a rate that the reaction temperature remained below −5° C. The reaction mixture was stirred at room temperature for 60 min. The precipitate was filtered, washed with water and air dried to afford 4-bromo-5-chloro-2-hydrazinylbenzoic acid, HCl (752 mg, 1.868 mmol, 46.8% yield) as a white solid.

A mixture of 4-bromo-5-chloro-2-hydrazinylbenzoic acid, HCl (1.0 g, 3.31 mmol) and cyclohexanone (0.650 g, 6.62 mmol) in HOAc (20 mL) was stirred at 110° C. for 18 hour. The precipitate was filtered and washed with HOAc and DCM. The crude material yielded 5-bromo-6-chloro-2,3,4,9-tetrahydro-1H-carbazole-8-carboxylic acid (893 g, 2582 mmol, 7.80E+04% yield) as a light green solid. $^1$H NMR (400 MHz, DMSO-$d_6$) δ 11.12 (s, 1H), 7.67 (s, 1H), 3.01 (br. s., 2H), 2.76 (br. s., 2H), 1.78 (br. s., 4H). LCMS: 1.21 min, M+H 329.

Intermediate 126B: Ethyl 4-bromo-3-chloro-9H-carbazole-1-carboxylate

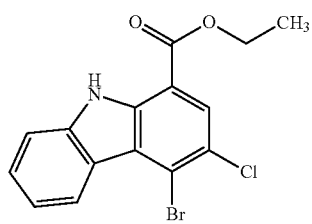

(126B)

To a solution of 5-bromo-6-chloro-2,3,4,9-tetrahydro-1H-carbazole-8-carboxylic acid, (Intermediate 126A) (2.27 g, 6.91 mmol) in THF (80 mL) was added DDQ (3.14 g, 13.82 mmol). The mixture was stirred at 60° C. for 18 hours. The mixture was concentrated to give 4-bromo-3-chloro-9H-carbazole-1-carboxylic acid. A mixture of 4-bromo-3-chloro-9H-carbazole-1-carboxylic acid and sulfuric acid (0.736 mL, 13.82 mmol) in EtOH (100 mL) was stirred at reflux for 18 hour. The mixture was concentrated. The crude product was subjected to ISCO flash chromatography (silica gel/hexane-EtOAc 100:0 to 50:50 gradient) to afford ethyl 4-bromo-3-chloro-9H-carbazole-1-carboxylate (760 mg, 2.048 mmol, 29.6% yield) as light brown solid. $^1$H NMR (400 MHz, chloroform-d) δ 10.12 (br. s., 1H), 8.82 (dd, J=8.1, 0.9 Hz, 1H), 8.23-8.08 (m, 1H), 7.65-7.48 (m, 2H), 7.37 (ddd, J=8.1, 6.6, 1.6 Hz, 1H), 4.52 (q, J=7.1 Hz, 2H), 1.55-1.47 (m, 3H).

Intermediate 126C: Ethyl 4-(1-(tert-butoxycarbonyl)hexahydro-1H-pyrrolo[3,4-b] pyridin-6(2H)-yl)-3-chloro-9H-carbazole-1-carboxylate

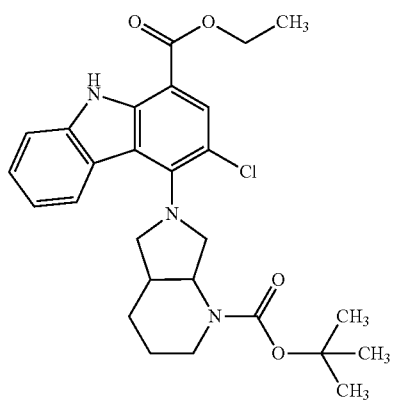

(126C)

A mixture of ethyl 4-bromo-3-chloro-9H-carbazole-1-carboxylate (200 mg, 0.567 mmol, 1-80), tert-butyl octahydro-1H-pyrrolo[3,4-b]pyridine-1-carboxylate (141 mg, 0.624 mmol), cesium carbonate (425 mg, 1.305 mmol), BINAP (17.66 mg, 0.028 mmol) and Pd$_2$(dba)$_3$ (26.0 mg, 0.028 mmol) in degassed 1,4-dioxane (3 mL) was stirred at 105° C. under nitrogen for 2 days. The mixture was diluted with EtOAc (15 mL) and was washed with a solution of aqueous saturated sodium bicarbonate (2×15 mL) and aqueous 1.0 M HCl (15 mL). The ethyl acetate layer was dried over sodium sulfate and concentrated. The crude product was subjected to ISCO flash chromatography (silica gel/hexane-EtOAc 100:0 to 50:50 gradient) to yield ethyl 4-(1-(tert-butoxycarbonyl) hexahydro-1H-pyrrolo[3,4-b]pyridin-6(2H)-yl)-3-chloro-9H-carbazole-1-carboxylate (198 mg, 0.358 mmol, 63.1% yield) as light brown gum. LCMS: 1.36 min, M+H 498.

Intermediate 126D: tert-Butyl 6-(1-carbamoyl-3-chloro-9H-carbazol-4-yl)octahydro-1H-pyrrolo[3,4-b]pyridine-1-carboxylate

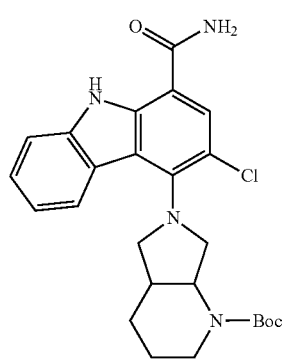

(126D)

A mixture of ethyl 4-(1-(tert-butoxycarbonyl)hexahydro-1H-pyrrolo[3,4-b] pyridin-6(2H)-yl)-3-chloro-9H-carbazole-1-carboxylate (198 mg, 0.398 mmol) and 2.0 M sodium hydroxide (1.988 mL, 3.98 mmol) in MeOH (15 mL) was stirred at 60° C. for 3 hour. The mixture was poured into a solution of 1.0 N aqueous HCl (60 mL) and was extracted with EtOAc (30 mL). The ethyl acetate layer was dried over sodium sulfate and concentrated to give 4-(1-(tert-butoxycarbonyl)octahydro-6H-pyrrolo[3,4-b]pyridin-6-yl)-3-chloro-9H-carbazole-1-carboxylic acid. LCMS: 1.17 min, M+H 470.

A mixture of 4-(1-(tert-butoxycarbonyl)octahydro-6H-pyrrolo[3,4-b]pyridin-6-yl)-3-chloro-9H-carbazole-1-carboxylic acid, ammonium chloride (213 mg, 3.98 mmol), BOP (176 mg, 0.398 mmol) and TEA (0.277 mL, 1.988 mmol) in DMF (5.0 mL) was stirred at room temperature for 2 hours. The mixture was diluted with EtOAc (15 mL) and was washed with a solution of aqueous saturated sodium bicarbonate (2×15 mL) and aqueous 1.0 M HCl (15 mL). The ethyl acetate layer was dried over sodium sulfate and concentrated. The crude product was subjected to ISCO flash chromatography (silica gel/hexane-EtOAc 100:0 to 0:100 gradient) to yield tert-butyl 6-(1-carbamoyl-3-chloro-9H-carbazol-4-yl)octahydro-1H-pyrrolo[3,4-b]pyridine-1-carboxylate (125 mg, 0.240 mmol, 60.3% yield) as white solid. LCMS: 1.13 min, M+H 469.

Intermediate 126E: 3-Chloro-4-(octahydro-6H-pyrrolo[3,4-b]pyridin-6-yl)-9H-carbazole-1-carboxamide

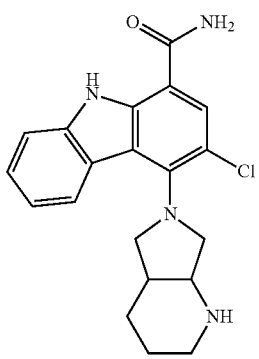

(126E)

To a solution of tert-butyl 6-(1-carbamoyl-3-chloro-9H-carbazol-4-yl)octahydro-1H-pyrrolo[3,4-b]pyridine-1-carboxylate (75 mg, 0.160 mmol) in DCM (1.0 mL) was added TFA (1.0 mL). The mixture was stirred at room temperature for 30 min. The mixture was concentrated to afford 3-chloro-4-(octahydro-6H-pyrrolo[3,4-b]pyridin-6-yl)-9H-carbazole-1-carboxamide.

Example 126

3-Chloro-4-(octahydro-6H-pyrrolo[3,4-b]pyridin-6-yl)-9H-carbazole-1-carboxamide, but-2-ynoic acid (13.45 mg, 0.160 mmol) and BOP (70.7 mg, 0.160 mmol) in DMF (3.0 mL) was added TEA (0.111 mL, 0.800 mmol). The mixture was stirred at room temperature for 60 min. The mixture was diluted with EtOAc (15 mL) and was washed with a solution of aqueous saturated sodium bicarbonate (2×15 mL) and aqueous 1.0 M HCl (15 mL). The ethyl acetate layer was dried over sodium sulfate and concentrated. The crude product was subjected to ISCO flash chromatography (silica gel/hexane-EtOAc 100:0 to 0:100 gradient) yielding Example 126. (65 mg, 0.142 mmol, 89% yield) as white solid. ¹H NMR (500 MHz, DMSO-d₆) δ 11.51 (d, J=3.7 Hz, 1H), 8.33-8.14 (m, 2H), 8.11-8.03 (m, 1H), 7.75 (d, J=8.1 Hz, 1H), 7.62-7.49 (m, 1H), 7.44 (s, 1H), 7.25 (t, J=7.5 Hz, 1H), 5.49-5.29 (m, 1H), 4.40-4.21 (m, 1H), 3.67-3.39 (m, 2H), 3.34-3.08 (m, 2H), 2.95-2.64 (m, 1H), 2.45-2.33 (m, 1H), 2.15-1.78 (m, 6H), 1.62-1.31 (m, 1H). LCMS: 0.94 min, M+H 435.

Examples 127 and 128

4-((4aS,7aS)-1-(But-2-ynoyl)octahydro-6H-pyrrolo[3,4-b]pyridin-6-yl)-3-chloro-9H-carbazole-1-carboxamide, and 4-((4aR,7aR)-1-(But-2-ynoyl)octahydro-6H-pyrrolo[3,4-b]pyridin-6-yl)-3-chloro-9H-carbazole-1-carboxamide (Single Isomers)

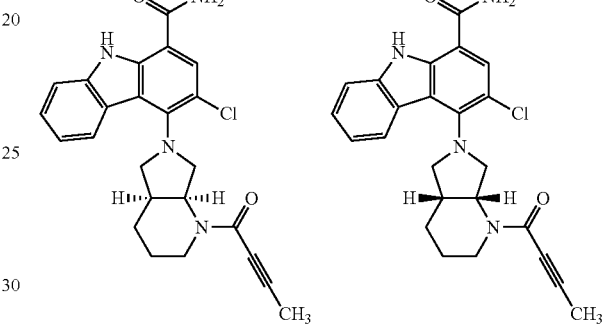

(127 and 128)

4-(1-(But-2-ynoyl)hexahydro-1H-pyrrolo[3,4-b]pyridin-6(2H)-yl)-3-chloro-9H-carbazole-1-carboxamide (65 mg) was separated by chiral super-critical fluid chromatography (CHIRALCEL® OJ (3×25 cm, 5 μm); Mobile Phase: CO₂-MeOH with 0.1% NH₄OH (67/33) at 160 mL/min; 100 bar, 40° C.; sample preparation: 85 mg in 6 mL MeOH with 0.1% NH₄OH. The first peak eluting from the column provided one enantiomer of 4-(1-(but-2-ynoyl)hexahydro-1H-pyrrolo[3,4-b]pyridin-6(2H)-yl)-3-chloro-9H-carbazole-1-carboxamide as a white powder (18 mg). The second peak eluting from the column provided the second enantiomer of 4-(1-(but-2-ynoyl)hexahydro-1H-pyrrolo[3,4-b]pyridin-6(2H)-yl)-3-chloro-9H-carbazole-1-carboxamide as a white powder (17 mg).

Example 129

3-Fluoro-4-((2-(prop-1-yn-1-yl)pyridin-4-yl)methyl)-9H-carbazole-1-carboxamide

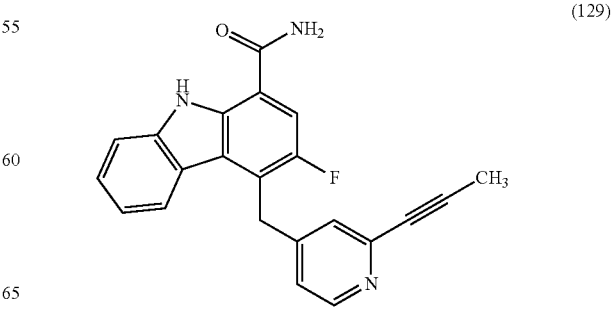

(129)

Intermediate 129A: Ethyl 4-bromo-3-fluoro-9H-carbazole-1-carboxylate

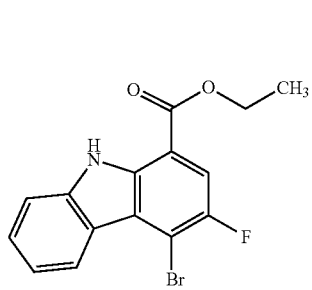

(129A)

Intermediate 129A was prepared according to the general procedure in Intermediate 126B using the acid intermediate (4-bromo-3-fluoro-9H-carbazole-1-carboxylic acid) in the preparation of Intermediate 8. $^1$H NMR (400 MHz, chloroform-d) δ 10.04 (br. s., 1H), 8.76 (d, J=7.9 Hz, 1H), 7.85 (d, J=9.3 Hz, 1H), 7.64-7.48 (m, 2H), 7.35 (ddd, 6.5, 1.7 Hz, 1H), 4.51 (q, J=7.1 Hz, 2H), 1.50 (t, J=7.2 Hz, 3H).

Intermediate 129B: Ethyl 3-fluoro-4-(4,4,5,5-tetramethyl-1,3,2-dioxaborolan-2-yl)-9H-carbazole-1-carboxylate

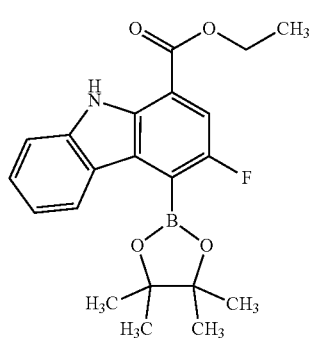

(129B)

A mixture of ethyl 4-bromo-3-fluoro-9H-carbazole-1-carboxylate (700 mg, 2.082 mmol), bis(pinacolato)diboron (555 mg, 2.186 mmol), potassium acetate (613 mg, 6.25 mmol) and PdCl$_2$(dppf)-CH$_2$Cl$_2$ adduct (85 mg, 0.104 mmol) in dioxane (10 mL) was stirred at 85° C. for 18 hour. The mixture was diluted with EtOAc (15 mL) and was washed with a solution of aqueous saturated sodium bicarbonate (2×15 mL) and aqueous 1.0 M HCl (15 mL). The ethyl acetate layer was dried over sodium sulfate and concentrated. The crude product was subjected to ISCO flash chromatography (silica gel/hexane-EtOAc 100:0 to 0:100 gradient) to yield ethyl 3-fluoro-4-(4,4,5,5-tetramethyl-1,3,2-dioxaborolan-2-yl)-9H-carbazole-1-carboxylate (522 mg, 1.226 mmol, 58.9% yield) as off-white solid. LCMS: 1.18 min, M+H 384.

Intermediate 129C: Ethyl 4-((2-chloropyridin-4-yl)methyl)-3-fluoro-9H-carbazole-1-carboxylate

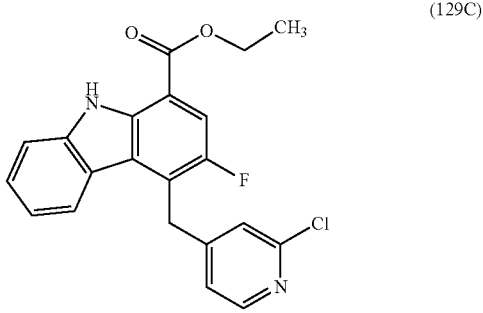 [SMILES: CCOC(=O)c1cc(F)c(Cc2ccnc(Cl)c2)c2c1[nH]c1ccccc12]

(129C)

To a solution of ethyl 3-fluoro-4-(4,4,5,5-tetramethyl-1,3,2-dioxaborolan-2-yl)-9H-carbazole-1-carboxylate (100 mg, 0.261 mmol), 1,1'-bis(di-tert-butylphosphino) ferrocene palladium dichloride (8.50 mg, 0.013 mmol) and 2.0 M potassium phosphate tribasic (0.391 mL, 0.783 mmol) in THF (1.0 mL) was added 2-chloro-4-(chloromethyl) pyridine (42.3 mg, 0.261 mmol), the mixture was stirred at room temperature in a sealed vial under nitrogen for 18 hour. The mixture was diluted with EtOAc (15 mL) and was washed with a solution of aqueous saturated sodium bicarbonate (15 mL). The ethyl acetate layer was dried over sodium sulfate and concentrated. The crude product was subjected to ISCO flash chromatography (silica gel/hexane-EtOAc 100:0 to 60:40 gradient) to yield ethyl 4-((2-chloropyridin-4-yl)methyl)-3-fluoro-9H-carbazole-1-carboxylate (75 mg, 0.186 mmol, 71.3% yield) as white solid. $^1$H NMR (400 MHz, chloroform-d) δ 10.12 (br. s., 1H), 8.25 (dd, J=5.1, 0.5 Hz, 1H), 7.97-7.82 (m, 2H), 7.62-7.45 (m, 2H), 7.26-7.17 (m, 2H), 7.11 (dd, J=5.1, 1.0 Hz, 1H), 4.68 (s, 2H), 4.53 (q, J=7.1 Hz, 2H), 1.56-1.45 (m, 3H). LCMS: 1.14 min, M+H 383.

Intermediate 129D: 4-((2-Chloropyridin-4-yl)methyl)-3-fluoro-9H-carbazole-1-carboxamide

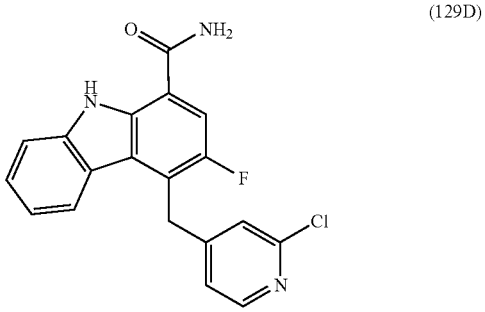 [SMILES: NC(=O)c1cc(F)c(Cc2ccnc(Cl)c2)c2c1[nH]c1ccccc12]

(129D)

A mixture of ethyl 4-((2-chloropyridin-4-yl)methyl)-3-fluoro-9H-carbazole-1-carboxylate (75 mg, 0.196 mmol) and lithium hydroxide (0.392 mL, 0.392 mmol) in THF (2.0 mL) was stirred at 60° C. for 18 hour. A solution of aqueous 1.0 N HCl (0.4 mL) was added to the mixture and the mixture was concentrated to give 4-((2-chloropyridin-4-yl)methyl)-3-fluoro-9H-carbazole-1-carboxylic acid. LCMS 5:0.94 min, M+H 355.

A mixture of 4-((2-chloropyridin-4-yl)methyl)-3-fluoro-9H-carbazole-1-carboxylic acid, ammonium chloride (52.4 mg, 0.980 mmol), BOP (87 mg, 0.196 mmol) and TEA (0.137 mL, 0.980 mmol) in DMF (2.0 mL) was stirred at room temperature for 30 min. The mixture was diluted with EtOAc (15 mL) and was washed with a solution of aqueous saturated sodium bicarbonate (2×15 mL) and aqueous 1.0 M HCl (15 mL). The ethyl acetate layer was dried over sodium sulfate and concentrated. The crude product was subjected to ISCO flash chromatography (silica gel/hexane-EtOAc 100:0 to 0:100 gradient) to yield 4-((2-chloropyridin-4-yl)methyl)-3-fluoro-9H-carbazole-1-carboxamide (67 mg, 0.170 mmol, 87% yield) as off-white solid. LCMS: 0.88 min, M+H 354.

Example 129

A mixture of 4-((2-chloropyridin-4-yl)methyl)-3-fluoro-9H-carbazole-1-carboxamide (20 mg, 0.057 mmol), tributyl (1-propynyl) tin (55.8 mg, 0.170 mmol), lithium chloride (7.19 mg, 0.170 mmol) and tetrakis(triphenylphosphine)palladium(0) (3.27 mg, 2.83 µmol) in DMF (1.0 mL) was stirred at 90° C. in a sealed vial under nitrogen for 18 hour. The mixture was diluted with EtOAc (15 mL) and was washed with a solution of aqueous saturated sodium bicarbonate (2×15 mL). The ethyl acetate layer was dried over sodium sulfate and concentrated. The crude product was purified by prep-HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-55% B over 25 minutes, then a 2-minute hold at 55% B; Flow: 20 mL/min) to yield 3-fluoro-4-((2-(prop-1-yn-1-yl)pyridin-4-yl)methyl)-9H-carbazole-1-carboxamide (14.1 mg, 0.037 mmol, 66.3% yield). $^1$H NMR (500 MHz, DMSO-d$_6$) δ 11.55 (s, 1H), 8.36 (d, J=5.0 Hz, 1H), 8.25 (br. s., 1H), 8.00-7.88 (m, 2H), 7.77 (d, J=8.1 Hz, 1H), 7.62 (br. s., 1H), 7.40 (t, J=7.6 Hz, 1H), 7.24-7.04 (m, 3H), 4.65 (br. s., 2H), 1.97 (s, 3H). LCMS: 0.71 min, M+H 358.

Example 130

5-((S)-3-(But-2-ynamido)piperidin-1-yl)-6-fluoro-2-(2-hydroxypropan-2-yl)-2,3,4,9-tetrahydro-1H-carbazole-8-carboxamide (Racemic)

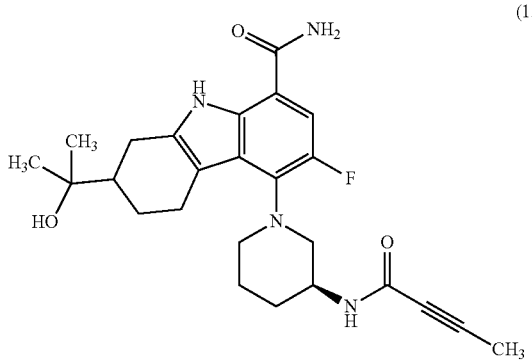

(130)

Intermediate 130A: Ethyl 5-bromo-8-cyano-6-fluoro-2,3,4,9-tetrahydro-1H-carbazole-2-carboxylate

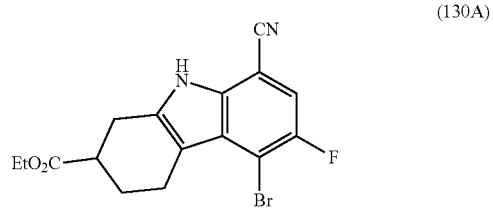 [SMILES: CCOC(=O)C1CCc2c([nH]c3c(C#N)cc(F)c(Br)c23)C1]

(130A)

To a homogeneous solution of ethyl 5-bromo-8-carbamoyl-6-fluoro-2,3,4,9-tetrahydro-1H-carbazole-2-carboxylate (1.00 g, 2.61 mmol) in tetrahydrofuran (6 mL) at room temperature was added phosphoryl trichloride (0.485 mL, 5.22 mmol) dropwise via syringe. The reaction mixture was stirred at room temperature for 5 days. The heterogeneous reaction mixture was concentrated under reduced pressure. The residue was diluted with ethyl acetate, and the resulting solid was collected by vacuum filtration, washed with ethyl acetate, and dried to give ethyl 5-bromo-8-cyano-6-fluoro-2,3,4,9-tetrahydro-1H-carbazole-2-carboxylate (0.699 g, 1.91 mmol, 73% yield) as a yellow solid. The product had a UPLC ret. time=1.40 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. LC/MS M+1=365.2 and 367.1.

Intermediate 130B: Ethyl 5-((S)-3-((tert-butoxycarbonyl)amino)piperidin-1-yl)-8-cyano-6-fluoro-2,3,4,9-tetrahydro-1H-carbazole-2-carboxylate

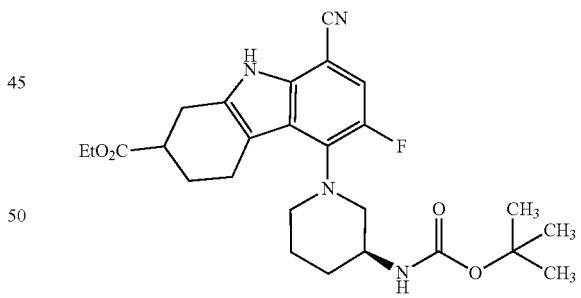

(130B)

A mixture of ethyl 5-bromo-8-cyano-6-fluoro-2,3,4,9-tetrahydro-1H-carbazole-2-carboxylate (0.699 g, 1.91 mmol), (S)-tert-butyl piperidin-3-ylcarbamate (0.460 g, 2.30 mmol), and (S)-tert-butyl piperidin-3-ylcarbamate (0.460 g, 2.30 mmol) in dioxane (10 mL) was degassed with vacuum and nitrogen (3×). BINAP (0.060 g, 0.096 mmol) was added followed by Pd$_2$(dba)$_3$ (0.088 g, 0.096 mmol), and the mixture was degassed (3×). The reaction mixture was immersed in an oil bath at 103° C. and stirred for ~24 h. After cooling to room temperature, the reaction mixture was diluted with ethyl acetate, washed with water, and washed with brine. The organic layer was collected, and the aqueous layers were sequentially extracted with ethyl acetate (2×).

The combined organic layers were dried over anhydrous sodium sulfate and concentrated under reduced pressure. The residue was purified by ISCO flash chromatography (40 g column; 0%-100% ethyl acetate in hexane) to give ethyl 5-((S)-3-((tert-butoxycarbonyl)amino)piperidin-1-yl)-8-cyano-6-fluoro-2,3,4,9-tetrahydro-1H-carbazole-2-carboxylate (0.718 g, 1.48 mmol, 77% yield) as a pale yellow solid. The product had a UPLC ret. time=1.48 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. LC/MS M+1=485.5.

Intermediate 130C: 5-((S)-3-Aminopiperidin-1-yl)-8-carbamoyl-6-fluoro-2,3,4,9-tetrahydro-1H-carbazole-2-carboxylic acid

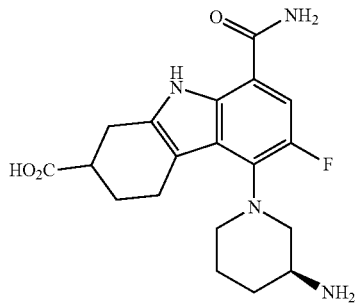

(130C)

A mixture of ethyl 5-((S)-3-(((benzyloxy)carbonyl)amino)piperidin-1-yl)-8-cyano-6-fluoro-2,3,4,9-tetrahydro-1H-carbazole-2-carboxylate (0.699 g, 1.348 mmol) and 90% aqueous sulfuric acid (9.98 ml, 168 mmol) was immersed in an oil bath at 60° C. and stirred for 60 min. To the stirred reaction mixture cooled to 0° C. was added an aqueous solution of sodium hydroxide (10M) (33.7 ml, 337 mmol) dropwise. A few additional drops of the sodium hydroxide solution was added until the pH was ~9. The pH was then dropped to ~5 with hydrochloric acid, and the suspension was filtered under reduced pressure. The solid was washed with water and dried well to give 5-((S)-3-aminopiperidin-1-yl)-8-carbamoyl-6-fluoro-2,3,4,9-tetrahydro-1H-carbazole-2-carboxylic acid (0.400 g, 1.07 mmol, 79% yield) as a light brown solid. The product had a UPLC ret. time=0.723 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. LC/MS M+1=375.2.

Intermediate 130D: Methyl 5-((S)-3-aminopiperidin-1-yl)-8-carbamoyl-6-fluoro-2,3,4,9-tetrahydro-1H-carbazole-2-carboxylate

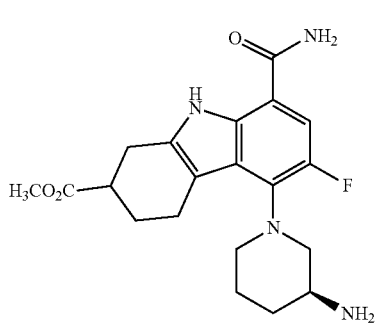

(130D)

To a solution of 5-((S)-3-aminopiperidin-1-yl)-8-carbamoyl-6-fluoro-2,3,4,9-tetrahydro-1H-carbazole-2-carboxylic acid (0.380 g, 1.02 mmol) in a mixture of methanol (2.5 mL) and dichloromethane (2.5 mL) at room temperature was added trimethylsilyldiazomethane (2M in ether; 0.558 mL, 1.12 mmol) dropwise, while being monitored by HPLC, until the reaction was nearly complete. The solvent was removed under reduced pressure, and the reaction mixture was diluted with ethyl acetate, washed with a saturated aqueous solution of sodium bicarbonate, washed with brine, and dried over anhydrous sodium sulfate. A precipitate that formed during the work up was collected and was found to be the acid starting material. The organic layer was dried over anhydrous sodium sulfate and concentrated to afford methyl 5-((S)-3-aminopiperidin-1-yl)-8-carbamoyl-6-fluoro-2,3,4,9-tetrahydro-1H-carbazole-2-carboxylate (0.269 g, 0.693 mmol, 68% yield) as a pale yellow solid. The product was had a UPLC ret. time=0.753 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. LC/MS M+1=389.2.

Intermediate 130E: 5-((S)-3-Aminopiperidin-1-yl)-6-fluoro-2-(2-hydroxypropan-2-yl)-2,3,4,9-tetrahydro-1H-carbazole-8-carboxamide

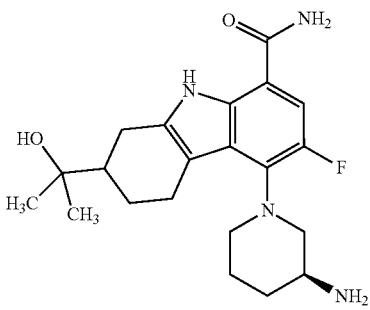

(130E)

To a solution of methyl 5-((S)-3-aminopiperidin-1-yl)-8-carbamoyl-6-fluoro-2,3,4,9-tetrahydro-1H-carbazole-2-carboxylate (0.269 g, 0.693 mmol) in tetrahydrofuran (5 mL) at −78° C. was added methyllithium (1.6 M in ether) (3 equiv.; 1.3 mL, 78 mmol) dropwise over 30 min. The reaction mixture was stirred at −78° C. for 45 min. An additional 3 equivalents of methyllithium (1.3 mL) was added over 25 min., and the reaction mixture was stirred at −78° C. for an additional 1.5 h. The reaction was quenched at −78° C. with a saturated aqueous solution of ammonium chloride was allowed to warm to room temperature. The mixture was diluted with ethyl acetate and washed with water, resulting in a solid. The solid was collected by vacuum filtration, washed with water, and dried well. The filtrate was extracted with ethyl acetate, washed with water, and washed with brine. The organ layer was dried over anhydrous sodium sulfate and concentrated under reduced pressure. Both recovered products were combined to give 5-((S)-3-aminopiperidin-1-yl)-6-fluoro-2-(2-hydroxypropan-2-yl)-2,3,4,9-tetrahydro-1H-carbazole-8-carboxamide (0.105 g, 0.270 mmol, 39.0% yield) as a pale yellow solid. The product had a UPLC retention time=0.745 min.—Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=389.2.

Example 130

A mixture of 5-((S)-3-aminopiperidin-1-yl)-6-fluoro-2-(2-hydroxypropan-2-yl)-2,3,4,9-tetrahydro-1H-carbazole-8-carboxamide (0.079 g, 0.203 mmol), but-2-ynoic acid (0.021 g, 0.244 mmol), HATU (0.108 g, 0.285 mmol), and Hunig's Base (0.124 mL, 0.712 mmol) in N,N-dimethylformamide (1.0 mL) was stirred at room temperature for 40 min. The mixture was diluted with ethyl acetate, washed with 10% aqueous lithium chloride (2×), and washed with brine. The organic layer was collected, and the aqueous layers were sequentially extracted with ethyl acetate (2×). The combined organic layers were dried over anhydrous sodium sulfate and concentrated. Purification by ISCO flash chromatography (4 g column; 0%-5% methanol in dichloromethane) afforded the product as a pale yellow solid. The compound was triturated with methanol with sonication and dried to give 5-((S)-3-(but-2-ynamido)piperidin-1-yl)-6-fluoro-2-(2-hydroxypropan-2-yl)-2,3,4,9-tetrahydro-1H-carbazole-8-carboxamide (0.0072 g, 0.015 mmol, 7.2% yield) as an off-white solid. The product had a UPLC ret. time=0.965 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=455.4.

Examples 131 and 132

5-((S)-3-(But-2-ynamido)piperidin-1-yl)-6-fluoro-2-(2-hydroxypropan-2-yl)-2,3,4,9-tetrahydro-1H-carbazole-8-carboxamide (Single Isomer)

(131 and 132)

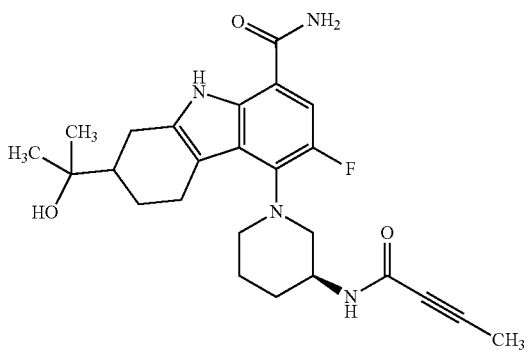

The filtrate from Example 130 was purified by reverse phase, preparative HPLC to give the two homochiral isomers:

Example 131 (Diastereomer 1) as a white solid. The product had a UPLC ret. time=0.967 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=455.3. $^1$H NMR (500 MHz, DMSO-$d_6$) δ 10.61 (s, 1H), 8.51 (br. s., 1H), 7.90 (br. s., 1H), 7.42-7.36 (m, 1H), 7.32 (br. s., 1H), 4.25-4.21 (m, 1H), 3.86-3.77 (m, 1H), 3.25-3.11 (m, 2H), 3.06 (d, J=11.3 Hz, 1H), 2.88 (dd, J=16.9, 4.5 Hz, 3H), 2.68-2.58 (m, 1H), 2.46-2.39 (m, 1H), 2.09 (d, J=7.9 Hz, 1H), 1.94 (s, 3H), 1.85 (br. s., 1H), 1.78-1.60 (m, 3H), 1.36-1.26 (m, 2H), and 1.13 (d, J=3.8 Hz, 6H).

Example 132 (Diastereomer 2) as a white solid. The product had a UPLC ret. time=0.973 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=455.3. $^1$H NMR (500 MHz, DMSO-$d_6$) δ 10.60 (s, 1H), 8.46 (br. s., 1H), 7.91 (br. s., 1H), 7.42-7.37 (m, 1H), 7.32 (br. s., 1H), 4.23 (s, 1H), 3.95-3.86 (m, 1H), 3.19-3.11 (m, 2H), 3.02 (br. s., 2H), 2.87 (dd, J=16.8, 4.7 Hz, 1H), 2.71 (d, J=10.7 Hz, 2H), 2.46-2.38 (m, 1H), 2.13-2.05 (m, 2H), 1.93 (s, 3H), 1.86 (br. s., 1H), 1.73 (br. s., 1H), 1.70-1.58 (m, 2H), 1.34-1.25 (m, 1H), and 1.13 (s, 6H).

TABLE 7

| Example | Structure | Starting Materials | Name | Mass Spectrum |
|---|---|---|---|---|
| 133 | 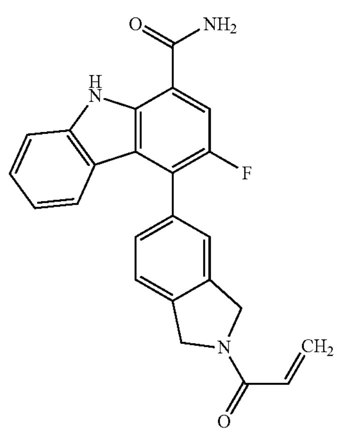 [SMILES: C=CC(=O)N1Cc2ccc(-c3c(F)cc(C(N)=O)c4[nH]c5ccccc5c34)cc2C1] | Intermediate 70 | 4-(2-acryloylisoindolin-5-yl)-3-fluoro-9H-carbazole-1-carboxamide | m/z 400 (M + H)$^+$ |

TABLE 7-continued

| Example | Structure | Starting Materials | Name | Mass Spectrum |
|---|---|---|---|---|
| 134 | 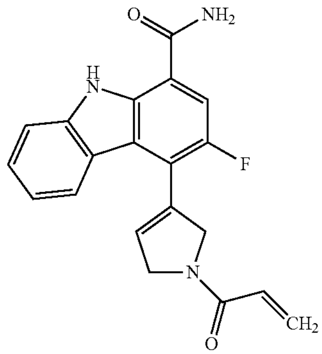 [SMILES: C=CC(=O)N1CC=C(c2c(F)cc(C(N)=O)c3[nH]c4ccccc4c23)C1] | Intermediate 71 | 4-(1-acryloyl-2,5-dihydro-1H-pyrrol-3-yl)-3-fluoro-9H-carbazole-1-carboxamide | m/z 350 (M + H)+ |
| 135 (racemate) | 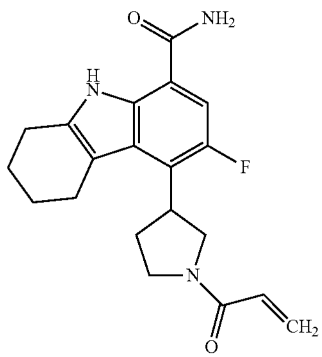 [SMILES: C=CC(=O)N1CCC(c2c(F)cc(C(N)=O)c3[nH]c4c(c23)CCCC4)C1] | Intermediate 73 | 5-(1-acryloylpyrrolidin-3-yl)-6-fluoro-2,3,4,9-tetrahydro-1H-carbazole-8-carboxamide | m/z 356 (M + H)+ |
| 136 homochiral | 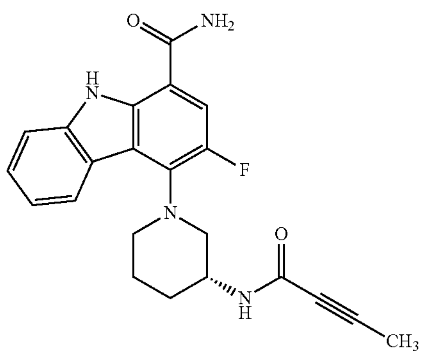 [SMILES: CC#CC(=O)N[C@@H]1CCCN(c2c(F)cc(C(N)=O)c3[nH]c4ccccc4c23)C1] | Intermediate 74 | (R)-4-(3-(but-2-ynamido)piperidin-1-yl)-3-fluoro-9H-carbazole-1-carboxamide | m/z 393 (M + H)+ |
| 137 (racemate) | 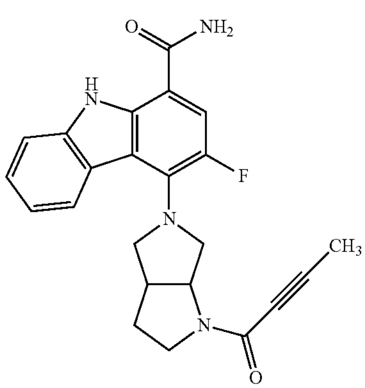 [SMILES: CC#CC(=O)N1CCC2CN(c3c(F)cc(C(N)=O)c4[nH]c5ccccc5c34)CC21] | Intermediate 76 | 4-(1-(but-2-ynoyl)hexahydropyrrolo[3,4-b]pyrrol-5(1H)-yl)-3-fluoro-9H-carbazole-1-carboxamide | m/z 405 (M + H)+ |

TABLE 7-continued

| Example | Structure | Starting Materials | Name | Mass Spectrum |
|---|---|---|---|---|
| 138 | 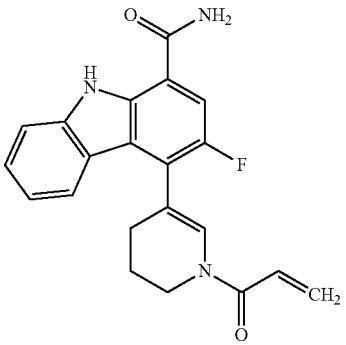 [SMILES: C=CC(=O)N1C=C(c2c(F)cc(C(N)=O)c3[nH]c4ccccc4c23)CCC1] | Intermediate 77 | 4-(1-acryloyl-1,4,5,6-tetrahydropyridin-3-yl)-3-fluoro-9H-carbazole-1-carboxamide | m/z 364 (M + H)+ |
| 139 (racemate) | 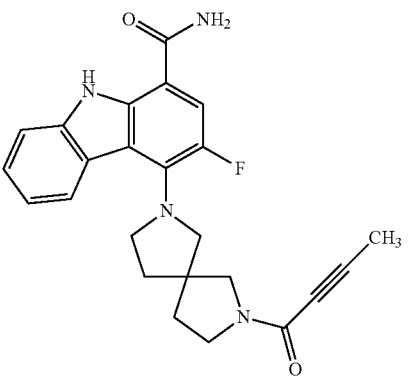 [SMILES: CC#CC(=O)N1CCC2(CCN(c3c(F)cc(C(N)=O)c4[nH]c5ccccc5c34)C2)C1] | Intermediate 78 | 4-(7-(but-2-ynoyl)-2,7-diazaspiro[4.4]nonan-2-yl)-3-fluoro-9H-carbazole-1-carboxamide | m/z 419 (M + H)+ |
| 140 (racemate) | 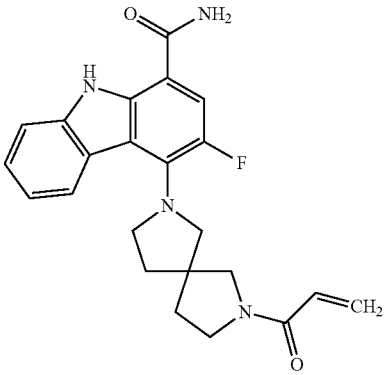 [SMILES: C=CC(=O)N1CCC2(CCN(c3c(F)cc(C(N)=O)c4[nH]c5ccccc5c34)C2)C1] | Intermediate 78 | 4-(7-acryloyl-2,7-diazaspiro[4.4]nonan-2-yl)-3-fluoro-9H-carbazole-1-carboxamide | m/z 407 (M + H)+ |
| 141 (racemate) | 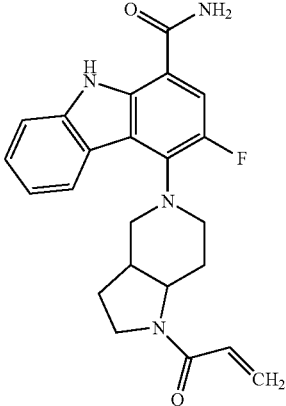 [SMILES: C=CC(=O)N1CCC2CN(c3c(F)cc(C(N)=O)c4[nH]c5ccccc5c34)CCC21] | Intermediate 79 | 4-(1-acryloyloctahydro-5H-pyrrolo[3,2-c]pyridin-5-yl)-3-fluoro-9H-carbazole-1-carboxamide | m/z 407 (M + H)+ |

TABLE 7-continued

| Example | Structure | Starting Materials | Name | Mass Spectrum |
|---|---|---|---|---|
| 142 (racemate) | 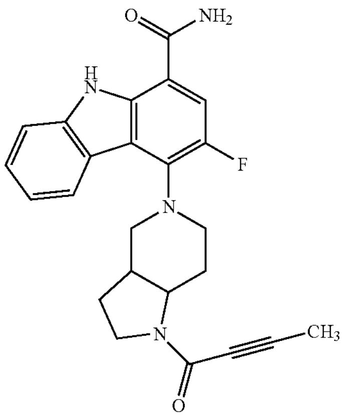 [SMILES: CC#CC(=O)N1CCC2CN(c3c(F)cc(C(N)=O)c4[nH]c5ccccc5c34)CCC21] | Intermediate 79 | 4-(1-(but-2-ynoyl) octahydro-5H-pyrrolo[3,2-c]pyridin-5-yl)-3-fluoro-9H-carbazole-1-carboxamide | m/z 419 (M + H)+ |

Additional Examples prepared by procedures described above or similar procedures to those known in the art, using the appropriate starting materials, are shown in Table 8.

TABLE 8

| Example | Structure | Name | Mass Spectrum |
|---|---|---|---|
| 143 | 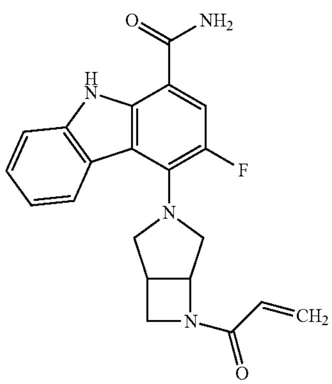 [SMILES: C=CC(=O)N1CC2CN(c3c(F)cc(C(N)=O)c4[nH]c5ccccc5c34)CC21] | 4-(6-acryloyl-3,6-diazabicyclo[3.2.0]heptan-3-yl)-3-fluoro-9H-carbazole-1-carboxamide | m/z 379 (M + H)+ |
| 144 | 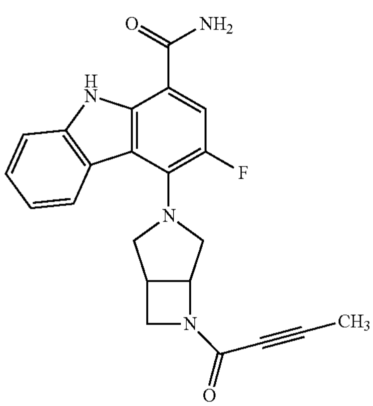 [SMILES: CC#CC(=O)N1CC2CN(c3c(F)cc(C(N)=O)c4[nH]c5ccccc5c34)CC21] | 4-(6-(but-2-ynoyl)-3,6-diazabicyclo[3.2.0]heptan-3-yl)-3-fluoro-9H-carbazole-1-carboxamide | m/z 391 (M + H)+ |

TABLE 8-continued

| Example | Structure | Name | Mass Spectrum |
|---|---|---|---|
| 145 | 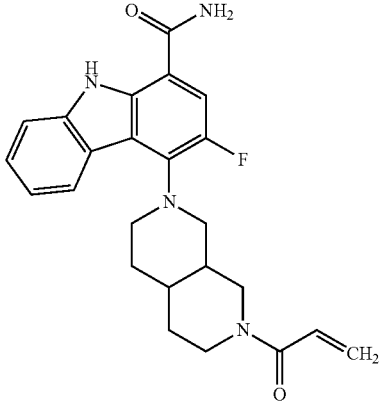 [SMILES: C=CC(=O)N1CCC2CCN(c3c(F)cc(C(N)=O)c4[nH]c5ccccc5c34)CC2C1] | 4-(7-acryloyloctahydro-2,7-naphthyridin-2(1H)-yl)-3-fluoro-9H-carbazole-1-carboxamide | m/z 421 (M + H)+ |
| 146 | 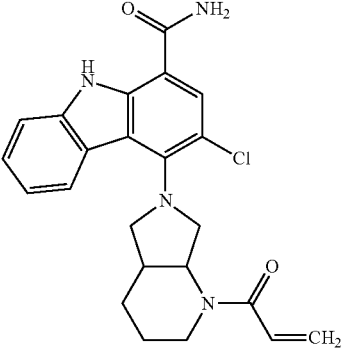 [SMILES: C=CC(=O)N1CCCC2CN(c3c(Cl)cc(C(N)=O)c4[nH]c5ccccc5c34)CC21] | 4-(1-acryloyloctahydro-6H-pyrrolo[3,4-b]pyridin-6-yl)-3-chloro-9H-carbazole-1-carboxamide | m/z 423 (M + H)+ |
| 147 (racemate) | 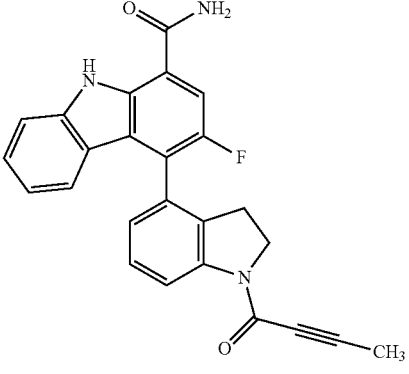 [SMILES: CC#CC(=O)N1CCc2c(-c3c(F)cc(C(N)=O)c4[nH]c5ccccc5c34)cccc21] | 4-(1-(but-2-ynoyl)indolin-4-yl)-3-fluoro-9H-carbazole-1-carboxamide | m/z 412 (M + H)+ |
| 148 | 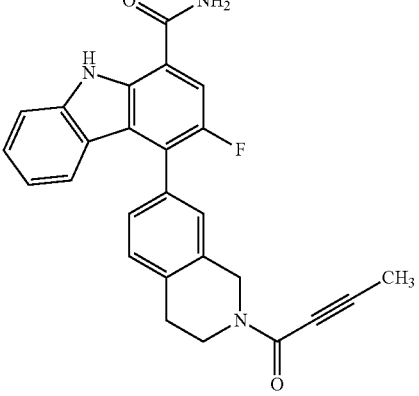 | 4-(2-(but-2-ynoyl)-1,2,3,4-tetrahydroisoquinolin-7-yl)-3-fluoro-9H-carbazole-1-carboxamide | m/z 426 (M + H)+ |

TABLE 8-continued

| Example | Structure | Name | Mass Spectrum |
|---------|-----------|------|---------------|
| 149 | 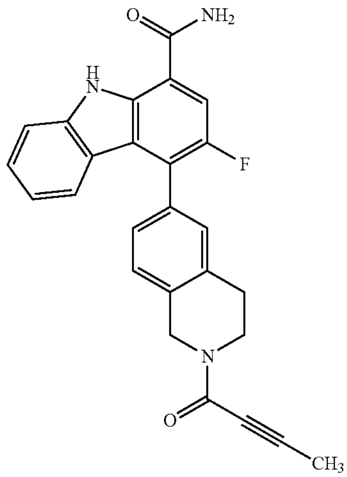 [SMILES: CC#CC(=O)N1CCc2cc(-c3c(F)cc(C(N)=O)c4[nH]c5ccccc5c34)ccc2C1] | 4-(2-(but-2-ynoyl)-1,2,3,4-tetrahydroisoquinolin-6-yl)-3-fluoro-9H-carbazole-1-carboxamide | m/z 426 (M + H)+ |
| 150 (racemate) | 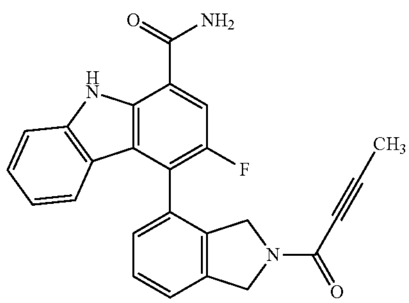 [SMILES: CC#CC(=O)N1Cc2cccc(-c3c(F)cc(C(N)=O)c4[nH]c5ccccc5c34)c2C1] | 4-(2-(but-2-ynoyl)isoindolin-4-yl)-3-fluoro-9H-carbazole-1-carboxamide | m/z 412 (M + H)+ |
| 151 | 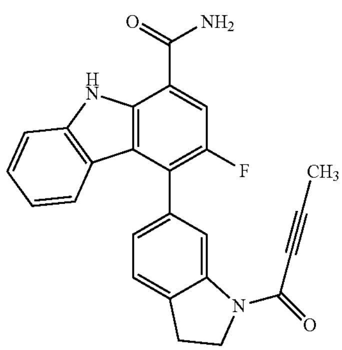 [SMILES: CC#CC(=O)N1CCc2ccc(-c3c(F)cc(C(N)=O)c4[nH]c5ccccc5c34)cc21] | 4-(1-(but-2-ynoyl)indolin-6-yl)-3-fluoro-9H-carbazole-1-carboxamide | m/z 412 (M + H)+ |
| 152 | 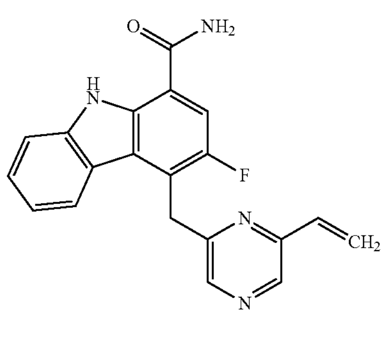 [SMILES: C=Cc1cncc(Cc2c(F)cc(C(N)=O)c3[nH]c4ccccc4c23)n1] | 3-fluoro-4-((6-vinylpyrazin-2-yl)methyl)-9H-carbazole-1-carboxamide | m/z 347 (M + H)+ |

TABLE 8-continued

| Example | Structure | Name | Mass Spectrum |
|---|---|---|---|
| 153 | 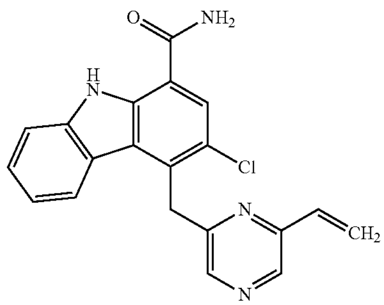 [SMILES: C=Cc1cncc(Cc2c(Cl)cc(C(N)=O)c3[nH]c4ccccc4c23)n1] | 3-chloro-4-((6-vinylpyrazin-2-yl)methyl)-9H-carbazole-1-carboxamide | m/z 363 (M + H)+ |
| 154 | 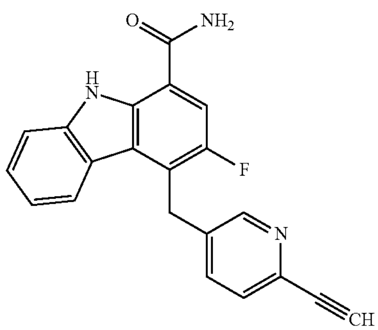 [SMILES: C#Cc1ccc(Cc2c(F)cc(C(N)=O)c3[nH]c4ccccc4c23)cn1] | 4-((6-ethynylpyridin-3-yl)methyl)-3-fluoro-9H-carbazole-1-carboxamide | m/z 344 (M + H)+ |
| 155 | 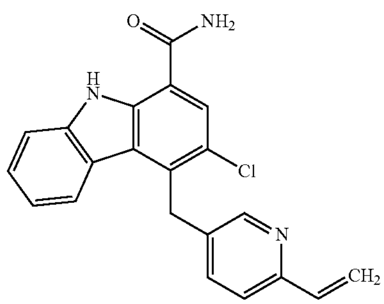 [SMILES: C=Cc1ccc(Cc2c(Cl)cc(C(N)=O)c3[nH]c4ccccc4c23)cn1] | 3-chloro-4-((6-vinylpyridin-3-yl)methyl)-9H-carbazole-1-carboxamide | m/z 362 (M + H)+ |
| 156 | 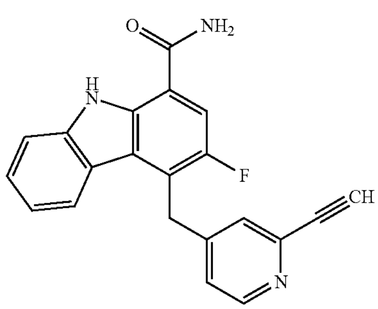 [SMILES: C#Cc1cc(Cc2c(F)cc(C(N)=O)c3[nH]c4ccccc4c23)ccn1] | 4-((2-ethynylpyridin-4-yl)methyl)-3-fluoro-9H-carbazole-1-carboxamide | m/z 344 (M + H)+ |
| 157 | 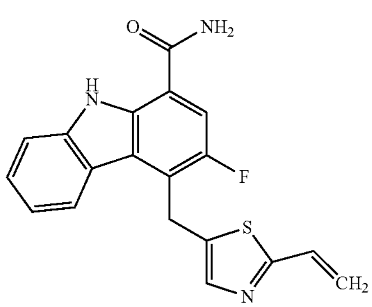 [SMILES: C=Cc1ncc(Cc2c(F)cc(C(N)=O)c3[nH]c4ccccc4c23)s1] | 3-fluoro-4-((2-vinylthiazol-5-yl)methyl)-9H-carbazole-1-carboxamide | m/z 352 (M + H)+ |

TABLE 8-continued

| Example | Structure | Name | Mass Spectrum |
|---|---|---|---|
| 158 | 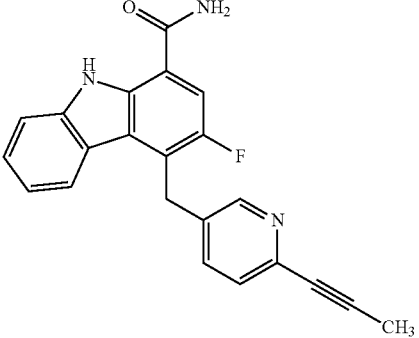 [SMILES: CC#Cc1ccc(Cc2c(F)cc(C(N)=O)c3[nH]c4ccccc4c23)cn1] | 3-fluoro-4-((6-(prop-1-yn-1-yl)pyridin-3-yl)methyl)-9H-carbazole-1-carboxamide | m/z 358 (M + H)+ |
| 159 | 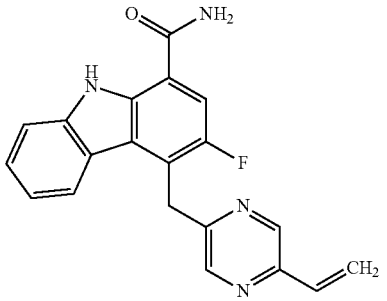 [SMILES: C=Cc1cnc(Cc2c(F)cc(C(N)=O)c3[nH]c4ccccc4c23)cn1] | 3-fluoro-4-((5-vinylpyrazin-2-yl)methyl)-9H-carbazole-1-carboxamide | m/z 347 (M + H)+ |
| 160 | 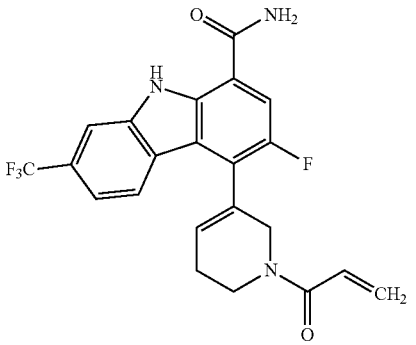 [SMILES: C=CC(=O)N1CCC=C(c2c(F)cc(C(N)=O)c3[nH]c4cc(C(F)(F)F)ccc4c23)C1] | 4-(1-acryloyl-1,2,5,6-tetrahydropyridin-3-yl)-3-fluoro-7-(trifluoromethyl)-9H-carbazole-1-carboxamide | m/z 432 (M + H)+ |
| 161 | 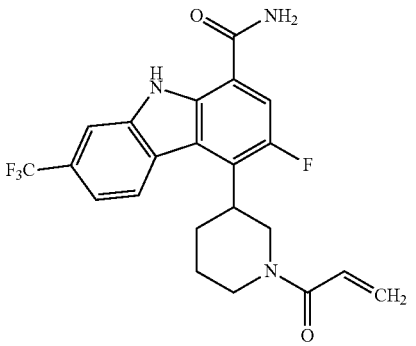 [SMILES: C=CC(=O)N1CCCC(c2c(F)cc(C(N)=O)c3[nH]c4cc(C(F)(F)F)ccc4c23)C1] | 4-(1-acryloylpiperidin-3-yl)-3-fluoro-7-(trifluoromethyl)-9H-carbazole-1-carboxamide, isomer 1 | m/z 434 (M + H)+ |

TABLE 8-continued

| Example | Structure | Name | Mass Spectrum |
|---|---|---|---|
| 162 | 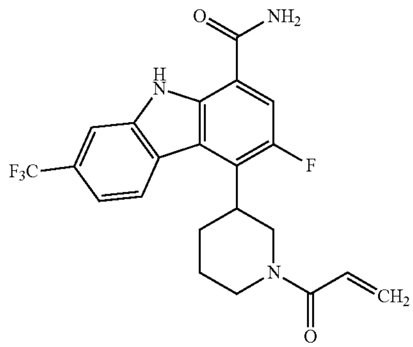 [SMILES: C=CC(=O)N1CCCC(c2c(F)cc(C(N)=O)c3[nH]c4cc(C(F)(F)F)ccc4c23)C1] | 4-(1-acryloylpiperidin-3-yl)-3-fluoro-7-(trifluoromethyl)-9H-carbazole-1-carboxamide; isomer 2 | m/z 434 (M + H)+ |
| 163 | 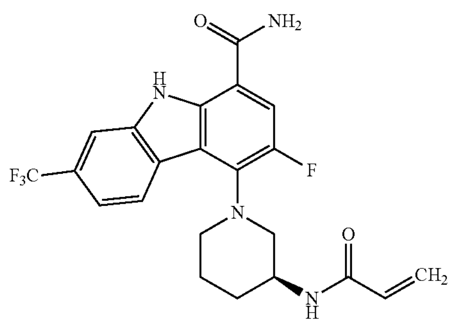 [SMILES: C=CC(=O)N[C@H]1CCCN(c2c(F)cc(C(N)=O)c3[nH]c4cc(C(F)(F)F)ccc4c23)C1] | (S)-4-(3-acrylamidopiperidin-1-yl)-3-fluoro-7-(trifluoromethyl)-9H-carbazole-1-carboxamide | m/z 449 (M + H)+ |
| 164 | 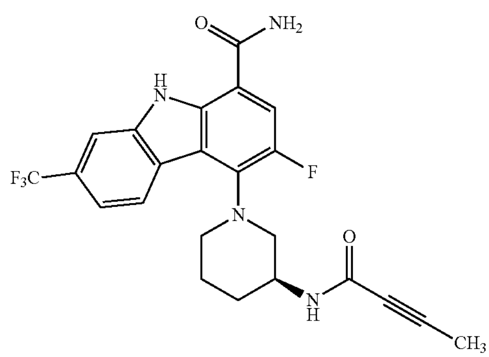 [SMILES: CC#CC(=O)N[C@H]1CCCN(c2c(F)cc(C(N)=O)c3[nH]c4cc(C(F)(F)F)ccc4c23)C1] | (S)-4-(3-(but-2-ynamido)piperidin-1-yl)-3-fluoro-7-(trifluoromethyl)-9H-carbazole-1-carboxamide | m/z 461 (M + H)+ |
| 165 | 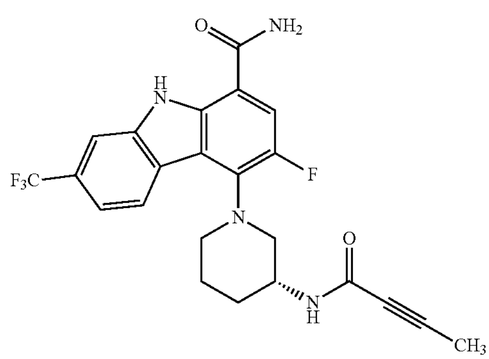 [SMILES: CC#CC(=O)N[C@@H]1CCCN(c2c(F)cc(C(N)=O)c3[nH]c4cc(C(F)(F)F)ccc4c23)C1] | (R)-4-(3-(but-2-ynamido)piperidin-1-yl)-3-fluoro-7-(trifluoromethyl)-9H-carbazole-1-carboxamide | m/z 461 (M + H)+ |

TABLE 8-continued

| Example | Structure | Name | Mass Spectrum |
|---|---|---|---|
| 166 | 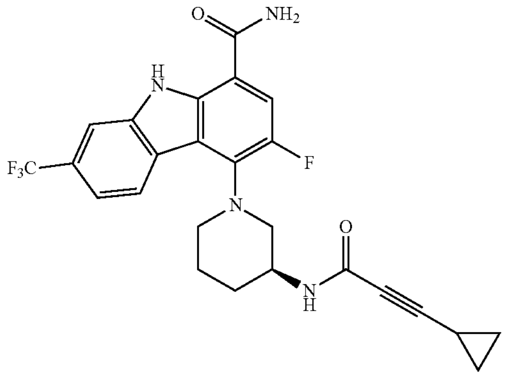 [SMILES: NC(=O)c1cc(F)c(N2CCC[C@H](NC(=O)C#CC3CC3)C2)c2c1[nH]c1cc(C(F)(F)F)ccc12] | (S)-4-(3-(3-cyclopropylpropiolamido)piperidin-1-yl)-3-fluoro-7-(trifluoromethyl)-9H-carbazole-1-carboxamide | m/z 487 (M + H)+ |
| 167 | 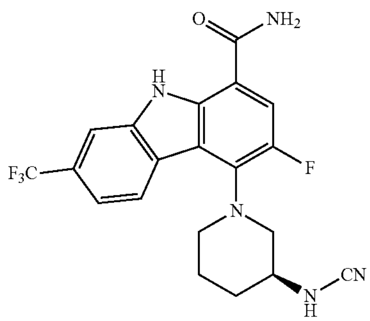 [SMILES: N#CN[C@H]1CCCN(c2c(F)cc(C(N)=O)c3[nH]c4cc(C(F)(F)F)ccc4c23)C1] | (S)-4-(3-cyanamidopiperidin-1-yl)-3-fluoro-7-(trifluoromethyl)-9H-carbazole-1-carboxamide | m/z 420 (M + H)+ |
| 168 | 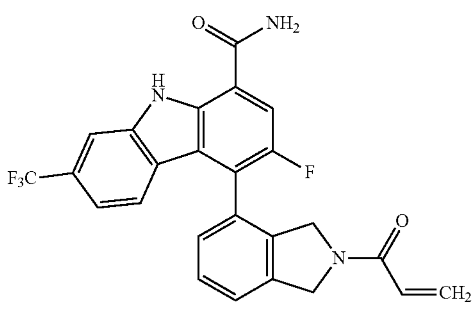 [SMILES: C=CC(=O)N1Cc2cccc(-c3c(F)cc(C(N)=O)c4[nH]c5cc(C(F)(F)F)ccc5c34)c2C1] | 4-(2-acryloylisoindolin-4-yl)-3-fluoro-7-(trifluoromethyl)-9H-carbazole-1-carboxamide | m/z 468 (M + H)+ |
| 169 | 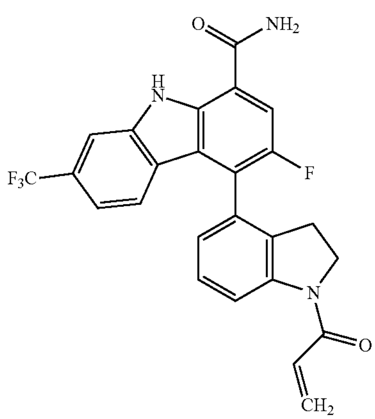 [SMILES: C=CC(=O)N1CCc2c(-c3c(F)cc(C(N)=O)c4[nH]c5cc(C(F)(F)F)ccc5c34)cccc21] | 4-(1-acryloylindolin-4-yl)-3-fluoro-7-(trifluoromethyl)-9H-carbazole-1-carboxamide | m/z 468 (M + H)+ |

TABLE 8-continued

| Example | Name | Mass Spectrum |
|---|---|---|
| 170 | 4-(1-acryloylindolin-6-yl)-3-fluoro-7-(trifluoromethyl)-9H-carbazole-1-carboxamide | m/z 468 (M + H)+ |
| 171 | 4-(1-acryloyl-1-azaspiro[4.4]nonan-7-yl)-3-fluoro-7-(trifluoromethyl)-9H-carbazole-1-carboxamide | m/z 475 (M + H)+ |
| 172 | (S)-4-(3-(but-2-ynamido)piperidin-1-yl)-3-fluoro-7-(4-methylpiperazine-1-carbonyl)-9H-carbazole-1-carboxamide | m/z 520 (M + H)+ |
| 173 | (S)-4-(3-(but-2-ynamido)piperidin-1-yl)-3-fluoro-N7,N7-dimethyl-9H-carbazole-1,7-dicarboxamide | m/z 465 (M + H)+ |

TABLE 8-continued

| Example | Structure | Name | Mass Spectrum |
|---|---|---|---|
| 174 | 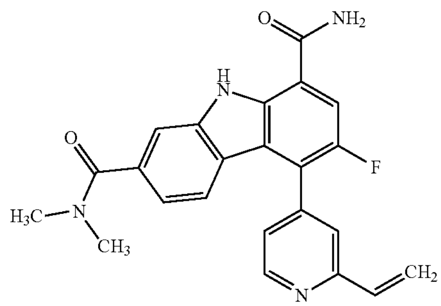 [SMILES: C=Cc1cc(-c2c(F)cc(C(N)=O)c3[nH]c4cc(C(=O)N(C)C)ccc4c23)ccn1] | 3-fluoro-N7,N7-dimethyl-4-(2-vinylpyridin-4-yl)-9H-carbazole-1,7-dicarboxamide | m/z 403 (M + H)+ |
| 175 | 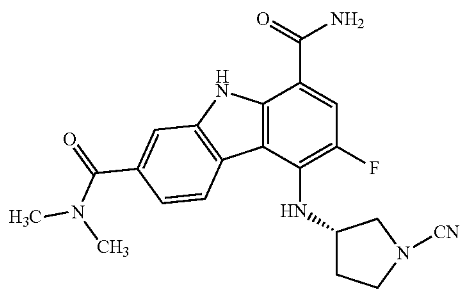 [SMILES: CN(C)C(=O)c1ccc2c(c1)[nH]c1c(C(N)=O)cc(F)c(N[C@H]3CCN(C#N)C3)c12] | (S)-4-((1-cyanopyrrolidin-3-yl)amino)-3-fluoro-N7,N7-dimethyl-9H-carbazole-1,7-dicarboxamide | m/z 409 (M + H)+ |
| 176 | 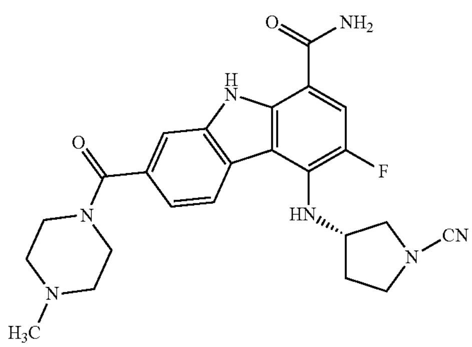 [SMILES: CN1CCN(C(=O)c2ccc3c(c2)[nH]c2c(C(N)=O)cc(F)c(N[C@H]4CCN(C#N)C4)c23)CC1] | (S)-4-((1-cyanopyrrolidin-3-yl)amino)-3-fluoro-7-(4-methylpiperazine-1-carbonyl)-9H-carbazole-1-carboxamide | m/z 465 (M + H)+ |
| 177 | 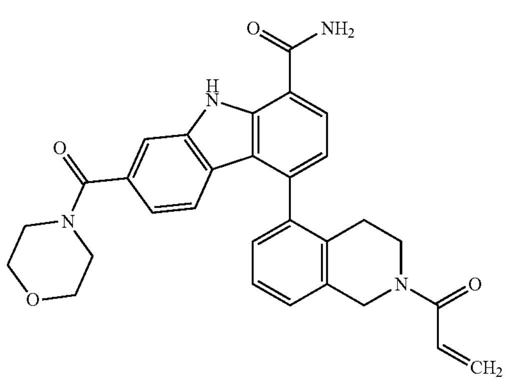 [SMILES: C=CC(=O)N1CCc2c(cccc2-c2ccc(C(N)=O)c3[nH]c4cc(C(=O)N5CCOCC5)ccc4c23)C1] | 4-(2-acryloyl-1,2,3,4-tetrahydroisoquinolin-5-yl)-7-(morpholine-4-carbonyl)-9H-carbazole-1-carboxamide | m/z 510 (M + H)+ |

TABLE 8-continued

| Example | Name | Mass Spectrum |
|---|---|---|
| 178 | 4-(2-(but-2-ynoyl)-1,2,3,4-tetrahydroisoquinolin-5-yl)-7-(morpholine-4-carbonyl)-9H-carbazole-1-carboxamide | m/z 522 (M + H)+ |
| 179 | 4-(2-cyano-1,2,3,4-tetrahydroisoquinolin-5-yl)-7-(morpholine-4-carbonyl)-9H-carbazole-1-carboxamide | m/z 481 (M + H)+ |
| 180 | 4-(1-acryloylindolin-6-yl)-3-fluoro-7-(2-hydroxyethyl)-9H-carbazole-1-carboxamide | m/z 444 (M + H)+ |
| 181 | 4-(1-cyanoindolin-6-yl)-3-fluoro-7-(2-hydroxyethyl)-9H-carbazole-1-carboxamide | m/z 415 (M + H)+ |

TABLE 8-continued

| Example | Structure | Name | Mass Spectrum |
|---|---|---|---|
| 182 (racemate) | 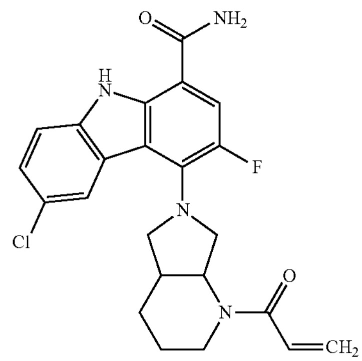 [SMILES: C=CC(=O)N1CCCC2CN(c3c(F)cc(C(N)=O)c4[nH]c5ccc(Cl)cc5c34)CC21] | 4-(1-acryloyloctahydro-6H-pyrrolo[3,4-b]pyridin-6-yl)-6-chloro-3-fluoro-9H-carbazole-1-carboxamide | m/z 441 (M + H)+ |
| 183 (racemate) | 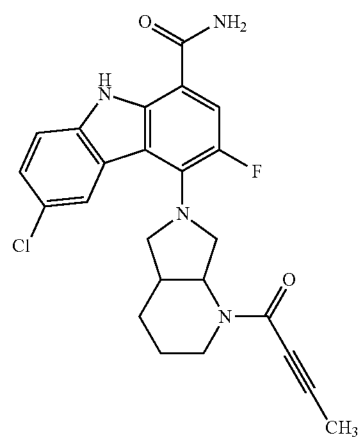 [SMILES: CC#CC(=O)N1CCCC2CN(c3c(F)cc(C(N)=O)c4[nH]c5ccc(Cl)cc5c34)CC21] | 4-(1-(but-2-ynoyl)octahydro-6H-pyrrolo[3,4-b]pyridin-6-yl)-6-chloro-3-fluoro-9H-carbazole-1-carboxamide | m/z 453 (M + H)+ |
| 184 racemic | 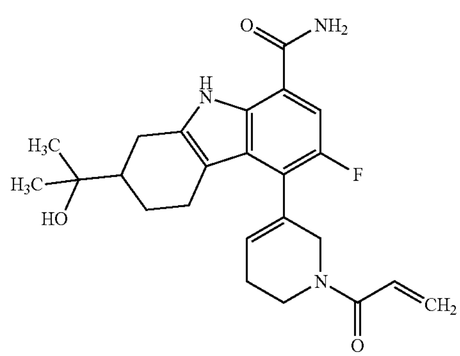 [SMILES: C=CC(=O)N1CCC=C(c2c(F)cc(C(N)=O)c3[nH]c4c(c23)CCC(C(C)(C)O)C4)C1] | 5-(1-acryloyl-1,2,5,6-tetrahydropyridin-3-yl)-6-fluoro-2-(2-hydroxypropan-2-yl)-2,3,4,9-tetrahydro-1H-carbazole-8-carboxamide | m/z 427 (M + H)+ |
| 185 | 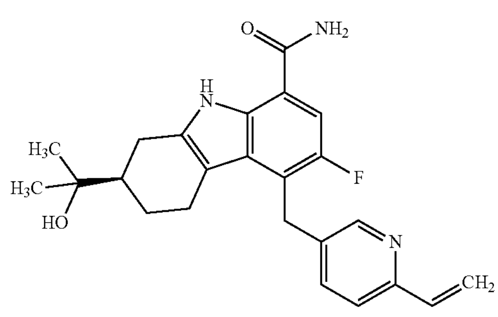 [SMILES: C=Cc1ccc(Cc2c(F)cc(C(N)=O)c3[nH]c4c(c23)CC[C@@H](C(C)(C)O)C4)cn1] | (R)-6-fluoro-2-(2-hydroxypropan-2-yl)-5-((6-vinylpyridin-3-yl)methyl)-2,3,4,9-tetrahydro-1H-carbazole-8-carboxamide | m/z 408 (M + H)+ |

TABLE 8-continued

| Example | Structure | Name | Mass Spectrum |
|---|---|---|---|
| 186 Isomer 1 | 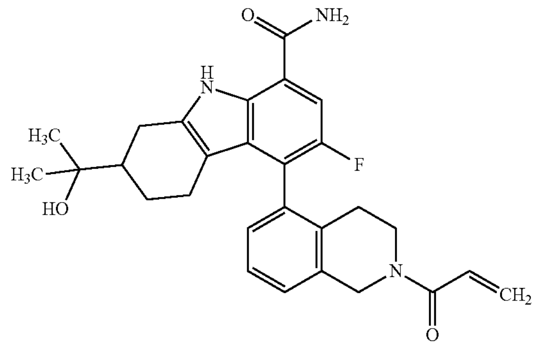 | 5-(2-acryloyl-1,2,3,4-tetrahydroisoquinolin-5-yl)-6-fluoro-2-(2-hydroxypropan-2-yl)-2,3,4,9-tetrahydro-1H-carbazole-8-carboxamide | m/z 459 (M + H)+ |
| 187 Isomer 2 | 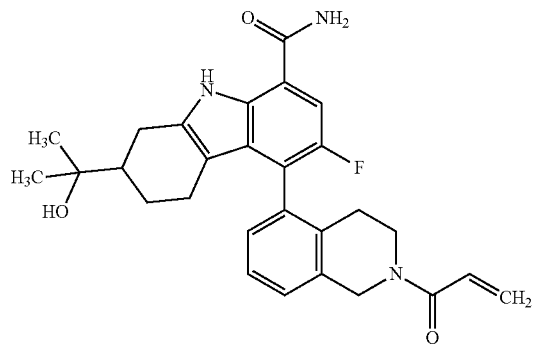 | 5-(2-acryloyl-1,2,3,4-tetrahydroisoquinolin-5-yl)-6-fluoro-2-(2-hydroxypropan-2-yl)-2,3,4,9-tetrahydro-1H-carbazole-8-carboxamide | m/z 459 (M + H)+ |
| 188 | 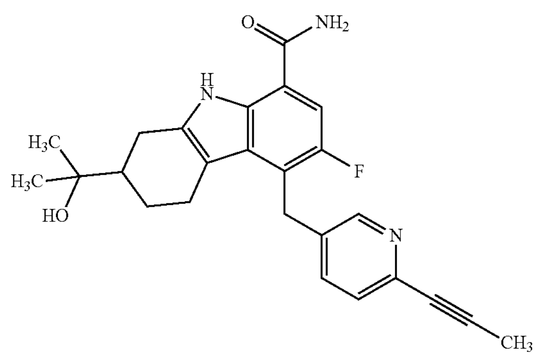 [SMILES: CC#Cc1ccc(Cc2c(F)cc(C(N)=O)c3[nH]c4c(c23)CCC(C(C)(C)O)C4)cn1] | 6-fluoro-2-(2-hydroxypropan-2-yl)-5-((6-(prop-1-yn-1-yl)pyridin-3-yl)methyl)-2,3,4,9-tetrahydro-1H-carbazole-8-carboxamide | m/z 420 (M + H)+ |
| 189 | 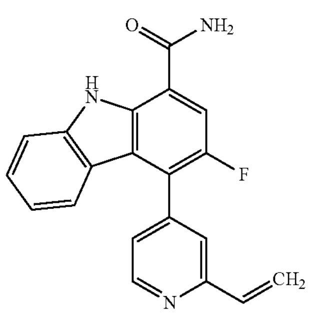 [SMILES: C=Cc1cc(-c2c(F)cc(C(N)=O)c3[nH]c4ccccc4c23)ccn1] | 3-fluoro-4-(2-vinylpyridin-4-yl)-9H-carbazole-1-carboxamide | m/z 332 (M + H)+ |

TABLE 8-continued

| Example | Structure | Name | Mass Spectrum |
|---------|-----------|------|---------------|
| 190 | 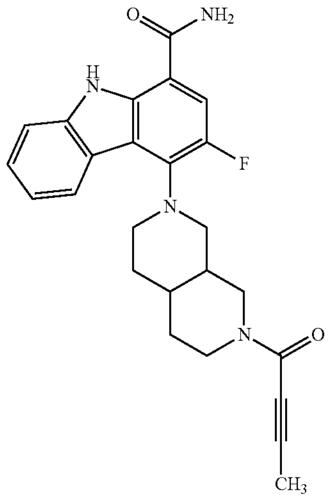 [SMILES: CC#CC(=O)N1CCC2CCN(c3c(F)cc(C(N)=O)c4[nH]c5ccccc5c34)CC2C1] | 4-(7-(but-2-ynoyl)octahydro-2,7-naphthyridin-2(1H)-yl)-3-fluoro-9H-carbazole-1-carboxamide | m/z 433 (M + H)+ |
| 191 | 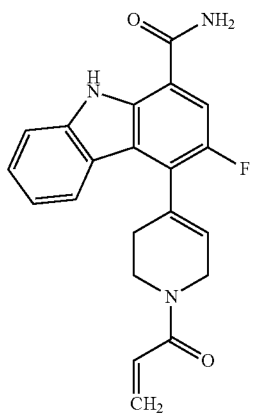 [SMILES: C=CC(=O)N1CC=C(c2c(F)cc(C(N)=O)c3[nH]c4ccccc4c23)CC1] | 4-(1-acryloyl-1,2,3,6-tetrahydropyridin-4-yl)-3-fluoro-9H-carbazole-1-carboxamide | m/z 364 (M + H)+ |
| 192 | 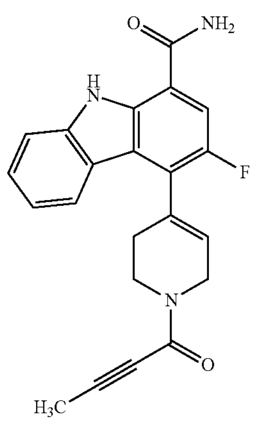 [SMILES: CC#CC(=O)N1CC=C(c2c(F)cc(C(N)=O)c3[nH]c4ccccc4c23)CC1] | 4-(1-(but-2-ynoyl)-1,2,3,6-tetrahydropyridin-4-yl)-3-fluoro-9H-carbazole-1-carboxamide | m/z 376 (M + H)+ |

TABLE 8-continued
| Example | Structure | Name | Mass Spectrum |
|---|---|---|---|
| 193 | 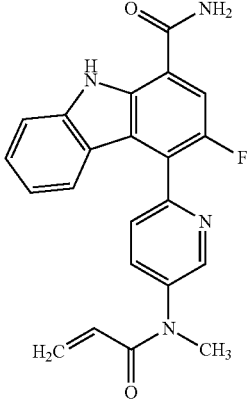 [SMILES: C=CC(=O)N(C)c1ccc(-c2c(F)cc(C(N)=O)c3[nH]c4ccccc4c23)nc1] | 3-fluoro-4-(5-(N-methylacrylamido)pyridin-2-yl)-9H-carbazole-1-carboxamide | m/z 389 (M + H)+ |
| 194 | 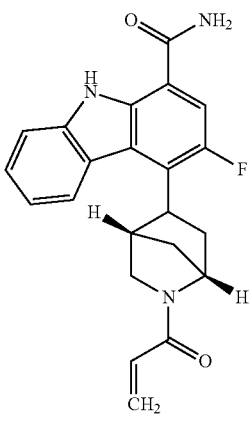 [SMILES: C=CC(=O)N1C[C@H]2C[C@@H]1CC2c1c(F)cc(C(N)=O)c2[nH]c3ccccc3c12] | 4-((1S,4S)-2-acryloyl-2-azabicyclo[2.2.1]heptan-5-yl)-3-fluoro-9H-carbazole-1-carboxamide | m/z 379 (M + H)+ |
| 195 | 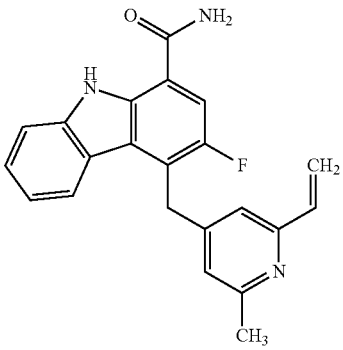 [SMILES: C=Cc1cc(Cc2c(F)cc(C(N)=O)c3[nH]c4ccccc4c23)cc(C)n1] | 3-fluoro-4-((2-methyl-6-vinylpyridin-4-yl)methyl)-9H-carbazole-1-carboxamide | m/z 360 (M + H)+ |
| 196 | 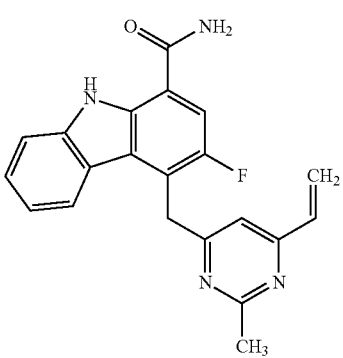 [SMILES: C=Cc1cc(Cc2c(F)cc(C(N)=O)c3[nH]c4ccccc4c23)nc(C)n1] | 3-fluoro-4-((2-methyl-6-vinylpyrimidin-4-yl)methyl)-9H-carbazole-1-carboxamide | m/z 361 (M + H)+ |

TABLE 8-continued
| Example | Structure | Name | Mass Spectrum |
|---|---|---|---|
| 197 | 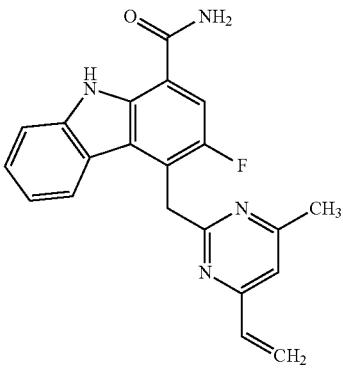 [SMILES: C=Cc1cc(C)nc(Cc2c(F)cc(C(N)=O)c3[nH]c4ccccc4c23)n1] | 3-fluoro-4-((4-methyl-6-vinylpyrimidin-2-yl)methyl)-9H-carbazole-1-carboxamide | m/z 361 (M + H)+ |
| 198 | 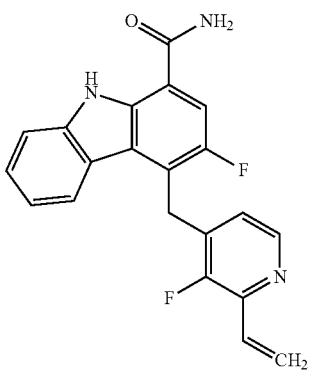 [SMILES: C=Cc1nccc(Cc2c(F)cc(C(N)=O)c3[nH]c4ccccc4c23)c1F] | 3-fluoro-4-((3-fluoro-2-vinylpyridin-4-yl)methyl)-9H-carbazole-1-carboxamide | m/z 364 (M + H)+ |
| 199 | 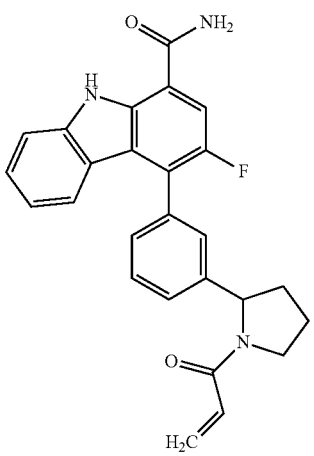 [SMILES: C=CC(=O)N1CCCC1c1cccc(-c2c(F)cc(C(N)=O)c3[nH]c4ccccc4c23)c1] | 4-(3-(1-acryloylpyrrolidin-2-yl)phenyl)-3-fluoro-9H-carbazole-1-carboxamide | m/z 428 (M + H)+ |

TABLE 8-continued

| Example | Structure | Name | Mass Spectrum |
|---|---|---|---|
| 200 | 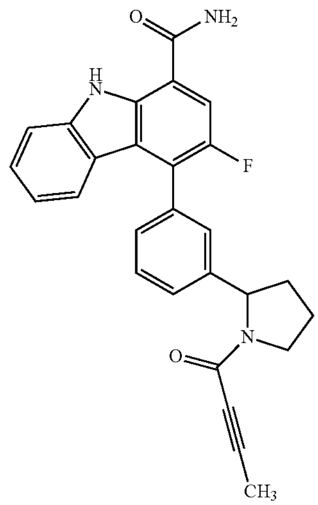 [SMILES: CC#CC(=O)N1CCCC1c1cccc(-c2c(F)cc(C(N)=O)c3[nH]c4ccccc4c23)c1] | 4-(3-(1-(but-2-ynoyl) pyrrolidin-2-yl)phenyl)-3-fluoro-9H-carbazole-1-carboxamide | m/z 440 (M + H)+ |
| 201 | 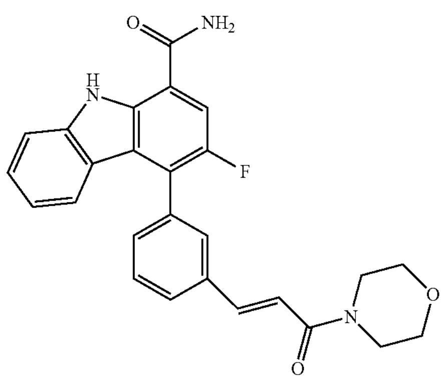 [SMILES: NC(=O)c1cc(F)c(-c2cccc(/C=C/C(=O)N3CCOCC3)c2)c2c1[nH]c1ccccc12] | (E)-3-fluoro-4-(3-(3-morpholino-3-oxoprop-1-en-1-yl)phenyl)-9H-carbazole-1-carboxamide | m/z 444 (M + H)+ |
| 202 | 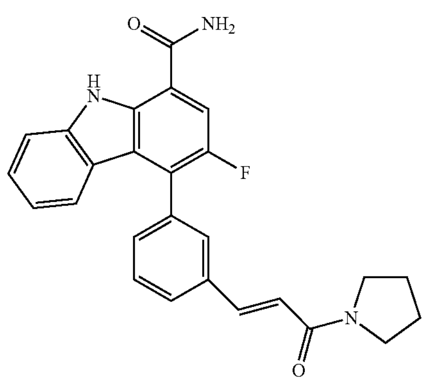 [SMILES: NC(=O)c1cc(F)c(-c2cccc(/C=C/C(=O)N3CCCC3)c2)c2c1[nH]c1ccccc12] | (E)-3-fluoro-4-(3-(3-oxo-3-(pyrrolidin-1-yl)prop-1-en-1-yl)phenyl)-9H-carbazole-1-carboxamide | m/z 428 (M + H)+ |

Example 203

5-(2-Acryloyl-1,2,3,4-tetrahydroisoquinolin-5-yl)-2-(2-hydroxypropan-2-yl)-2,3,4,9-tetrahydro-1H-carbazole-8-carboxamide

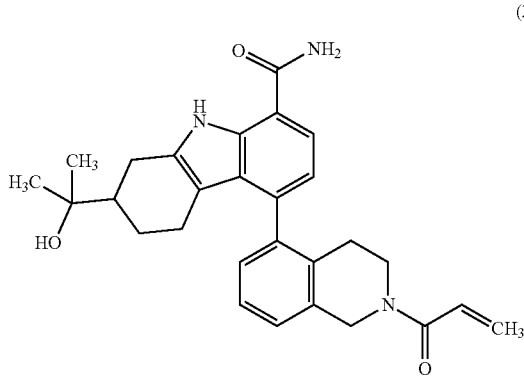

(203)

Intermediate 203A: tert-Butyl 5-(8-carbamoyl-2-(2-hydroxypropan-2-yl)-2,3,4,9-tetrahydro-1H-carbazol-5-yl)-3,4-dihydroisoquinoline-2(1H)-carboxylate

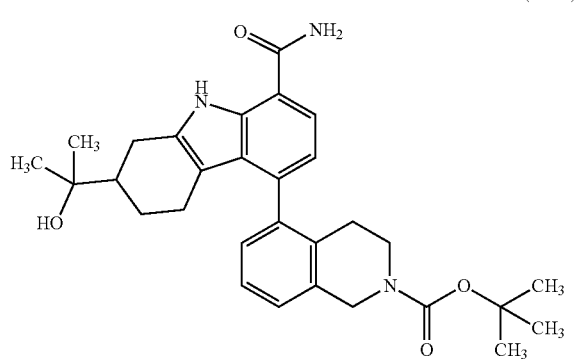

(203A)

A mixture of 5-bromo-2-(2-hydroxypropan-2-yl)-2,3,4,9-tetrahydro-1H-carbazole-8-carboxamide (homochiral enantiomer 1, see U.S. Pat. No. 8,084,620, Example 73-1 0.177 g, 0.504 mmol), tert-butyl 5-(4,4,5,5-tetramethyl-1,3,2-dioxaborolan-2-yl)-3,4-dihydroisoquinoline-2(1H)-carboxylate (0.217 g, 0.605 mmol), tripotassium phosphate (2 M in water) (0.76 mL, 1.512 mmol), and tetrahydrofuran (3 mL) was degassed with vacuum and nitrogen (3×). 1,1'-Bis(di-tert-butylphosphino) ferrocene palladium dichloride (0.016 g, 0.025 mmol) was added, and the reaction mixture was degassed (2×). The reaction mixture was stirred at room temperature overnight. The reaction mixture was diluted with ethyl acetate, washed with water, washed with brine, and dried over anhydrous sodium sulfate. Concentration under reduce pressure followed by purification by ISCO flash chromatography (12 g column; 0%-100% ethyl acetate in hexane) afforded tert-butyl 5-(8-carbamoyl-2-(2-hydroxypropan-2-yl)-2,3,4,9-tetrahydro-1H-carbazol-5-yl)-3,4-dihydroisoquinoline-2(1H)-carboxylate (0.208 g, 0.409 mmol, 81% yield) as a pale yellow solid. The product had a UPLC ret. time=1.22 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=504.4.

Intermediate 203B: 2-(2-Hydroxypropan-2-yl)-5-(1,2,3,4-tetrahydroisoquinolin-5-yl)-2,3,4,9-tetrahydro-1H-carbazole-8-carboxamide

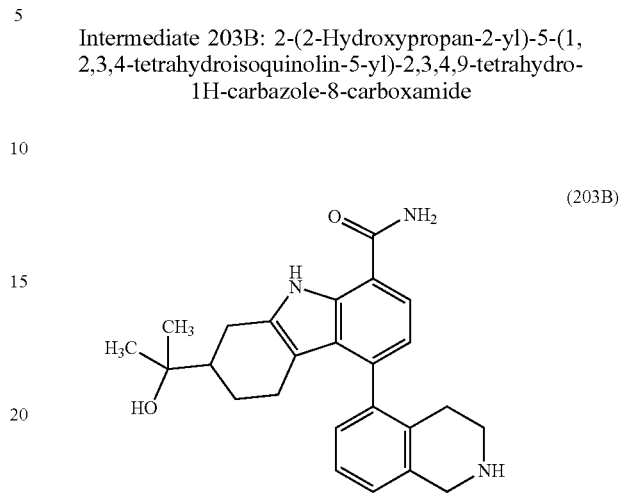

(203B)

A mixture of tert-butyl 5-(8-carbamoyl-2-(2-hydroxypropan-2-yl)-2,3,4,9-tetrahydro-1H-carbazol-5-yl)-3,4-dihydroisoquinoline-2(1H)-carboxylate (0.208 g, 0.413 mmol) and trifluoroacetic acid (3 mL) was stirred at room temperature for 45 min. The reaction mixture was concentrated under reduced pressure, and the residue was diluted with ethyl acetate and washed with 1.5M aqueous potassium phosphate (dibasic) (2×). The organic layer was collected, and the aqueous layers were sequentially extracted with ethyl acetate (2×). The combined organic layers were dried over anhydrous sodium sulfate. Concentration under reduced pressure afforded 2-(2-hydroxypropan-2-yl)-5-(1,2,3,4-tetrahydroisoquinolin-5-yl)-2,3,4,9-tetrahydro-1H-carbazole-8-carboxamide (0.163 g, 0.404 mmol, 98% yield) as a pale yellow solid. The product had a UPLC ret. time=0.777 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=404.3.

Example 203

To a mixture of 2-(2-hydroxypropan-2-yl)-5-(1,2,3,4-tetrahydroisoquinolin-5-yl)-2,3,4,9-tetrahydro-1H-carbazole-8-carboxamide (0.163 g, 0.404 mmol) and Hunig's Base (0.282 mL, 1.62 mmol) in tetrahydrofuran (3.0 mL) at room temperature was added acryloyl chloride (0.033 mL, 0.404 mmol). The reaction mixture was stirred for 20 min. The reaction mixture was diluted with dichloromethane, washed with water, and dried over anhydrous sodium sulfate. Concentration under reduce pressure followed by purification by ISCO flash chromatography (12 g column; gradient: 0%-5% methanol in dichloromethane) provided 5-(2-acryloyl-1,2,3,4-tetrahydroisoquinolin-5-yl)-2-(2-hydroxypropan-2-yl)-2,3,4,9-tetrahydro-1H-carbazole-8-carboxamide (0.055 g, 0.118 mmol, 29% yield) as a white solid. The product had a UPLC ret. time=0.958 min. —Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=458.3. $^1$H NMR (500 MHz, DMSO-$d_6$) δ 10.75 (s, 1H), 8.01 (br. s., 1H), 7.59 (dd, J=7.5, 4.7 Hz, 1H), 7.32 (br. s., 1H), 7.29-7.22 (m, 2H), 7.08 (dd, J=5.5, 2.7 Hz, 1H), 6.93 (dd, J=16.6, 10.5

Hz, 0.4H), 6.79 (dd, J=16.6, 10.4 Hz, 0.6H), 6.75-6.68 (m, 1H), 6.13 (dd, J=16.6, 2.1 Hz, 1H), 5.75-5.64 (m, 1H), 4.92-4.81 (m, 1H), 4.81-4.67 (m, 1H), 4.15 (s, 1H), 3.79-3.68 (m, 1H), 3.67-3.52 (m, 1H), 2.88 (d, J=16.5 Hz, 1H), 2.47-2.23 (m, 3H), 1.93-1.69 (m, 3H), 1.61-1.50 (m, 1H), and 1.07 (s, 6H).

Example 204

5-(2-Acryloyl-1,2,3,4-tetrahydroisoquinolin-5-yl)-2-(2-hydroxypropan-2-yl)-2,3,4,9-tetrahydro-1H-carbazole-8-carboxamide

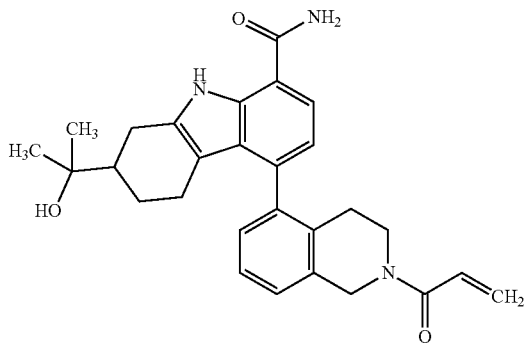

(204)

Intermediate 204A: tert-Butyl 5-(8-carbamoyl-2-(2-hydroxypropan-2-yl)-2,3,4,9-tetrahydro-1H-carbazol-5-yl)-3,4-dihydroisoquinoline-2(1H)-carboxylate

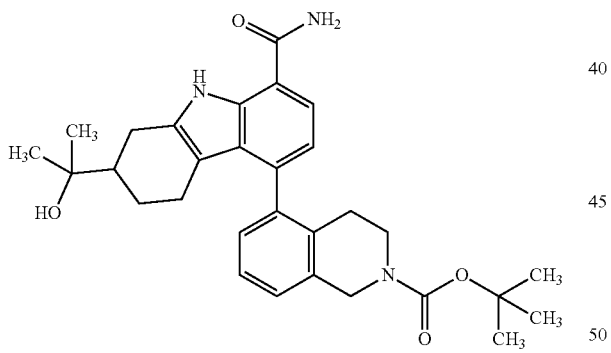

(204A)

A mixture of 5-bromo-2-(2-hydroxypropan-2-yl)-2,3,4,9-tetrahydro-1H-carbazole-8-carboxamide (homochiral enantiomer 2, see U.S. Pat. No. 8,084,620, Example 73-1) 0.185 g, 0.527 mmol), tert-butyl 5-(4,4,5,5-tetramethyl-1,3,2-dioxaborolan-2-yl)-3,4-dihydroisoquinoline-2(1H)-carboxylate (0.227 g, 0.632 mmol), tripotassium phosphate (2 M in water) (0.79 mL, 1.58 mmol), and tetrahydrofuran (3 mL) was degassed with vacuum and nitrogen (3x). 1,1'-Bis(di-tert-butylphosphino)ferrocene palladium dichloride (0.017 g, 0.026 mmol) was added, and the reaction mixture was degassed (2x). The reaction mixture was stirred at room temperature overnight. The reaction mixture was diluted with ethyl acetate, washed with water, washed with brine, and dried over anhydrous sodium sulfate. Concentration under reduce pressure followed by purification by ISCO flash chromatography (12 g column; 0%-100% ethyl acetate in hexane) afforded tert-butyl-5-(8-carbamoyl-2-(2-hydroxypropan-2-yl)-2,3,4,9-tetrahydro-1H-carbazol-5-yl)-3,4-dihydroisoquinoline-2(1H)-carboxylate (0.250 g, 0.491 mmol, 93% yield) as a pale yellow solid. The product had a UPLC ret. time=1.22 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. LC/MS M+1=504.4.

Intermediate 204B: 2-(2-Hydroxypropan-2-yl)-5-(1,2,3,4-tetrahydroisoquinolin-5-yl)-2,3,4,9-tetrahydro-1H-carbazole-8-carboxamide

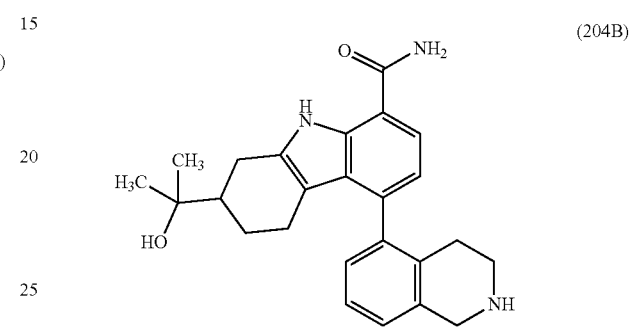

(204B)

A mixture of tert-butyl 5-(8-carbamoyl-2-(2-hydroxypropan-2-yl)-2,3,4,9-tetrahydro-1H-carbazol-5-yl)-3,4-dihydroisoquinoline-2(1H)-carboxylate (0.250 g, 0.496 mmol) and trifluoroacetic acid (3 mL) was stirred at room temperature for 45 min. The reaction mixture was concentrated under reduced pressure, and the residue was diluted ethyl acetate and washed with 1.5M aqueous potassium phosphate (dibasic) (2x). The organic layer was collected, and the aqueous layers were sequentially extracted with ethyl acetate (2x). The combined organic layers were dried over anhydrous sodium sulfate. Concentration under reduced pressure afforded 2-(2-hydroxypropan-2-yl)-5-(1,2,3,4-tetrahydroisoquinolin-5-yl)-2,3,4,9-tetrahydro-1H-carbazole-8-carboxamide (0.180 g, 0.446 mmol, 90% yield) as an off-white solid. The product had a UPLC ret. time=0.777 min.—Column: PHENOMENEX® Kinetex C18 2.1×50 mm (1.5 min. gradient); Solvent A=10% MeCN, 90% H$_2$O, 0.1% TFA; Solvent B=90% MeCN, 10% H$_2$O, 0.1% TFA. LC/MS M+1=404.3.

Example 204

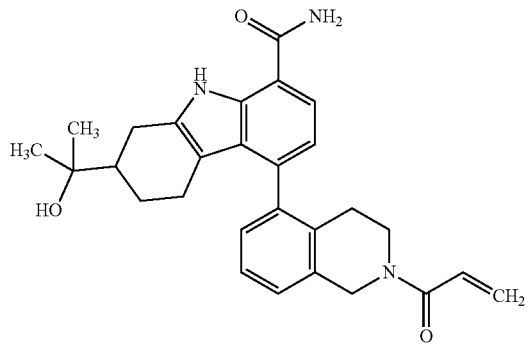

(203C)

To a mixture of 2-(2-hydroxypropan-2-yl)-5-(1,2,3,4-tetrahydroisoquinolin-5-yl)-2,3,4,9-tetrahydro-1H-carbazole-8-carboxamide (0.180 g, 0.446 mmol) and Hunig's Base (0.312 mL, 1.784 mmol) in tetrahydrofuran (3.0 mL) at room temperature was added acryloyl chloride (0.036 mL, 0.446 mmol). The reaction mixture was stirred for 20 min. HPLC and LCMS indicated that the reaction was complete. The reaction mixture was diluted with dichloromethane, washed with water, and dried over anhydrous sodium sulfate. Concentration under reduce pressure followed by purification by ISCO flash chromatography (12 g column; gradient: 0%-5% methanol in dichloromethane) provided 5-(2-acryloyl-1,2,3,4-tetrahydroisoquinolin-5-yl)-2-(2-hydroxypropan-2-yl)-2,3,4,9-tetrahydro-1H-carbazole-8-carboxamide (0.078 g, 0.167 mmol, 37.5% yield) as a white solid. The product had a UPLC ret. time=0.962 min.—Column: PHENOMENEX® Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=458.4. $^1H$ NMR (500 MHz, DMSO-$d_6$) δ 10.75 (s, 1H), 8.01 (br. s., 1H), 7.59 (dd, J=7.5, 4.7 Hz, 1H), 7.32 (br. s., 1H), 7.29-7.22 (m, 2H), 7.08 (dd, J=5.5, 2.7 Hz, 1H), 6.93 (dd, J=16.6, 10.5 Hz, 0.4H), 6.79 (dd, J=16.6, 10.4 Hz, 0.6H), 6.75-6.68 (m, 1H), 6.13 (dd, J=16.6, 2.1 Hz, 1H), 5.75-5.64 (m, 1H), 4.92-4.81 (m, 1H), 4.81-4.67 (m, 1H), 4.15 (s, 1H), 3.79-3.68 (m, 1H), 3.67-3.52 (m, 1H), 2.88 (d, J=16.5 Hz, 1H), 2.47-2.23 (m, 3H), 1.93-1.69 (m, 3H), 1.61-1.50 (m, 1H), and 1.07 (s, 6H).

Biological Assays

The pharmacological properties of the compounds of this invention may be confirmed by a number of biological assays. The exemplified biological assays, which follow, have been carried out with compounds of the invention.

Human Recombinant Btk Enzyme Assay

To V-bottom 384-well plates were added test compounds, human recombinant Btk (1 nM, Invitrogen Corporation), fluoresceinated peptide (1.5 ATP (20 and assay buffer (20 mM HEPES pH 7.4, 10 mM $MgCl_2$, 0.015% Brij 35 surfactant and 4 mM DTT in 1.6% DMSO), with a final volume of 30 μL. After incubating at room temperature for 60 min, the reaction was terminated by adding 45 μL of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required for inhibiting 50% of kinase activity ($IC_{50}$). Compounds were dissolved at 10 mM in DMSO and evaluated at eleven concentrations.

Ramos FLIPR Assay

Ramos RA1 B cells (ATCC CRL-1596) at a density of $2 \times 10^6$ cells/mL in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, room temperature, 5 min) and resuspended at room temperature in RPMI minus phenol red with 50 mM HEPES and 10% FBS to a density of $1 \times 10^6$ cells/mL. 150 μL aliquots (150,000 cells/well) were plated into 96 well poly-D-lysine coated assay plates (BD 35 4640) and briefly centrifuged (Beckmann GS-CKR 800 rpm, 5 min, without brake). Next, 50 μL compound dilutions in 0.4% DMSO/RPMI minus phenol red+50 mM HEPES+10% FBS were added to the wells and the plate was incubated at room temperature in the dark for 1 hour. The assay plate was briefly centrifuged as above prior to measuring calcium levels. Using the FLIPR1 (Molecular Devices), cells were stimulated by adding goat anti-human IgM (Invitrogen AHI0601) to 2.5 μg/mL. Changes in intracellular calcium concentrations were measured for 180 seconds and percent inhibition was determined relative to peak calcium levels seen in the presence of stimulation only. The Ramos assay measures the ability of a compound to move through the cell membrane into the cell interior. A lower $IC_{50}$ value indicates a greater ability to move into the cell interior.

Table 9 shows the Btk $IC_{50}$ values obtained from the evaluation of Examples 1-66, 69, 72-100, and 112-202 in the human recombinant Btk enzyme assay and the Ramos $IC_{50}$ values obtained from the evaluation of Examples 1-12, 14-65, 69, 72, 74-90, 92-96, 98-100, 112-126, 128-129, 131-140, 144, 155-156, 159-170, 172, 174-177, 179-183, and 186-187 in the Ramos FLIPR assay.

TABLE 9

| Example | Btk $IC_{50}$ value (nM) | Ramos $IC_{50}$ value (nM) |
|---|---|---|
| 1 | 0.17 | 5.1 |
| 2 | 0.27 | 6.0 |
| 3 | 0.86 | 58 |
| 4 | 0.46 | 7.1 |
| 5 | 0.31 | 28 |
| 6 | 0.13 | 3.7 |
| 7 | 0.21 | 12 |
| 8 | 0.078 | 5.4 |
| 9 | 0.43 | 150 |
| 10 | 0.21 | 4.6 |
| 11 | 0.43 | 27 |
| 12 | 0.11 | 9.8 |
| 13 | 0.079 | — |
| 14 | 0.21 | 420 |
| 15 | 0.076 | 4.8 |
| 16 | 0.088 | 240 |
| 17 | 0.10 | 6.0 |
| 18 | 0.20 | 16 |
| 19 | 1.1 | 15 |
| 20 | 0.66 | 43 |
| 21 | 1.1 | 33 |
| 22 | 0.26 | 5.9 |
| 23 | 0.32 | 5.7 |
| 24 | 0.15 | 11 |
| 25 | 0.43 | 17 |
| 26 | 0.18 | 8.8 |
| 27 | 0.14 | 18 |
| 28 | 0.11 | 17 |
| 29 | 0.12 | 8.8 |
| 30 | 0.12 | 12 |
| 31 | 0.069 | 27 |
| 32 | 0.16 | 32 |
| 33 | 0.046 | 110 |
| 34 | 0.051 | 200 |
| 35 | 0.24 | 28 |
| 36 | 0.25 | 19 |
| 37 | 0.16 | 23 |
| 38 | 0.061 | 6.8 |
| 39 | 0.52 | 31 |
| 40 | 0.33 | 17 |
| 41 | 0.16 | 41 |
| 42 | 1.1 | 16 |
| 43 | 0.52 | 84 |
| 44 | 1.9 | 30 |
| 45 | 0.19 | 9.5 |
| 46 | 0.099 | 6.0 |
| 47 | 0.095 | 7.9 |
| 48 | 0.095 | 25 |
| 49 | 0.11 | 19 |

TABLE 9-continued

| Example | Btk IC$_{50}$ value (nM) | Ramos IC$_{50}$ value (nM) |
| --- | --- | --- |
| 50 | 0.29 | 27 |
| 51 | 0.34 | 91 |
| 52 | 0.27 | 5.0 |
| 53 | 0.21 | 9.8 |
| 54 | 1.1 | 18 |
| 55 | 0.26 | 15 |
| 56 | 0.27 | 10 |
| 57 | 0.075 | 11 |
| 58 | 0.10 | 7.9 |
| 59 | 0.13 | 1.9 |
| 60 | 0.047 | 3.4 |
| 61 | 0.77 | 26 |
| 62 | 0.97 | 13 |
| 63 | 0.38 | 2.4 |
| 64 | 1.2 | 68 |
| 65 | 0.58 | 35 |
| 66 | 0.37 | — |
| 69 | 0.073 | 2.8 |
| 72 | 0.67 | 47 |
| 73 | 0.12 | — |
| 74 | 0.21 | 38 |
| 75 | 0.067 | 2.9 |
| 76 | 0.052 | 6.4 |
| 77 | 0.48 | 26 |
| 78 | 0.35 | 12 |
| 87 | 0.10 | 30 |
| 88 | 0.51 | 580 |
| 89 | 0.23 | 14 |
| 90 | 0.19 | 19 |
| 91 | 0.19 | — |
| 92 | 0.17 | 9.0 |
| 95 | 0.049 | 3.0 |
| 96 | 0.10 | 9.4 |
| 97 | 0.087 | — |
| 98 | 0.35 | 10.7 |
| 99 | 0.050 | 2.8 |
| 100 | 0.12 | 2.2 |
| 112 | 0.2 | 18 |
| 113 | 0.3 | 81 |
| 114 | 0.3 | 10 |
| 115 | 0.1 | 19 |
| 116 | 0.4 | 9 |
| 117 | 0.2 | 56 |
| 118 | 0.07 | 3 |
| 119 | 0.09 | 1 |
| 120 | 0.2 | 45% at 0.3 μM |
| 121 | 0.1 | 0.6 |
| 122 | 0.6 | 16 |
| 123 | 0.2 | 0.7 |
| 124 | 0.4 | 7 |
| 125 | 0.07 | 0.5 |
| 126 | 0.3 | 19 |
| 127 | 1.0 | — |
| 128 | 0.3 | 6 |
| 129 | 0.3 | 20 |
| 130 | 0.1 | — |
| 131 | 0.3 | 0.6 |
| 132 | 0.2 | 4 |
| 133 | 1.0 | 30% at 0.3 μM |
| 134 | 0.2 | 1 |
| 135 | 2.0 | 35 |
| 136 | 0.8 | 26 |
| 137 | 0.6 | 66 |
| 138 | 0.5 | 2 |
| 139 | 0.4 | 54 |
| 140 | 0.3 | 62 |
| 141 | 12.0 | — |
| 142 | 50.0 | — |
| 143 | 0.3 | — |
| 144 | 2.0 | 4 |
| 145 | 0.6 | — |
| 146 | 0.2 | — |
| 147 | 2.0 | — |
| 148 | 256.0 | — |
| 149 | 130.0 | — |
| 150 | 477.0 | — |
| 151 | 22.0 | — |
| 152 | 76.0 | — |
| 153 | 308.0 | — |
| 154 | 0.6 | — |
| 155 | 0.5 | 42 |
| 156 | 0.3 | 3 |
| 157 | 0.9 | — |
| 158 | 3.0 | — |
| 159 | 3.0 | 32 |
| 160 | 0.05 | 0.8 |
| 161 | 0.09 | 40% at 0.3 μM |
| 162 | 0.8 | 17 |
| 163 | 0.1 | 4 |
| 164 | 0.2 | 24 |
| 165 | 2.0 | 58 |
| 166 | 0.2 | 9 |
| 167 | 8.0 | 72 |
| 168 | 0.7 | 95 |
| 169 | 0.8 | 25 |
| 170 | 0.2 | 9 |
| 171 | 6.0 | — |
| 172 | 0.1 | 5 |
| 173 | 0.2 | — |
| 174 | 4.0 | 40% at 0.3 μM |
| 175 | 0.8 | 70 |
| 176 | 0.8 | 87 |
| 177 | 0.2 | 8 |
| 178 | 5.0 | — |
| 179 | 1.0 | 193 |
| 180 | 0.1 | 12 |
| 181 | 1.0 | 14 |
| 182 | 0.2 | 5 |
| 183 | 0.8 | 62 |
| 184 | 0.6 | — |
| 185 | 0.4 | — |
| 186 | 0.5 | 3 |
| 187 | 0.6 | 5 |
| 188 | 6.0 | — |
| 189 | 8.0 | — |
| 190 | 51.0 | — |
| 191 | 0.4 | — |
| 192 | 1.0 | — |
| 193 | 2.0 | — |
| 194 | 9.0 | — |
| 195 | 0.3 | — |
| 196 | 3.0 | — |
| 197 | 0.7 | — |
| 198 | 2.0 | — |
| 199 | 3.0 | — |
| 200 | 95.0 | — |
| 201 | 96.0 | — |
| 202 | 54.0 | — |

Table 10 shows the Btk IC$_{50}$ values from the evaluation of Comparative Examples 101 to 111 in the human recombinant Btk enzyme assay and the Ramos IC$_{50}$ values from the evaluation of Comparative Examples 101 to 105 and 110 obtained from the Ramos FLIPR assay.

TABLE 10

| Comparative Example | Btk IC$_{50}$ value (nM) | Ramos IC$_{50}$ value (nM) |
| --- | --- | --- |
| 101 | 7.3 | 59 |
| 102 | 5.1 | 140 |
| 103 | 1.4 | 570 |
| 104 | 11 | 92 |
| 105 | 4.1 | 29 |
| 106 | 75 | — |
| 107 | 16 | — |
| 108 | 14 | — |
| 109 | 240 | — |
| 110 | 19 | 800 |
| 111 | 30 | — |

The compounds of Formula (IIa) as exemplified by the tested examples in Table 9 have been compared to Comparative Examples 101 to 111, and have been found to be especially advantageous. As shown in Tables 9 and 10, in the reported tests, Examples 1-12, 14-65, 69, 72, 74-78, 87, 89-90, 92, 95-96 and 98-100 of this invention show the surprising advantage of the combination of improved Btk inhibition activity and improved penetration into the cell interior, as characterized by the Btk $IC_{50}$ values and the Ramos $IC_{50}$ values, respectively. Examples 1-12, 14-65, 69, 72, 74-78, 87, 89-90, 92, 95-96 and 98-100 have a combination of Btk $IC_{50}$ values of less than 2 nM in the reported Btk assay and Ramos $IC_{50}$ values of less 450 nM in the Ramos FLIPR assay. In contrast, Comparative Examples 101 to 102 and 104 to 111 have been found to have Btk $IC_{50}$ values of greater than 4.0 nM. Comparative Example 103 had been found to have a combination of a Btk $IC_{50}$ value of 1.4 and a Ramos $IC_{50}$ values of 570 nM.

Human Whole Blood Btk Inactivation Assay

Human whole blood (0.2 mL) containing ACD-A as anticoagulant was incubated with a test compound at various concentrations for 60 min. Lysates were prepared by adding lysis buffer (0.2 mL, Cell Signaling, Cat. #9803) containing 40 nM of the compound of Example 88. After shaking for 1 h at room temperature, lysates were transferred to a 96-well streptavidin-coated plate (Pierce, Cat. #15120), incubated for 1 h more, and washed 3 times with PBS containing 0.05% Tween 20. Mouse anti-Btk antibody (BD Biosciences, Cat. #611116) was added, followed by incubation for 1 h more. The plate was washed again, then a horse radish peroxidase (HRP)-linked goat anti-mouse IgG (Invitrogen, Cat. #G21040) was added. The plate was incubated for 1 h more and washed as described above. 3,3',5,5'-Tetramethylbenzidine was added to the plate, and the reaction was stopped after 15 min by the addition of $H_2SO_4$. The absorbance was measured and the percent inactivation, as measured by the amount of Btk available to be complexed with the compound of Example 88 and captured on the streptavidin-coated plate, was calculated versus control wells without test compound.

Results obtained from evaluation of Example 5 in the human whole blood inactivation assay are shown in Table 11.

TABLE 11

| Concentration of Example 5 (nM) | % Inactivation of Btk at 60 min |
| --- | --- |
| 0 | 0 |
| 0.7 | 0 |
| 3.1 | 25 |
| 12.5 | 33 |
| 50 | 70 |
| 200 | 98 |

Human Recombinant Btk Dissociation Dialysis Assay

A test compound was incubated with human recombinant Btk (100 nM) for 1.5 h at a concentration of 25 times the $IC_{50}$ of Btk inhibition or 200 nM (whichever was greater). The incubation was performed in assay buffer (20 mM HEPES pH 7.5, 10 mM $MgCl_2$, 2 mM dithiothreitol, 50 µg/mL bovine serum albumen and 0.015% Brij 35). The reaction mixture was then dialyzed twice for 6 h each time against 1 L of assay buffer. The dialyzed reaction mixture (0.5 µL) was then diluted into a solution (100 µL) of ATP (2 mM) and substrate peptide (5 µM Src-tide, AnaSpec) such that the final Btk concentration was 1 nM (along with any inhibitor still bound). The assay was performed in matrix polypropylene 384-well plates. The reaction progress curve was monitored on the Caliper LABCHIP® by electrophoretic separation of the substrate and phosphorylated product (pressure −1.2 psi, downstream voltage −500 V, upstream voltage −2300 V). Reaction velocity was measured over the linear phase and percent recovery of Btk activity was assessed at 2 h by comparing the fraction of phosphorylated peptide product relative to a DMSO-treated Btk control reaction containing no Example inhibitor. A control reaction with no Btk was also used to measure the background signal. A reversible inhibitor would show nearly complete recovery of Btk activity, while an irreversible inhibitor, would show little or no recovery of Btk activity.

TABLE 12

| Example | Btk $IC_{50}$ value (nM) | % recovery of Btk inhibition |
| --- | --- | --- |
| 18 | 0.2 | 4.5 |
| 37 | 0.16 | 3.5 |
| 101 | 7.3 | 101 |
| 102 | 5.1 | 75 |
| 103 | 1.4 | 77 |
| 104 | 11 | 97 |
| 105 | 4.1 | 99 |
| 106 | 75 | 102 |
| 107 | 16 | 95 |
| 108 | 14 | 117 |
| 109 | 240 | 100 |
| 110 | 19 | 102 |

Results obtained from evaluation of Comparative Examples 101-110 and for Examples 18 and 37 in the human recombinant Btk dissociation dialysis assay are shown in Table 12. These results show that Examples 18 and 37 bind to the enzyme with less than 5% recovery of Btk inhibition, indicating that these compounds form covalent bonds with human recombinant Btk and that the binding to the human recombinant Btk was irreversible. In contrast, Comparative Examples 101 through 110 were found to have significant (>75%) recovery of the Btk inhibition activity, indicating that the binding to the human recombinant Btk was reversible.

The invention claimed is:

1. A compound of Formula (I)

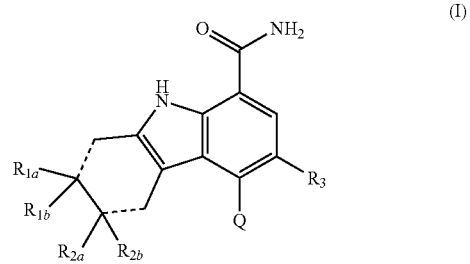

or a salt thereof, wherein:

the two dotted lines represent either two single or two double bonds; and $R_{1b}$ and $R_{2b}$ are present only if said two dotted lines are two single bonds;

Q is:

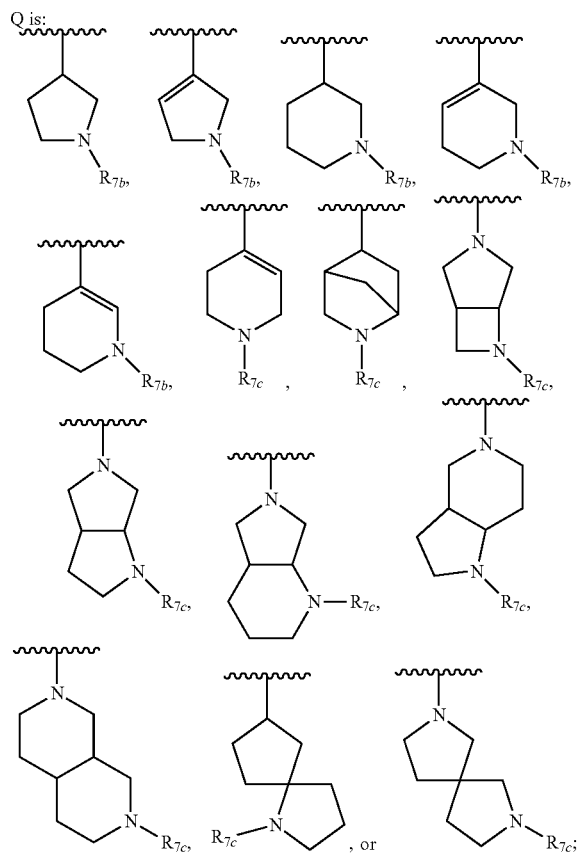

$R_{1a}$ is H, —CN, —CF$_3$, —CH$_3$, —CR$_{8a}$R$_{8b}$OH, —CR$_{8a}$R$_{8b}$CR$_{8a}$R$_{8b}$OH, —CH(OH)CH$_2$OH, NHR$_9$, —C(O)NR$_{10a}$R$_{10b}$, —C(O)(morpholinyl), —C(O)(piperazinyl), or C(O)(methyl piperazinyl);

$R_{1b}$, when present, is H or —CH$_3$, provided that if $R_{1a}$ is H then $R_{1b}$ is also H; $R_{2a}$ is H, F, or Cl, provided that if $R_{1a}$ is other than H then $R_{2a}$ is H;

$R_{2b}$, when present, is the same as $R_{2a}$;

$R_3$ is H, F, or Cl;

$R_{7b}$ is —C(O)CH=CH$_2$;

$R_{7c}$ is —C(O)CH=CH$_2$ or —C(O)C≡CR$_{12}$;

$R_{8a}$ is H or —CH$_3$;

$R_{8b}$ is H or —CH$_3$;

$R_9$ is C$_{1-4}$ alkyl;

$R_{10a}$ and $R_{10b}$ are independently H or —CH$_3$; and $R_{12}$ is H, C$_{1-4}$ alkyl, or cyclopropyl.

2. The compound according to claim 1 or a salt thereof, wherein:

$R_{1a}$ is H, —CF$_3$, —CH$_3$, —CR$_{8a}$R$_{8b}$OH, —CR$_{8a}$R$_{8b}$CR$_{8a}$R$_{8b}$OH, —NHR$_9$, —C(O)NR$_{10a}$R$_{10b}$, —C(O)(piperazinyl), or —C(O)(methyl piperazinyl);

$R_{1b}$ is H;

$R_{2a}$ is H or F, provided that if $R_{1a}$ is other than H then $R_{2a}$ is H;

$R_{2b}$, when present, is the same as $R_{2a}$;

$R_3$ is F or Cl;

$R_{7b}$ is —C(O)CH=CH$_2$;

$R_{7c}$ is —C(O)CH=CH$_2$ or —C(O)C≡CR$_{12}$;

$R_{8a}$ is H or —CH$_3$;

$R_{8b}$ is H or —CH$_3$;

$R_{10a}$ and $R_{10b}$ are independently H or —CH$_3$; and $R_{12}$ is H, C$_{1-4}$ alkyl, or cyclopropyl.

3. The compound according to claim 1 or a salt thereof, wherein $R_3$ is F.

4. The compound according to claim 1 or a salt thereof, having the structure of Formula (Ia):

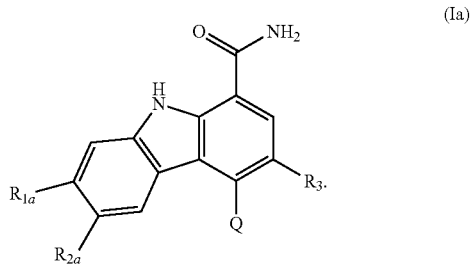

(Ia)

5. The compound according to claim 1 or a salt thereof, having the structure of Formula (Ib):

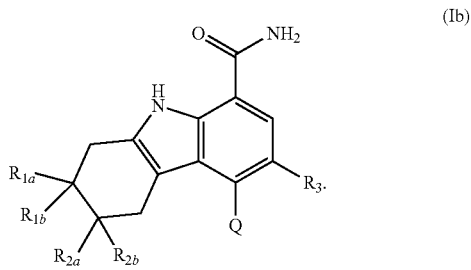

(Ib)

6. The compound according to claim 1 or a salt thereof, wherein Q is:

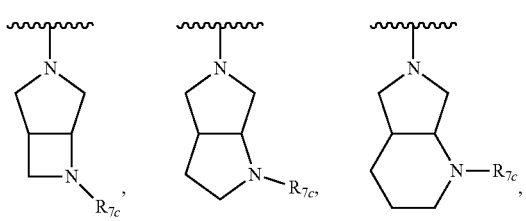

7. The compound according to claim 1 or a salt thereof, wherein said compound is:

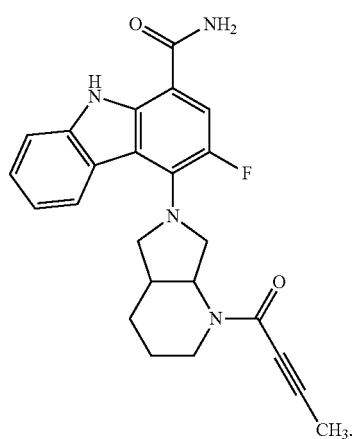 [SMILES: CC#CC(=O)N1CCCC2CN(c3c(F)cc(C(N)=O)c4[nH]c5ccccc5c34)CC21]

8. The compound according to claim 1 or a salt thereof, wherein said compound is:

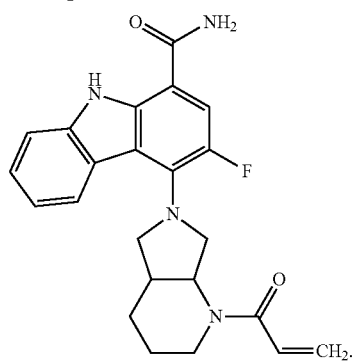

9. The compound according to claim 5 or a salt thereof, wherein Q is:

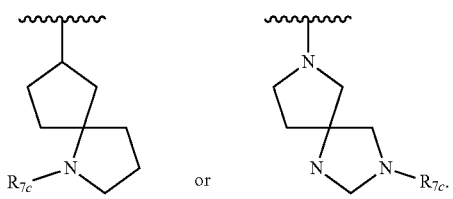

10. The compound according to claim 1 or a salt thereof, wherein said compound is:

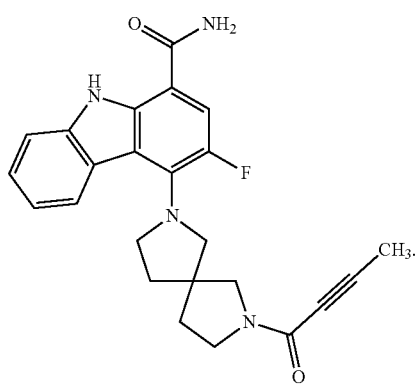 [SMILES: CC#CC(=O)N1CCC2(CCN(c3c(F)cc(C(N)=O)c4[nH]c5ccccc5c34)C2)C1]

11. The compound according to claim 1 or a salt thereof, wherein Q is:

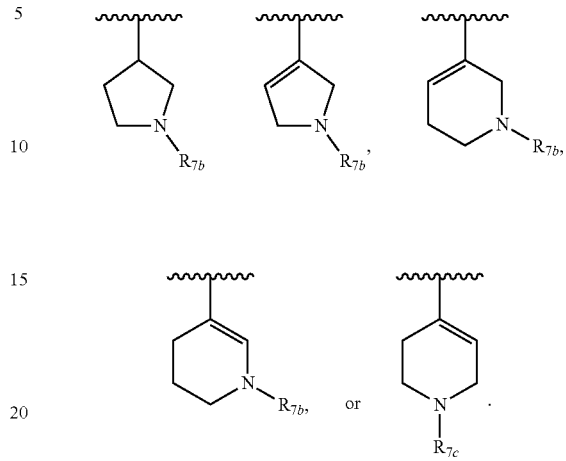

12. The compound according to claim 1 or a salt thereof, wherein said compound is:

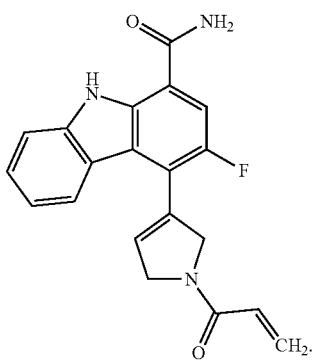 [SMILES: C=CC(=O)N1CC=C(c2c(F)cc(C(N)=O)c3[nH]c4ccccc4c23)C1]

13. The compound according to claim 1 or a salt thereof, wherein said compound is:

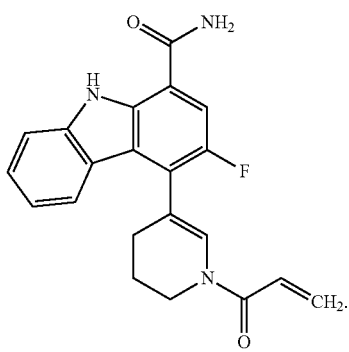 [SMILES: C=CC(=O)N1C=C(c2c(F)cc(C(N)=O)c3[nH]c4ccccc4c23)CCC1]

14. The compound according to claim 1 or a salt thereof, wherein Q is:

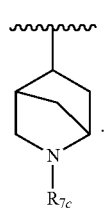

15. The compound according to claim 1 or a salt thereof, wherein said compound is:

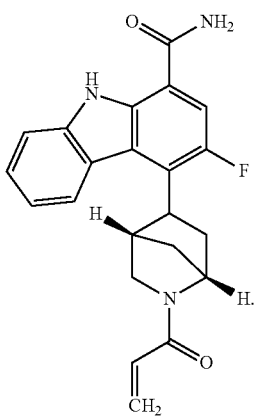

16. The compound according to claim 1 or a salt thereof, wherein the compound is selected from:
   4-(1-acryloyl-1,2,5,6-tetrahydropyridin-3-yl)-3-fluoro-9H-carbazole-1-carboxamide (96);
   (RS)-4-(1-acryloylpiperidin-3-yl)-3-fluoro-9H-carbazole-1-carboxamide (97);
   4-(1-acryloylpiperidin-3-yl)-3-fluoro-9H-carbazole-1-carboxamide, single enantiomers (98 and 99);
   4-(1-acryloylpyrrolidin-3-yl)-3-fluoro-9H-carbazole-1-carboxamide (112);
   4-(1-acryloylpyrrolidin-3-yl)-3-fluoro-9H-carbazole-1-carboxamide (113 and 114);
   cis-4-(1-(but-2-ynoyl)octahydro-6H-pyrrolo[3,4-b]pyridin-6-yl)-3-fluoro-9H-carbazole-1-carboxamide (115);
   cis-4-(1-(but-2-ynoyl)octahydro-6H-pyrrolo[3,4-b]pyridin-6-yl)-3-fluoro-9H-carbazole-1-carboxamide (116 and 117);
   cis-4-(1-acryloyloctahydro-6H-pyrrolo[3,4-b]pyridin-6-yl)-3-fluoro-9H-carbazole-1-carboxamide (119-121);
   cis-4-(1-acryloylhexahydropyrrolo[3,4-b]pyrrol-5 (1H)-yl)-3-fluoro-9H-carbazole-1-carboxamide (123);
   cis-4-(1-acryloylhexahydropyrrolo[3,4-b]pyrrol-5 (1H)-yl)-3-fluoro-9H-carbazole-1-carboxamide (124 and 125);
   4-(1-(but-2-ynoyl)octahydro-6H-pyrrolo[3,4-b]pyridin-6-yl)-3-chloro-9H-carbazole-1-carboxamide (126);
   4-((4aS, 7aS)-1-(but-2-ynoyl)octahydro-6H-pyrrolo[3,4-b]pyridin-6-yl)-3-chloro-9H-carbazole-1-carboxamide and 4-((4aR,7aR)-1-(but-2-ynoyl)octahydro-6H-pyrrolo[3,4-b]pyridin-6-yl)-3-chloro-9H-carbazole-1-carboxamide (127 and 128);
   4-(1-acryloyl-2,5-dihydro-1H-pyrrol-3-yl)-3-fluoro-9H-carbazole-1-carboxamide (134);
   5-(1-acryloylpyrrolidin-3-yl)-6-fluoro-2,3,4,9-tetrahydro-1H-carbazole-8-carboxamide (135);
   4-(1-(but-2-ynoyl)hexahydropyrrolo[3,4-b]pyrrol-5(1H)-yl)-3-fluoro-9H-carbazole-1-carboxamide (137);
   4-(1-acryloyl-1,4,5,6-tetrahydropyridin-3-yl)-3-fluoro-9H-carbazole-1-carboxamide (138);
   4-(7-(but-2-ynoyl)-2,7-diazaspiro[4.4] nonan-2-yl)-3-fluoro-9H-carbazole-1-carboxamide (139);
   4-(7-acryloyl-2,7-diazaspiro [4.4]nonan-2-yl)-3-fluoro-9H-carbazole-1-carboxamide (140);
   4-(1-acryloyloctahydro-5H-pyrrolo[3,2-c]pyridin-5-yl)-3-fluoro-9H-carbazole-1-carboxamide (141);
   4-(1-(but-2-ynoyl)octahydro-5H-pyrrolo[3,2-c]pyridin-5-yl)-3-fluoro-9H-carbazole-1-carboxamide (142);
   4-(6-acryloyl-3,6-diazabicyclo[3.2.0]heptan-3-yl)-3-fluoro-9H-carbazole-1-carboxamide (143);
   4-(6-(but-2-ynoyl)-3,6-diazabicyclo[3.2.0] heptan-3-yl)-3-fluoro-9H-carbazole-1-carboxamide (144);
   4-(7-acryloyloctahydro-2,7-naphthyridin-2(1H)-yl)-3-fluoro-9H-carbazole-1-carboxamide (145);
   4-(1-acryloyloctahydro-6H-pyrrolo[3,4-b] pyridin-6-yl)-3-chloro-9H-carbazole-1-carboxamide (146);
   4-(1-acryloyl-1,2,5,6-tetrahydropyridin-3-yl)-3-fluoro-7-(trifluoromethyl)-9H-carbazole-1-carboxamide (160);
   4-(1-acryloylpiperidin-3-yl)-3-fluoro-7-(trifluoromethyl)-9H-carbazole-1-carboxamide (161 and 162);
   4-(1-acryloyl-1-azaspiro[4.4]nonan-7-yl)-3-fluoro-7-(trifluoromethyl)-9H-carbazole-1-carboxamide (171);
   4-(1-acryloyloctahydro-6H-pyrrolo[3,4-b]pyridin-6-yl)-6-chloro-3-fluoro-9H-carbazole-1-carboxamide (182);
   4-(1-(but-2-ynoyl)octahydro-6H-pyrrolo[3,4-b]pyridin-6-yl)-6-chloro-3-fluoro-9H-carbazole-1-carboxamide (183);
   5-(1-acryloyl-1,2,5,6-tetrahydropyridin-3-yl)-6-fluoro-2-(2-hydroxypropan-2-yl)-2,3,4,9-tetrahydro-1H-carbazole-8-carboxamide (184);
   4-(7-(but-2-ynoyl)octahydro-2,7-naphthyridin-2(1H)-yl)-3-fluoro-9H-carbazole-1-carboxamide (190);
   4-(1-acryloyl-1,2,3,6-tetrahydropyridin-4-yl)-3-fluoro-9H-carbazole-1-carboxamide (191);
   4-(1-(but-2-ynoyl)-1,2,3,6-tetrahydropyridin-4-yl)-3-fluoro-9H-carbazole-1-carboxamide (192); and
   4-((1S,4S)-2-acryloyl-2-azabicyclo[2.2.1]heptan-5-yl)-3-fluoro-9H-carbazole-1-carboxamide (194).

17. A pharmaceutical composition comprising a compound according to claim 1 and a pharmaceutically acceptable carrier.

18. A pharmaceutical composition comprising a compound according to claim 7 and a pharmaceutically acceptable carrier.

19. A pharmaceutical composition comprising a compound according to claim 7 and a pharmaceutically acceptable carrier.

20. A pharmaceutical composition comprising a compound according to claim 10 and a pharmaceutically acceptable carrier.

21. A pharmaceutical composition comprising a compound according to claim 12 and a pharmaceutically acceptable carrier.

22. A pharmaceutical composition comprising a compound according to claim 13 and a pharmaceutically acceptable carrier.

23. A pharmaceutical composition comprising a compound according to claim 15 and a pharmaceutically acceptable carrier.

* * * * *

UNITED STATES PATENT AND TRADEMARK OFFICE
CERTIFICATE OF CORRECTION

| | | Page 1 of 1 |
|---|---|---|
| PATENT NO. | : 11,053,197 B2 | |
| APPLICATION NO. | : 16/859103 | |
| DATED | : July 6, 2021 | |
| INVENTOR(S) | : Saleem Ahmad et al. | |

It is certified that error appears in the above-identified patent and that said Letters Patent is hereby corrected as shown below:

On the Title Page

Item (72) Column 1 (Inventors), Line 6, Delete "Scott Hunter," and insert -- Scott Hunter Watterson, --, therefor.

In the Claims

In Claim 1, Column 249, Line 37, delete "NHR$_9$," and insert -- —NHR$_9$, --, therefor.

In Claim 1, Column 249, Line 39, delete "C(O)(" and insert -- —C(O)( --, therefor.

In Claim 11, Column 252, Line 5-11 (Approx.), after " 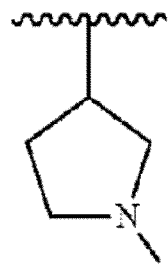" insert -- , --.

In Claim 16, Column 253, Line 50 (Approx.), delete "-5 (1H)-" and insert -- -5(1H)- --, therefor.

In Claim 16, Column 253, Line 52, delete "-5 (1H)-" and insert -- -5(1H)- --, therefor.

In Claim 16, Column 253, Line 57, delete "4-((4aS, 7aS)-" and insert -- 4-((4aS,7aS)- --, therefor.

In Claim 16, Column 253, Line 64-65, delete "-tetrahy dro-" and insert -- -tetrahydro- --, therefor.

In Claim 19, Column 254, Line 51, delete "claim 7" and insert -- claim 8 --, therefor.

Signed and Sealed this
Seventh Day of December, 2021

Drew Hirshfeld
*Performing the Functions and Duties of the
Under Secretary of Commerce for Intellectual Property and
Director of the United States Patent and Trademark Office*